(12) United States Patent
Ott et al.

(10) Patent No.: US 11,634,448 B2
(45) Date of Patent: Apr. 25, 2023

(54) METABOLIC LABELING AND MOLECULAR ENHANCEMENT OF BIOLOGICAL MATERIALS USING BIOORTHOGONAL REACTIONS

(71) Applicant: The General Hospital Corporation, Boston, MA (US)

(72) Inventors: Harald C. Ott, Wenham, MA (US); Xi Ren, Malden, MA (US); Jordan P. Bloom, Charlestown, MA (US); Taufiek Konrad Rajab, Hirrlingen (DE)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/624,399

(22) Filed: Jun. 15, 2017

(65) Prior Publication Data
US 2017/0362266 A1 Dec. 21, 2017

Related U.S. Application Data

(60) Provisional application No. 62/350,259, filed on Jun. 15, 2016.

(51) Int. Cl.
| | |
|---|---|
| A61K 31/655 | (2006.01) |
| C12N 5/06 | (2006.01) |
| C07H 13/04 | (2006.01) |
| A61L 27/38 | (2006.01) |
| A61L 27/54 | (2006.01) |
| C12N 5/07 | (2010.01) |
| A61K 35/22 | (2015.01) |
| A61K 35/34 | (2015.01) |
| A61K 35/36 | (2015.01) |
| A61K 35/407 | (2015.01) |
| A61K 35/42 | (2015.01) |
| A61K 35/44 | (2015.01) |
| A61L 27/36 | (2006.01) |

(52) U.S. Cl.
CPC ........... *C07H 13/04* (2013.01); *A61K 31/655* (2013.01); *A61K 35/22* (2013.01); *A61K 35/34* (2013.01); *A61K 35/36* (2013.01); *A61K 35/407* (2013.01); *A61K 35/42* (2013.01); *A61K 35/44* (2013.01); *A61L 27/3633* (2013.01); *A61L 27/383* (2013.01); *A61L 27/3808* (2013.01); *A61L 27/3813* (2013.01); *A61L 27/3826* (2013.01); *A61L 27/54* (2013.01); *C12N 5/06* (2013.01); *A61L 2300/256* (2013.01); *A61L 2300/406* (2013.01); *A61L 2300/414* (2013.01); *A61L 2300/42* (2013.01)

(58) Field of Classification Search
CPC ..... C07H 13/04; A61L 27/36; A61L 27/3633; A61L 27/56; A61K 35/44; A61K 35/42; A61K 31/655; A61K 35/36; A61K 35/34; A61K 35/22; A61K 35/407; A61K 9/0019; A61K 31/7004; C12N 5/06
See application file for complete search history.

(56) References Cited

U.S. PATENT DOCUMENTS

| | | |
|---|---|---|
| 6,479,064 B1 | 11/2002 | Atala |
| 6,753,181 B2 | 6/2004 | Atala |
| 6,803,031 B2 | 10/2004 | Rabinowitz et al. |
| 8,470,520 B2 | 6/2013 | Ott et al. |
| 8,790,920 B2 | 7/2014 | Freyman |
| 9,005,885 B2 | 4/2015 | Ott |
| 9,127,242 B2 | 9/2015 | Guertin et al. |
| 2002/0042658 A1 | 4/2002 | Tyagi |
| 2002/0115208 A1 | 8/2002 | Mitchell et al. |
| 2003/0087428 A1 | 5/2003 | Wolfinbarger et al. |
| 2005/0256588 A1 | 11/2005 | Sawa et al. |
| 2007/0244568 A1 | 10/2007 | Matsuda et al. |
| 2007/0275363 A1 | 11/2007 | Bertram et al. |
| 2008/0095662 A1 | 4/2008 | Konertz et al. |
| 2008/0267878 A1 | 10/2008 | Robillard et al. |
| 2009/0142836 A1 | 6/2009 | Wang et al. |
| 2009/0192528 A1 | 7/2009 | Higgins et al. |
| 2010/0247433 A1* | 9/2010 | Tirrell ................ A61K 49/0002 424/1.65 |

(Continued)

FOREIGN PATENT DOCUMENTS

| | | | |
|---|---|---|---|
| CN | 101511389 | 8/2009 | |
| CN | 101925675 | 12/2010 | |
| CN | 102112162 | 6/2011 | |
| CN | 102313801 | 1/2012 | |
| DE | 102015100171 | 9/2015 | |
| EP | 2623609 A2 * | 7/2013 | .............. C12P 21/00 |
| EP | 2641616 | 9/2013 | |

(Continued)

OTHER PUBLICATIONS

Neves et al. Imaging Cell Surface Glycosylation in Vivo Using "Double Click" Chemistry. Bioconjugate Chem. 2013;24:934-941.*

(Continued)

*Primary Examiner* — Lynn Y Fan
(74) *Attorney, Agent, or Firm* — Fish & Richardson P.C.

(57) ABSTRACT

The present application provides methods of functionalizing an organ or tissue of a mammal by administering a nutrient (e.g., peracetylated N-azido galactosamine Ac4GalNAz) to the mammal or by culturing an organ or tissue in a bioreactor containing such nutrient. The present application also provides methods of selectively functionalizing extracellular matrix (ECM) of an organ or tissue of a mammal by administering a nutrient (e.g., peracetylated N-azido galactosamine Ac4GalNAz) to the mammal. In some aspects, the present application provides a decellularized scaffold of a mammalian organ or tissue comprising an extracellular matrix, wherein the extracellular matrix of the decellularized scaffold is functionalized with a chemical group that is reactive in a bioorthogonal chemical reaction, such as an azide chemical group. The present application also provides biological prosthetic mesh and mammalian organs and tissues for transplantation prepared according to the methods of the application.

13 Claims, 51 Drawing Sheets
(44 of 51 Drawing Sheet(s) Filed in Color)

(56) References Cited

U.S. PATENT DOCUMENTS

| | | |
|---|---|---|
| 2010/0272782 A1 | 10/2010 | Owens et al. |
| 2010/0318108 A1 | 12/2010 | Datta et al. |
| 2011/0045566 A1 | 2/2011 | Wang et al. |
| 2012/0028335 A1 | 2/2012 | Agnew |
| 2012/0149887 A1 | 6/2012 | Sawa et al. |
| 2013/0177972 A1 | 7/2013 | Green et al. |
| 2014/0205565 A1 | 7/2014 | Matheny |
| 2015/0079143 A1 | 3/2015 | Lelkes et al. |
| 2015/0197600 A1 | 7/2015 | Becker et al. |
| 2015/0238656 A1 | 8/2015 | Orlando et al. |
| 2015/0291925 A1 | 10/2015 | Ott |
| 2015/0297798 A1 | 10/2015 | Badylak et al. |
| 2015/0306148 A1 | 10/2015 | Barakat et al. |
| 2015/0344842 A1 | 12/2015 | Sheu et al. |
| 2016/0015503 A1 | 1/2016 | Guttadauro |
| 2016/0053213 A1 | 2/2016 | Takei et al. |
| 2016/0089477 A1 | 3/2016 | Valmikinathan et al. |
| 2017/0015963 A1 | 1/2017 | Ott |
| 2017/0073645 A1 | 3/2017 | Ren et al. |

FOREIGN PATENT DOCUMENTS

| | | |
|---|---|---|
| WO | WO 2002/040630 | 5/2002 |
| WO | WO 2007/039858 | 4/2007 |
| WO | WO 2009/002772 | 12/2008 |
| WO | WO 2010/141803 | 12/2010 |
| WO | WO 2012016044 | 2/2012 |
| WO | WO 2012016048 | 2/2012 |
| WO | WO 2013/093921 | 6/2013 |
| WO | WO 2014/008844 | 1/2014 |
| WO | WO 2016/036764 | 3/2016 |
| WO | WO 2016/061450 | 4/2016 |

OTHER PUBLICATIONS

Nagib DA. The Career of Carolyn Bertozzi. www.princeton.edu. 2008;1-40.*

Azagarsamy et al. Bioorthogonal Click Chemistry: An Indispensable Tool to Create Multifaceted Cell Culture Scaffolds. ACS Macro Lett. 2013;2:5-9.*

Crapo et al. An overview of tissue and whole organ decellularization processes. Biomaterials. 2011;32(12):3233-3243.*

Badylak et al., "Whole-Organ Tissue Engineering: Decellularization and Recellularization of Three-Dimensional Matrix Scaffolds," Annu Rev Biomed Eng., 2011, 13: 27-53.

Banerjee et al., "Chemoselective attachment of small molecule effector functionality to human adenoviruses facilitates gene delivery to cancer cells," Journal of the American Chemical Society, Oct. 2010, 132: 13615-13617.

Bao et al., "Hemocompatibility improvement of perfusion-decellularized clinical-scale liver scaffold through heparin immobilization," Scientific Reports, Jun. 2015, 5:10756.

Bellows et al., "The effect of bacterial infection on the biomechanical properties of biological mesh in a rat model," PLoS One, Jun. 2011, 6: e21228.

Bilsel and Abci, "The search for ideal hernia repair; mesh materials and types," International Journal of Surgery, 2012, 10: 317-321.

Boyce et al., "Metabolic cross-talk allows labeling of O-linked β-N-acetylglucosamine-modified proteins via the N-acetylgalactosamine salvage pathway," PNAS, Feb. 2011, 108: 3141-3146.

Bribriesco et al., "Experimental models of lung transplantation," Front Biosci (Elite Ed), Jan. 2013, 5:266-72.

Cai and Janda, "A chemoenzymatic approach toward the preparation of site-specific antibody-drug conjugates," Tetrahedron Letters, Jun. 2015, 23: 3172-3175.

Cai et al., "Corrigendum to A chemoenzymatic approach toward the preparation of site-specific antibody-drug conjugates," Tetrahedron Lett, 2015, 56: 3172-3175.

Chang et al., "Copper-free click chemistry in living animals," PNAS, Feb. 2010, 107: 1821-1826.

Chang et al., "Imaging Cell Surface Glycans with Bioorthogonal Chemical Reporters," Journal of the American Chemical Society, Jul. 2007, 129: 8400-8401.

Chang et al., "Metabolic Labeling of Sialic Acids in Living Animals with Alkynyl Sugars," Angewandte Chemie International Edition, 2009, 48: 4030-4033.

Chiu and Radisic, "Scaffolds with covalently immobilized VEGF and Angiopoietin-1 for vascularization of engineered tissues," Biomaterials, 2010, 31: 226-241.

Cohen et al., "Real-Time Bioluminescence Imaging of Glycans on Live Cells," Journal of the American Chemical Society, 2010, 132: 8563-8565.

Collage and Rosengart, "Abdominal wall infections with in situ mesh," Surg. Infect., 2010,11: 311-8.

Crapo et al., "An overview of tissue and whole organ decellularization processes," Biomaterials, Apr. 2011, 32: 3233-3243.

Darehzereshki et al., "Biologic versus nonbiologic mesh in ventral hernia repair: a systematic review and meta-analysis," World J. Surg, 2014, 38: 40-50.

Davidenko et al., "Control of crosslinking for tailoring collagen-based scaffolds stability and mechanics," Acta Biomaterialia, 2015, 25: 131-142.

Dube et al., "Probing mucin-type O-linked glycosylation in living animals," PNAS, Mar. 2006, 103: 4819-4824.

Gilbert et al., "Decellularization of tissues and organs," Biomaterials, 2006, 27(9):3675-83.

Gilpin et al., "Perfusion decellularization of human and porcine lungs: Bringing the matrix to clinical scale," Journal of Heart and Lung Transplantation, Mar. 2014, 33: 298-308.

Grover et al., "Crosslinking and composition influence the surface properties, mechanical stiffness and cell reactivity of collagen-based films," Acta Biomaterialia, 2012, 8: 3080-3090.

Grover et al., "The interplay between physical and chemical properties of protein films affects their bioactivity," Journal of Biomedical Materials Research Part A , Sep. 2012,100: 2401-2411.

Guyette et al., "Bioengineering Human Myocardium on Native Extracellular Matrix," Circulation Research, Jan. 2016, 118(1):56-72.

Guyette et al., "Perfusion decellularization of whole organs," Nat Protoc, 2014, 9: 1451-1468.

Halaweish et al., "Novel in vitro model for assessing susceptibility of synthetic hernia repair meshes to Staphylococcus aureus infection using green fluorescent protein-labeled bacteria and modern imaging techniques," Surg. Infect, 2010, 11: 449-454.

Hang et al., "A metabolic labeling approach toward proteomic analysis of mucin-type O-linked glycosylation," PNAS, 2003, 100: 14846-14851.

Hang et al., "Probing Glycosyltransferase Activities with the Staudinger Ligation," J. Am. Chem. Soc, 2004, 126: 6-7.

Hao et al., "Introducing Bioorthogonal Functionalities into Proteins in Living Cells," Accounts Of Chemical Research, 2011, 44: 742-751.

Hinz et al., "Noncanonical Amino Acid Labeling in Vivo to Visualize and Affinity Purify Newly Synthesized Proteins in Larval Zebrafish," ACS Chemical Neuroscience, 2012, 3: 40-49.

Hong et al., "Analysis and Optimization of Copper-Catalyzed Azide-Alkyne Cycloaddition for Bioconjugation," Angewandte Chemie (International ed. in English), 2009, 48: 9879-9883.

Hubbard et al., "Cell surface glycoproteomic analysis of prostate cancer-derived PC-3 cells," Bioorganic & Medicinal Chemistry Letters, Sep. 2011, 21: 4945-4950.

Invitation to Pay Additional Fees and, Where Applicable, Protest Fee in Application No. PCT/US2017/37710, dated Aug. 8, 2017.

Jao and Salic, "Exploring RNA transcription and turnover in vivo by using click chemistry," PNAS, 2008, 105: 15779-15784.

Jao et al., "Metabolic labeling and direct imaging of choline phospholipids in vivo," PNAS, 2009, 106: 15332-15337.

Jiang et al., "Tracking surface glycans on live cancer cells with single molecule sensitivity," Angew Chem Int Ed Engl, 2014, 53: 1-6.

Kierzek et al., "Microarrays for identifying binding sites and probing structure of RNAs," Nucl. Acids Res, Jan. 2015, 43: 1-12.

(56) References Cited

OTHER PUBLICATIONS

Ko et al., "Bioengineered transplantable porcine livers with re-endothelialized vasculature," Biomaterials, Feb. 2015, 40:72-9.
Laughlin and Bertozzi, "In Vivo Imaging of Caenorhabditis elegans Glycans," ACS Chemical Biology, 2009, 4: 1068-1072.
Laughlin and Bertozzi, "Metabolic labeling of glycans with azido sugars and subsequent glycan-profiling and visualization via Staudinger ligation," Nat Protoc, 2007, 2: 2930-2944.
Laughlin et al., "In vivo imaging of membrane-associated glycans in developing zebrafish," May 2008, 320: 664-7.
Letschert et al., "Super-Resolution Imaging of Plasma Membrane Glycans," Angew Chem Int Ed Engl, 2014, 53: 10921-10924.
Liao et al, "Effects of decellularization on the mechanical and structural properties of the porcine aortic valve leaflet," Biomaterials, Mar. 2008, 29(8):1065-74.
Liu et al., "Dynamic Monitoring of Newly Synthesized Proteomes: Up-Regulation of Myristoylated Protein Kinase A During Butyric Acid Induced Apoptosis," Angew. Chem. Int. Ed, 2011, 50: 6776-6781.
Liu et al., "Imaging protein synthesis in cells and tissues with an alkyne analog of puromycin," PNAS, 2012, 109: 413-418.
Ma et al., "Crosslinking strategies for preparation of extracellular matrix-derived cardiovascular scaffolds," Regenerative Biomaterials, Nov. 2014, 1(1):81-9.
Maghsoudlou et al., "Preservation of microarchitecture and angiogenic potential in a pulmonary acellular matrix obtained using intermittent intra-tracheal flow of detergent enzymatic treatment," Biomaterials, Sep. 2013, 34(28):6638-48.
Moller et al., "N-Glycans of Recombinantly Expressed Human Lactotransferrin by Metabolic Oligosaccharide Engineering," 2011, 30: 334-336.
Ngoka, Sample prep for proteomics of breast cancer: proteomics and gene ontology reveal dramatic differences in protein solubilization preferences of radioimmunoprecipitation assay and urea lysis buffers. Proteome Science, 2008, 6: 30.
Nichols et al., "Production and assessment of decellularized pig and human lung scaffolds," Tissue Eng Part A, Sep. 2013, 19 (17-18):2045-62.
Niederwieser et al., "Two-Color Glycan Labeling of Live Cells by a Combination of Diels-Alder and Click Chemistry," Angew Chem Int Ed Engl, 2013, 52: 4265-4268.
Olde Damink et al., "Cross-linking of dermal sheep collagen using a watersoluble Carbodiimide," Biomaterials, 1996, 17: 765-773.
O'Neill et al., "Decellularization of human and porcine lung tissues for pulmonary tissue engineering," Ann Thorac Surg, Sep. 2013, 96(3):1046-55.
Ott et al., "Perfusion-decellularized matrix: using nature's platform to engineer a bioartificial heart," Nat. Med, Feb. 2008, 14: 213-221.
Ott et al., "Regeneration and orthotopic transplantation of a bioartificial lung," Nat Med, 2010, 16: 927-933.
Pasque, "Standardizing thoracic organ procurement for transplantation," J Thorac Cardiovasc Surg, Jan. 2010, 139(1):13-7.
Pathigoolla et al., "A versatile solvent-free azide-alkyne click reaction catalyzed by in situ generated copper nanoparticles," Applied Catalysis A: General, Feb. 2013, 453: 151-158.
Perez and Bode, "Click Chemistry for the Simple Determination of Fatty-Acid Uptake and Degradation: Revising the Role of Fatty-Acid Transporters," ChemBioChem, Jul. 2015, 16 (11): 1588-1591.
Petersen et al., "Tissue-Engineered Lungs for in Vivo Implantation," Science, Jul. 2010, 329: 538-541.
Pieper et al., "Preparation and characterization of porous cross-linked collagenous matrices containing bioavailable chondroitin sulphate," Biomaterials, 1999, 20: 847-858.
Pouilly et al., "Evaluation of analogues of GalNAc as substrates for enzymes of the mammalian GalNAc salvage pathway," ACS Chem Biol, Apr. 2012, 7: 753-60.
Presolski et al., "Copper-Catalyzed Azide-Alkyne Click Chemistry for Bioconjugation", Curr Protoc Chem Biol, 2011, 3(4): 153-162.

Ren et al., "Engineering pulmonary vasculature in decellularized rat and human lungs," Nature Biotechnology, Oct. 2015, 33: 1097-1102.
Reyes-Ortega et al., "Smart heparin-based bioconjugates synthesized by a combination of ATRP and click chemistiy," Polymer Chemistiy, 2013, 15 pages.
Rinaldi et al., "Solvent-Free Copper-Catalyzed Azide-Alkyne Cycloaddition under Mechanochemical Activation," Molecules, 2015, 20: 2837-2849.
Salic and Mitchison, "A chemical method for fast and sensitive detection of DNA synthesis in vivo," PNAS, 2008, 105: 2415-2420.
Santner et al., "Efficient access to 3'-terminal azide-modified RNA for inverse click-labeling patterns," Bioconjug Chem, Jan. 2014, 25(1): 188-195.
Sawant et al., "A versatile toolbox for posttranscriptional chemical labeling and imaging of RNA," Nucleic Acids Research, 2015, 1-12.
Schiapparelli et al., "Direct Detection of Biotinylated Proteins by Mass Spectrometry," Journal of Proteome Research, 2014, 13: 3966-3978.
Shen et al., "Vascular endothelial growth factor immobilized in collagen scaffold promotes penetration and proliferation of endothelial cells," Acta Biomaterialia, 2008, 4: 477-489.
Slade et al., "Identifying the CHO Secretome using Mucin-type O-Linked Glycosylation and Click-chemistry," J. Proteome Res, 2012, 11: 6175-6186.
Song and Ott, "Bioartificial lung engineering," Am J Transplant, Feb. 2012, 2(2):283-8.
Song et al., "Regeneration and experimental orthotopic transplantation of a bioengineered kidney," Nature Medicine, May 2013, 19(5):646-51.
Spate et al., Rapid Labeling of Metabolically Engineered Cell-Surface Glycoconjugates with a Carbamate-Linked Cyclopropene Reporter, Bioconjugate Chem, 2014, 25: 147-154.
Teebken et al., "Tissue engineering of vascular grafts: human cell seeding of decellularised porcine matrix," Eur. J. Vasc. Endovasc. Surg, 2000, 19:381-86.
Teo and Wells, "Monitoring protein O-linked b-N-acetylglucosamine status via metabolic labeling and copper-free click chemistry," Anal Biochem, Nov. 2014, 464: 70-72.
Ullrich et al., "Bio-orthogonal labeling as a tool to visualize and identify newly synthesized proteins in Caenorhabditis elegans," Nat. Protocols, 2014, 9: 2237-2255.
Uygun et al., "Organ reengineering through development of a transplantable recellularized liver graft using decellularized liver matrix," Nature Medicine, Jul. 2010, 16(7): 814-820.
Wilson et al., "A cellular Matrix: A Biomaterials Approach for Coronary Artery Bypass and Heart Valve Replacement," Ann Thorac Surg, 1995, 60: S353-358.
Wissink et al., "Immobilization of heparin to EDC/NHS-crosslinked collagen. Characterization and in vitro evaluation," Biomaterials, Jan. 2001, 22: 151-163.
Witte et al., "Live-cell MRI with Xenon Hyper-CEST Biosensors Targeted to Metabolically Labeled Cell-Surface Glycans," Feb. 2015, 54: 2806-2810.
Yang, "Evaluation of the release rate of bioactive recombinant human epidermal growth factor from crosslinking collagen sponges," Journal of Materials Science, 2008,19: 1433-1440.
Ying and Branchaud, "Design of a reversible biotin analog and applications in protein labeling, detection, and isolation," Chem Commun (Camb), Aug. 2011, 47: 8593-8595.
Zaro et al., "Robust in-gel fluorescence detection of mucin-type O-linked glycosylation," Bioorganic & Medicinal Chemistiy Letters, 2011, 21: 5062-5066.
Zerkowski et al., "Clickable Lipids: Azido and Alkynyl Fatty Acids and Triacylglycerols," Journal of the American Oil Chemists' Society, 2009, 86: 1115-1121.
Zhao et al., "Labeling of Enveloped Virus via Metabolic Incorporation of Azido Sugars," Bioconjugate Chemistry, 2015, 26: 1868-1872.
Zhou et al., "Bioengineering Human 20 Lung Grafts on Porcine Matrix," Annals of Surgery, 2017, 1-7.

(56) References Cited

OTHER PUBLICATIONS

Azagarsamy and Anseth, "Bioorthogonal Click Chemistry: An Indispensable Tool to Create Muitifaceted Cell Culture Scaffolds," ACS Macro Lett, 2013, 2(1): 5-9.
Armstrong and Perriman, "Strategies for cell membrane functionalization," Exp Biol Med, May 2016, 241(10): 1098-106.
Sletten and Bertozzi, "Bioorthogonal Chemistry: Fishing for Selectivity in a Sea of Functionality azide," Angew Chem Int Ed Engl, 2009, 48(38): 6974-98.
Ruff et al., "clickECM; Development of a cell-derived extracellular matrix with azide Functionalities," Acta Biomater, Apr. 2017, 52: 159-170.
International Search Report and Written Opinion in International Application No. PCT/US 17/37710, dated Oct. 31, 2017, 31 pages.
Chemlabs.princeton.edu [online], "The Career of Carolyn Bertozzi," Nov. 12, 2008, [retrieved on Feb. 13, 2020], retrieved from: URL < http://chemlabs.princeton.edu/macmillan/wp-content/uploads/sites/6/DAN_Bertozzi.pdf>, 40 pages.
EP Extended European Search Report in European Appln. 17814104.0, dated Feb. 13, 2020, 10 pages.
Neves et al., "Imaging sialylated tumor cell glycans in vivo," FASEB journal: official publication of the Federation of American Societies for Experimental Biology, Aug. 2011, 25(8):2528-2537.
APBioCellOrganelles.Weebly.com [online], "AP Biology—Cell Organelles—ECM," Jul. 21, 2015, retrieved on Mar. 16, 2021, retrieved from URL <http://apbiocellorganelles.weebly.com/ecm.html>, 4 pages.
AU Office Action in Australian Appln. No. 2017286715, dated Feb. 15, 2021, 9 pages.
CNOA in Chinese Appln. No. 201780049920.4, dated Nov. 4, 2020, 14 pages (with English Translation).
Frantz et al., "The extracellular matrix at a glance," Journal of Cell Science, 2010, 123(24):4195-4200.
JP Office Action in Japanese Appln. No. 2018-565708, dated Dec. 1, 2020, 4 pages (with English translation).
KhanAcademy.org [online], "The extracellular matrix and cell wall," available on or before 2016, retrieved May 4, 2021, retrieved from URL <https://www.khanacademy.org/science/ap-biology/cell-structure-and-function/membrane-permeability/a/the-extracellular-matrix-and-cell-wall>, 11 pages.
Ruff et al., "clickECM—a new approach to covalently immobilize human ECM on artificial surfaces," Frontiers Event Abstract, published online Mar. 30, 2016, retrieved from URL <https://www.frontiersin.org/Community/AbstractDetails.aspx?ABS_DOI=10.3389/conf.FBIOE.2016.01.00633&eid=2893&sname=10th_World_Biomaterials_Congress>, 2 pages.
Office Action in Korean Appln. No. 10-2019-7000956, dated Feb. 3, 2022, 15 pages (with English translation).
CN Office Action in Chinese Appln. No. 201780049920.4, dated Jul. 22, 2021, 18 pages (with English translation).
Xenotransplantation, Dou (ed.), People's Military Medical Press, Jan. 31, 2014, p. 336 (with English translation).
Notice of Allowance in Chinese Appln. No. 201780049920.4, dated Apr. 6, 2022, 5 pages (with English translation).
Notice of Allowance in Japanese Appln. No. 2018-565708, dated May 9, 2022, 5 pages (with English translation).
Office Action in Korean Appln. No. 10-2019-7000956, dated Aug. 29, 2022, 8 pages (with English translation).
Wang et al., "'Click' Immobilization of a VEGF-Mimetic Peptide on Decellularized Endothelial Extracellular Matrix to Enhance Angiogenesis," ACS Appln. Mater. Interfaces, 2014, 6:8401-8406.
Zhao et al., "Research progress of generating organ decellularization scaffold by perfusion method," Chinese Journal of Clinical Anatomy, 2013, 31(6):727-730, 5 pages (with English abstract).

\* cited by examiner

FIG. 1C

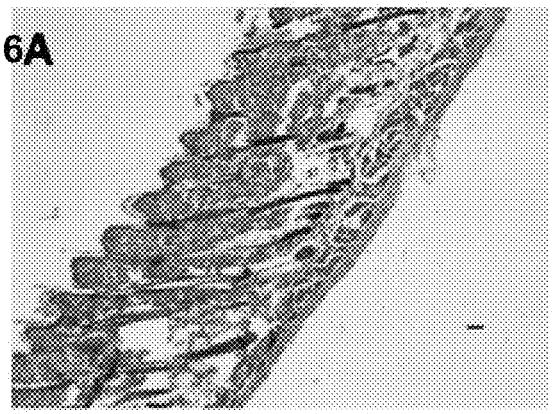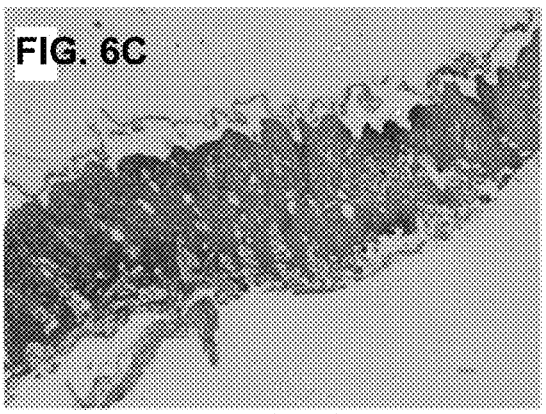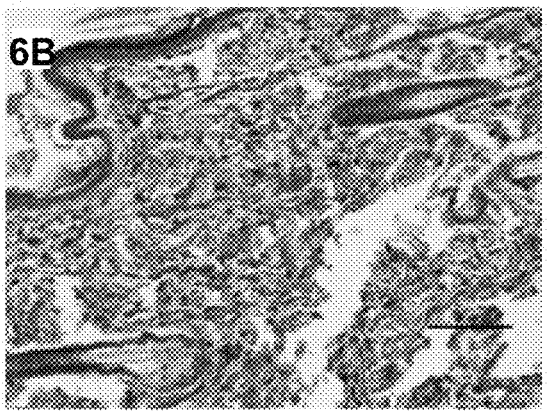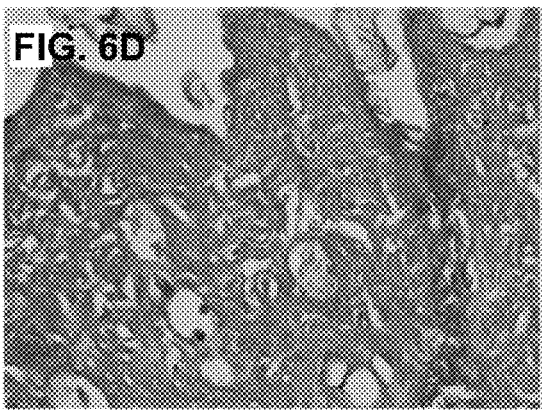

FIG. 16

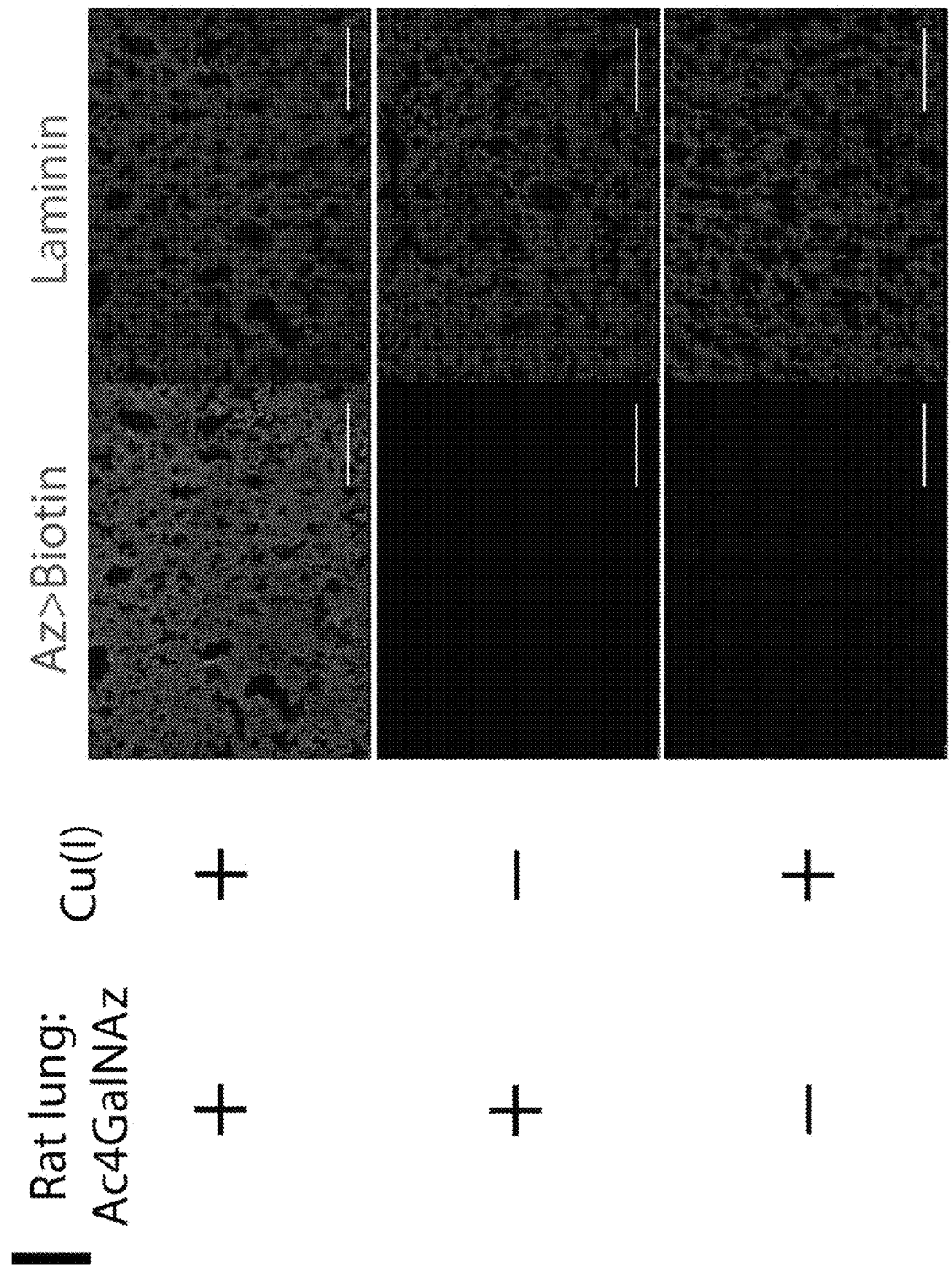

METABOLIC LABELING AND MOLECULAR ENHANCEMENT OF BIOLOGICAL MATERIALS USING BIOORTHOGONAL REACTIONS

CLAIM OF PRIORITY

This application claims the benefit of U.S. Provisional Application No. 62/350,259, filed Jun. 15, 2016. The entire contents of the foregoing are hereby incorporated by reference.

TECHNICAL FIELD

This invention relates to metabolic labeling and further functionalization of mammalian organs and tissues.

BACKGROUND

Prosthetic meshes are a common solution to numerous clinical problems with the most frequent being hernia repair. While synthetic prosthetic meshes are strong and offer low recurrence rates, an increase in mesh-related complications, including infection, has been demonstrated. (Darehzereshki, A. et al. World J. Surg. 38, 40-50 (2014)) Synthetic meshes are contraindicated in the setting of active infection and are relatively contraindicated in patients at high risk for infection or in operations at high risk of contamination.

Biological prosthetics have been developed using a variety of tissue sources and processing techniques. Most of these meshes are composed of decellularized extracellular matrix (ECM), which has been sterilized and often fixed. The most commonly used meshes come from porcine small intestine (Surgisis®), porcine dermis (Strattice®, Permacol™) or cadaveric human dermis (Alloderm®, Allomax™). These biologic prosthesis have an increased resistance to infection, yet failure rates and bacterial infection of these materials persist. (Darehzereshki, A. et al. World J. Surg. 38, 40-50 (2014); Bellows, C. F., Wheatley, B. M., Moroz, K., Rosales, S. C. & Morici, L. PLoS One 6, (2011)) Furthermore, the biomechanical properties of biologic mesh significantly decline after bacterial colonization. (Bellows, C. F., Wheatley, B. M., Moroz, K., Rosales, S. C. & Morici, L. PLoS One 6, (2011)) Mesh infection complicates 1-8% of hernia repairs, which is most commonly due to *Staphylococcus* spp., especially *Staphylococcus aureus*, *Streptococcus* spp. (including group *B Streptococci*) and other *Staphylococcus* species. (Collage, R. D. & Rosengart, M. R. Surg. Infect. (Larchmt). 11, 311-8 (2010)) Vancomycin is a glycopeptide antibiotic that is bactericidal to both Staphylococcal and Streptococcal microbes including Methicillin-resistant *Staphylococcus aureus* (MRSA) which is responsible for more than half of all mesh infections. (Collage, R. D. & Rosengart, M. R. Abdominal wall infections with in situ mesh. Surg. Infect. (Larchmt). 11, 311-8 (2010)) Systemic treatment with Vancomycin requires intravenous infusions and continuous therapeutic drug level monitoring to ensure efficacy and avoid harmful renal toxicity.

Organ transplantation is the definitive treatment to end stage organ failure. However, it is limited by donor organ shortage. Organ regeneration based on decellularized organ scaffolds provides an alternative source of viable grafts for transplantation. This concept has been demonstrated in the rodent model in the regeneration of heart (Ott, H et al. Nature Medicine 14(2):213-21 (2008)), lung (Ott, H. et al. Nature Medicine 16(8):927-33 (2010); Petersen, T. et al. Science 329(5991):538-41 (2010)), liver (Uygun, B. et al. Nature Medicine 16(7): 814-820 (2010)) and kidney (Song, J. et al. Nature Medicine 19(5):646-51 (2013)). This strategy is also being upscaled to the decellularization and regeneration of human-sized organs (Ko, I et al. Biomaterials 40:72-9 (2014); Ren, X. et al. Nature Biotechnology 33, 1097-1102 (2015); Guyette, J. et al. Circulation Research 118(1):56-72 (2016)). The decellularized organ scaffolds are primarily composed of extracellular matrix, which is one of the essential components defining an organ's anatomical, mechanical and biochemical features. Functionalization of decellularized organ scaffolds through immobilization of bioactive molecules held the promise to facilitate organ regeneration and improve in vivo performance of the regenerated grafts. However, the current technologies to functionalize decellularized organ scaffold is based on random crosslinking chemistry and is not selective (Ma, B. et al. Regenerative Biomaterials 1(1):81-9 (2014); Bao, J. et al. Scientific Reports 5:10756 (2015)), which dramatically alters the mechanical and biochemical features of the biomaterials.

Organ (e.g. lung) transplants represent a final hope for many patients experiencing conditions typified by organ (e.g. lung) failure, e.g., chronic obstructive pulmonary disease (COPD), cystic fibrosis, lung cancer, and congenital lung diseases, among others. Typical wait time for an organ (e.g. lung) transplant can be two years or more, resulting in a 30% mortality rate for those on the waiting list. Despite its widespread potential, the continuing success of organ transplantation depends upon an adequate supply of organs. It is increasingly apparent that the number of organs obtained in the traditional way from brain-stem dead donors has reached a plateau. Moreover, ischemia/reperfusion injury is a frequent consequence after organ transplantation and influences short term as well as long-term graft outcome. Clinically ischemia/reperfusion injury is associated with delayed graft function, graft rejection, chronic rejection and chronic graft dysfunction. Microbial exposure and tissue damage that accompany transplantation result in the release of both pathogen- and damage-associated complications (e.g., blood clotting), as well as the generation of cross-reactive alloreactive T cells.

SUMMARY

In some aspects, the present disclosure provides a method of functionalizing an extracellular matrix of an organ or tissue of a mammal, the method comprising:
  (i) selecting the mammal for functionalizing the extracellular matrix of the organ or tissue; and
  (ii) administering a nutrient to the mammal, wherein the nutrient is functionalized with a chemical group that is reactive in a biorthogonal chemical reaction.

In some aspects, the present disclosure provides a method of functionalizing an extracellular matrix of an organ or tissue of a mammal, the method comprising:
  (i) harvesting the organ or tissue; and
  (ii) culturing the organ or tissue using media comprising a nutrient functionalized with a chemical group that is reactive in a biorthogonal chemical reaction.

In some aspects, the present disclosure provides a method of preparing an organ or tissue for transplantation, the method comprising:
  (i) administering to a donor subject a nutrient functionalized with a chemical group that is reactive in a biorthogonal chemical reaction;
  (ii) surgically removing the organ or tissue from the donor subject; and (iii) treating the isolated organ or tissue with a preservation solution comprising biologically active molecule functionalized with a reactive chemical group complimentary to the reactive chemical group of the functionalized nutrient.

In some aspects, the organ or tissue is bovine, porcine, murine or human organ or tissue.

In some aspects, the organ or tissue is selected from the group consisting of carotid artery, lung, heart, liver, kidney and skin.

In some aspects, the chemical group that is reactive in a bioorthogonal chemical reaction is selected from the group consisting of an azide ($-N_3$), an alkyne, a nitrone, an isocyanide, a cyclopropene and a tetrazine.

In some aspects, the chemical group that is reactive in a bioorthogonal chemical reaction is selected from an azide ($-N_3$) and an alkyne.

In some aspects, the chemical group that is reactive in a bioorthogonal chemical reaction is an azide ($-N_3$).

In some aspects, the nutrient is selected from the group consisting of saccharide, amino acid, fatty acid, and triglyceride.

In some aspects, the nutrient is a monosaccharide.

In some aspects, the nutrient functionalized with a chemical group that is reactive in a biorthogonal chemical reaction is selected from the group consisting of azide-labeled galactosamine, azide-labeled glucosamine and azide-labeled mannosamine.

In some aspects, the nutrient functionalized with a chemical group that is reactive in a biorthogonal chemical reaction is selected from Ac4GalNAz, Ac4ManNAz and Ac4GlcNAz.

In some aspects, the nutrient functionalized with a chemical group that is reactive in a biorthogonal chemical reaction is tetraacylated N-azidoacetylgalactosamine (Ac4GalNAz).

In some aspects, the nutrient is administered by intraperitoneal injection, subcutaneous injection or by the intratracheal route.

In some aspects, the nutrient is administered by intraperitoneal injection.

In some aspects, the present disclosure provides a decellularized scaffold of a mammalian organ or tissue comprising a functionalized extracellular matrix, wherein the extracellular matrix is functionalized by any one of methods described herein.

In some aspects, the present disclosure provides a decellularized scaffold of a mammalian organ or tissue comprising an extracellular matrix, wherein the extracellular matrix of the decellularized scaffold is chemoselectively functionalized with at least one biologically active molecule.

In some aspects, the present disclosure provides a method of preparing the decellularized scaffold, the method comprising reacting the decellularized scaffold as described herein with a biologically active molecule functionalized with a reactive chemical group complimentary to the reactive chemical group of the functionalized extracellular matrix.

In some aspects, the present disclosure provides a method of preparing a biological prosthetic mesh, the method comprising reacting the decellularized scaffold as described herein with a biologically active molecule functionalized with a reactive chemical group complimentary to the reactive chemical group of the functionalized extracellular matrix.

In some embodiments, the reacting comprises infusion of the decellularized scaffold with the biologically active molecule (e.g., infusion of the scaffold with a buffer solution containing the biologically active molecule).

In some aspects, the complementary reactive chemical group is an azide ($-N_3$), an alkyne, a nitrone, an isocyanide, a cyclopropene or a tetrazine.

In some aspects, the alkyne is an aliphatic alkyne or a cyclooctyne.

In some aspects, the cyclooctyne is dibenzocyclooctyne (DBCO), difluorobenzocyclooctyne (DIFBO), biarylazacyclooctynone (BARAC), dibenzocyclooctyne (DIBO), difluorinated cyclooctyne (DIFO), monofluorinated cyclooctyne (MOFO), dimethoxyazacyclooctyne (DIMAC) or arylless octyne (ALO).

In some aspects, the alkyne is an aliphatic alkyne and the reacting is carried out in the presence of copper (I) catalyst.

In some aspects, the alkyne is cyclooctyne and the reacting is carried out under copper-free conditions.

In some aspects, the biologically active molecule is a growth factor, a peptide, an antibody, an anticoagulant or an antibiotic.

In some aspects, the anticoagulant is a coumarin, a heparin, a pentasaccharide inhibitor of factor Xa, a direct factor Xa inhibitor or a direct thrombin inhibitor.

In some aspects, the anticoagulant is heparin.

In some aspects, the antibiotic is a quinolone, a β-lactam, a cephalosporin, a penicillin, a carbapenem, a lipopetide, an aminoglycoside, a glycopeptide, a macrolide, an ansamycin or a sulfonamide.

In some aspects, the antibiotic is vancomycin.

In some aspects, the antibody is an antibody specific against tumor necrosis factor-alpha (TNF-α).

In some aspects, the biologically active molecule functionalized with a reactive chemical group complimentary to the reactive chemical group of the functionalized extracellular matrix is selected from heparin-alkyne, heparin-alkyne-biotin (HeparinAB), vancomycin-alkyne, heparin-DBCO, vancomycin-DBCO, anti-TNF-α-alkyne and anti-TNF-α-DBCO.

In some aspects the present disclosure provides a method of preparing a mammalian organ or tissue for transplantation, the method comprising seeding the decellularized scaffold of a mammalian organ or tissue as described herein with recipient-derived cells to obtain the organ or tissue for transplantation.

In some aspects, the recipient-derived cells are selected from epithelial cells, endothelial cells, stromal cells, muscle cells and neurons.

In some aspects, the organ or tissue is prepared by any one of methods described herein.

In some aspects the present disclosure provides a mammalian organ or tissue for transplantation, wherein the organ or tissue is prepared by any one of the methods as described herein.

In some aspects the present disclosure provides a biological prosthetic mesh bioorthogonally functionalized with at least one biologically active molecule, wherein the biological prosthetic mesh is prepared by any one of the methods described herein.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 1C shows azide tags on the glycosaminoglycans or glycoproteins preserved in the ECM after decellularization. Diagram shows the lung as an example.

FIG. 6A shows low power view of cadaveric epigastric flap (hematoxylin and eosin (H&E) staining).

FIG. 6B shows high power view of cadaveric epigastric flap (hematoxylin and eosin (H&E) staining).

FIG. 6C shows low power view of decellularized epigastric flap (hematoxylin and eosin (H&E) staining).

FIG. 6D shows high power view of decellularized epigastric flap (hematoxylin and eosin (H&E) staining).

FIG. 16 shows detection of azide labeling in decellularized rat liver scaffolds after in vivo metabolic engineering using Ac4GalNAz.

Azide ligands were detected using biotin-alkyne click reaction with and without Cu(I) catalyst, followed by streptavidin staining. Acellular lung ECM was co-stained with Laminin (scale bar: 200 μm).

Figure 26A:
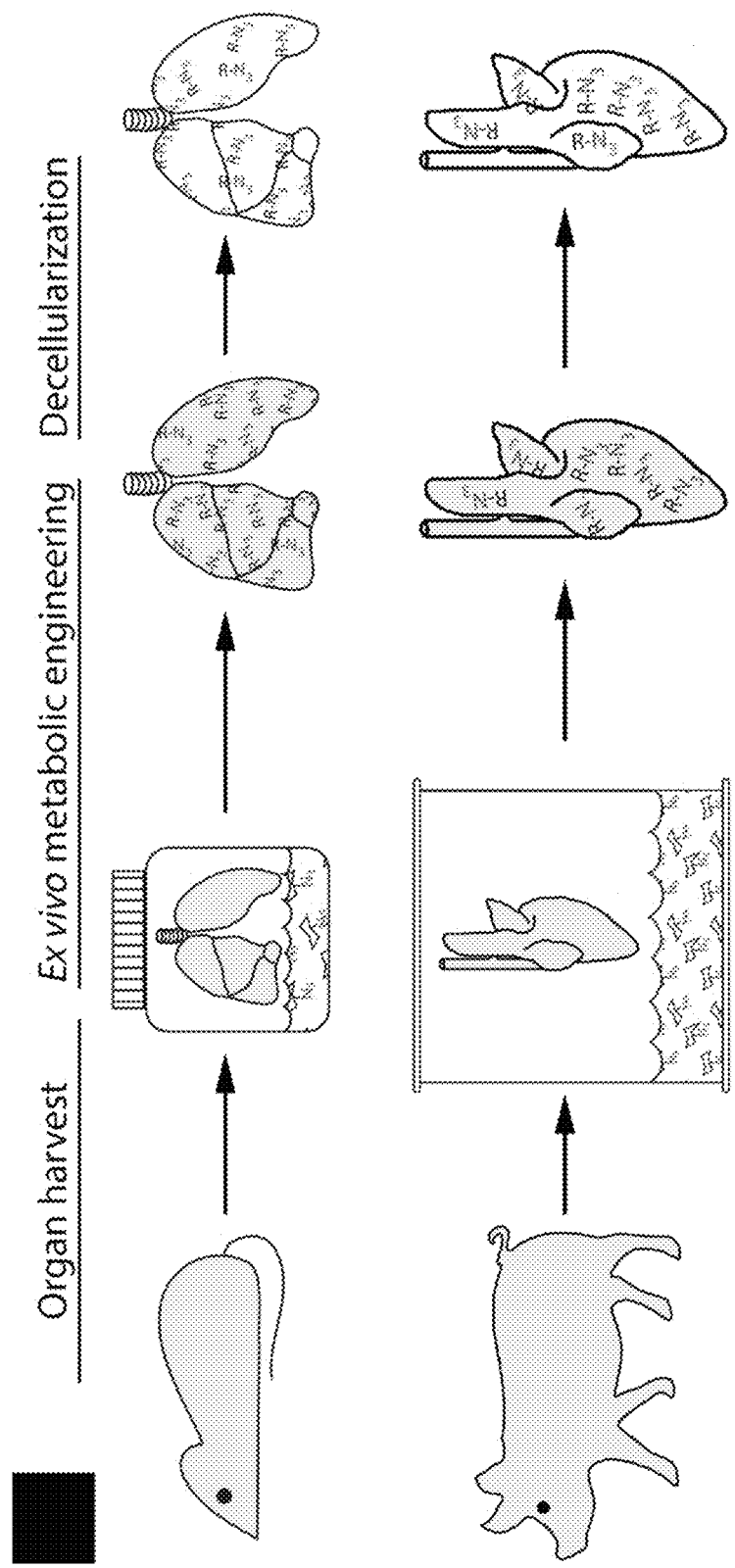
FIG. 26A is a diagram of ex vivo metabolic engineering of rat and porcine lung ECM. Briefly, the freshly isolated rat lung or porcine left lung was cultured ex vivo in the bioreactor for 24 hours in the presence of Ac4GalNAz (50 μM) or DMSO (control without Ac4GalNAz), and decellularized.
Figure 26C:
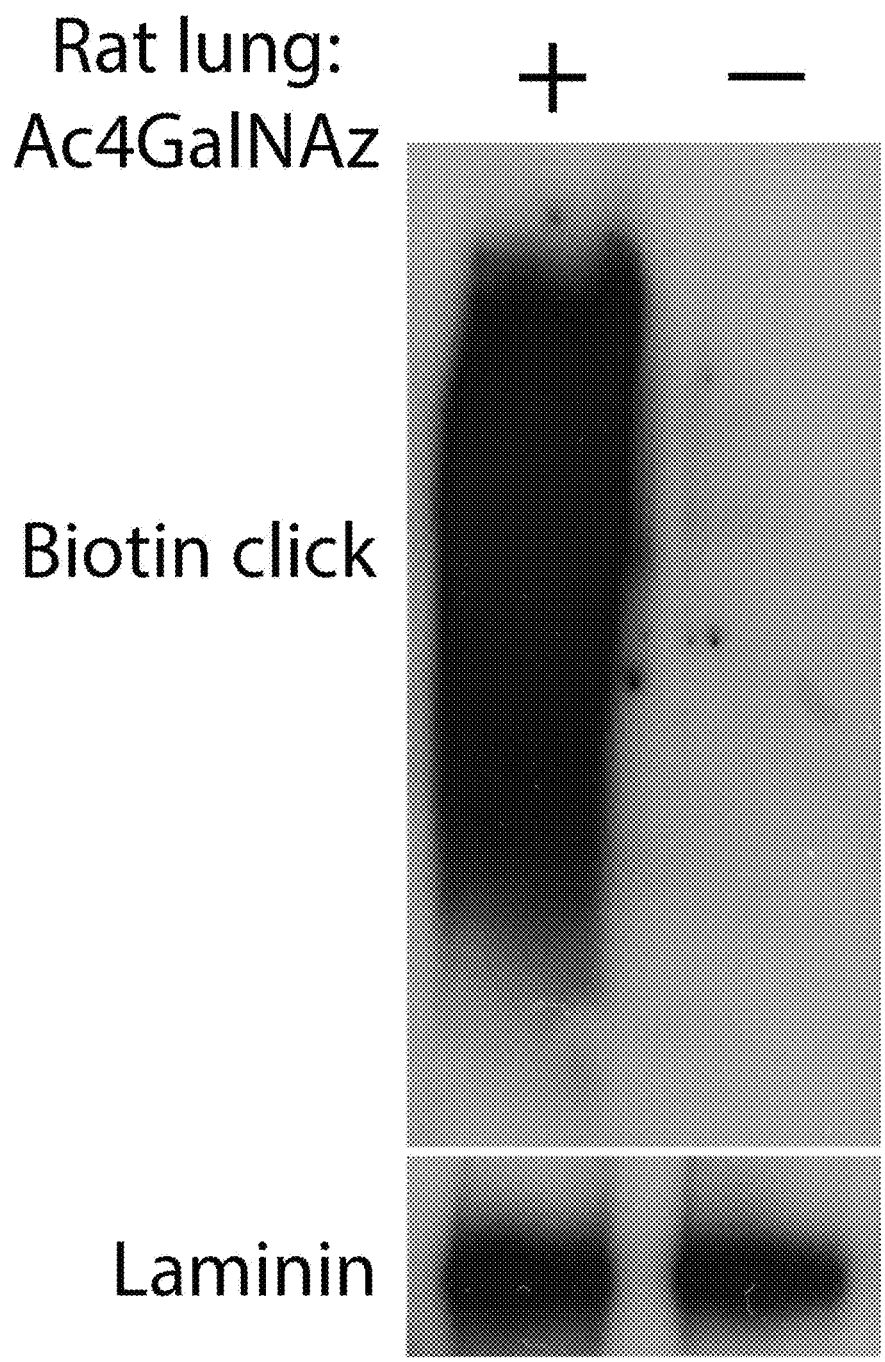
FIG. 26B contains images showing detection of azide ligands in acellular rat lungs after ex vivo metabolic engineering using Ac4GalNAz or DMSO (n=3 for each group).

FIG. 26C is a Western blot showing detection of azide-biotin-streptavidin labeling in the ECM proteins extracted from acellular rat lungs after ex vivo metabolic engineering using Ac4GalNAz or DMSO (n=3 for each group). Laminin Western blot served as loading control.

Figure 26D:
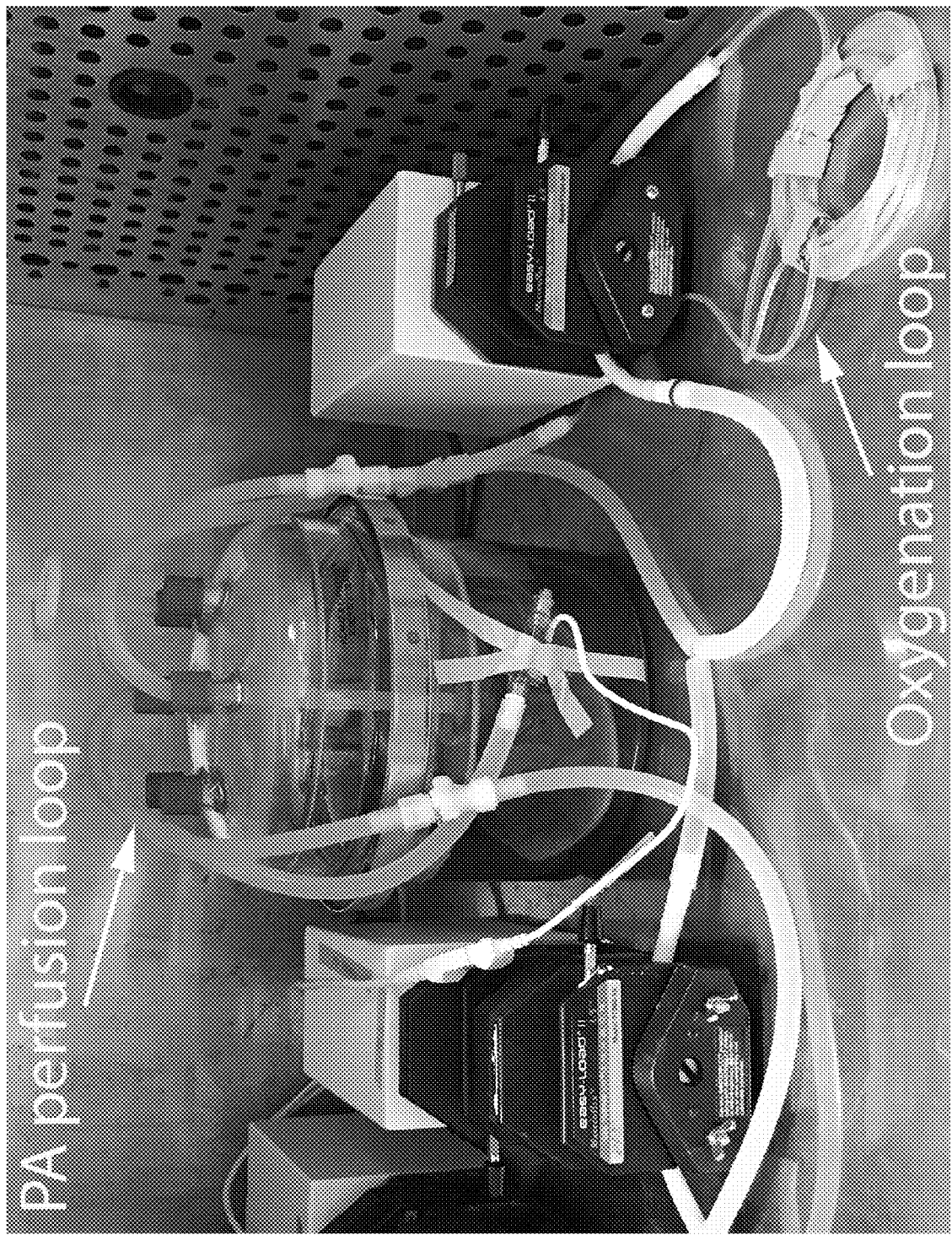

FIG. 26D is an image showing porcine left lung undergoing ex vivo culture and metabolic engineering.

Figure 26E:
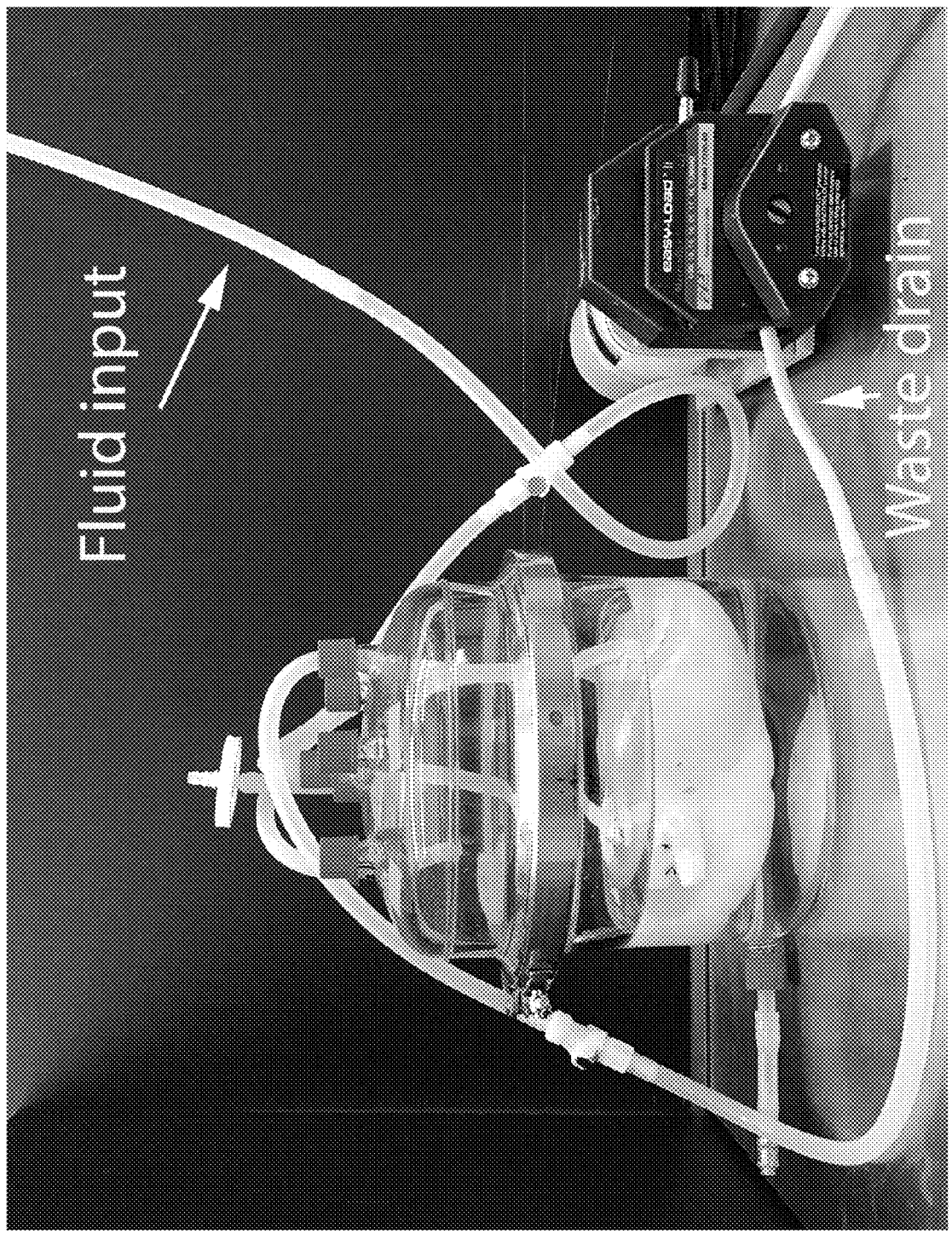

FIG. 26E is an image showing porcine left lung undergoing ex vivo decellularization.

Figure 26F:
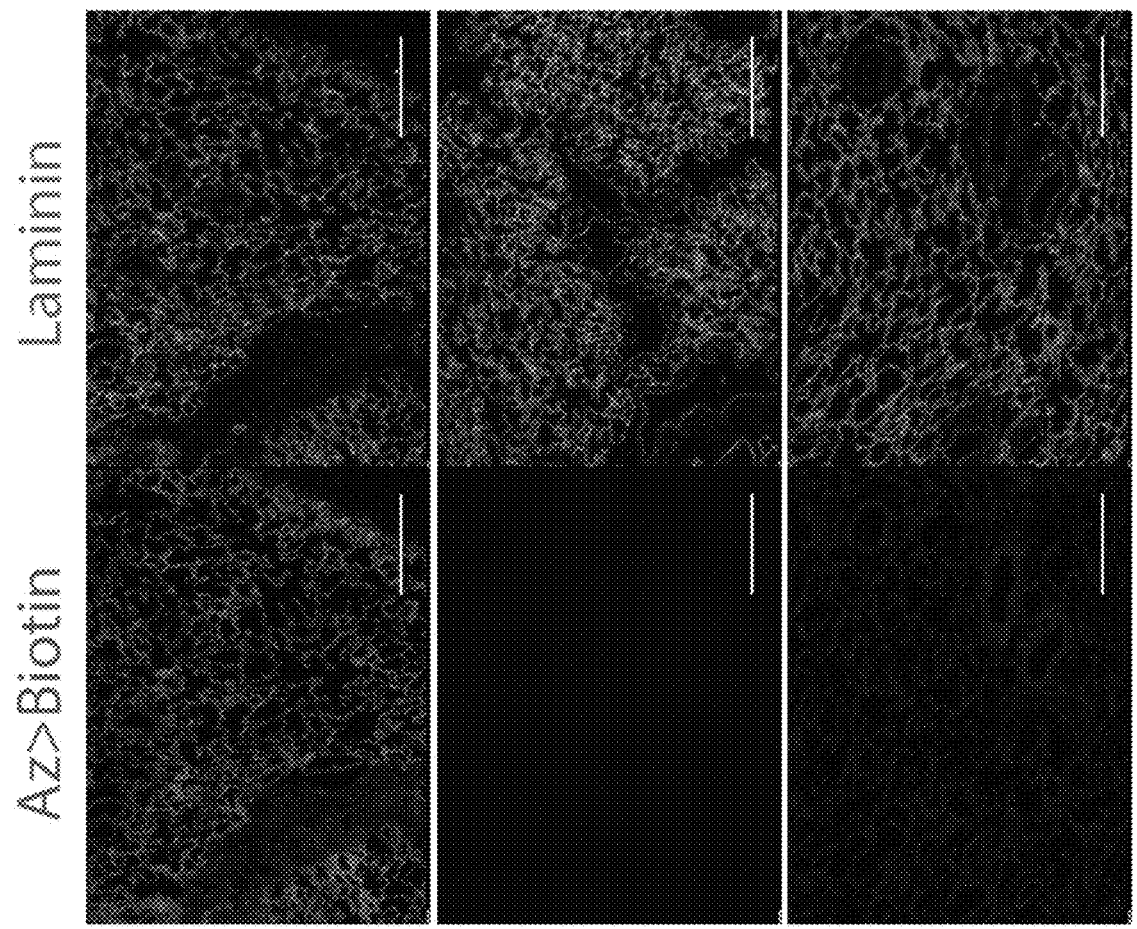

FIG. 26F is an image showing detection of azide ligands in an acellular porcine left lung after ex vivo metabolic engineering using Ac4GalNAz or DMSO (three representative areas of the Ac4GalNAz or DMSO porcine lung were analyzed; scale bar: 200 μm).

Figure 26G:

FIG. 26G is a Western blot showing detection of azide-biotin-streptavidin labeling in the ECM proteins extracted from an acellular porcine left lung after ex vivo metabolic engineering using Ac4GalNAz or DMSO (three representative areas of the Ac4GalNAz or DMSO porcine lung were analyzed).

Figure 26H:
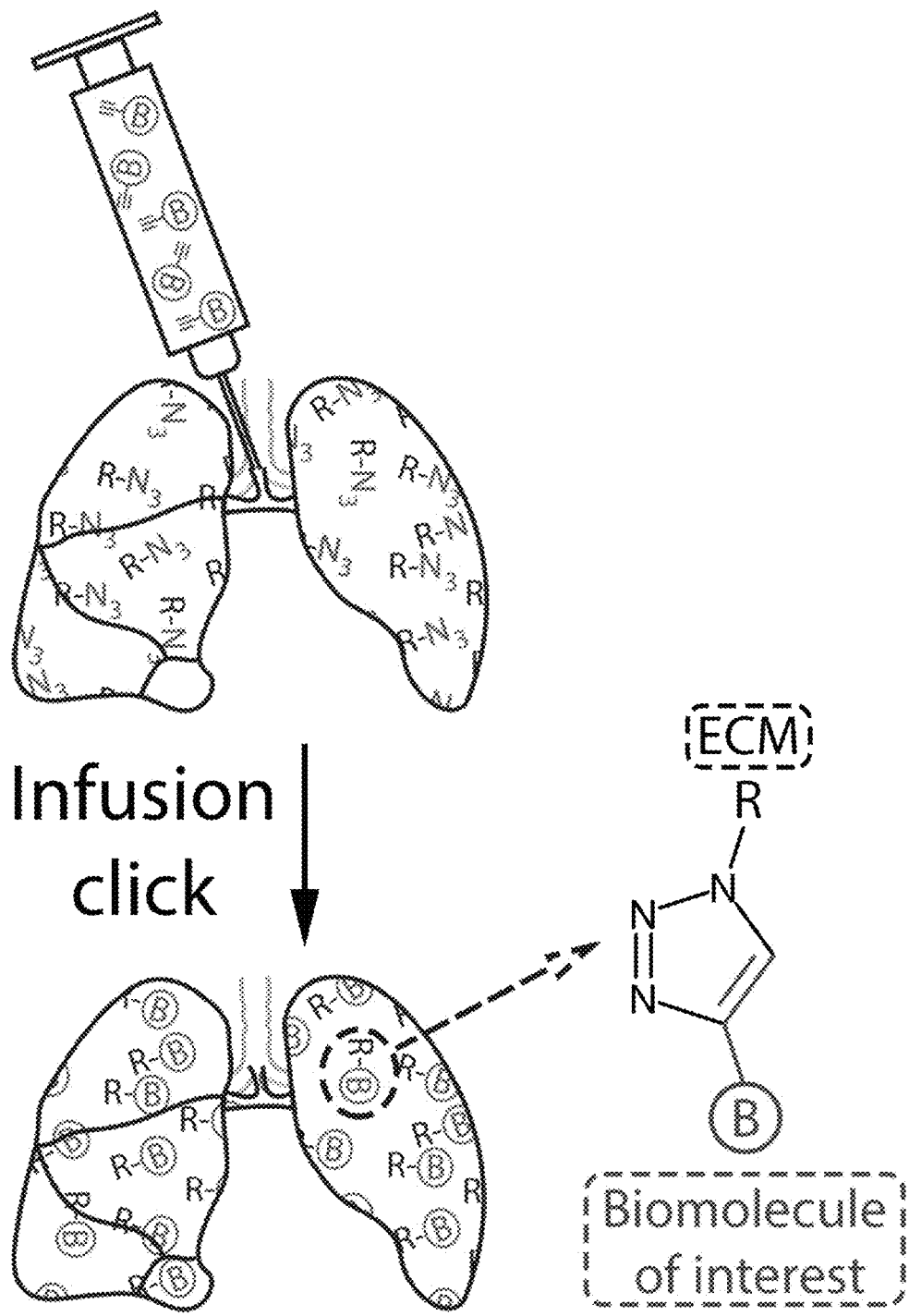

FIG. 26H is a diagram of whole-organ infusion click reaction allowing immobilization of alkyne-labeled biomolecules of interest onto intact azide-labeled acellular organ scaffolds (diagram showing the lung as an example).

Figure 26I:
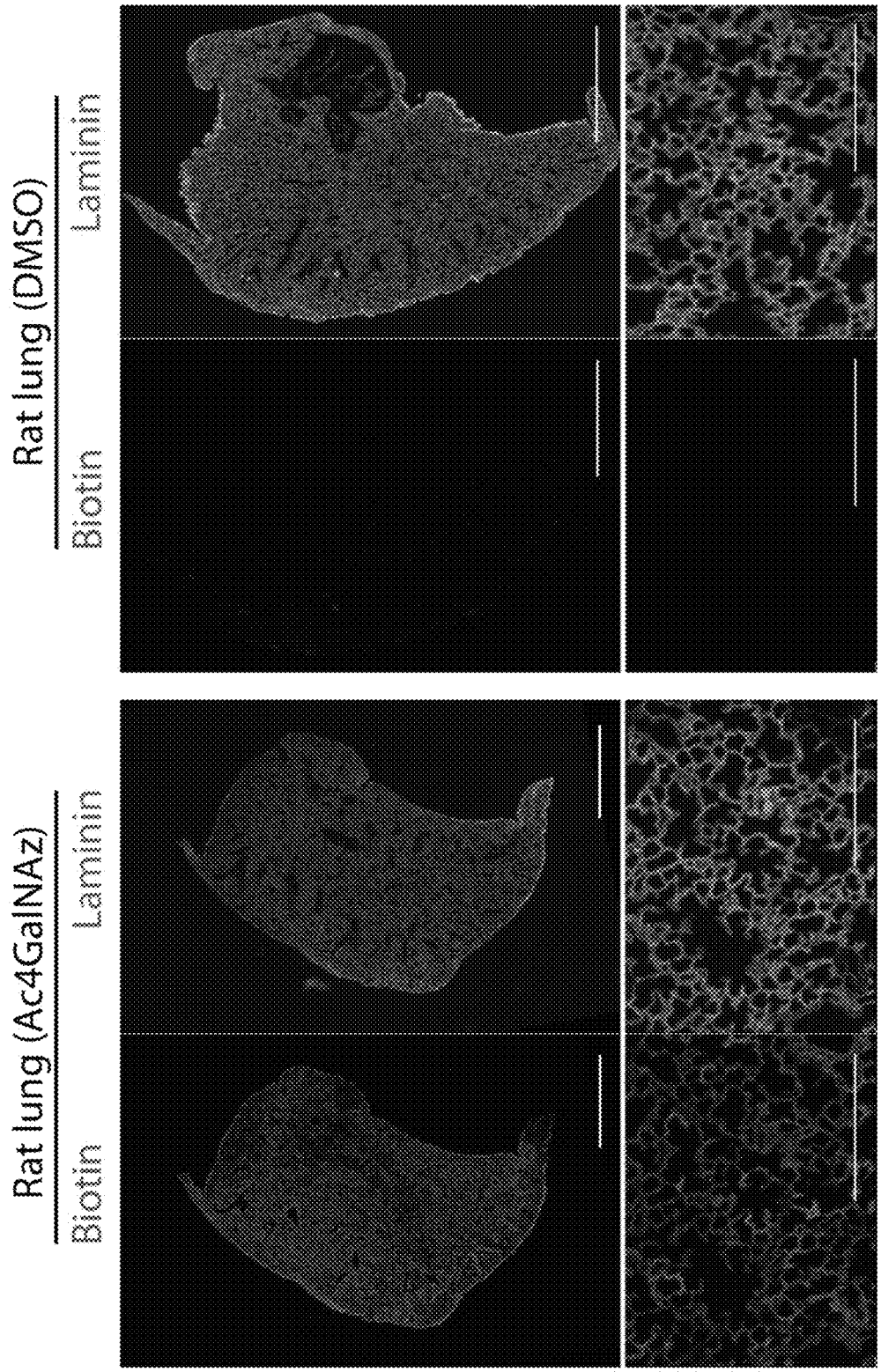

FIG. 26I contains images showing Biotin-Alkyne infusion click reaction in acellular rat lungs after ex vivo metabolic engineering using Ac4GalNAz or DMSO, followed by streptavidin staining of biotin and Laminin co-staining (scale bar of upper images: 2000 μm; scale bar of lower images: 200 μm).

Figure 27A:
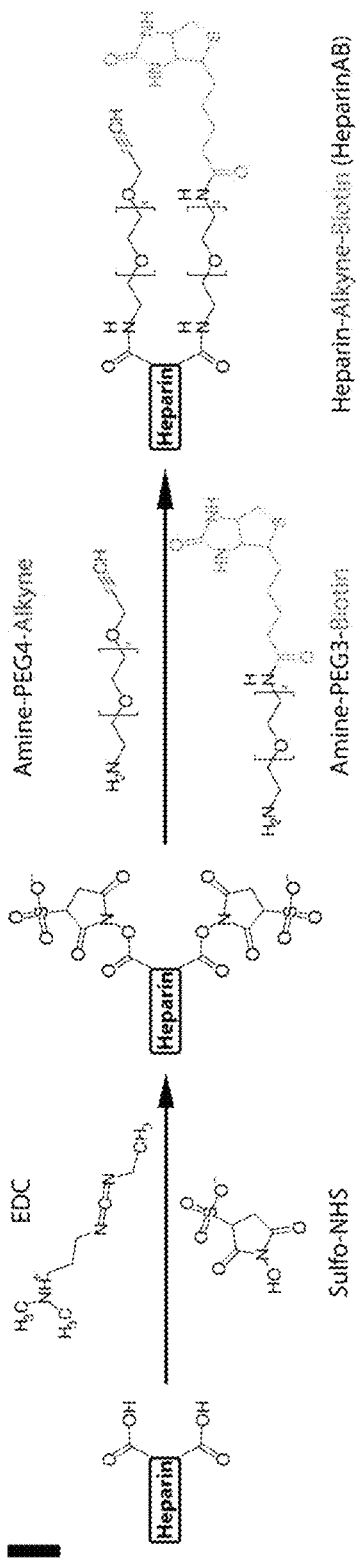

FIG. 27A is a diagram showing preparation of clickable Heparin-Alkyne-Biotin (Heparin-AB). Briefly, carboxyl groups in heparin were activated to be amine-reactive by EDC and Sulfo-NHS, and conjugated with Amine-PEG4-Alkyne and Amine-PEG3-Biotin.

Figure 27B:
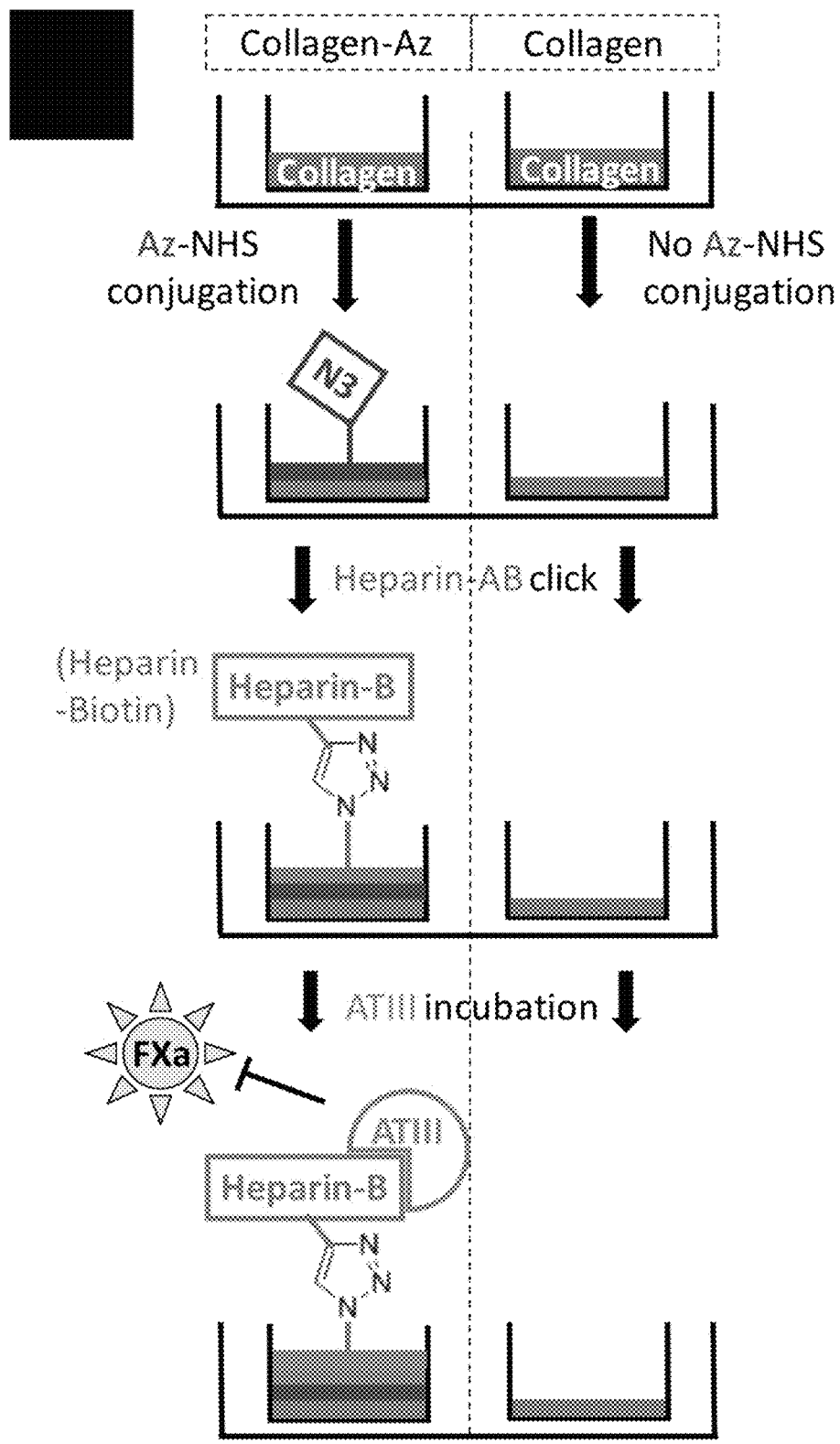

FIG. 27B is a diagram showing Collagen-Azide (Collagen-Az) plate assay. Briefly, we conjugated azide groups onto Collagen I-coated tissue culture plate using Azido-PEG4-NHS Ester (Az-NETS), which allowed immobilization of Heparin-AB via the click reaction onto the plate for visualization and bioactivity assessment. Click-immobilized Heparin-Biotin (Heparin-B) further bound and immobilized ATIII, and potentiated the ATIII activity in inhibiting Factor Xa (FXa).

Figure 27C:
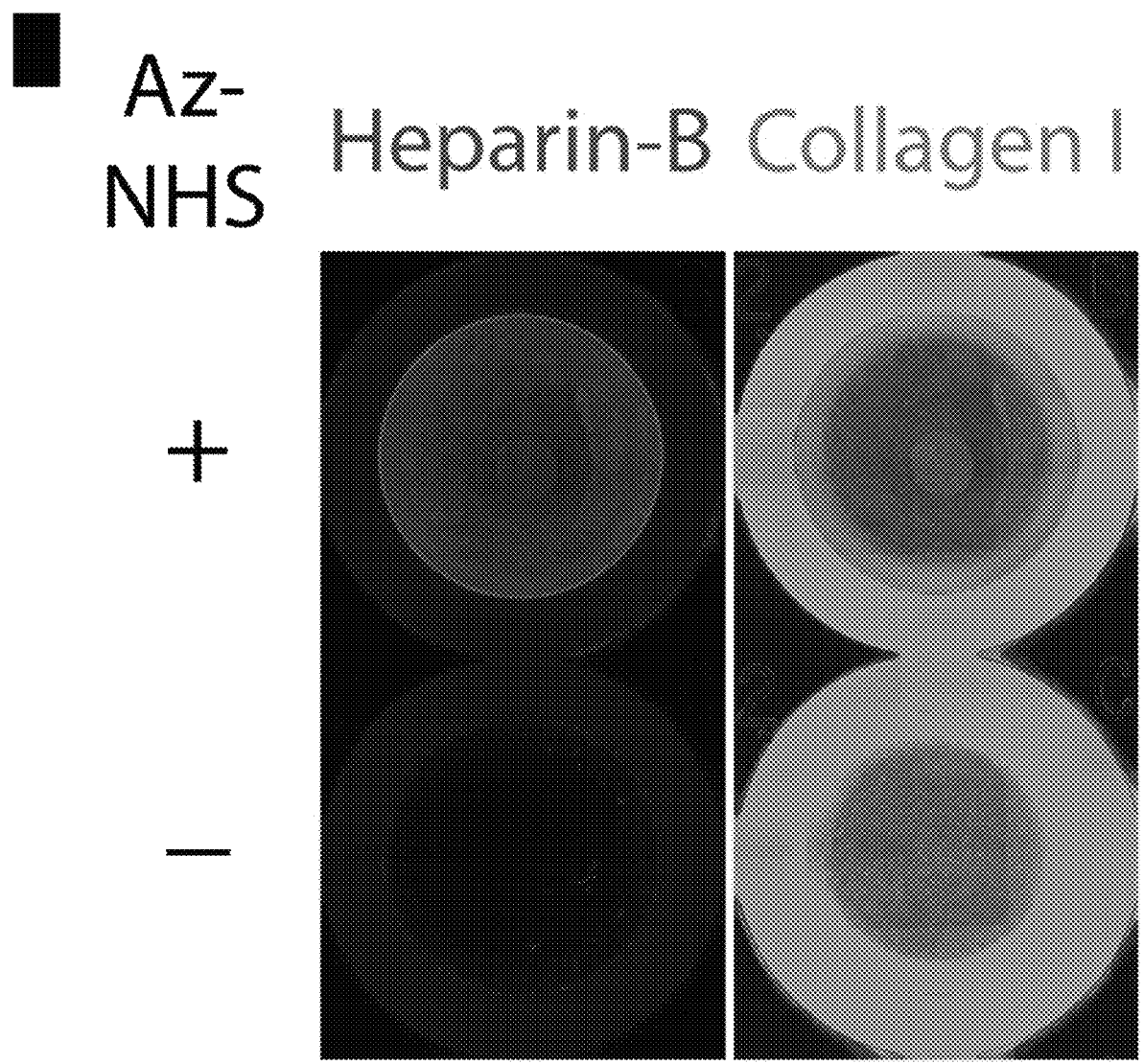

FIG. 27C contains images of representative Collagen wells with and without Az-NETS conjugation after streptavidin staining of click-immobilized Heparin-B. Collagen I was co-stained to indicate the ECM.

Figure 27D:
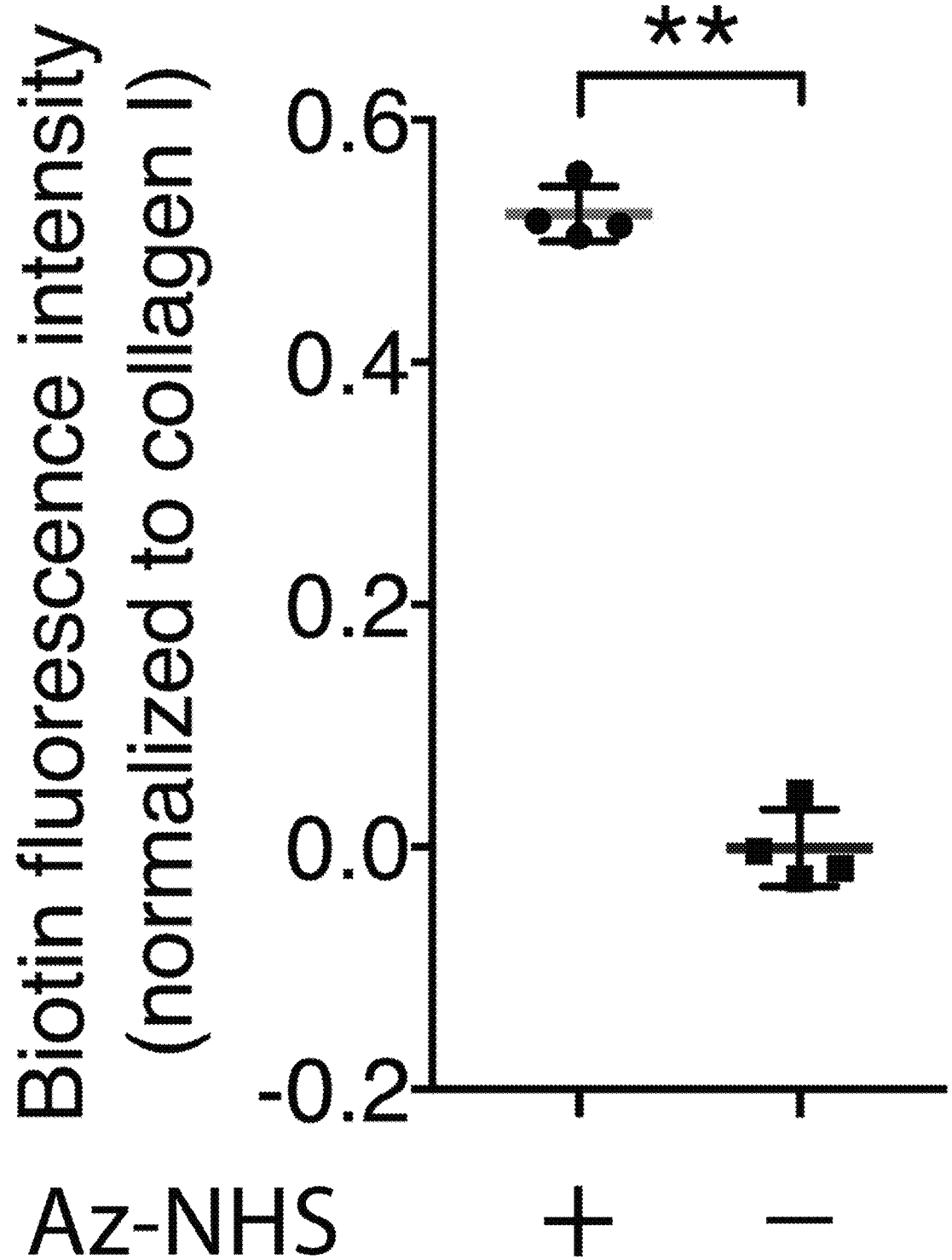

FIG. 27D is a line plot showing quantification of immobilized Heparin-B on Collagen wells with and without Az-NETS conjugation (n=4 for each group). ** P<0.01.

Figure 27E:
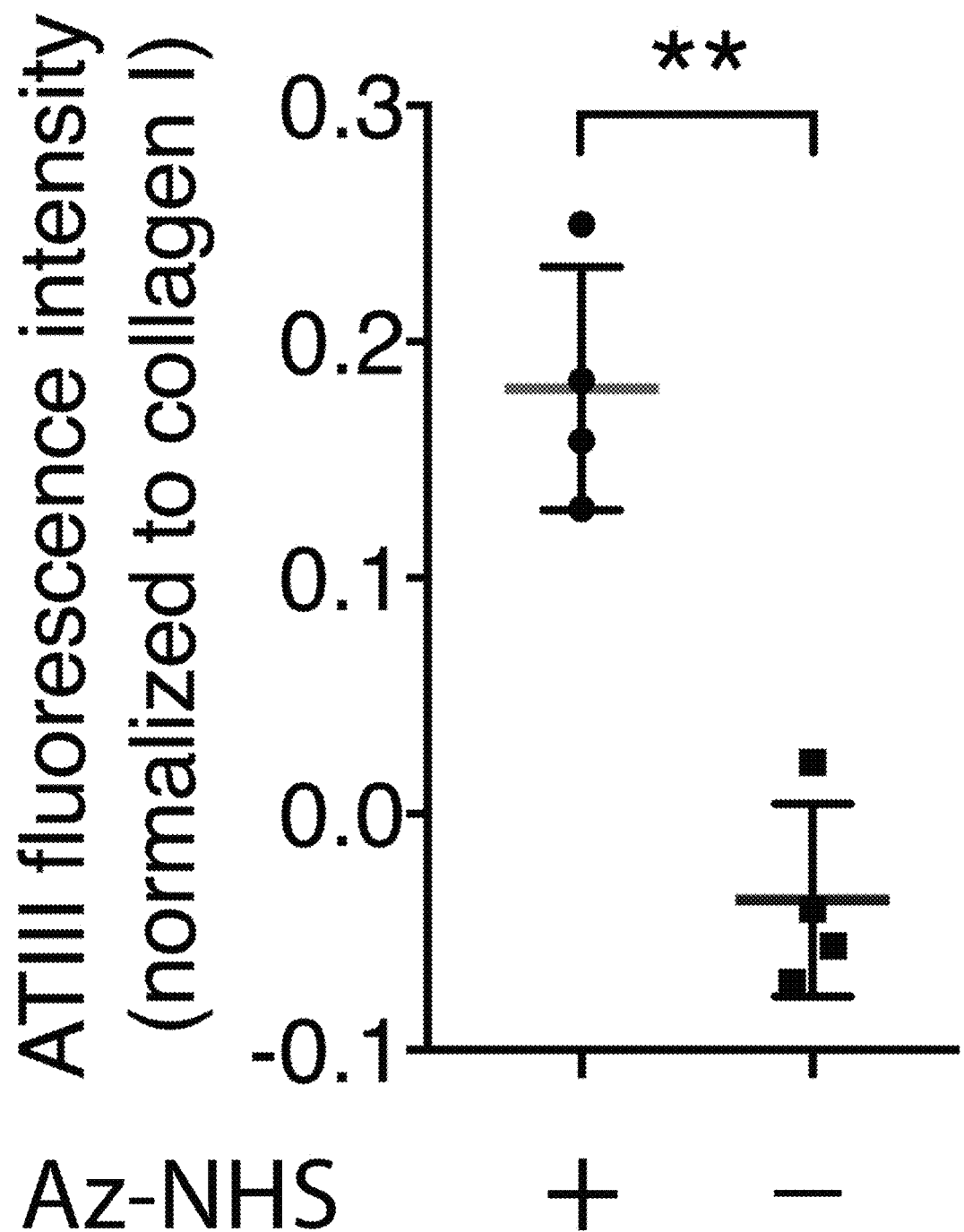

FIG. 27E is a line plot showing quantification of immobilized ATIII on Collagen wells with and without Az-NETS conjugation (n=4 for each group). ** P<0.01.

Figure 27F:
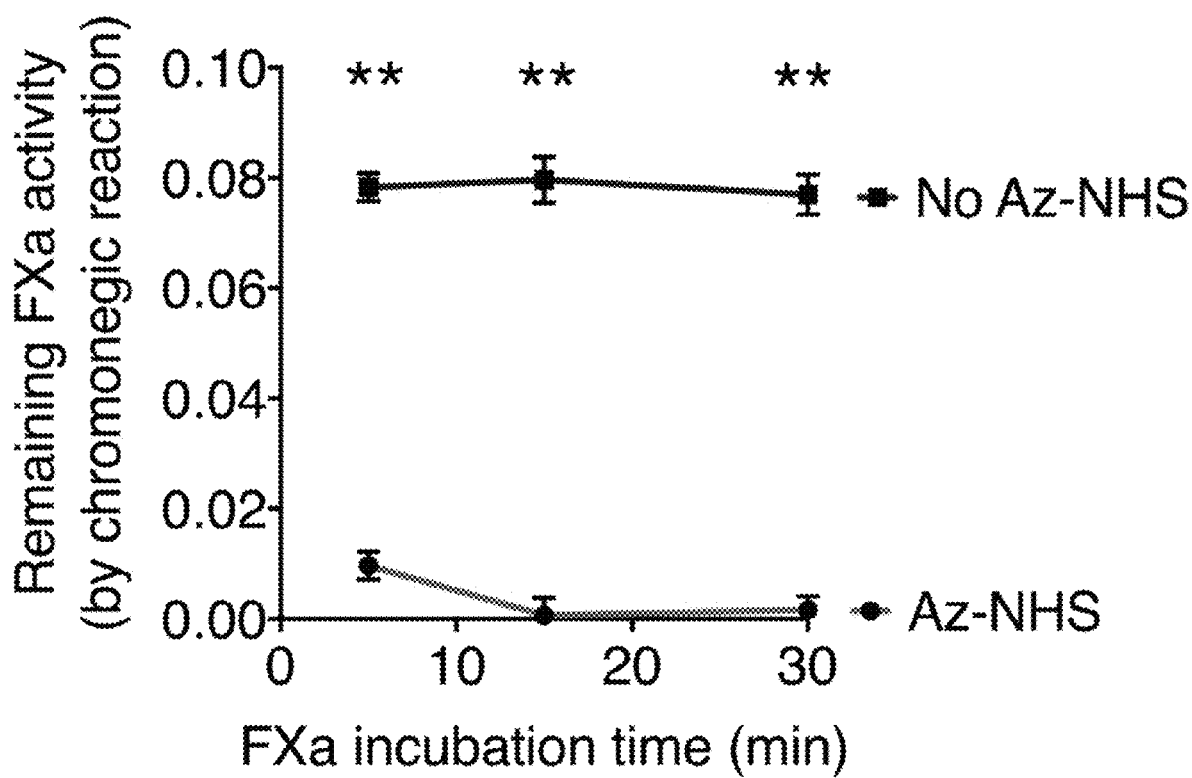

FIG. 27F is a line plot showing quantification of remaining FXa activity using a chromogenic reaction with substrate S2222 after incubation in Collagen wells for 5, 15 and 30 minutes. Collagen wells were with and without Az-NETS conjugation, and incubated sequentially with Heparin-AB click reaction mix and ATIII (as shown in FIG. 27B). **P<0.01.

Figure 27G:
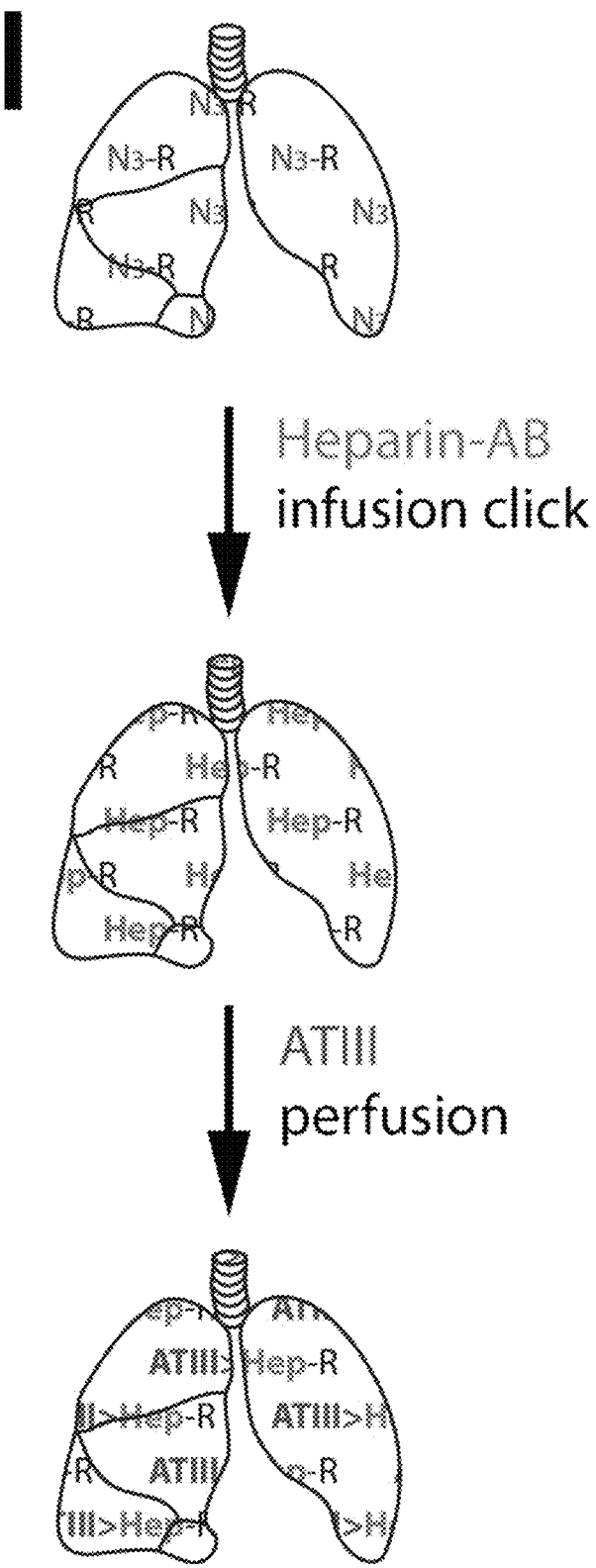

FIG. 27G is a diagram of Heparin-AB immobilization onto the ex vivo metabolically engineered azide-labeled rat lung by infusion click reaction, and subsequent immobilization of ATIII.

Figure 27H:
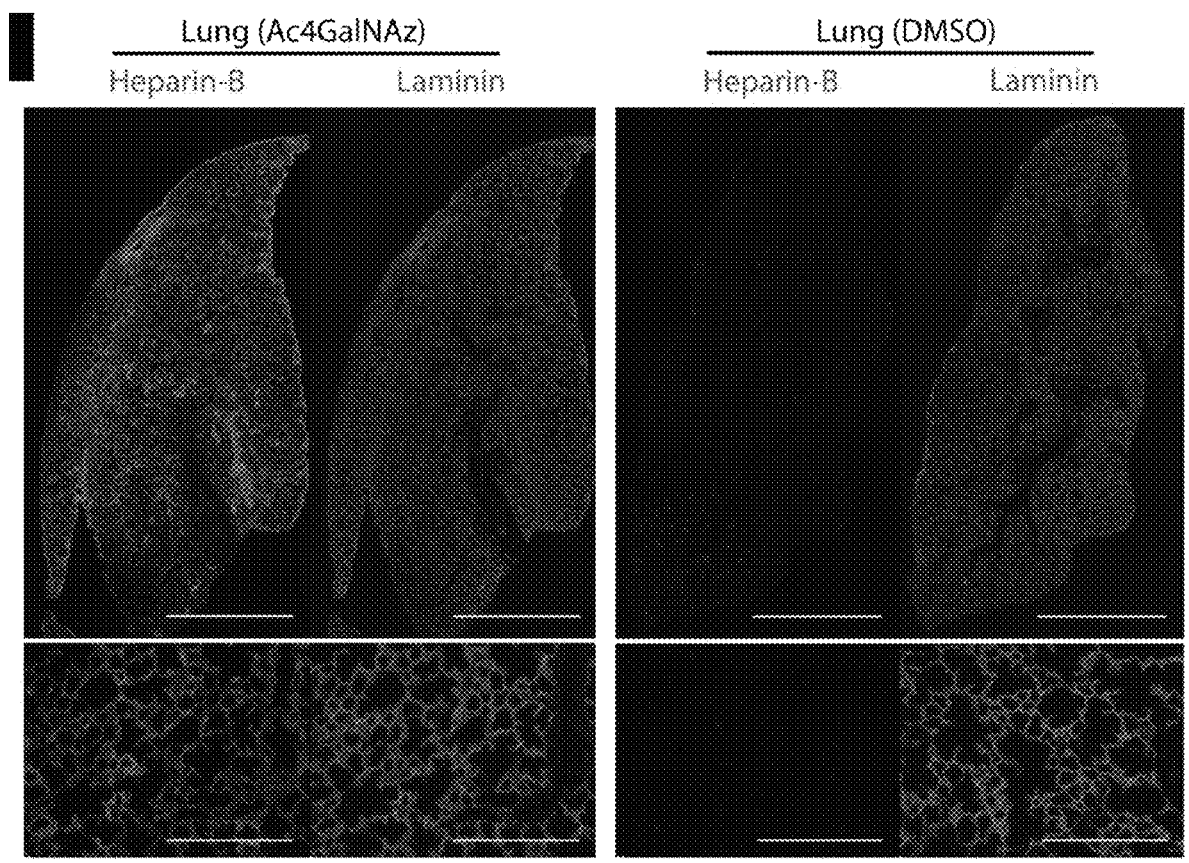

FIG. 27H contains images showing Streptavidin staining and visualization of click-immobilized Heparin-B on acellular rat lungs with and without ex vivo Ac4GalNAz metabolic engineering. Acellular lung ECM was co-stained with Laminin (scale bar of upper images: 2000 μm; scale bar of lower images: 200 μm).

Figure 27I:
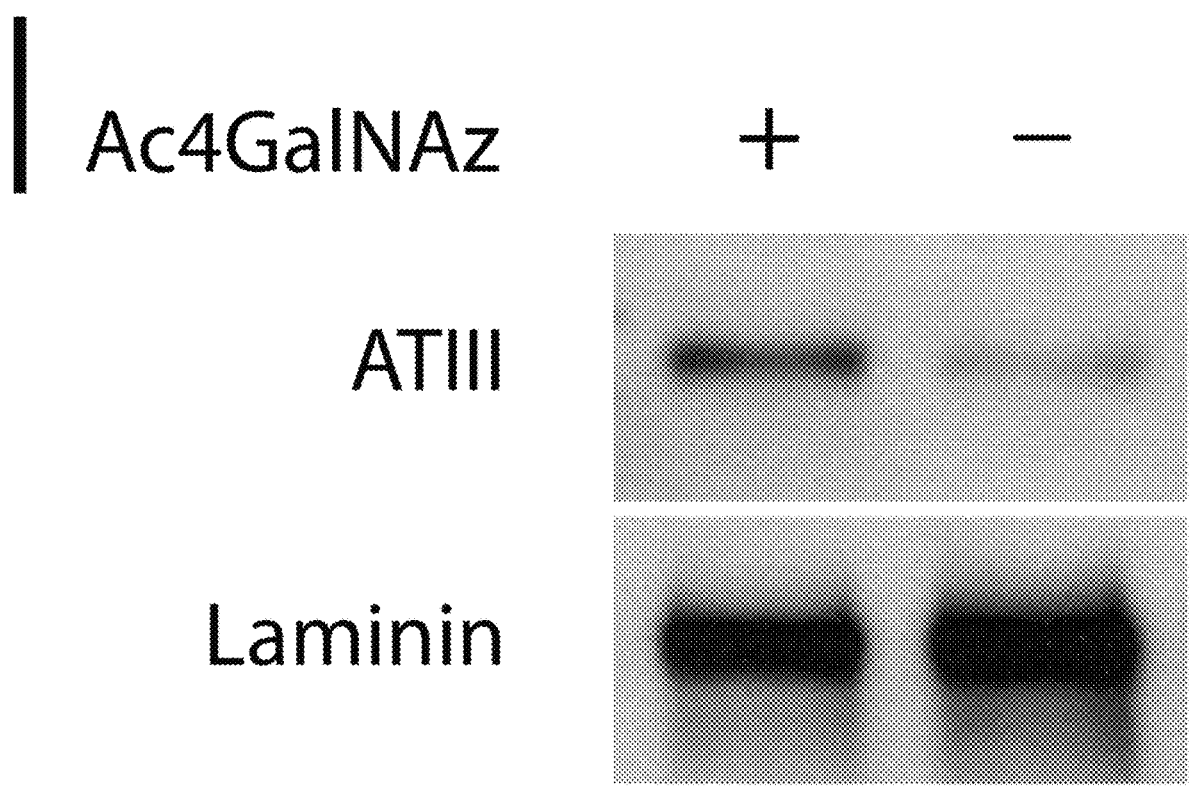

FIG. 27I is a Western blot showing analysis of ATIII immobilized on Heparin-B-clicked acellular rat lungs with and without ex vivo Ac4GalNAz metabolic engineering. Laminin Western blot served as loading control.

Figure 27J:
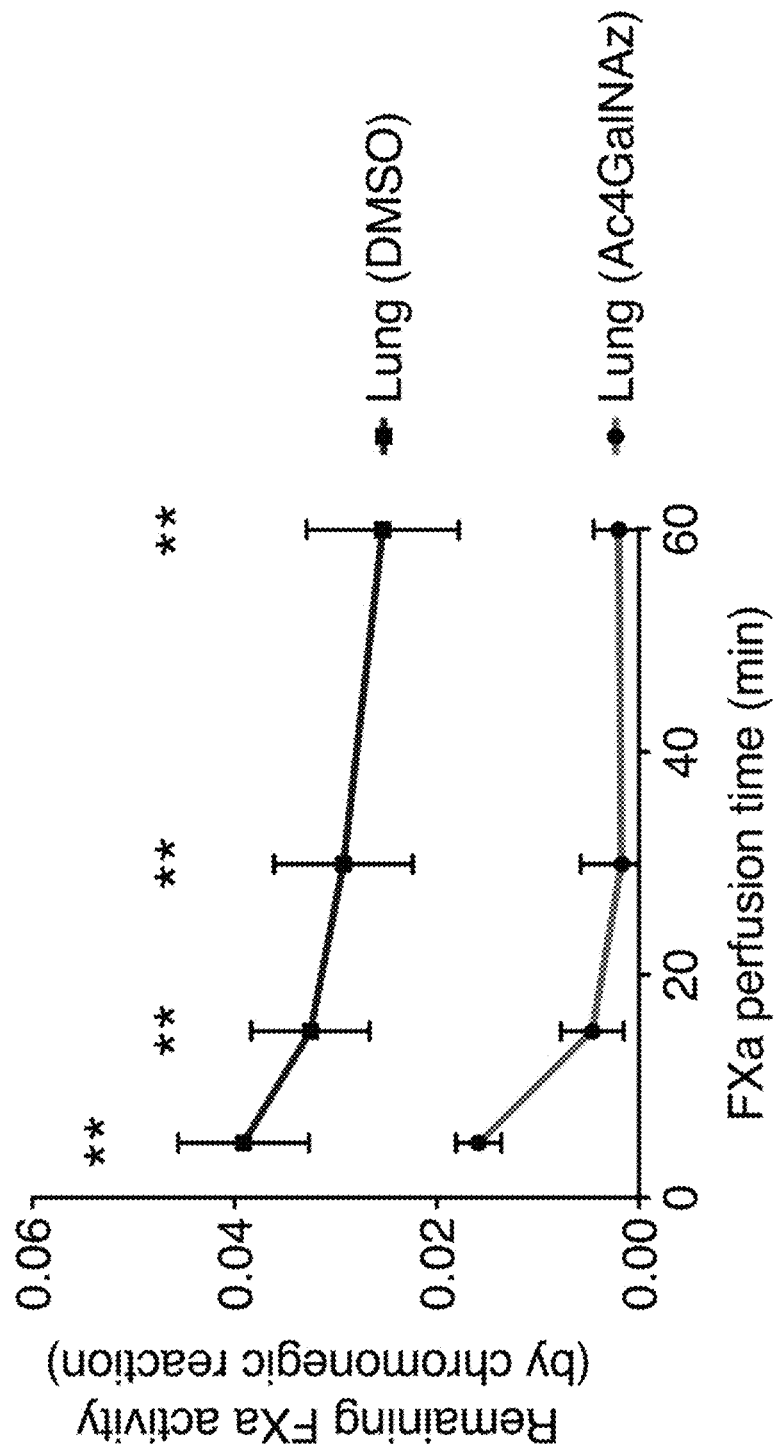

FIG. 27J is a line plot showing quantification of remaining FXa activity using a chromogenic reaction with substrate S2222 after perfusion in acellular rat lungs for 5, 15, 30 and 60 minutes. Acellular rat lungs with and without ex vivo Ac4GalNAz metabolic engineering were incubated sequentially with Heparin-AB click reaction mix and ATIII (as shown in FIG. 27G) before the FXa perfusion and inhibition assay. ** P<0.01.

Figure 28:
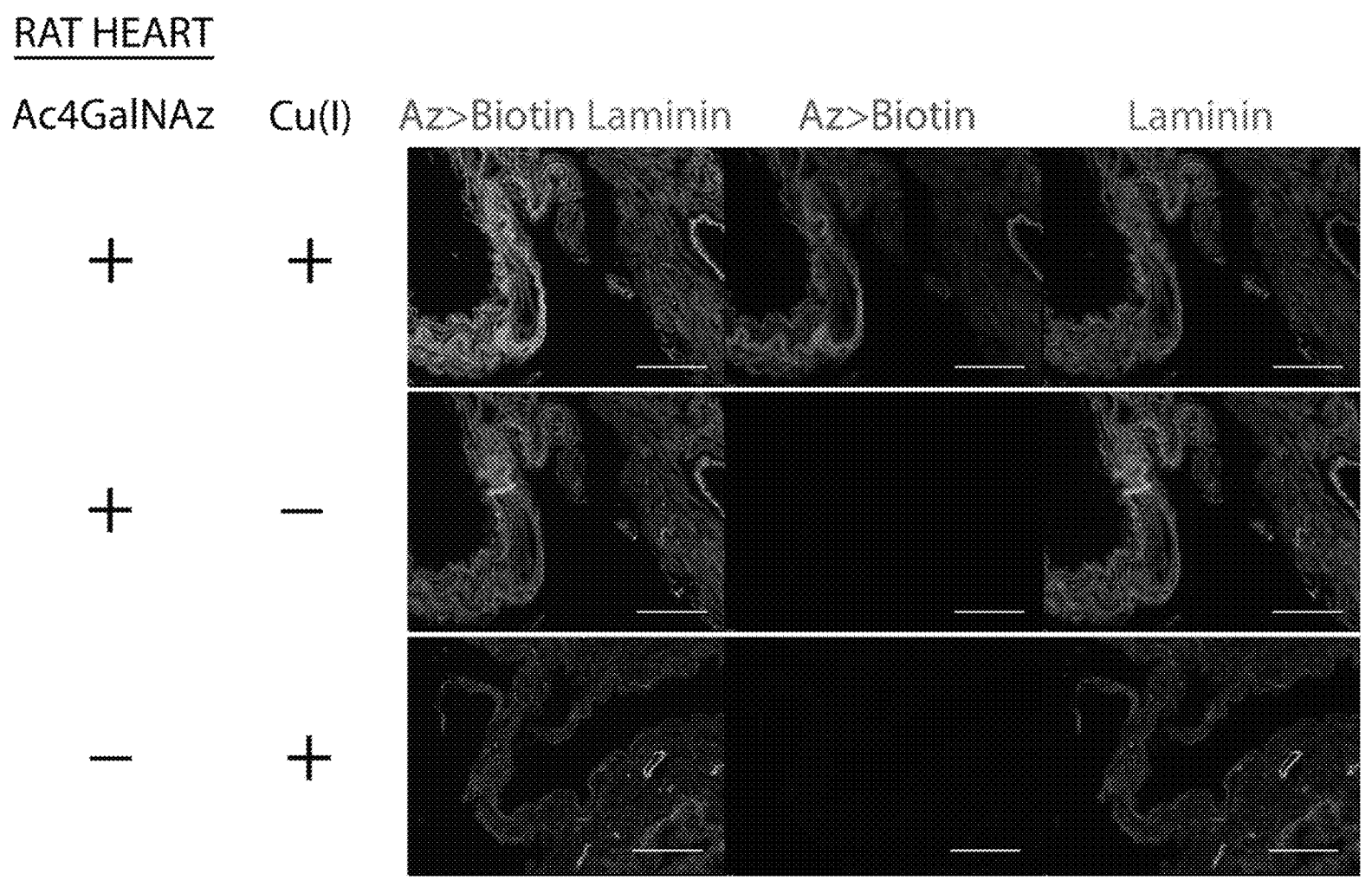

FIG. 28 contains images showing detection of azide ligands in acellular rat hearts after in vivo metabolic engineering using Ac4GalNAz or DMSO (control without Ac4GalNAz). Azide ligands were detected using biotin-alkyne click reaction with and without Cu(I) catalyst, followed by staining with fluorophore-conjugated streptavidin. Acellular heart ECM was co-stained with Laminin (n=3 for each group; scale bar: 200 μm).

Figure 29:
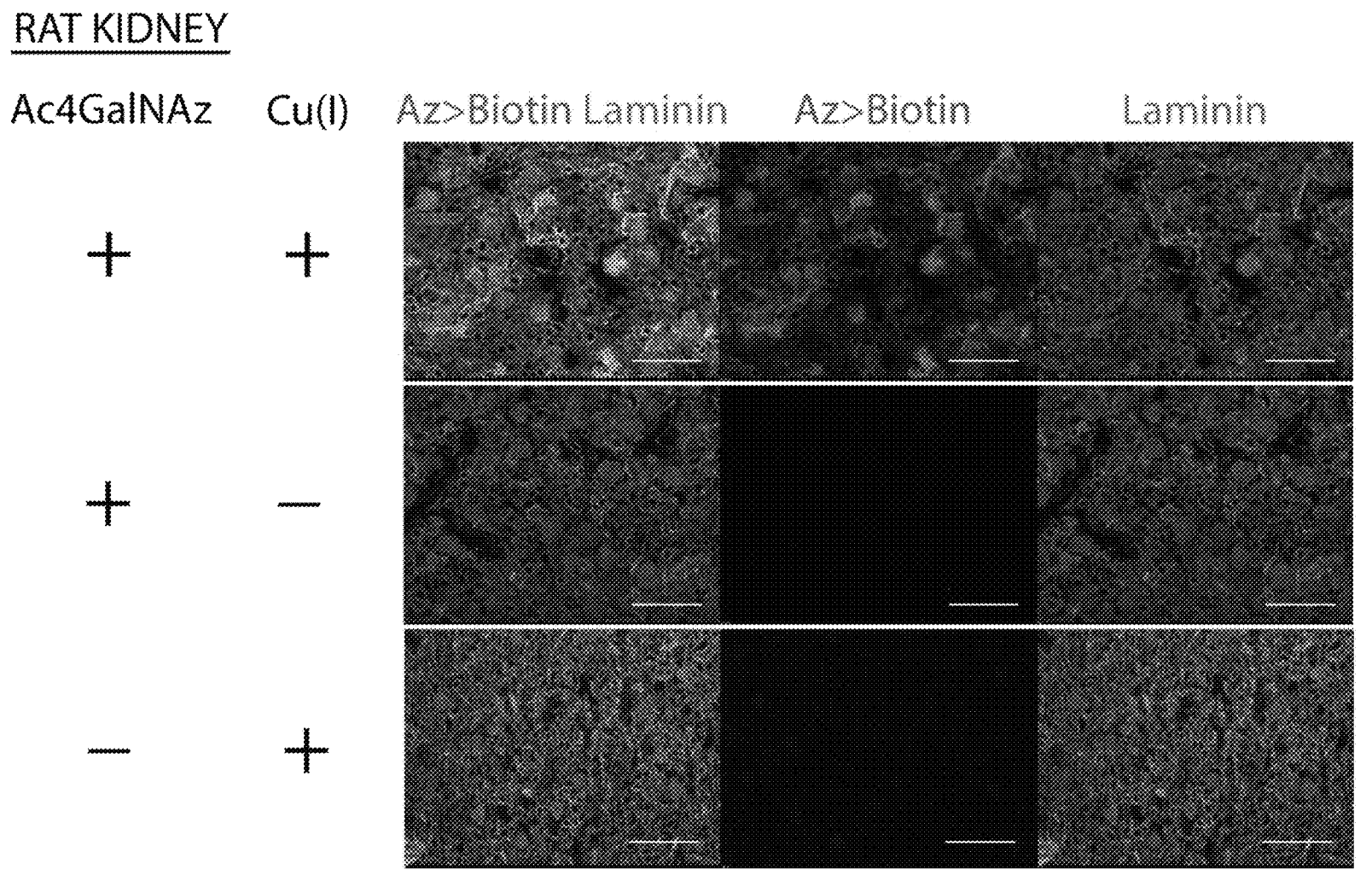

FIG. 29 contains images showing detection of azide ligands in acellular rat kidneys after in vivo metabolic engineering using Ac4GalNAz or DMSO (control without Ac4GalNAz). Azide ligands were detected using biotin-alkyne click reaction with and without Cu(I) catalyst, followed by staining with fluorophore-conjugated streptavidin. Acellular kidney ECM was co-stained with Laminin (n=3 for each group; scale bar: 200 μm).

Figure 30:
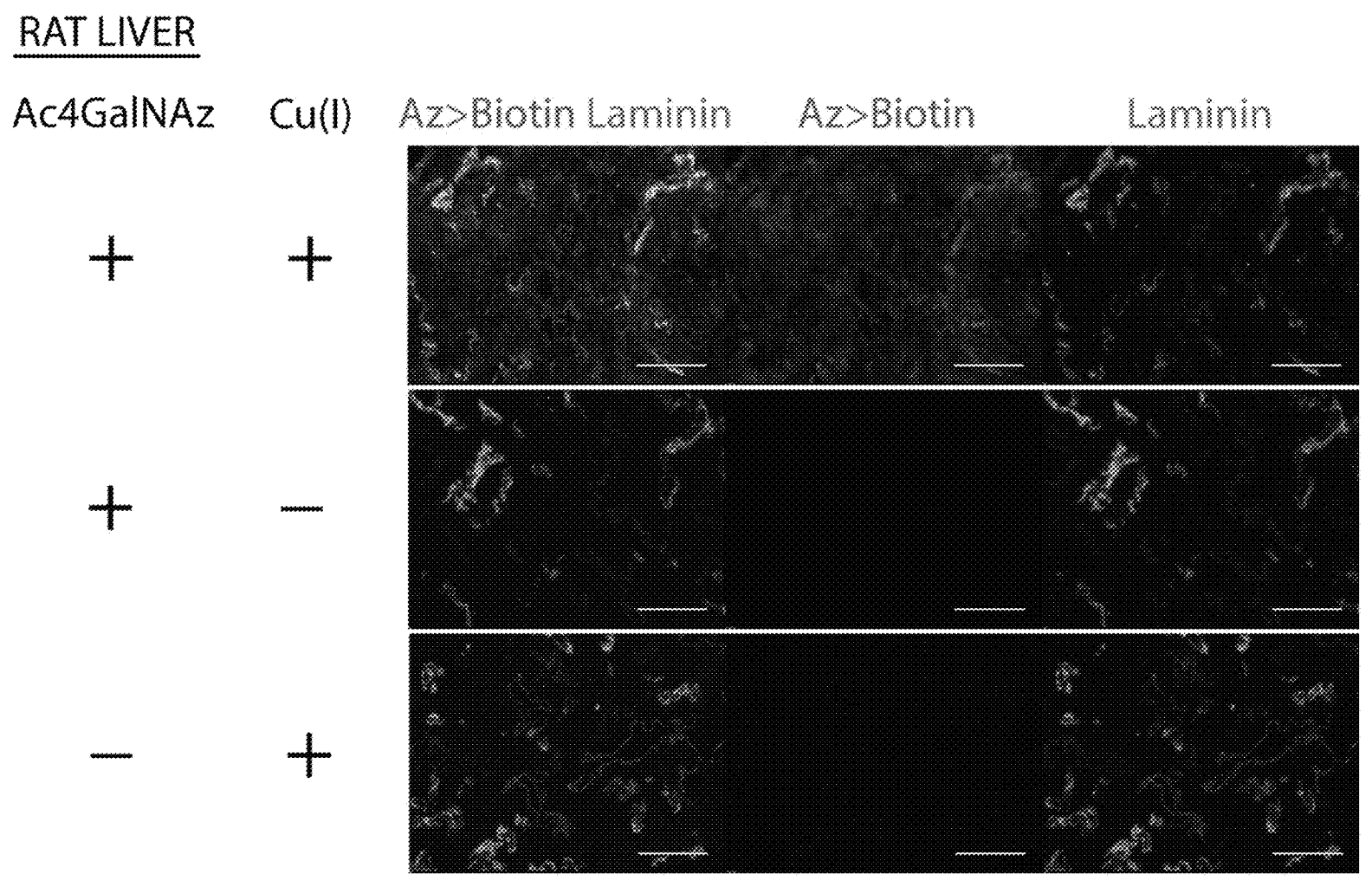

FIG. 30 contains images showing detection of azide ligands in acellular rat livers after in vivo metabolic engineering using Ac4GalNAz or DMSO (control without Ac4GalNAz). Azide ligands were detected using biotin-alkyne click reaction with and without Cu(I) catalyst, followed by staining with fluorophore-conjugated streptavidin. Acellular liver ECM was co-stained with Laminin (n=3 for each group; scale bar: 200 μm).

Figure 31:
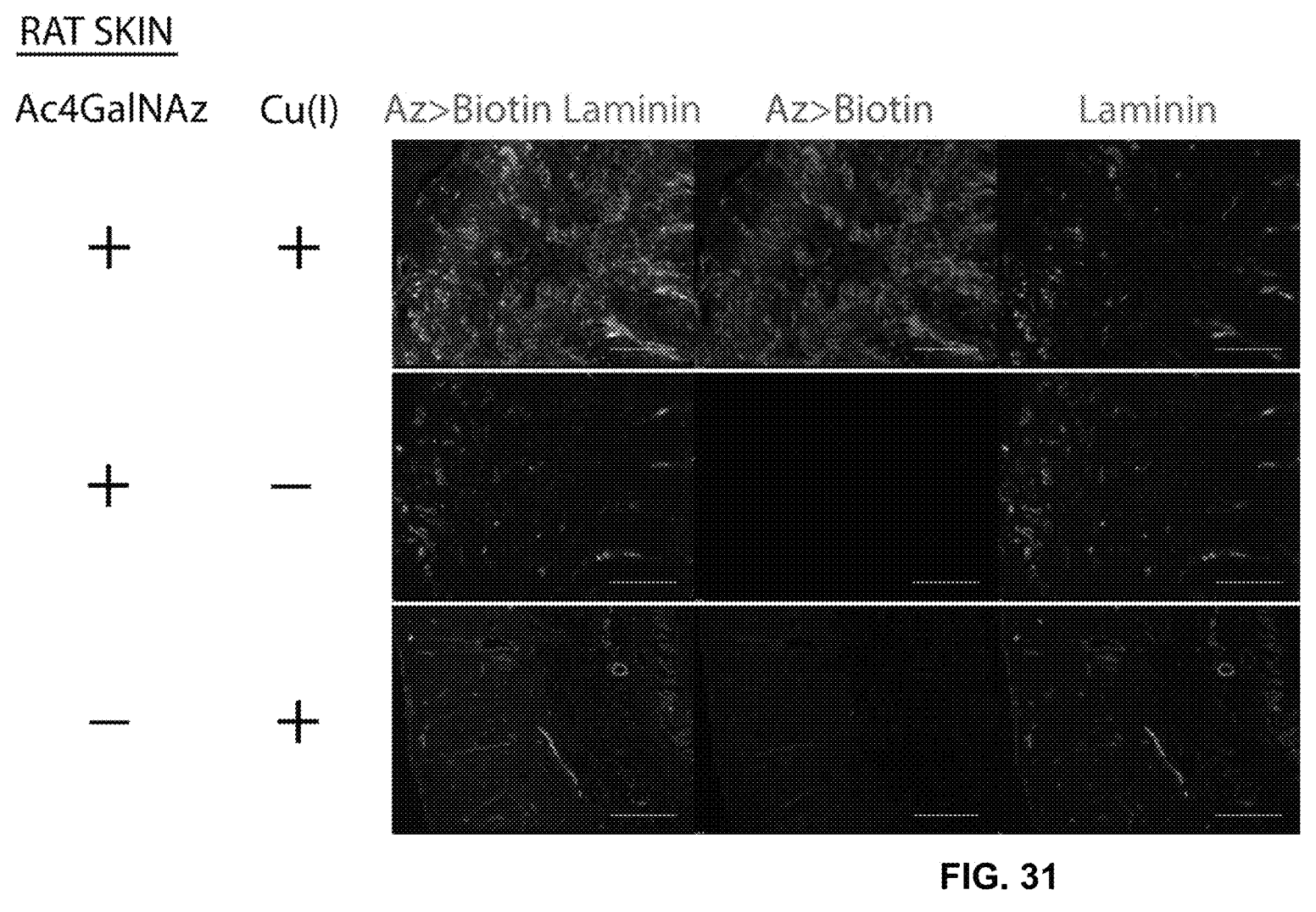

FIG. 31 contains images showing detection of azide ligands in acellular rat skin after in vivo metabolic engineering using Ac4GalNAz or DMSO (control without Ac4GalNAz). Azide ligands were detected using biotin-alkyne click with and without Cu(I) catalyst, followed by staining with fluorophore-conjugated streptavidin. Acellular skin ECM was co-stained with Laminin (n=3 for each group; scale bar: 200 μm).

Figure 32:
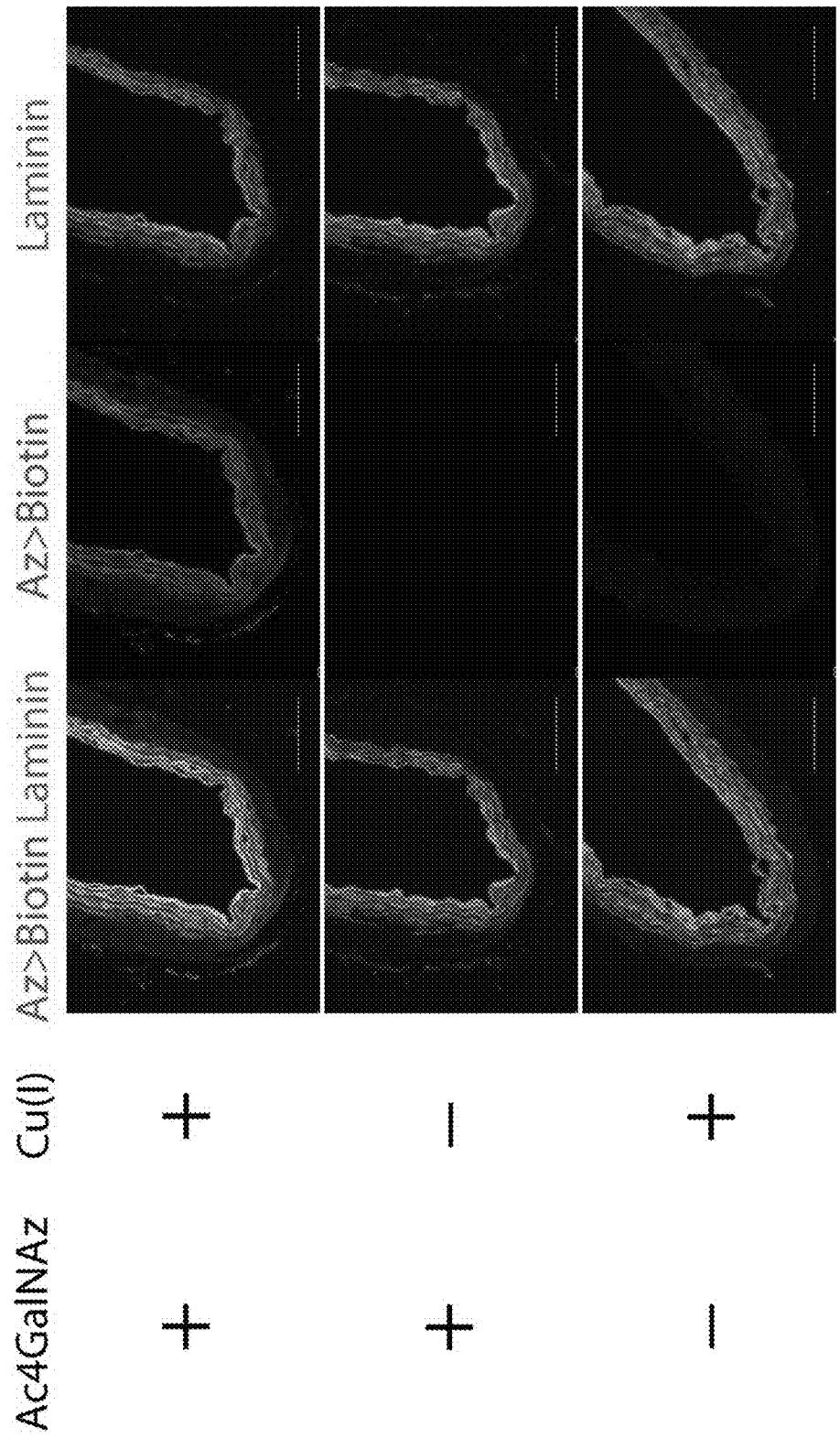

FIG. 32 contains images showing detection of azide ligands in acellular rat carotid arteries after in vivo metabolic engineering using Ac4GalNAz or DMSO (control without Ac4GalNAz). Azide ligands were detected using biotin-alkyne click with and without Cu(I) catalyst, followed by staining with fluorophore-conjugated streptavidin. Acellular carotid artery ECM was co-stained with Laminin (n=3 for each group; scale bar: 100 μm).

DETAILED DESCRIPTION

The present application relates to selective, covalent modification of native extracellular matrix (ECM) without random crosslinking of the functional groups of extracellular matrix. The native matrix is produced by whole-organ or tissue decellularization through, for example, detergent perfusion, or subjecting tissue (e.g., lung tissue) to repeated freeze-thaw cycles. Selective modification may be first achieved by, for example, placing azide tags onto organ/tissue ECM by administering (e.g. feeding or by injection) to the donor animals azide-labeled sugars, which remain in the ECM scaffolds after decellularization. In another example, placing azide tags onto organ/tissue ECM may be achieved by culturing tissue (e.g. lung tissue) with media containing azide-labeled sugars. Alkyne-labeled biomolecules can then be conjugated onto the azide tags on the decellularized organ/tissue scaffolds by the highly selective copper-catalyzed or copper-free click reaction. Various biomolecules and small-molecules may be immobilized onto azide-labeled decellularized organ/tissue scaffolds, for example, by conjugating the biomolecules of interest with an alkyne group. The methods of the present application allow for enhanced cell engraftment on the ECM by immobilizing the ECM, for example, with growth factors/peptides (e.g. VEGF, FGF), reduced thrombogenicity by immobilizing the ECM, for example, with anticoagulation reagents (e.g. heparin), and reduced risk of infection by immobilizing ECM, for example, with antibiotics (e.g. vancomycin).

Immobilization of biomolecules, such as growth factors and heparin, on synthetic or natural materials has mainly been performed using carbodiimide reagents (e.g. 1-ethyl-3-(3-dimethylaminopropyl)carbodiimide (EDC))/N-hydroxysuccinimide (HNS)-mediated crosslinking chemistry[1-3]. Conventional methods for ECM biomaterial functionalization usually involve crosslinking chemistry utilizing the native amino acid residues within the biomaterials, such as lysine residues[3, 9-10] For example, EDC/HNS crosslinking chemistry depends on the reaction between activated carboxyl groups with primary amines. Both carboxyl and amine groups are prevalent in proteins (e.g. collagen), which are major components of ECM. Because of the large abundance of these reactive amino acid residues within the native ECM, these crosslinking conjugation reactions are lacking specificity[11-15]. Therefore, if applied to native extracellular matrix, the non-selective EDC/NHS chemistry causes undesired crosslinking of the matrix and dramatically changes the biochemical and mechanical properties of the ECM. The methods of the present application allow for selective modification of native ECM through the chemoselective click chemistry. Copper-catalyzed or copper-free click chemistry is the conjugation reaction between azide and alkyne functional groups. Azide and alkyne functionalities are not present in biological molecules, hence the reaction between biological molecules functionalized with an azide and molecules with an alkyne functional group is highly specific (biorthogonal). While EDC/NHS chemistry need to be done under extreme chemical conditions that are usually incompatible with biological or living systems (e.g. extreme pH, organic solvents), copper-catalyzed or copper-free click chemistry can be performed in regular biological buffers. Therefore, the methods of the present application can be advantageously used for biomaterial functionalization.

Attributed to the biological and chemical inertness of azide and alkyne moieties in natural biological systems, the conjugation, e.g., between azide- and alkyne-modified biomolecules is highly specific. However, the application of click chemistry to functionalizing decellularized ECM biomaterials has been hindered by the lack of methods for biocompatible and efficient incorporation of click-reactive ligands, such as azide or alkyne, into the ECM. In vivo metabolic engineering approaches have been developed to incorporate click-reactive ligands into amino acids, glycans, lipids and nucleic acids[16-25]. These studies have focused on the labeling of cellular components, and little attention has been given to the feasibility, efficacy and stability of the metabolic labeling of the ECM of tissues and organs. Described herein is a metabolic engineering approach to incorporate, e.g., click-reactive azide ligands into the ECM of tissues and organs via in vivo metabolic engineering.

In some aspects, the present application relates to a novel method to make antibiotic coated biologic mesh by isolating dermal matrix and using selective, covalent modification of native extracellular matrix (ECM) to immobilize an antibiotic (e.g. vancomycin). Click chemistry, also called azide-alkyne Huisgen cycloaddition, uses Copper (Cu) as a catalyst at room temperature. Unlike other methods used to immobilize biomolecules, the methods described herein avoid any off-target crosslinking. The successful reaction requires the native ECM of the donor animal to be labeled with an azide, a functional group that is otherwise not found in the body. To accomplish this, the animals are administered (e.g. intraperitoneally injected) with an azide-labeled sugar for specific time intervals prior to end-point tissue harvest. The injected azide-labeled carbohydrate is incorporated into the ECM and labels the glycoaminoglycans or glycoproteins with the azide group necessary for the click reaction. A simple modification to Vancomycin by conjugating the molecule with an alkyne functional group allows the antibiotic to be covalently bound to the ECM through the click reaction between the alkyne group on Vancomycin with the azide group on the ECM.

In some aspects, the present application provides improved donor organ grafts (e.g., lung graft), by immobilizing biologically active molecules onto the donor organs using bioorthogonal chemical reactions between an alkyne and an azide (e.g., between DBCO and azide). TNF-alpha is one of the main causes of ischemia/reperfusion injury after organ transplantation, and blockade/neutralization of TNF-alpha signaling is beneficial to ameliorate ischemia/reperfusion injury after organ transplantation. In some aspects, methods disclosed in the present application allow for immobilization of anti-TNF-alpha antibody onto the donor organ during its cold preservation, thus neutralizing TNF-alpha produced during ischemia/reperfusion and advantageously protecting the donor lung graft and improve its transplantation outcomes.

Definitions

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the terms "decellularized" and "acellular" are used interchangeably and are defined as the complete or near complete absence of detectable intracellular, endothelial cells, epithelial cells, and nuclei in histologic sections using standard histological staining procedures. Preferably, but not necessarily, residual cell debris also has been removed from the decellularized organ or tissue.

As used herein, the term "biorthogonal" is used to refer to a chemical reaction that can occur in vitro and in vivo in living systems without interfering with native biochemical processes. In some embodiments, biorthogonal reaction may occur between two or more biological molecules, such as growth factors, enzymes, extracellular proteins, and nucleic acids. In some embodiments, biorthogonal reaction may occur between a biological molecule and a xenobiotic. In some embodiments, biorthogonal reaction may occur between two or more xenobiotics. In some embodiments, biorthogonal chemical reaction is 1,3-dipolar cycloaddition between an azide and an alkyne. In some embodiments, biorthogonal chemical reaction is a reaction between a nitrone and an alkyne. In some embodiments, biorthogonal chemical reaction is Staudinger reaction between an azide and a phosphine.

As used herein, the term "chemoselective" is used to refer to selective reactivity of one functional group with another in the presence of other functional groups.

As used herein, the term "preventing" means to completely or almost completely stop an disease or condition (e.g., an infection, ischemia or reperfusion injury) from occurring, for example when the patient or subject is predisposed to an condition or is at risk of a disease or condition. Preventing can also include inhibiting, i.e., arresting the development, of a condition.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans. In some embodiments, the subject may be a donor of an organ or tissue or a recipient of an organ or tissue.

As used herein, the term "bioorthogonally attached" is used to describe two or more molecules coupled together using a bioorthogonal chemical reaction.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "$C_{n-m}$ alkynyl" or "alkynyl" refers to an alkyl group having one or more triple carbon-carbon bonds (wherein "n to m" refer to the number of carbon atoms that the alkynyl group may contain). In some embodiments, alkynyl group is aliphatic. Example aliphatic alkynyl groups include, but are not limited to, ethynyl, propyn-1-yl, propyn-2-yl, and the like. In some embodiments, the aliphatic alkynyl moiety contains 2 to 6, 2 to 4, or 2 to 3 carbon atoms. In some embodiments, the alkynyl group is —C≡CH or $CH_2C$≡CH. In some embodiments, alkynyl group is cyclic (e.g., cyclooctyne or cyclononyne). In some embodiments, cyclooctyne is selected from DBCO, MOFO, DIFO, OCT, DIMAC, ALO and BCN as described herein.

As used herein, the term "click reaction" refers to a high-yielding and highly specific reaction between two or more substrates having low activation energy barrier. In some embodiments, click reaction refers to a reaction between an alkyne-bearing molecule and an azide-bearing molecule. In other embodiments, click reaction refers to a reaction between an alkene-bearing molecule and a tetrazine-bearing molecule. In yet other embodiments, click reaction refers to a reaction between an alkene-bearing molecule and an azide-bearing molecule.

As used herein, the term "nutrient" refers to a molecule that is metabolized by a living system (e.g., an animal or a plant) for survival and growth. As used herein, a nutrient may be a carbohydrate (e.g., saccharide (e.g., monosaccharide, oligosaccharide, polysaccharide)), an amino acid, a peptide, a protein, a fatty acid, a triglyceride, a vitamin or a co-factor.

As used herein, the term "extracellular matrix (ECM)" refers to a collection of extracellular biomolecules that provide structural support (e.g., physical scaffolding) and biochemical cues for the surrounding cells and tissues. In some embodiments, collagen (e.g., type I, II, III, IV, V, VI, VII, VIII, IX, X, XI, XII, XIII and/or XIV) is the main component of the extracellular matrix. In some embodiments, the fibers of the extracellular matrix also comprise elastins, glycosaminoglycans, proteoglycans, fibronectins and/or laminins. In some embodiments, ECM, is derived from native tissues and organs by removing all cellular components while leaving behind the matter outlining the microanatomy.

As used herein, the term "culturing" refers to an in vitro/ex vivo experimental technique that allows to maintain the cells of an isolated organ or a tissue (or a part of an organs or a tissue) in condition suitable for metabolism. In some embodiments, culturing preserves the function of on an organ or a tissue. This may be accomplished by treating the organ or tissue at about 37° C. with a media comprising a nutrient or a plurality of nutrients.

As used herein, the terms "isolated organ", "isolated tissue", "harvested organ" or "harvested tissue" refer to an organ or tissue (e.g., heart, liver, kidney, lung, blood vessel or skin) that was surgically removed from the donor subject for reuse (e.g., organ or tissue transplantation to the recipient subject).

As used herein, the terms "organ transplantation" or "tissue transplantation" refer to surgically removing an organ or tissue from donor subject and placing the organ or tissue to the recipient subject. In some embodiments, when the donor subject is the recipient subject, the organ or tissue transplantation is referred to as "autografting". In some embodiments, when the donor subject and the recipient subject belong to the same species (e.g., when the donor subject is human and the recipient subject is human), the organ or tissue transplantation is referred to as "allografting". In some embodiments, when the donor subject and the recipient subject belong to different species (e.g., when the donor subject is porcine and the recipient subject is human), the organ or tissue transplantation is referred to as "xeno-grafting".

As used herein, the terms "biological prosthetic mesh" and "prosthetic mesh" refers to prosthetic biomaterial (e.g., a flat sheet comprising a mesh layer) useful, for example, in incisional hernia repair to encourage tissue attachment. In some embodiments, the mesh refers to a class of flexible sheets that permit the growth of tissue through openings in the mesh after the surgery has been completed to enhance attachment to surrounding tissue.

As used herein, the term "scaffold" refers to a material providing structural support for the surrounding tissues in vitro and in vivo (e.g., for cell attachment and tissue formation). In some embodiments, scaffold is a matrix upon which cells may be cultured (e.g., survive and proliferate).

As used herein, the term "complementary reactive group" refers to the functional group that is commonly known to react with another functional group to form a chemical bond. For example, in a reaction forming a 1,2,3-triazole ring, when the first reactive functional group is an azide, the complementary reactive group is an alkyne. On the other hand, when the first reactive functional group is an alkyne, the complementary reactive functional group is an azide.

Methods of the Present Disclosure

In some embodiments, the present disclosure provides a method of functionalizing an extracellular matrix of an organ or tissue of a mammal comprising administering to the mammal a nutrient that is functionalized with a chemical group that is reactive in a biorthogonal chemical reaction.

In some embodiments, the present disclosure provides a method of functionalizing an extracellular matrix of an organ or tissue of a mammal comprising (i) selecting the mammal for functionalizing the extracellular matrix of the organ or tissue; and (ii) administering a nutrient to the mammal, wherein the nutrient is functionalized with a chemical group that is reactive in a biorthogonal chemical reaction.

In some embodiments, the present disclosure provides a method of functionalizing an extracellular matrix of an organ or tissue of a mammal, the method comprising (i) harvesting the organ or tissue; and (ii) culturing the organ or tissue using media comprising a nutrient functionalized with a chemical group that is reactive in a biorthogonal chemical reaction.

In some embodiments, the present disclosure provides a decellularized scaffold of a mammalian organ or tissue comprising an extracellular matrix functionalized with a chemical group that is reactive in a biorthogonal chemical reaction.

In some embodiments, the present disclosure provides a decellularized scaffold of a mammalian organ or tissue comprising an extracellular matrix, wherein the extracellular matrix of the decellularized scaffold is chemoselectively functionalized with a biologically active molecule.

In some embodiments, the present disclosure provides a method of preparing a decellularized scaffold of a mammalian organ or tissue comprising an extracellular matrix bioorthogonally functionalized with a biologically active molecule, the method comprising reacting the decellularized scaffold of a mammalian organ or tissue comprising an extracellular matrix functionalized with a chemical group that is reactive in a biorthogonal chemical reaction with a biologically active molecule functionalized with a reactive chemical group complimentary to the reactive chemical group of the functionalized extracellular matrix.

In some embodiments, the present disclosure provides a method of preparing a biological prosthetic mesh comprising reacting the decellularized scaffold of a mammalian organ or tissue comprising an extracellular matrix functionalized with a chemical group that is reactive in a biorthogonal chemical reaction with a biologically active molecule functionalized with a reactive chemical group complimentary to the reactive chemical group of the functionalized extracellular matrix.

In some embodiments, the present disclosure provides a method of preparing an organ or tissue for transplantation, the method comprising (i) administering to a donor subject a nutrient functionalized with a chemical group that is reactive in a biorthogonal chemical reaction; (ii) surgically removing the organ or tissue from the donor subject; and (iii) treating the isolated organ or tissue with a preservation solution comprising biologically active molecule functionalized with a reactive chemical group complimentary to the reactive chemical group of the functionalized nutrient.

In some embodiments, the present disclosure provides an organ or tissue for transplantation, wherein the organ or tissue is functionalized with a biologically active molecule as described herein.

Nutrient Functionalized with a Chemical Group that is Reactive in a Biorthogonal Chemical Reaction In some embodiments, the nutrient functionalized with a chemical group that is reactive in a biorthogonal chemical reaction is a carbohydrate (e.g., saccharide), an amino acid, a peptide, a protein, a fatty acid, a nucleic acid, a nucleoside, a nucleotide or a triglyceride. For example, the nutrient may be a natural amino acid (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine) or an unnatural amino acid (e.g., formylmethionine, selenocysteine, pyrrolysine, γ-aminobutyric acid (GABA), p-aminobenzoic acid, aminolevulinic acid, dehydroalanine, aminoisobutyric acid, lanthionine, alloisoleucine, norvaline, ornithine, allothreonine, or sarcosine). In some embodiments, the nutrient is a peptide comprising from about 2 to about 50 amino acids. In some embodiments, the nutrient is a peptide comprising 5 or more, 10 or more, 15 or more, 20 or more or 25 or more amino acids. In another example, the nutrient is a protein. In some embodiments, the peptide or a protein may comprise any one of the amino acids described herein.

In another example, the nutrient functionalized with a chemical group that is reactive in a biorthogonal chemical reaction may be a fatty acid (e.g., saturated fatty acid such as enanthic, caprylic, pelargonic, capric, undecylic, lauric, tridecylic, myristic, pentadecylic, palmitic, margaric, stearic, nonadecylic, arachidic, heneicosylic, behenic, tricosylic, lignoceric, pentacosylic, cerotic, heptacosylic, montanic, nonacosylic, melissic, henatriacontylic, lacceroic, psyllic, geddic, ceroplastic, hexatriacontylic, heptatriacontanoic or octatriacontanoic acid; or, e.g., mono-unsaturated fatty acid such as crotonic, myristoleic, palmitoleic, sapienic, oleic, elaidic, vaccenic, gadoleic, eicosenoic, erucic, or nervonic acid; or, e.g., di-unsaturated fatty acid such as linoleic, eicosadienoic, or docosadienoic acid; or, e.g., tri-unsaturated fatty acid such as linolenic, pinolenic, eleostearic, mead, dihomo-γ-linolenic or eicosatrienoic acid; or, e.g., tetra-unsaturated fatty acid such as stearidonic, arachidonic, eicosatetraenoic, or adrenic acid; or, e.g., penta-unsaturated fatty acid such as bosseopentaenoic, eicosapentaenoic, ozubondo, sardine, or tetracosanolpentaenoic acid; or, e.g., hexa-unsaturated fatty acid such as docosahexaenoic or nisinic acid). In another example, the nutrient functionalized with a chemical group that is reactive in a biorthogonal chemical reaction may be a triglyceride (e.g., an ester consisting of glycerol and three fatty acids as described herein). In some embodiments, the triglyceride is an ester of glycerol and oleic acid, palmitic acid and stearic acid.

In another example, the nutrient functionalized with a chemical group that is reactive in a biorthogonal chemical reaction may be a carbohydrate such as a saccharide (e.g., monosaccharide, disaccharide, oligosaccharide, or polysaccharide). In some embodiments, the monosaccharide is a pentose (e.g., D- or L-pentose) such as arabinose, lyxose, ribose, ridulose, xylulose, or xylose. In some embodiments, the monosaccharide is a hexose (e.g., D- or L-hexose) such as allose, altrose, glucose, mannose, gulose, idose, galactose, talose, psicose, fructose, sorbose or tagatose. In some embodiments, the disaccharise is sucrose, lactulose, lactose, maltose, trehalose, cellobiose, chitobiose, kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, or xylobiose.

In another example, the nutrient functionalized with a chemical group that is reactive in a biorthogonal chemical reaction may be a nucleic acid (e.g., deoxyribonucleic acid (DNA) or ribonucleic acid (RNA)).

In another example, the nutrient functionalized with a chemical group that is reactive in a biorthogonal chemical reaction may be a nucleoside. In some embodiments, the nucleoside is ribonucleoside (e.g., adenosine, guanosine, 5-methyluridine, uridine, or cytidine). In some embodiments, the nucleoside is deoxyribonucleoside (e.g., deoxyadenosine, deoxyguanosine, thymidine, deoxyuridine, or deoxycytidine). In another example, the nutrient functionalized with a chemical group that is reactive in a biorthogonal chemical reaction may be a nucleotide (e.g., a monophosphate, a diphosphate or a triphosphate of any one of the nucleosides described herein). For example, a nucleotide may be ATP, GTP, CTP or UTP.

In some embodiments the monosaccharide functionalized with a chemical group that is reactive in a biorthogonal chemical reaction is an amino sugar or derivative thereof (e.g., galactosamine, glucosamine, N-acetyl-D-glucosamine, daunosamine, neuraminic acid, sialic acid, N-acetylmannosamine (ManNAc), N-acetylglucosamine (GlcNAc), N-acetylgalactosamine (GalNAc), β-D-galactosamine pentaacetate, β-D-glucosamine pentaacetate, or β-D-mannosamine pentaacetate). In an example, the monosaccharide is sulfoquinovose.

In some embodiments, the chemical group is any one of chemical groups that is reactive in Huisgen cycloaddition (also known as [3+2] cycloaddition of alkynes and azides to form triazoles, or "click" reaction). In some embodiments, the chemical group is any one of chemical groups that is reactive in Staudinger ligation (i.e., a reaction between an azide and a phosphine), a reaction of oxanorbornadienes and azides to from triazoles, an inverse-demand Diels-Alder reaction of tetrazines (e.g., dipyridyl tetrazines) and trans-cycloctynes, inverse-demand Diels-Alder reaction of tetrazines (e.g., monoaryl tetrazines) and norbornenes, a reaction of tetrazines and cyclopropenes, a reaction of cyclopropenes and nitrile imines, a photoinduced 1,3-dipolar cycloaddition of tetrazoles and alkenes, a 1,3-dipolar cycloaddition of nitrile oxides and norbornenes, a [4+1] cycloaddition isocyanides and tetrazines or a 1,3-cycloaddition of nitrones and alkynes.

In some embodiments, the chemical group that is reactive in a biorthogonal chemical reaction is an azide ($-N_3$), an alkyne (e.g., $-C\equiv CH$), a cyclooctyne, a cyclooctene, a nitrone, an isocyanide, a cyclopropene, a norborene, a diphenylphosphine, nitrile imine, a tetrazole, a nitrile oxide, or a tetrazine. In some embodiments, the chemical group that is reactive in a biorthogonal chemical reaction is an azide ($-N_3$) or an alkyne. In some embodiments, the chemical group that is reactive in a biorthogonal chemical reaction is an azide ($-N_3$). In some embodiments, the chemical group that is reactive in a biorthogonal chemical reaction is an alkyne.

In some embodiments, the nutrient functionalized with a chemical group that is reactive in a biorthogonal chemical reaction is selected from L-azidooalanine, L-azidohomoalanine, L-homopropargylglycine, (2S)—N-Fmoc-5-azidopentanoic acid, (R)-N-Fmoc-2-(2'-propynyl)alanine, (S)—N-Fmoc-2-(2'-propynyl)alanine, (S)—N-Fmoc-2-(4'-azidobutyl)alanine, (S)—N-Fmoc-2-(5'-azidopentyl)alanine, (S)—N-Fmoc-2-(6'-azidohexyl)alanine, 2-Amino-3-mercapto-N-(prop-2-ynyl)propionamide, 2-Amino-N-(3-azidopropyl)-3-mercaptopropionamide, Boc-D-propargylglycine, Boc-Lys($N_3$)—OH, Boc-azidolysine, Fmoc-4-azidophenylalanine and Fmoc-D-propargylglycine.

In some embodiments, the nutrient functionalized with a chemical group that is reactive in a biorthogonal chemical reaction is any one of azide-modified RNA molecules described in Nucl. Acids Res. (2015), 1-12, the disclosure of which is incorporated herein by reference in its entirety. In some embodiments, the nutrient functionalized with a chemical group that is reactive in a biorthogonal chemical reaction is 3'-terminal azide-modified RNA (e.g., as described in Bioconjug Chem. 2014 Jan. 15; 25(1): 188-195, the disclosure of which is incorporated herein by reference in its entirety).

In some embodiments, the nutrient functionalized with a chemical group that is reactive in a biorthogonal chemical reaction is an azido nucleoside. In some embodiments, the azido nucleoside is 3'-azido-3'-deoxythymidine or a compound of the following formulae:

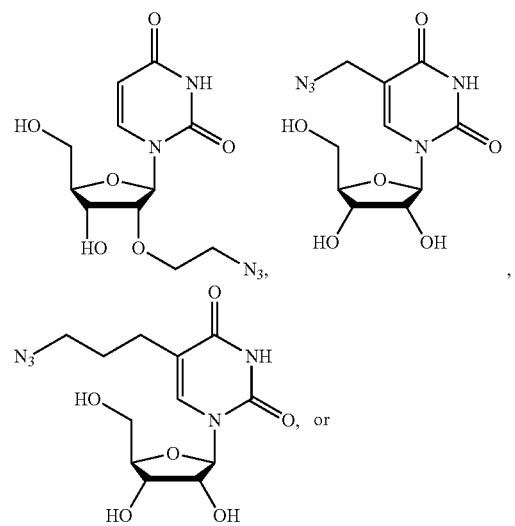

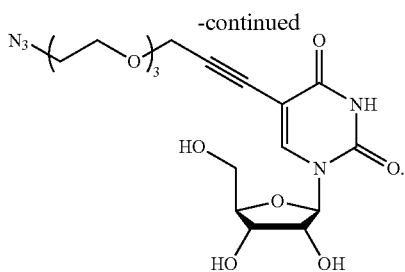

In some embodiments, the nutrient functionalized with a chemical group that is reactive in a biorthogonal chemical reaction is an alkyne nucleoside. In some embodiments, the alkyne nucleoside is (2'S)-2'-deoxy-2'-fluoro-5-ethynyluridine, 5-ethynyl-2'-deoxycytidine or 5-ethynyl-2'-deoxyuridine.

In some embodiments, the nutrient functionalized with a chemical group that is reactive in a biorthogonal chemical reaction is an azido nucleotide. In some embodiments, the azido nucleotide is 8-azido-AMP, 8-azido-ADP, 8-azido-ATP, γ-(2-azidoethyl)-ATP, γ-(6-azidohexyl)-ATP, γ-[(6-azidohexyl)-imido]-ATP, $N^6$-(6-azido)hexyl-ATP, $N^6$-(6-azido)hexyl-3'-dATP, $N^6$-(6-Azido)hexyl-dATP, 5-DBCO-PEG$_4$-dCTP, 5-DBCO-PEG$_4$-dUTP, 3'-azido-2',3'-ddATP, azide-PEG$_4$-aminoallyl-dUTP, 5-azido-C$_3$-UTP, 5-azido-PEG$_4$-UTP, 5-azido-PEG$_4$-CTP, pCp-azide, AzTMP, AzTTP, 2'-azido-2'-deoxyadenosine-5'-triphosphate, 2'-azido-2'-deoxycytidine-5'-triphosphate, 2'-azido-2'-deoxyguanosine-5'-triphosphate, or 2'-azido-2'-deoxyuridine-5'-triphosphate.

In some embodiments, the nutrient functionalized with a chemical group that is reactive in a biorthogonal chemical reaction is an alkyne nucleotide. In some embodiments, the alkyne nucleotide is $N^6$-propargyl-ATP, 5-TCO-PEG$_4$-dUTP, 5-trans-Cyclooctene-PEG$_4$-dUTP, γ-[(propargyl)-imido]-ATP, γ-propargyl-ATP, γ-[(propargyl)-imido]-ATP, 2-ethynyl-ATP (2-EATP), C8-alkyne-dCTP, C8-alkyne-dUTP, 5-ethynyl-UTP (5-EUTP) or 5-ethynyl-dUTP (5-EdUTP).

In some embodiments, the nutrient functionalized with a chemical group that is reactive in a biorthogonal chemical reaction is an azido fatty acid (e.g., ω-azido fatty acid) or an alkynyl fatty acid. In some embodiments, the nutrient functionalized with a chemical group that is reactive in a biorthogonal chemical reaction is a fatty acid derivative of formula Z—(Y)$_x$COOR, wherein Y is —CH$_2$— or —CH═CH—, Z is —N$_3$ or alkynyl, x is an integer from 1 to 20 (e.g., n is 6 or 7), and R is H or C$_{1-6}$ alkyl. In some embodiments, the azido fatty acid or the alkynyl fatty acid is any one of azido fatty acids or the alkynyl fatty acids described in Journal of the American Oil Chemists' Society, 2009, 86, 1115-1121.

In some embodiments, the azido fatty acid is any one of azido fatty acids described in ChemBioChem, 2015, 16 (11), 1588-1591, the disclosure of which is incorporated herein by reference in its entirety. In some embodiments, the azido fatty acid is selected from 12-azidododecanoic acid, 11-azidoundecanoic acid, 9-azidononanoic acid, 13-azidotridecanoic acid, 5-(1-azido-hexane-6-thia)pentanoic acid, 2-(1-azido-nonane-9-thia)acetic acid, 4-(1-azido-octane-6-thia)propionic acid, 9-(1-azido-ethane-2-oxa)nonanoic acid, 8-(1-azido-propane-3-oxa)octanoic acid, 5-(1-azido-hexane-6-oxa)pentanoic acid, and 2-(1-azido-nonane-9-oxa)acetic acid. In some embodiments, the alkynyl fatty acid is selected from 15-hexadecynoic acid, 17-octadecynoic acid, and 5Z,8Z,11Z,14Z-eicosatetraen-19-ynoic acid.

In some embodiments, the nutrient functionalized with a chemical group that is reactive in a biorthogonal chemical reaction is an alkynyl saccharide (e.g., alkynyl sugar). In some embodiments, the alkynyl saccharide is any one of the alkynyl saccharides described, for example, in US 2012/0149887, the disclosure of which is incorporated herein by reference in its entirety. In some embodiments, the alkynyl saccharide is selected from alkynyl fucose and alkynyl ManNAc.

In some embodiments, alkynyl fucose is 1,2,3,4-tetraacetyl alkynyl fucose of the following formula:

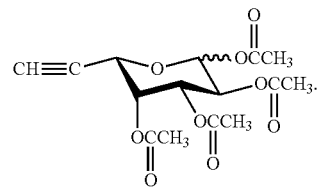

In some embodiments, alkynyl ManNAc is 1,3,4,6-tetra-O-acetyl-N-4-pentynoylmannosamine of the following formula:

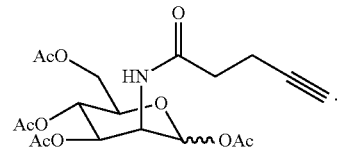 [SMILES: C#CCCC(=O)NC1C(OC(C)=O)OC(COC(C)=O)C(OC(C)=O)C1OC(C)=O]

In some embodiments, the nutrient functionalized with a chemical group that is reactive in a biorthogonal chemical reaction is an alkyne-labeled galactosamine, an alkyne-labeled glucosamine or an alkyne-labeled mannosamine.

In some embodiments, the nutrient functionalized with a chemical group that is reactive in a biorthogonal chemical reaction is selected from 1-azido-1-deoxy-β-D-galactopyranoside, 2-azido-D-galactose tetraacetate, 6-azido-6-deoxy-D-galactose, α-D-mannopyranosyl azide tetraacetate, 2,3,4-tri-O-acetyl-β-D-xylopyranosyl azide, 2-acetamido-2-deoxy-β-D-glucopyranosyl azide, 2-azido-β-D-glucose tetraacetate, 6-azido-6-deoxy-D-glucose, 1,3,4,6-tetra-O-acetyl-2-azido-2-deoxy-D-galactopyranose, 1,3,4,6-tetra-O-acetyl-2-azido-2-deoxy-D-glucopyranose, 1,6-anhydro-2-azido-2-deoxy-β-D-glucopyranose, 1,6-anhydro-2-azido-4-O-benzyl-2-deoxy-β-D-glucopyranose, 1,6-di-O-acetyl-2-azido-3,4-di-O-benzyl-2-deoxy-α-D-glucopyranose, 2,3,4,6-tetra-O-acetyl-α-D-mannopyranosyl azide, 2,3,4,6-tetra-O-acetyl-β-D-glucopyranosyl azide, 2,3,4-tri-O-acetyl-1-azido-1-deoxy-β-D-glucopyranuronic acid methyl ester, 2,3,4-tri-O-acetyl-6-azido-6-deoxy-β-D-glucopyranosyl azide, 2,3,4-tri-O-acetyl-6-azido-6-deoxy-β-D-glucopyranosylamine, 2-acetamido-3,4,6-tri-O-acetyl-2-deoxy-β-D-glucopyranosyl azide, 2-azido-2-deoxy-D-galactopyranose 1,3,4,6-tetraacetate, 2-azido-2-deoxy-D-glucopyranose 1,3,4,6-tetraacetate, 2-chloro-4-nitrophenyl 2-azido-2-deoxy-β-D-galactopyranoside, 2-fluoro-4-nitrophenyl 2-azido-2-deoxy-β-D-galactopyranoside, 3-O-acetyl-1,6-anhydro-2-azido-2',3'-di-O-benzyl-4',6'-O-benzylidene-2-deoxy-3-D-cellobiose, 3-O-acetyl-2-azido-2',3'-di-O-benzyl-4',6'-O-benzylidene-2-deoxy-cellobiosan, 6,6'-diazido-6,6'-dideoxy-α,α-D-trehalose, 6-azido-6-deoxy-2,3-O-isopropylidene-α-L-sorbofuranose, 6-azido-6-deoxy-D- galactose, 6-azido-6-deoxy-D-glucopyranose, 6-azido-6-deoxy-L-galactose, 6-azido-6-deoxy-α-D-glucopyranosyl 6-azido-6-deoxy-α-D-glucopyranoside, 6-azido-6-deoxy-β-D-glucopyranosylamine, 6-azido-D-fucose, 6-azido-L-fucose, 6-O-acetyl-2-azido-3,4-di-O-benzyl-2-deoxy-D-glucopyranose, methyl (6-O-acetyl-2-azido-3,4-di-O-benzyl-2-deoxy-α-D-glucopyranosyl)-(1→4)-methyl 2,3-di-O-benzyl-β-D-glucopyranosyluronate-(1→4)-3,6-di-O-acetyl-2-azido-2-deoxy-α-D-glucopyranosyl-(1→4)-methyl 2-O-acetyl-3-O-benzyl-α-L-idopyranosyluronate-(1→4)-6-O-acetyl-3-O-benzyl-2-benzyloxycarbonylamino-2-deoxy-α-D-glucopyranoside, methyl 2,3,4-tri-O-acetyl-1-deoxy-β-D-glucopyranuronosyl azide, methyl 2,3,4-tri-O-acetyl-6-azido-6-deoxy-α-D-glucopyranoside, α-D-mannopyranosyl azide, α-D-xylopyranosyl azide, β-D-glucopyranosyl azide, and β-D-xylopyranosyl azide.

In some embodiments, the nutrient functionalized with a chemical group that is reactive in a biorthogonal chemical reaction is an azide-labeled galactosamine, an azide-labeled glucosamine or an azide-labeled mannosamine.

In some embodiments, the nutrient functionalized with a chemical group that is reactive in a biorthogonal chemical reaction is tetraacylated N-azidoacetylglucosamine (Ac4GlcNAz):

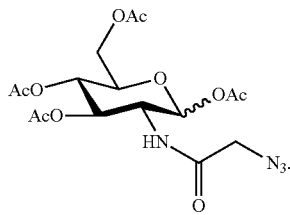

In some embodiments, the nutrient functionalized with a chemical group that is reactive in a biorthogonal chemical reaction is tetraacylated N-azidoacetylmannosamine (Ac4ManNAz):

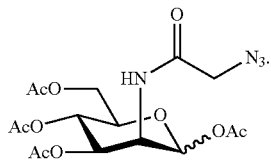

In some embodiments, the nutrient functionalized with a chemical group that is reactive in a biorthogonal chemical reaction is tetraacylated N-azidoacetylgalactosamine (Ac4GalNAz):

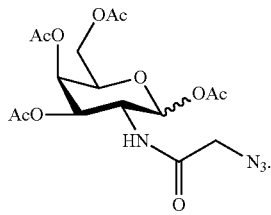

Metabolic Organ Labeling In Vivo (Animal Feeding)

In some embodiments, the nutrient functionalized with a chemical group that is reactive in a biorthogonal chemical reaction may be administered to a mammal by oral, rectal, nasal, topical (including buccal and sublingual), or parenteral (including intraperitoneal, subcutaneous, intramuscular, intravenous and intradermal) route. In some embodiments, the nutrient may be administered to the mammal with food or in a unit dosage from (e.g., tablets, capsules, sachets, powder, granules, sustained release capsules, or liposomes) that may be prepared by any methods well known in the art of pharmacy. When administered orally, the nutrient may be administered with commonly used carriers such as lactose and corn starch. If desired, common sweetening and/or flavoring and/or coloring agents may be added, and various diluents and excipients commonly known in the art may be used (e.g., alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and polyethylene glycol).

In some embodiments, the nutrient may be administered to the mammal by intramuscular, intravenous, intraperitoneal (i.p.), or subcutaneous injection. In some embodiments, the nutrient may be administered by intraperitoneal injection. Compositions suitable for an injection (e.g., intraperitoneal or subcutaneous injection) include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The sterile injectable preparation may also be a sterile injectable solution or suspension in a non-toxic parenterally-acceptable diluent or solvent, for example, as a solution in 1,3-butanediol. In some embodiments, the solvent is water, DMSO or mixtures thereof (e.g., about 10/90, about 20/80, about 30/70, about 40/60, about 50/50, about 60/40, about 70/30, about 80/20, or about 90/10 DMSO/water). Among other acceptable vehicles and solvents that may be employed are mannitol, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant. In some embodiments, the nutrient may be administered to the mammal by inhalation or nebulization (e.g., intratracheal, intranasal administration, or delivery by way of the lungs). In some embodiments, the nutrient may be administered by spray or aerosol (e.g., nasal aerosol or inhaler). Compositions for inhalation and/or nebulization comprising a nutrient (as well as the devices for administration of these compositions) may be prepared according to methods and techniques well-known in the art of pharmaceutical formulations and may be prepared (e.g., using any one of excipients described herein) as solutions (e.g., aqueous or saline solutions), solid formulations, employing benzyl alcohol or other suitable preservatives, absorption promoters to enhance bioavailability, fluorocarbons, propellants (e.g., butane or propane) and/or other solubilizing or dispersing agents known in the art. See, e.g.: Rabinowitz J D and Zaffaroni A C, U.S. Pat. No. 6,803,031, assigned to Alexza Molecular Delivery Corporation. In some embodiments, the particle size of the nutrient is reduced for inhalation administration. In some embodiments, the particle size may be reduced by dry-milling or wet-milling the nutrient (e.g., using ball mill, jet mill, pin mill, fluid energy mill, rod mill, roller mill, crusher mill, spex-type mill, attritor-type mill, siebtechnik mill, simoloyer mill, or hicom mill). In some embodiments, the particle size of the nutrient, on the particle volume average basis, is from about 10 nm to about 1000 nm, from about 20 nm to about 900 nm, from about 30 nm to about 800 nm, from about 40 nm to about 700 nm, from about 50 nm to about 600 nm, from about 60 nm to about 500 nm, from about 70 nm to about 400 nm, from about 70 nm to about 300 nm, from about 100 nm to about 200 nm.). In some embodiments, the particle size of the nutrient, of the particle volume average basis, is about 100 nm, about 200 nm, about 300 nm, about 400 nm, about 500 nm, about 600 nm, about 700 nm, about 800 nm, about 900 nm, or about 1000 nm. In some embodiments, the particle size of the nutrient, on the particle volume average basis, is from about 1 µm to about 100 µm, from about 1 µm to about 90 µm, from about 1 µm to about 80 µm, from about 1 µm to about 70 µm, from about 1 µm to about 60 µm, from about 1 µm to about 50 µm, from about 1 µm to about 40 µm, from about 1 µm to about 30 µm, from about 1 µm to about 20 µm, or from about 1 µm to about 10 µm. In some embodiments, the particle size of the nutrient, on the particle volume average basis, is about 1 µm, about 5 µm, about 10 µm, about 20 µm, about 25 µm, about 30 µm, about 40 µm, about 50 µm, about 75 µm, about 100 µm, about 150 µm, or about 200 µm. The size of the particles of the nutrient is the median particle size, determined as the median particle diameter on an equivalent spherical particle volume basis. It is understood that "median" describes the particle size that divides the population in half such that 50% of the population is greater than or less than this size.

In some embodiments, the dose of the nutrient functionalized with a chemical group that is reactive in a biorthogonal chemical reaction may be from about 100 mg to about 1000 g, from about 100 mg to about 900 g, from about 100 mg to about 800 g, from about 100 mg to about 700 g, from about 100 mg to about 600 g, from about 100 mg to about 500 g, from about 100 mg to about 400 g, from about 100 mg to about 350 g, from about 100 mg to about 300 g, from about 100 mg to about 200 g, from about 100 mg to about 100 g, from about 100 mg to about 50 g, from about 100 mg to about 40 g, 100 mg to about 30 g, 100 mg to about 20 g, from about 200 mg to about 15 g, from about 300 mg to about 10 g, from about 400 mg to about 9 g, from about 500 mg to about 8 g, from about 600 mg to about 7 g, from about 700 mg to about 6 g, from about 800 mg to about 5 g, from about 900 mg to about 4 g, or from about 1 g to about 3 g. In some embodiments, the dose is about 100 mg, about 150 mg, about 200 mg, about 250 mg, about 300 mg, about 350 mg, about 400 mg, about 450 mg, about 500 mg, about 550 mg, about 600 mg, about 700 mg, about 800 mg, about 900 mg, about 1 g, about 2 g, about 3 g, about 4 g, about 5 g, about 6 g, about 7 g, about 8 g, about 9 g, about 10 g, about 15 g, about 20 g, about 25 g, about 30 g, about 40 g, about 50 g, about 60 g, about 70 g, about 80 g, about 90 g, about 100 g, about 150 g, about 200 g, about 250 g, about 300 g, about 350 g, about 400 g, about 500 g, about 600 g, about 700 g, about 800 g, about 900 g, or about 1000 g. In some embodiments, the dose of the nutrient functionalized with a chemical group that is reactive in a biorthogonal chemical reaction per body weight of the subject may be from about 10 mg/kg to about 10 g/kg, from about 10 mg/kg to about 7.5 g/kg, from about 10 mg/kg to about 5 g/kg, from about 50 mg/kg to about 4 g/kg, from about 100 mg/kg to about 3 g/kg, from about 150 mg/kg to about 2 g/kg, from about 200 mg/kg to about 1 g/kg, from about 250 mg/kg to about 900 mg/kg, from about 300 mg/kg to about 800 mg/kg, from about 350 mg/kg to about 700 mg/kg, or from about 400 mg/kg to about 600 mg/kg. In some embodiments, the dose of the nutrient functionalized with a chemical group that is reactive in a biorthogonal chemical reaction may be about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 120 mg/kg, about 150 mg/kg, about 175 mg/kg, about 200 mg/kg, about 225 mg/kg, about 250 mg/kg, about 275 mg/kg, about 300 mg/kg, about 350 mg/kg, about 400 mg/kg, about 500 mg/kg, about 750 mg/kg, about 1 g/kg, about 2 g/kg, about 3 g/kg, about 4 g/kg, about 5 g/kg, about 6 g/kg, about 7 g/kg, about 8 g/kg, about 9 g/kg, or about 10 g/kg. In some embodiments, the dose of the nutrient is about 300 mg/kg body weight.

In some embodiments, the nutrient is administered once daily, twice daily or thrice daily. In some embodiments, the nutrient is administered once daily.

In some embodiments, when the nutrient is administered by intraperitoneal injection, the volume of injection is from about 100 µL to about 2000 mL, from about 100 µL to about 1900 mL, from about 100 µL to about 1800 mL, from about 100 µL to about 1750 mL, from about 100 µL to about 1700 mL, from about 100 µL to about 1600 mL, from about 100 µL to about 1500 mL, from about 100 µL to about 1250 mL, from about 100 µL to about 1000 mL, from about 100 µL to about 900 mL, from about 100 µL to about 800 mL, from about 100 µL to about 700 mL, from about 100 µL to about 600 mL, from about 100 µL to about 500 mL, from about 100 µL to about 400 mL, from about 100 µL to about 300 mL, from about 100 µL to about 200 mL, from about 100 µL to about 150 mL, from about 100 µL to about 100 mL, from about 100 µL to about 50 mL, from about 100 µL to about 40 mL, from about 100 µL to about 20 mL, from about 100 µL to about 15 mL, from about 150 µL to about 12 mL, from about 200 µL to about 10 mL, from about 250 µL to about 5 mL, from about 300 µL to about 4 mL, from about 400 µL to about 3 mL, from about 500 µL to about 2 mL, or from about 500 µL to about 1 mL. In some embodiments, the volume of injection is about 50 µL, about 100 µL, about 150 µL, about 200 µL, about 250 µL, about 300 µL, about 500 µL, about 1 mL, about 2 mL, about 4 mL, about 7.5 mL, or about 10 mL.

In some embodiments, the nutrient functionalized with a chemical group that is reactive in a biorthogonal chemical reaction may be administered to a mammal for about 1 day, about 2 days, about 3 days, about 4 days, about 5 days, about 6 days, about 7 days, about 8 days, about 9 days, or about 10 days prior to end-point organ or tissue harvest. In some embodiments, the nutrient may be administered to the mammal for about 3 to about 7 days. In some embodiments, the nutrient may be administered to the mammal for about 3 days. In other embodiments, the nutrient may be administered to the mammal for about 7 days.

In some embodiments, the nutrient functionalized with a chemical group that is reactive in a biorthogonal chemical reaction is Ac4GalNAz and the nutrient is administered to the mammal by intraperitoneal injection once daily in a dose of about 300 mg/kg in about 70% aqueous DMSO for about 3 days or about 7 days.

Metabolic Organ Labeling Ex Vivo (Organ Culturing)

In some embodiments, in order to functionalize the unfunctionalized isolated organ or tissue of a mammal (e.g., the extracellular matrix of the organ or tissue), the isolated organ or tissue may be cultured using media comprising a nutrient functionalized with a chemical group that is reactive in a biorthogonal chemical reaction as described herein.

Any growth or culturing media known in the art to sustain and promote cell growth may be used for functionalizing the extracellular matrix of the organs and tissues as described herein. In some embodiments, the culturing media comprises the aqueous solvent, electrolytes (e.g., NaCl, KCl, $KH_2PO_4$, $MgSO_4$, $Na_2CO_3$, $NaHCO_3$), nutrients (e.g., amino acids (e.g., any one of the amino acids described herein), glucose), vitamins (e.g., folic acid, nicotinamide, riboflavin, $B_{12}$), minerals (e.g., iron, magnesium), or glutamine (e.g., L-glutamine). In some embodiments, the media comprises human albumin, hetastarch, dextran, pyridoxine, or pyridoxal. In some embodiments, the media comprises Ham's F-12 nutrient mixture. In some embodiments, the media comprises a component selected from calcium chloride dihydrate, copper sulphate pentahydrate, ferric sulphate heptahydrate, magnesium chloride anhydrous, potassium chloride, sodium bicarbonate, sodium chloride, sodium phosphate dibasic anhydrous, zinc sulphate tetrahydrate, glycine, L-alanine, L-arginine hydrochloride, L-asparagine anhydrous, L-aspartic acid, L-cysteine hydrochloride, L-glutamic acid, L-histidine hydrochloride monohydrate, L-isoleucine, L-leucine, L-lysine hydrochloride, L-methionine, L-phenylalanine, L-proline, L-serine, L-threonine, L-tryptophan, L-tyrosine disodium salt, L-valine, biotin, choline chloride, D-Ca-pantothenate, folic acid, nicotinamide, pyridoxine hydrochloride, riboflavin, thiamine hydrochloride, vitamin B12, i-Inositol, D-glucose, hypoxanthine sodium salt, linoleic acid, lipoic acid, phenol red sodium salt, putrescine dihydrochloride, sodium pyruvate, and thymidine.

In some embodiments, the media comprises glucose in a concentration from about 10 mg/L to about 10000 mg/L, from about 20 mg/L to about 9000 mg/L, from about 30 mg/L to about 8000 mg/L, from about 40 mg/L to about 7000 mg/L, from about 50 mg/L to about 6000 mg/L, from about 60 mg/L to about 5000 mg/L, from about 70 mg/L to about 4000 mg/L, from about 80 mg/L to about 3000 mg/L, from about 90 mg/L to about 2000 mg/L, from about 100 mg/L to about 1000 mg/L, from about 200 mg/L to about 1000 mg/L, from about 300 mg/L to about 1000 mg/L, from about 400 mg/L to about 1000 mg/L, from about 500 mg/L to about 1000 mg/L, from about 600 mg/L to about 1000 mg/L, from about 2000 mg/L to about 6000 mg/L, from about 3000 mg/L to about 5000 mg/L or from about 3500 mg/L to about 4500 mg/L. In some embodiments, the media comprises glucose in a concentration of about 500 mg/L, about 600 mg/L, about 700 mg/L, about 800 mg/L, about 900 mg/L, about 1000 mg/L, about 2000 mg/L, about 3000 mg/L, about 4000 mg/L, about 4500 mg/L or about 5000 mg/L.

In some embodiments, the media comprises L-glutamine in a concentration from about 0.1 gm/L to about 1.1 gm/L, from about 0.2 gm/L to about 1.0 gm/L, from about 0.3 gm/L to about 0.9 gm/L, from about 0.4 gm/L to about 0.8 gm/L, or from about 0.5 gm/L to about 0.7 gm/L. In some embodiments, the media comprises L-glutamine in a concentration of about 0.1 gm/L, about 0.2 gm/L, about 0.3 gm/L, about 0.4 gm/L, about 0.5 gm/L, about 0.6 gm/L, or about 0.7 gm/L. In some embodiments, the concentration of L-glutamine is about 0.584 gm/L.

In some embodiments, the culturing media comprises fetal bovine serum (FBS). In some embodiments, the concentration (w/w %) of FBS in the culturing media is from about 1% to about 30%, from about 5% to about 20%, or from about 10% to about 15%. In some embodiments, the concentration of FBS in the culturing media is about 5%, about 10%, about 15%, or about 20%.

In some embodiments, the media comprises an antibiotic (e.g., any one of the antibiotics described herein). In some embodiments, the antibiotic is penicillin-streptomycin. In some embodiments, the antibiotic is gentamicin-amphotericin B. In some embodiments, when the antibiotic is penicillin-streptomycin, the media comprises from about 10 units/mL to about 500 units/ml of penicillin and from about 10 µg/ml to about 500 µg/ml of streptomycin, from about 20 units/mL to about 400 units/ml of penicillin and from about 20 µg/ml to about 400 µg/ml of streptomycin, from about 30 units/mL to about 300 units/ml of penicillin and from about 30 µg/ml to about 300 µg/ml of streptomycin, from about 40 units/mL to about 200 units/ml of penicillin and from about 40 µg/ml to about 200 µg/ml of streptomycin, or from about 50 units/mL to about 100 units/ml of penicillin and from about 50 µg/ml to about 100 µg/ml of streptomycin. In some embodiments, when the antibiotic is penicillin-streptomycin, the media comprises 100 units/ml of penicillin and about 100 µg/ml of streptomycin. In some embodiments, when the antibiotic is gentamicin-amphotericin B, the media comprises from about 1 µg/ml to about 20 µg/ml of gentamicin and from about 0.1 µg/ml to about 0.5 µg/ml of amphotericin B, from about 5 µg/ml to about 15 µg/ml of gentamicin and from about 0.12 µg/ml to about 0.4 µg/ml of amphotericin B, or from about 8 µg/ml to about 12 µg/ml of gentamicin and from about 0.15 µg/ml to about 0.35 µg/ml of amphotericin B. In some embodiments, when the antibiotic is gentamicin-amphotericin B, the media comprises about 10 µg/ml of gentamicin and about 0.25 µg/ml of amphotericin B.

In some embodiments, the media comprises a nutrient functionalized with a chemical group that is reactive in a biorthogonal chemical reaction. In some embodiments, the nutrient functionalized with a chemical group that is reactive in a biorthogonal chemical reaction in the media is any one of the nutrients described herein. In some embodiments, the concentration of the nutrient in the media is from about 1 µM to about 1000 µM, from about 2 µM to about 900 µM, from about 3 µM to about 800 µM, from about 4 µM to about 700 µM, from about 5 µM to about 600 µM, from about 6 µM to about 500 µM, from about 7 µM to about 400 µM, from about 8 µM to about 300 µM, from about 9 µM to about 200 µM, from about 10 µM to about 100 µM, from about 20 µM to about 90 µM, from about 25 µM to about 80 µM, from about 30 µM to about 70 µM, or from about 40 µM to about 60 µM. In some embodiments, the concentration of the nutrient in the media is about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, v, about 80 µM, about 85 µM, about 90 µM or about 100 µM.

In some embodiments, the culturing media is Eagle's minimal essential medium, Glasgow's Minimal Essential Medium, Roswell Park Memorial Institute medium, Dulbecco's modified Eagle's medium (DMEM), or Dulbecco/Vogt modified Eagle's minimal essential medium. In some embodiments, the media is DMEM/F-12.

In some embodiments, the media comprises Ac4GalNAz at a concentration of about 50 μM. In some embodiments, the media comprises about 10 w/w % fetal bovine serum, Ac4GalNAz at a concentration of about 50 μM and Penicillin-Streptomycin (1:100 dilution of a stock of 10,000 units/mL of penicillin and 10,000 μg/mL of streptomycin) or Gentamicin-Amphotericin B (1:500 dilution of a stock with 5 mg/ml Gentamicin, 125 μg/ml Amphotericin B).

Figure 21:
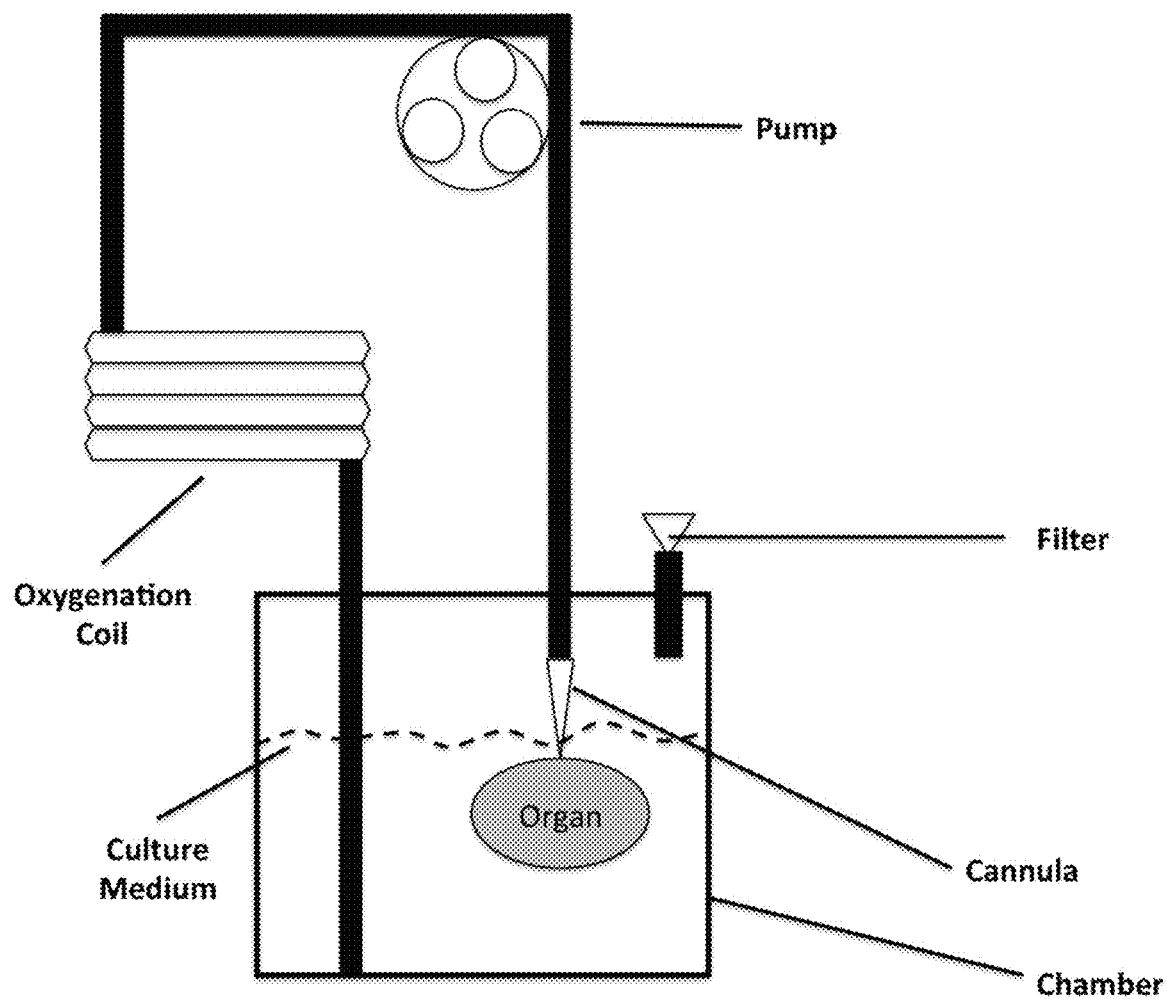
FIG. 21 is a diagram showing a bioreactor useful for culturing isolated organs.

In some embodiments, the organ or tissue is cultured in a bioreactor. In some embodiments, the bioreactor is any bioreactor known in the art to be suitable for culturing organs and tissues, or fragments thereof. In some embodiments, the bioreactor is any one of the bioreactors described, for example, in US 2016/0053213, U.S. Pat. No. 9,127,242, WO 2009/002772, US 2007/0275363, or US 2013/0177972, the disclosures of which are incorporated herein by reference in their entirety. In some embodiments, the bioreactor that may be used for organ or tissue culturing is depicted in FIG. 21. Referring to FIG. 21, the bioreactor comprises a chamber comprising a culturing media and an isolated organ or tissue in the culturing media, an oxygenation coil providing oxygen to the culturing media, a filter, a pump and a cannula for continuous supply of the culturing media to the organ or tissue. For most organs or tissues, the cannula may be connected to the main artery feeding the isolated organ or tissue. For blood vessels, such as carotid artery, the cannula is connected to one end of the blood vessel. Oxygenation coil provides efficient exchange of oxygen and carbon dioxide between the perfusate and the surrounding environment, such as the incubator. A pump allows for constant rate perfusion. In some embodiments, the culturing of the organ or tissue comprises perfusion of the organ or tissue with a media comprising a nutrient functionalized with a chemical group that is reactive in a biorthogonal chemical reaction. If necessary, the rate of perfusion can also be adjusted to perform pressure-controlled perfusion. Filter is provided for equilibrating pressure and gas content between the inside of the chamber and the surrounding environment, such as the incubator.

In some embodiments, the organ or tissue is perfused with the media at a constant perfusion rate. In some embodiments, the media perfusion rate is from about 0 mL/min to about 1000 mL/min, from about 1 mL/min to about 900 mL/min, from about 2 mL/min to about 800 mL/min, from about 3 mL/min to about 700 mL/min, from about 4 mL/min to about 600 mL/min, from about 5 mL/min to about 500 mL/min, from about 6 mL/min to about 400 mL/min, from about 7 mL/min to about 300 mL/min, from about 8 mL/min to about 200 mL/min, from about 9 mL/min to about 100 mL/min, or from about 10 mL/min to about 100 mL/min. In some embodiments, the media perfusion rate is from about 0 mL/min to about 10 mL/min, from about 0 mL/min to about 7.5 mL/min, from about 0 mL/min to about 5 mL/min, from about 0 mL/min to about 2.5 mL/min, or from about 0.1 mL/min to about 0.2 mL/min. In some embodiments, the media perfusion rate is from about 0 mL/min to about 50 mL/min, from about 0.5 mL/min to about 40 mL/min, from about 1 mL/min to about 30 mL/min, from about 2 mL/min to about 25 mL/min, from about 4 mL/min to about 20 mL/min, or from about 5 mL/min to about 15 mL/min. In some embodiments, the media perfusion rate is about 0.1 mL/min, about 0.2 mL/min, about 0.5 mL/min, about 1 mL/min, about 2 mL/min, about 5 mL/min, about 7.5 mL/min, about 10 mL/min, about 15 mL/min, or about 20 mL/min. In some embodiments, the organ is rat lung and the perfusion rate is about 5 mL/min. In some embodiments, the organ is lobe of human lung and the perfusion rate is about 10 mL/min. In some embodiments, the organ is rat epigastric flaps and the perfusion rate is about 0.2 mL/min.

In some embodiments, the organ or tissue is cultured for a time period from about 1 hour to about 10 days, from about 6 hours to about 9 days, from about 12 hours to about 8 days, from about 18 hours to about 7 days, from about 24 hours to about 6 days. From about 2 days to about 5 days, or from about 3 days to about 4 days. In some embodiments, the organ or tissue is cultured for about 1 hour, about 6 hours, about 12 hours, about 18 hours, about 24 hours, about 1 day, about 2 days, about 3 days, about 4 days, about 5 days, about 6 days, or about a week.

Organ Harvesting (Cadaveric Organs, Organs for Transplantation)

In some embodiments, the organ or tissue is a human organ or tissue. In some embodiments, the organ or tissue is a non-human organ or tissue. In some embodiments, the organ or tissue, or a portion thereof, is bovine (e.g., Bovidae family, Bovinae subfamily of the Animalia kingdom), porcine (e.g., Suidae family, Suinae subfamily of the Animalia kingdom), primate (e.g., monkey or ape), ovine (e.g., Bovidae family, Caprinae subfamily of the Animalia kingdom), murine (e.g., Muridae family, Murinae subfamily of the Animalia kingdom) or human organ or tissue. The organ or tissue may be a small animal or a large animal organ or tissue. In some embodiments, the organ or tissue is a mouse, a rat, a pig (wild or domestic), a boar, a cow, a bull, a bison, a buffalo, a rabbit, a hare, a dog, a cat, a horse, a goat (e.g., domestic goat), a sheep (e.g., domestic sheep), a gorilla, a chimpanzee, or an orangutan organ or tissue. In some embodiments, the organ or tissue is taken from a male or a female subject species. In some embodiments, the organ or tissue is taken from a growing or an aged subject.

In some embodiments, the organ or tissue is selected from the group consisting of limb (e.g., upper extremity such as an arm, or lower extremity such as a leg), bone, tongue, stomach, small intestine (e.g., duodenum, jejunum, ileum), large intestine, liver, gallbladder, pancreas, trachea, lung (e.g., right lung or left lung), bronchi, diaphragm, kidney, bladder, fallopian tubes, uterus, blood vessel, lymphatic vessel, artery (e.g., aorta, pulmonary artery, umbilical artery, brachiocephalic artery, carotid artery, subclavian artery), vein (e.g., inferior vena cava, abdominal vena cava, subclavian vein), spleen, heart, cartilage, muscle tissue (e.g., smooth muscle, cardiac muscle, skeletal muscle), cartilage, epithelium, tendon, ligament, and skin (e.g., skin flap). In some embodiments, the organ or tissue is selected from the group consisting of carotid artery, lung, heart, liver, kidney and skin.

Methods and materials to isolate donor organs (e.g., lungs) from human and animal donor subjects are known in the art. Depending on the sex, age and general health condition of the subject, possibly other therapeutic treatments, a skilled surgeon would be able to select appropriate timing, methods and/or instruments to surgically remove (e.g., harvest) an organ or tissue. For example, appropriate methods are described in Pasque M K et al. Standardizing thoracic organ procurement for transplantation. J Thorac Cardiovasc Surg. 2010 January; 139(1):13-7. and Bribriesco A C et al Experimental models of lung transplantation. Front Biosci (Elite Ed). 2013 Jan. 1; 5:266-72. Any appropriate method to isolate organs or tissues as described herein can be used.

Preparing Decellularized Tissue and Organ Scaffolds

In some embodiments, the method of functionalizing an extracellular matrix of an organ or tissue of a mammal comprises (i) administering to the mammal a nutrient that is functionalized with a chemical group that is reactive in a biorthogonal chemical reaction as described herein; and further comprises (ii) harvesting the organ or tissue as described herein; and (iii) decellularizing the organ or tissue to obtain the decellularized scaffold comprising functionalized extracellular matrix of the organ or tissue.

In some embodiments, the method of functionalizing an extracellular matrix of an organ or tissue of a mammal comprises (i) selecting the mammal for functionalizing the extracellular matrix of the organ or tissue; (ii) administering to the mammal a nutrient functionalized with a chemical group that is reactive in a biorthogonal chemical reaction as described herein; and further comprises (iii) harvesting the organ or tissue as described herein, and (iv) decellularizing the organ or tissue to obtain the decellularized scaffold comprising functionalized extracellular matrix of the organ or tissue.

In some embodiments, the method of functionalizing an extracellular matrix of an organ or tissue of a mammal comprises (i) harvesting the organ or tissue as described herein; (ii) culturing the organ or tissue using media comprising a nutrient functionalized with a chemical group that is reactive in a biorthogonal chemical reaction as described herein, and further comprises (iii) decellularizing the organ or tissue to obtain the decellularized scaffold comprising functionalized extracellular matrix of the organ or tissue.

In some embodiments, the organ or tissue may be decellularized according to using methods and materials for a preparing a decellularized organ or tissue matrix known in the art. Any appropriate materials can be used to prepare such a matrix. In some embodiments, an organ or tissue matrix can be an acellular tissue scaffold developed from decellularized organ or tissue. For example, tissue such as a human lung, e.g., one or a pair of human lungs or portions thereof, or, e.g., human, porcine, bovine, primate, or ovine cadaveric lungs or portions thereof, can be decellularized by an appropriate method to remove native cells from the tissue while maintaining morphological integrity and vasculature of the tissue or tissue portion and preserving extracellular matrix (ECM) proteins. Methods for decellularizing mammalian organs and tissues are described, e.g., in O'Neill J D et al., Decellularization of human and porcine lung tissues for pulmonary tissue engineering. *Ann Thorac Surg.* 2013 September; 96(3):1046-55; Nichols J E et al., Production and assessment of decellularized pig and human lung scaffolds, *Tissue Eng Part A.* 2013 September; 19 (17-18):2045-62; Gilpin S E et al., Perfusion decellularization of human and porcine lungs: Bringing the matrix to clinical scale. *Journal of Heart and Lung Transplantation.* In press; Song J J et al., Bioartificial lung engineering. *Am J Transplant.* 2012 February; 12(2):283-8; Guyette, J. P. et al. Perfusion decellularization of whole organs. *Nat Protoc* 9, 1451-1468 (2014), Ott H C et al., Regeneration and orthotopic transplantation of a bioartificial lung. *Nat Med.* 2010 August; 16 (8):927-33; WO 2016/036764, US 2015/0306148, WO 2014/008844, U.S. Pat. Nos. 8,470,520, 8,790,920, US 2005/0256588, U.S. Pat. No. 6,479,064, WO 2002/040630, US 2002/0115208, U.S. Pat. No. 6,753,181, US 2015/0344842, US 2015/0238656, US 2011/0045566, US 2008/0095662, and US 2007/0244568, the disclosures of the foregoing are incorporated by reference herein in their entirety. Exemplary decellularization methods can include subjecting tissue (e.g., lung tissue) to repeated freeze-thaw cycles, for example using liquid nitrogen. In other cases, a tissue can be subjected to (e.g., perfused with) an anionic or ionic cellular disruption medium such as sodium dodecyl sulfate (SDS), sodium deoxycholate (SDC), 3-((3-cholamidopropyl) dimethylammonio)-1-propanesulfonate (CHAPS), polyethylene glycol (PEG), or TritonX. The tissue can also be treated with (e.g., perfused with) a nuclease solution (e.g., ribonuclease, deoxyribonuclease), or a phospholipase solution, and washed in sterile phosphate buffered saline with mild agitation. Exemplary methods are known in the art e.g., O'Neill J D et al., Decellularization of human and porcine lung tissues for pulmonary tissue engineering. *Ann Thorac Surg.* 2013 September; 96(3):1046-55. In some cases, decellularization can be performed by flushing the vessels, ducts, and/or cavities of the organ or tissue using methods and materials known in the art. For example, as described in Maghsoudlou P et al., Preservation of microarchitecture and angiogenic potential in a pulmonary acellular matrix obtained using intermittent intra-tracheal flow of detergent enzymatic treatment. *Biomaterials.* 2013 September; 34(28):6638-48. Following the flushing step, the organ or tissue can be perfused via the line with a cellular disruption medium as described above for example 1% SDS in deionized water. Perfusion through the tissue can be anterograde or retrograde, and directionality can be alternated to improve perfusion efficiency. Depending upon the size and weight of an organ or tissue and the particular anionic or ionic detergent(s) and concentration of anionic or ionic detergent(s) in the cellular disruption medium, a tissue generally is perfused from about 2 to about 12 hours per 10 grams of tissue with cellular disruption medium. Including washes, an organ may be perfused for up to about 12 to about 72 hours per 10 grams of tissue. Perfusion generally is adjusted to physiologic conditions including flow rate and pressure, e.g., pressure between 5-100 mmHg, and flow rate between 0.1-10 times the physiologic cardiac output of the source organism or individual.

In an exemplary method, a decellularization method includes perfusing a detergent, e.g., (1) 0.1% SDS (2) 2%, sodium deoxycholate (SDC), or (3) 8 mmol/liter (3)3[(3-cholamidopropyl)dimethylammonio]-1-propanesulfonate (CHAPS) (pH 12) detergent, through the pulmonary artery at a constant pressure of 30 cm $H_2O$. The protocol for all 3 detergents includes: (1) a 10-minute initial antegrade wash with phosphate-buffered saline (PBS), (2) detergent perfusion for the time required to visualize an opaque translucent matrix (indicative of decellularization) plus an additional 20% of that initial time (e.g., 70 minutes+14 minutes), (3) 15-minute deionized $H_2O$ wash, and (4) an additional 172-hour PBS wash with added antibiotics and antimycotics. This decellularization method, e.g., can include an additional wash of 1% Triton-X following the deionized $H_2O$. The SDC protocol can include a 0.1% Triton-X perfusion before SDC and a 1 mol/liter NaCl wash after SDC.

Similarly, porcine and human organ and tissue (e.g., lung) decellularization methods can include perfusion of a detergent or other decellularization agent though the pulmonary artery at constant pressure, followed by sequential washing with $H_2O$, 1% Triton-X solution, and PBS. Similar to rat lungs, decellularization can be deemed complete upon visual inspection and the appearance of an opaque translucent matrix. Variability in the starting organ, mainly due to extensiveness of pre-flushing during harvest and any resulting clots can contribute to the required length of perfusion. In general, the time of decellularization perfusion can vary e.g., from 4 to 7 days.

Decellularized scaffold of an organ or tissue can consist essentially (e.g., at least: 85% pure, 90% pure, 92% pure, 95% pure, 96% pure, 97% pure, 98% pure, and 99% pure by weight) of the extracellular matrix (ECM) component of all or most regions of the tissue, including ECM components of the vascular tree. ECM components can include any or all of the following or any combination of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. In some embodiments, decellularized organ or tissue (e.g., lung) matrix retains an intact decellularized vasculature. Preserving a substantially intact decellularized vasculature enables connection of the tissue matrix to a subject's vascular system upon transplantation. In addition, a decellularized tissue matrix can be further treated with, for example, irradiation (e.g., UV, gamma) to reduce or eliminate the presence of any type of microorganism remaining on or in a decellularized tissue matrix.

Methods for obtaining decellularized tissue matrices using physical, chemical, and enzymatic means are known in the art, see, e.g., Liao et al, *Biomaterials* 29(8):1065-74 (2008); Gilbert et al., *Biomaterials* 27(9):3675-83 (2006); Teebken et al., *Eur J. Vasc. Endovasc. Surg.* 19:381-86 (2000). See also U.S. Pat. Publication Nos. 2009/0142836; 2005/0256588; 2007/0244568; and 2003/0087428.

Bioactive Molecules for Molecular Enhancement of Organs and Tissues and the Decellularized Tissue/Organ Scaffolds In some embodiments, the biologically active molecule is selected from the group consisting of therapeutic biomolecules (e.g., polypeptides, proteins, lipoproteins, glycoproteins, polysaccharides (e.g., oligosaccharides), polynucleotides and nucleic acids, or analogs or derivatives of such molecules), therapeutic proteins (e.g., antibodies, hormones, transmembrane proteins, growth factors, enzymes, or structural proteins), or therapeutic small-molecules.

In some embodiments, the biologically active molecule is useful in treating or preventing a bacterial infection. In some embodiments, the biologically active molecule is useful in treating or preventing an inflammatory disease or condition. In some embodiments, the biologically active molecule is useful in treating or preventing an organ transplant rejection (e.g., treating acute kidney transplant rejection). In some embodiments, the biologically active molecule is useful in preventing a condition selected from ischemia and reperfusion injury after organ transplantation.

In some embodiments, the biologically active molecule is a small-molecule drug. Small molecule drugs are low molecular weight organic compounds (typically about 2000 daltons or less).

In some embodiments, the small-molecule drug is a quinolone antibiotic (e.g., levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, ruflaxocin, temafloxacin, tosufloxacin, trovafloxacin, or besifloxacin).

In some embodiments, the small-molecule drug is a β-lactam antibiotic (e.g., penicillin or cephalosporin class antibiotic).

In some embodiments, the small-molecule drug is a penicillin antibiotic (e.g., penicillin G, penicillin V, procaine penicillin, and benzathine penicillin, ampicillin, and amoxicillin, benzylpenicillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, or pivampicillin).

In some embodiments, the small-molecule drug is a cephalosporin antibiotic (e.g., of cefazolin, cefuroxime, ceftazidime, cephalexin, cephaloridine, cefamandole, cefsulodin, cefonicid, cefoperazine, cefoprozil, or ceftriaxone).

In some embodiments, the small-molecule drug is a carbapenem antibiotic (e.g., thienamycin, tomopenem, lenapenem, tebipenem, razupenem, imipenem, meropenem, ertapenem, doripenem, panipenem (betamipron), or biapenem).

In some embodiments, the small-molecule drug is a lipopeptide antibiotic (e.g., polymyxin B, colistin (polymyxin E), or daptomycin).

In some embodiments, the small-molecule drug is a glycopeptide antibiotic (e.g., vancomycin, teicoplanin, telavancin, ramoplanin, daptomycin, decaplanin, or bleomycin).

In some embodiments, the biologically active molecule is vancomycin. Vancomycin (CAS Registry No. 1404-90-6) is a compound of formula:

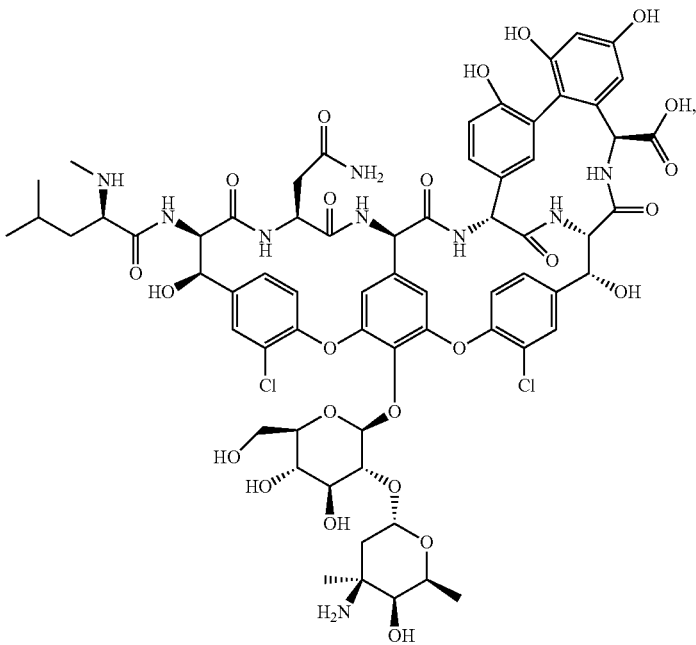 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O)c3ccc(c(Cl)c3)Oc3cc2cc(c3O[C@@H]2O[C@H](CO)[C@@H](O)[C@H](O)[C@H]2O[C@H]2C[C@](C)(N)[C@H](O)[C@H](C)O2)Oc2ccc(cc2Cl)[C@H]1O]

or a pharmaceutically acceptable salt thereof.

In some embodiments, the small-molecule drug is a macrolide antibiotic (e.g., azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin or cineromycin B)

In some embodiments, the small-molecule drug is an ansamycin antibiotic (e.g., streptovaricin, geldanamycin, herbimycin, rifamycin, rifampin, rifabutin, rifapentine or rifamixin).

In some embodiments, the small-molecule drug is a sulfonamide antibiotic (e.g., sulfanilamide, sulfacetarnide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole or phthalyl sulfathiazole).

In some embodiments, an antibiotic is useful in treating an infection caused by *Staphylococcus* spp., especially *Staphylococcus aureus* and methicillin-resistant *Staphylococcus aureus* (MRSA), *Streptococcus* spp. (including group *B Streptococci*), *E.* spp., *K. pneumoniae*, *P aeruginosa*, *A. baumannii*, *E. faecium*, *E. faecalis*, *B. subtilis*, or *B. anthracis*.

In some embodiments, an antibiotic is useful in treating an infection caused by *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis,* or *Staphylococcus saprophyticus.*

In some embodiments, the small-molecule drug is an inhibitor of coagulation cascade (e.g., anticoagulant), such as heparin, aspirin, clopidogrel, ticlopidine, cilostazol, dipyridamole, pentoxifylline, abciximab, eptifibatide, tirofiban, fondaparinux, idraparinux, rivoroxaban, hirudin, lepirudin, bivalirudin, argatroban, avoralstat or dagitran. In some embodiments, anticoagulant is a vitamin K antagonist (e.g., coumarin, warfarin, acenocoumarol, phenprocoumon, atromentin, or phenindione). In some embodiments, anticoagulant is a low-molecular-weight derivative of heparin (e.g., enoxaparin, dalteparin or tinzaparin)

In some embodiments, the small-molecule drug is an antifibrinolytic agent (e.g., aminocaproic acid, tranexamic acid, bisobrin, aprotinin, amicar, cyklokapron, trasylol).

In some embodiments, the small-molecule drug is an anti-inflammatory agent (e.g., acetaminophen, aspirin, codeine, fentanyl, ibuprofen, indomethacin, ketodolac, morphine, naproxen, phenacetin, piroxicam, a steroidal analgesic, sufentanyl, sunlindac or tenidap)

In some embodiments, the biologically active molecule is a growth factor, for example, adrenomedullin, angiopoietin, autocrine motility factor, bone morphogenetic proteins (BMPs), brain-derived neurotrophic factor (BDNF), epidermal growth factor (EGF), erythropoietin (EPO), fibroblast growth factor (FGF), foetal bovine somatotrophin (FBS), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), nerve growth factor (NGF), platelet-derived growth factor (PDGF) (e.g., "healing factor"), thrombopoietin (TPO), T-cell growth factor (TCGF), transforming growth factor alpha (TGF-α), tumor necrosis factor-alpha (TNF-α), vascular endothelial growth factor (VEGF), or placental growth factor (PGF).

In some embodiments, the biologically active molecule is a cytokine, such as transforming growth factor-beta (TGF-beta), interferons (e.g., interferon-alpha, interferon-beta, interferon-gamma), colony stimulating factors (e.g., granulocyte colony stimulating factor (GM-CSF)), and thymic stromal lymphopoietin (TSLP). In some embodiments, the interferon is interferon-αcon1, interferon-alpha2a, interferon-α2b, interferon-αn3, interferon-β1a, or interferon-γ1b. In some embodiments, the cytokine is an interleukin, such as interleukin-1, interleukin-2, interleukin-3, interleukin-4, interleukin-5, interleukin-6, interleukin-7, or interleukin-8.

In some embodiments, the biologically active molecule is an immunosuppressive drug (e.g., fingolimod, cytokines, interferons and the like). In some embodiments, the immunisupressive drug may be used to prevent rejection of transplanted organs and tissues.

In some embodiments, the biologically active molecule is an antithrombolytic agent (e.g., tissue plasminogen activator, streptokinase, alteplase, reteplase, tenecteplase, anistreplase or urokinase, and functional derivatives thereof).

In some embodiments, the biologically active molecule is an antibody. In some embodiments, the antibody is specific against tumor necrosis factor-alpha (TNF-α) (e.g., adalimumab). In some embodiments, the antibody specific against tumor necrosis factor-alpha (TNF-α) is any one of TNF-α antibodies described in US 2004/0260069 or U.S. Pat. No. 7,227,003, the disclosures of which is incorporated herein by reference in their entirety. In some embodiments, the biologically active molecule is an antibody that is useful in treating or preventing an inflammatory disease or condition (e.g., adalimumab, alemtuzumab, atlizumab, basiliximab, canakinumab, certolizumab, certolizumab pegol, daclizumab, muromonab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, or briakinumab).

In some embodiments, the biologically active molecule is albumin, human albumin, or immunoglobulin. In some embodiments, the biologically active molecule is factor VIIa, factor VIII, factor IX, antithrombin III, protein C, drotrecogin-α, filgrastim, pegfilgrastim, sargramostim, or oprelvekin.

In some embodiments, any one of the biologically active molecules described herein comprises at least one reactive functional group. In some aspects of these embodiments, the functional group is hydroxyl group (—OH), keto group (—C(=O)—), aldehyde group (—C(=O)H), amino group (—NH$_2$), thiol group (—SH) (e.g., a cysteine residue), carboxylic acid (—C(=O)OH), a carboxylic ester group (—C(=O)O—C$_{1-3}$ alkyl), a sulfonic acid group (—S(=O)$_2$OH), or a phosphonate group (—P(=O)(OH)$_2$). These functional groups may be used, for example, for conjugating the biologically active molecule with a suitable reagent comprising a functional group that is reactive in a bioorthogonal chemical reaction as described herein.

Functionalization of Biomolecules with a Functional Group that is Reactive in a Bioorthogonal Chemical Reaction.

In some embodiments, any one of the biomolecules described herein may be functionalized with a chemical group that is reactive in a bioorthogonal chemical reaction using a reagent comprising a chemical group that is reactive in a bioorthogonal chemical reaction. In some embodiments, the reactive chemical group is complementary to the reactive chemical group of the functionalized nutrient (e.g., any one of the functionalized nutrients described herein). In some embodiments, when the reactive chemical group of the functionalized nutrient is an azide, the biologically active molecule may be functionalized with an alkyne (e.g., aliphatic alkyne or cycloalkyne) reactive group. In some embodiments, when the reactive chemical group of the functionalized nutrient is an alkyne (e.g., aliphatic alkyne or cycloalkyne), the biologically active molecule may be functionalized with an azide reactive group. In some embodiments, the nutrient is Ac4GalNAz and the biologically active molecule may be functionalized with an alkyne (e.g., aliphatic alkyne or cycloalkyne) reactive chemical group as described herein.

In some embodiments, the chemical group is any one of chemical groups that is reactive in Huisgen cycloaddition (also known as [3+2] cycloaddition of alkynes and azides to form triazoles, or "click" reaction). In some embodiments, the chemical group is any one of chemical groups that is reactive in Staudinger ligation (i.e., a reaction between an azide and a phosphine), a reaction of oxanorbornadienes and azides to from triazoles, an inverse-demand Diels-Alder reaction of tetrazines (e.g., dipyridyl tetrazines) and trans-cyclooctynes, inverse-demand Diels-Alder reaction of tetrazines (e.g., monoaryl tetrazines) and norbornenes, a reaction of tetrazines and cyclopropenes, a reaction of cyclopropenes and nitrile imines, a photoinduced 1,3-dipolar cycloaddition of tetrazoles and alkenes, a 1,3-dipolar cycloaddition of nitrile oxides and norbornenes, a [4+1] cycloaddition isocyanides and tetrazines or a 1,3-cycloaddition of nitrones and alkynes.

In some embodiments, the chemical group that is reactive in a biorthogonal chemical reaction is an azide (—N$_3$), an aliphatic alkyne (e.g., —C≡CH), a cyclooctyne, a cyclooctene, a nitrone, an isocyanide, a cyclopropene, a norborene, a diphenylphosphine, nitrile imine, a tetrazole, a nitrile oxide, or a tetrazine. In some embodiments, the chemical group that is reactive in a biorthogonal chemical reaction is an azide (—N$_3$) or an alkyne. In some embodiments, the chemical group that is reactive in a biorthogonal chemical reaction is an azide (—N$_3$). In some embodiments, the chemical group that is reactive in a biorthogonal chemical reaction is an alkyne.

In some embodiments, a reagent comprising a chemical group that is reactive in a bioorthogonal chemical reaction is a compound of Formula (I):

F-L-B (I), wherein F is the reactive chemical group selected from N$_3$, —C≡CH, —CH$_2$—C≡CH, —O—NH$_2$, cyclooctyne, cyclooctene, nitrone, an isocyanide, a cyclopropene, a norborene, a diphenylphosphine, nitrile, imine, a tetrazole, a nitrile oxide, and a tetrazine.

In some embodiments, a reagent comprising an alkyne functionality is a compound of Formula (Ia):

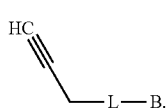 (Ia)

In some embodiments, a reagent comprising an azide functionality is a compound of Formula (Ib):

 (Ib).

In some embodiments of any one of Formulae disclosed herein:

L is absent or

L is a linker selected from $C_{1-20}$ alkylene and any one of the following Formulae:

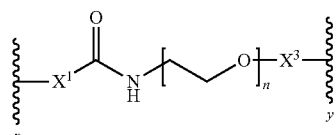

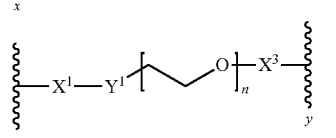

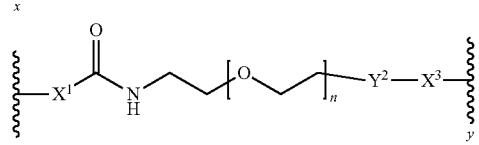

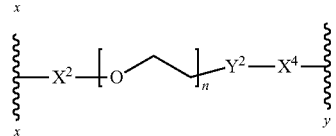

$X^1$ is absent or $X^1$ is $C_{1-6}$ alkylene;
$X^2$ is absent or $X^2$ is $C_{1-6}$ alkylene;
$X^3$ is $C_{1-6}$ alkylene;
$X^4$ is absent or $X^4$ is $C_{1-6}$ alkylene;
$Y^1$ is absent or selected from —O— and —NH—;
$Y^2$ is absent or selected from —O— and —NH—;
n is an integer independently selected from 1, 2, 3, 4, 5, 6, 7, 8, 9 and 10;
x indicates a point of attachment to alkyne functionality and y indicates point of attachment to B;
B is a functional group independently selected from halogen, —OH, —O—NH$_2$, —NH$_2$, —SH, —C(=O)OH, —C(=O)H, —O—C$_{1-3}$ alkyl, a group of Formula:

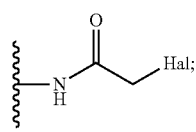

an activated phenol ester of any one of the following Formulae:

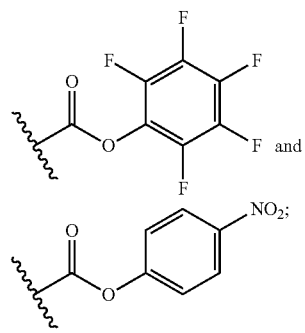

a NHS ester of the following Formula:

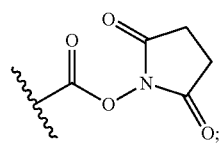

and a maleimide of any one of the following Formulae:

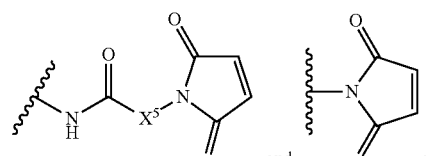

Hal is a halogen selected from I, Br and Cl; and
$X^5$ is $C_{1-6}$ alkylene;

In some embodiments, halogen is I, Br or Cl. In some aspects of these embodiments, halogen is I.

In some embodiments, B is a functional group of Formula:

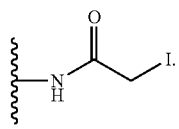 [SMILES: *NC(=O)CI]

In some embodiments, B is a functional group of Formula:

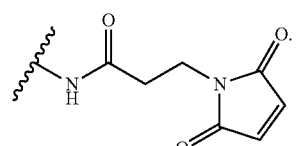

In some embodiments, $X^1$ is absent. In some embodiments, $X^1$ is methylene, ethylene, propylene, butelene, or hexylene. In some embodiments, $X^1$ is ethylene.

In some embodiments, $X^2$ is absent. In some embodiments, $X^2$ is methylene, ethylene, propylene, butelene, or hexylene. In some embodiments, $X^2$ is methylene.

In some embodiments, $X^3$ is methylene, ethylene, propylene, butelene, or hexylene. In some embodiments, $X^3$ is ethylene.

In some embodiments, $X^4$ is absent. In some embodiments, $X^4$ is methylene, ethylene, propylene, butelene, or hexylene. In some embodiments, $X^4$ is ethylene.

In some embodiments, $Y^1$ is absent. In some embodiments, $Y^1$ is —O—. In some embodiments, $Y^1$ is —NH—. In some embodiments, $Y^2$ is absent. In some embodiments, $Y^2$ is —O—. In other embodiments, $Y^2$ is —NH—.

In some embodiments, $X^5$ is methylene, ethylene, propylene, butelene, or hexylene. In some embodiments, $X^5$ is ethylene. In some embodiments, $X^5$ is propylene.

In some embodiments, n is 1. In some embodiments, n is 3. In some embodiments, n is 6. In some embodiments, n is 10.

In some embodiments, the compound of Formula (I) is selected from any one of the following compounds:

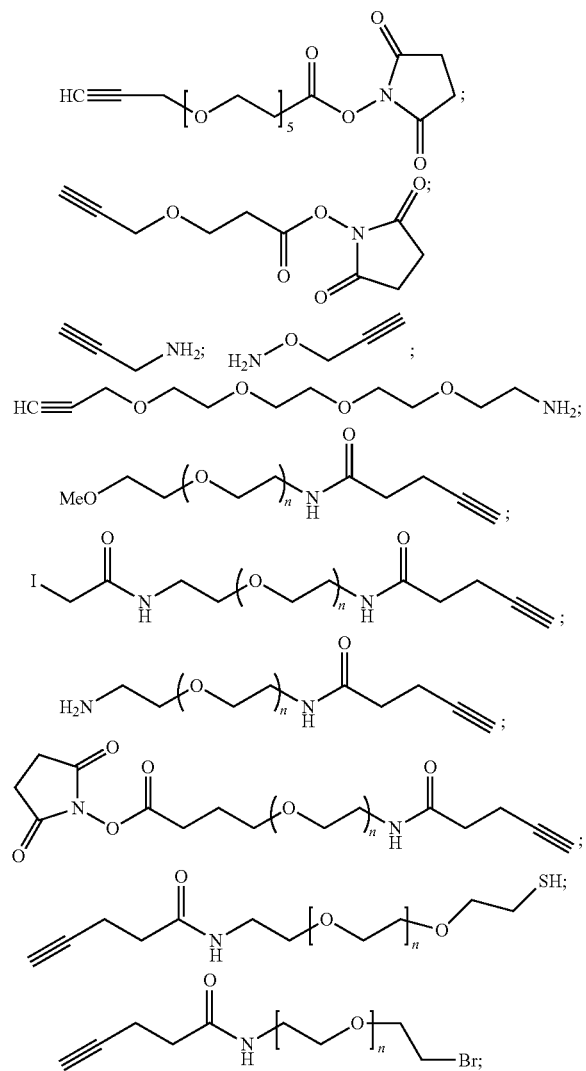

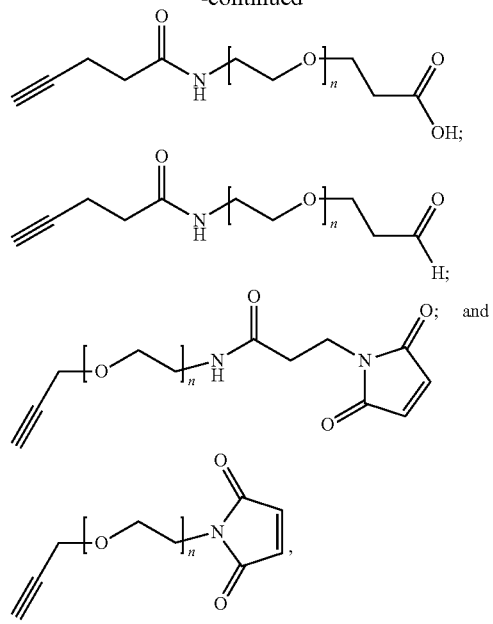

wherein n is as described herein.

In some embodiments, reagent comprising an alkyne functionality is alkyne-$PEG_5$-N-hydroxysuccinimidyl ester. In some embodiments, reagent comprising an alkyne functionality is amino-PEG4-alkyne. In some embodiments, reagent comprising an alkyne functionality is selected from any one of the following reagents:

HC≡C—$CH_2$-$PEG_n$-$NH_2$;

HC≡C—$CH_2$-$PEG_n$-$CH_2CH_2$COONHS Ester;

HC≡C—$CH_2$-$PEG_n$-OH;

HC≡C—$CH_2$-$PEG_n$-$CH_2CH_2$COOH;

HC≡C—$CH_2$-$PEG_n$-SH.

In some embodiments, reagent comprising an azide functionality is selected from any one of the following reagents:

$N_3$-$PEG_n$-$NH_2$;

$N_3$-$PEG_n$-$CH_2CH_2$COONHS Ester;

$N_3$-$PEG_n$-OH;

$N_3$-$PEG_n$-$CH_2CH_2$COOH;

$N_3$-$PEG_n$-SH.

In some embodiments, a reagent comprising an alkyne functionality is a compound of Formula (II):

$$A\text{-}L\text{-}B \qquad (II),$$

wherein:

A is a cyclooctyne-containing moiety of any one of the following Formulae:

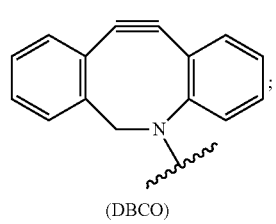

(DBCO)

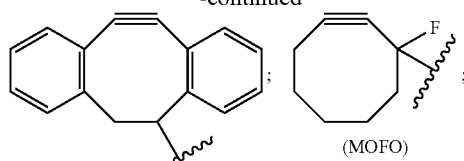
(MOFO)
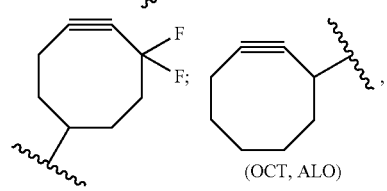
(DIFO)    (OCT, ALO)
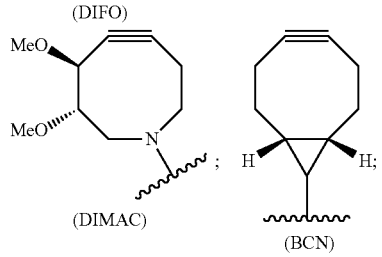
(DIMAC)    (BCN)
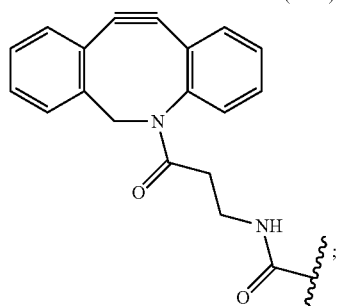
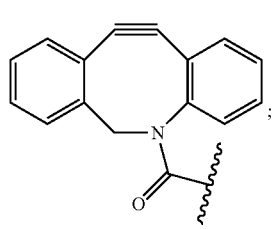
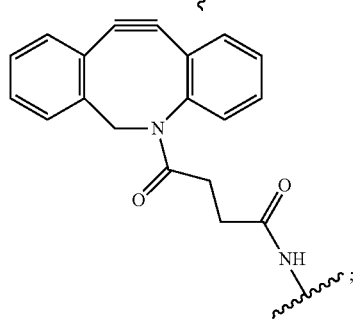
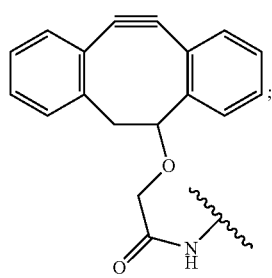
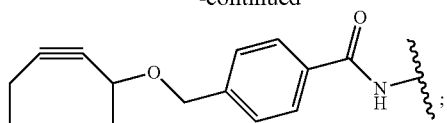
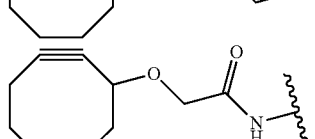
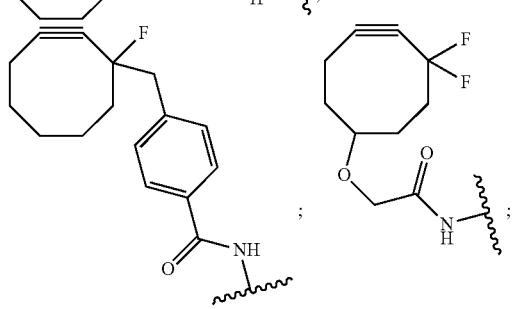
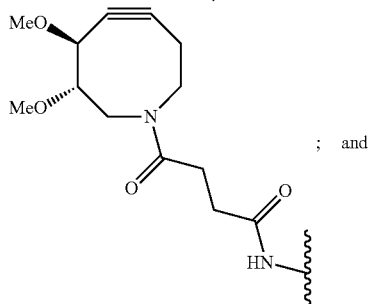
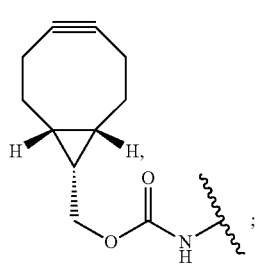
; and
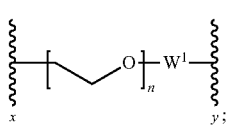
L is absent or a linker selected from $C_{1-20}$ alkylene and any one of the following Formulae:
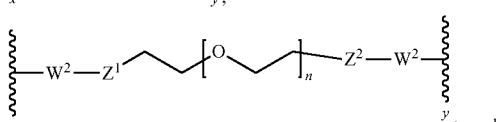
; and
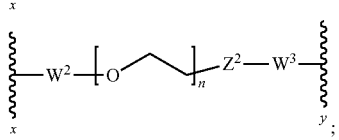
$W^1$ is absent or $C_{1-6}$ alkylene;
$W^2$ is $C_{1-6}$ alkylene;

$Z^1$ is selected from —O—, —NH—, —(C=O)—, and —C(=O)NH—;

$Z^2$ is selected from —O—, —NH—, —(C=O)—, and —C(=O)NH—;

$W^3$ is $C_{1-6}$ alkylene;

n is an integer independently selected from 1, 2, 3, 4, 5, 6, 7, 8, 9 and 10;

x indicates a point of attachment to the cycloalkyne and y indicates point of attachment to B;

B is a functional group independently selected from halogen, —OH, —O—NH$_2$, —NH$_2$, —SH, —C(=O)OH, —C(=O)H, —O—C$_{1-3}$ alkyl, a group of Formula:

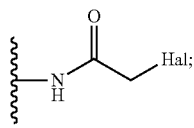

an activated phenol ester of any one of the following Formulae:

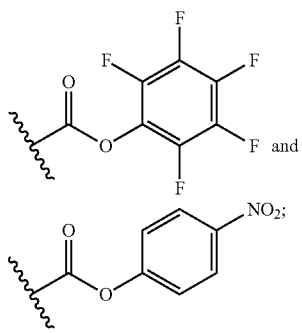

a NHS ester of any one of the following Formulae:

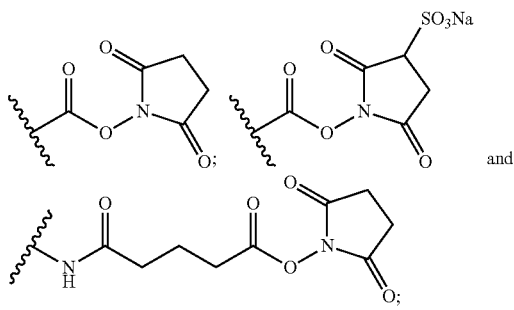

and a maleimide of any one of the following Formulae:

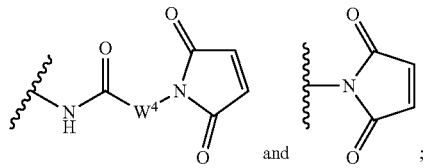

Hal is a halogen selected from I, Br and Cl; and $W^4$ is $C_{1-6}$ alkylene;

In some embodiments, halogen is I, Br or Cl. In some aspects of these embodiments, halogen is I.

In some embodiments, B is a functional group of Formula:

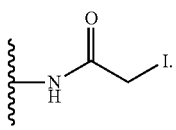

In some embodiments, B is a functional group of Formula:

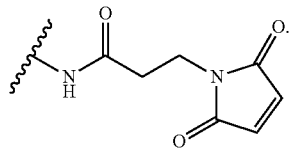 [SMILES: *NC(=O)CCN1C(=O)C=CC1=O]

In some embodiments, $W^1$ is methylene, ethylene, propylene, butelene, or hexylene. In some embodiments, $W^1$ is ethylene.

In some embodiments, $W^2$ is methylene, ethylene, propylene, butelene, or hexylene. In some embodiments, $W^2$ is ethylene.

In some embodiments, $Z^1$ is —O—. In some embodiments, $Z^1$ is —NH—. In some embodiments, $Z^1$ is —C(=O)NH—.

In some embodiments, $Z^2$ is —O—. In some embodiments, $Z^2$ is —NH—.

In some embodiments, $W^3$ is methylene, ethylene, propylene, butelene, or hexylene. In some embodiments, $W^3$ is ethylene.

In some embodiments, $W^4$ is methylene, ethylene, propylene, butelene, or hexylene. In some embodiments, $W^4$ is ethylene.

In some embodiments, n is 1. In some embodiments, n is 3. In some embodiments, n is 6. In some embodiments, n is 10.

In some embodiments, the compound of Formula (II) is selected from any one of the following compounds:

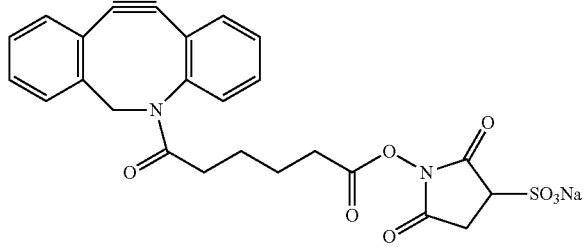

-continued
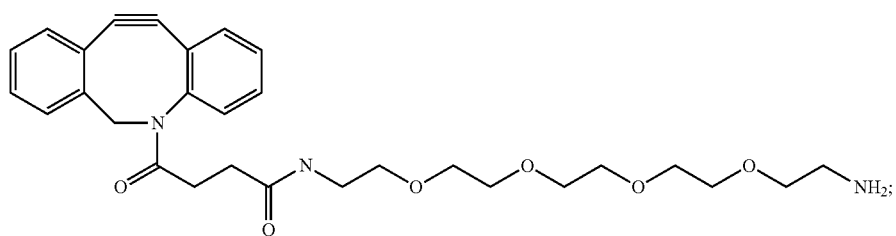
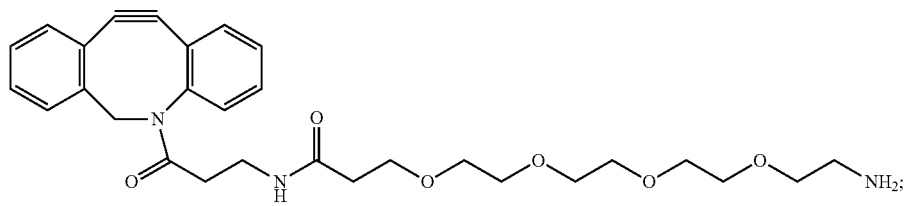
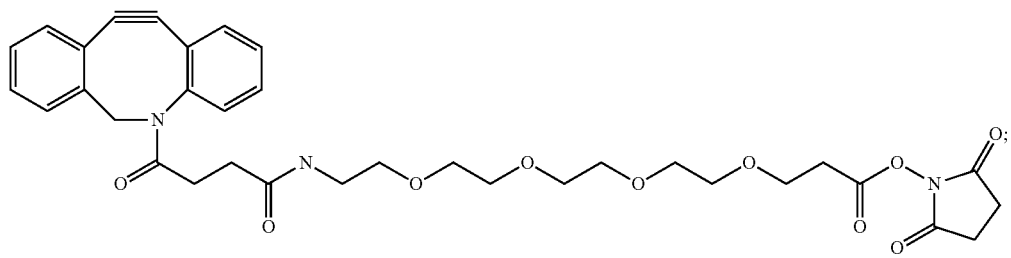
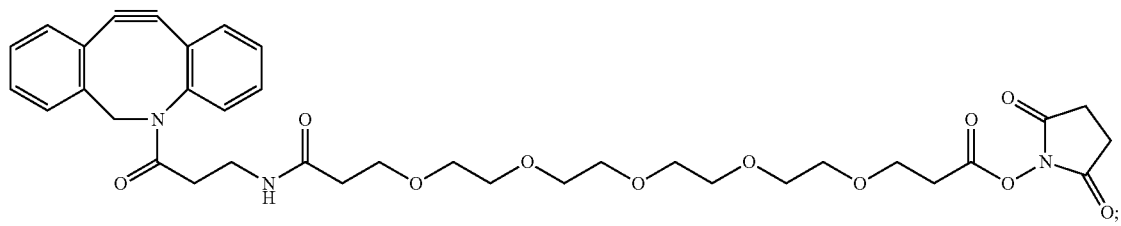
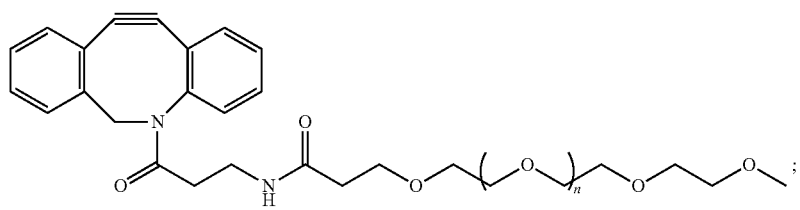
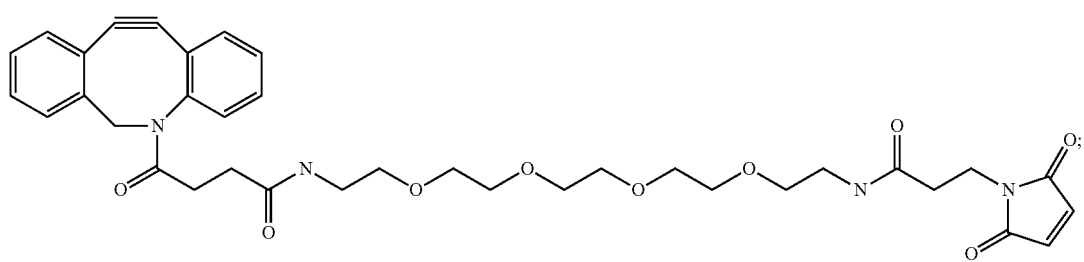

-continued

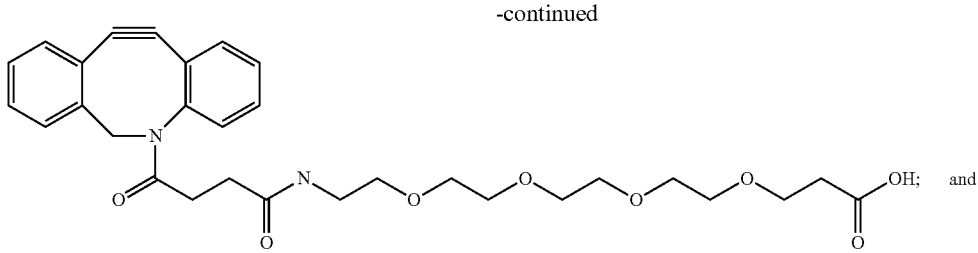

and

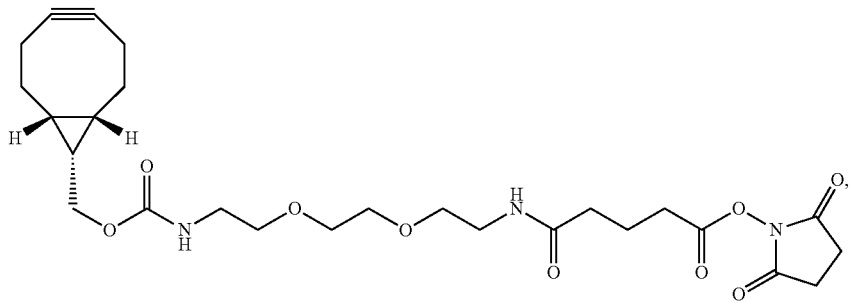

wherein n is as described herein.

In some embodiments, reagent comprising a cycloalkyne functionality is DBCO-PEG$_5$-NHS ester. In some embodiments, reagent comprising a cycloalkyne functionality is DBCO-PEG$_4$-amine.

In some embodiments, the reagent comprising a NHS ester functional group is useful for conjugating the alkyne or cyclooctyne reactive chemical group to a biologically active molecule comprising a primary amine group.

In some embodiments, the reagent comprising an amine functional group is useful for conjugating the alkyne or cyclooctyne reactive chemical group to a biologically active molecule comprising a keto group (—C(=O)—), an aldehyde group (—C(=O)H), a carboxylic acid group (—C(=O)OH), a sulfonic acid group (—S(=O)$_2$OH), or a phosphonate group (—P(=O)(OH)$_2$).

In some embodiments, the reagent comprising a maleimide functional group is useful for conjugating the alkyne or cyclooctyne functionality to a biologically active molecule comprising a thiol group (e.g., cysteine residue).

The reagents of Formulae (I), (Ia), (Ib) and Formula (II) can be conjugated to any one of biologically active molecules described herein according to any of numerous possible synthetic routes. The person skilled in the art knows how to select and implement appropriate synthetic routes. Suitable synthetic methods of starting materials, intermediates and products may be identified by reference to the literature, including reference sources such as: Carreira, et al. (Ed.) *Science of Synthesis*, Vols. 1-48 (2001-2010); Katritzky, et al. (Ed.) *Comprehensive Organic Functional Group Transformations*, (Pergamon Press, 1996); Katritzky et al. (Ed.); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006).

In some embodiments, growth factors, such as basic fibroblast growth factor (bFGF) and vascular endothelial growth factor (VEGF), can be conjugated with alkyne or cycloalkyne (e.g., DBCO) functionality by using the alkyne or cycloalkyne-containing reagent comprising a N-hydroxysuccinimidyl ester (NHS ester). A PEG linker of various lengths or an alkylene linker, or both, can be introduced between alkyne or cycloalkyne functionality of the reagent and the NHS ester (e.g., as described for compounds of Formula (I) and Formula (II)). This approach is applicable to many other growth factors and other proteins that contain primary amines.

In some embodiments, antibodies can be conjugated with alkyne or cycloalkyne (e.g., DBCO) functionality by using the alkyne or cycloalkyne-containing reagent comprising maleimide. A PEG linker of various lengths or an alkylene linker, or both, can be introduced between alkyne or cycloalkyne functionality of the reagent and the NHS ester (e.g., as described for compounds of Formula (I) and Formula (II)). This approach is applicable to antibodies and other proteins that cysteine residues.

In some embodiments, antibiotics, such as vancomycin, may be conjugated with azide, aliphatic alkyne or cycloalkyne (e.g., DBCO) functionality by using the azide, aliphatic alkyne or cycloalkyne-containing reagent comprising NHS ester. Vancomycin has only one free primary amine, and can be conjugated with alkyne by reacting with alkyne-conjugated NHS ester or conjugated with DBCO by reacting with DBCO-conjugated NHS ester. A PEG linker of various lengths or an alkylene linker, or both, may be introduced between alkyne or cycloalkyne functionality of the reagent and the NHS ester (e.g., as described for compounds of Formulae (I), (Ia), (Ib) and Formula (II)).

In some embodiments, the biologically active molecule functionalized with a chemical group reactive in a bioorthogonal chemical reaction is vancomycin-azide.

In some embodiments, the biologically active molecule functionalized with a chemical group reactive in a bioorthogonal chemical reaction is vancomycin-alkyne of the following formula:

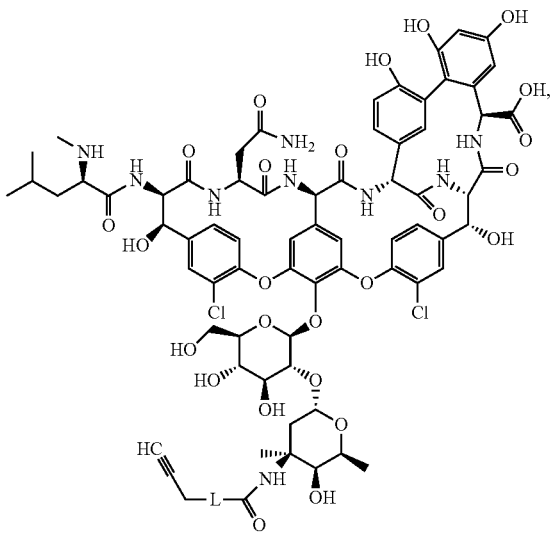

wherein L is as described herein for Formula (Ia).

In some embodiments, the biologically active molecule functionalized with a chemical group reactive in a bioorthogonal chemical reaction is vancomycin-cyclooctyne of the following formula:

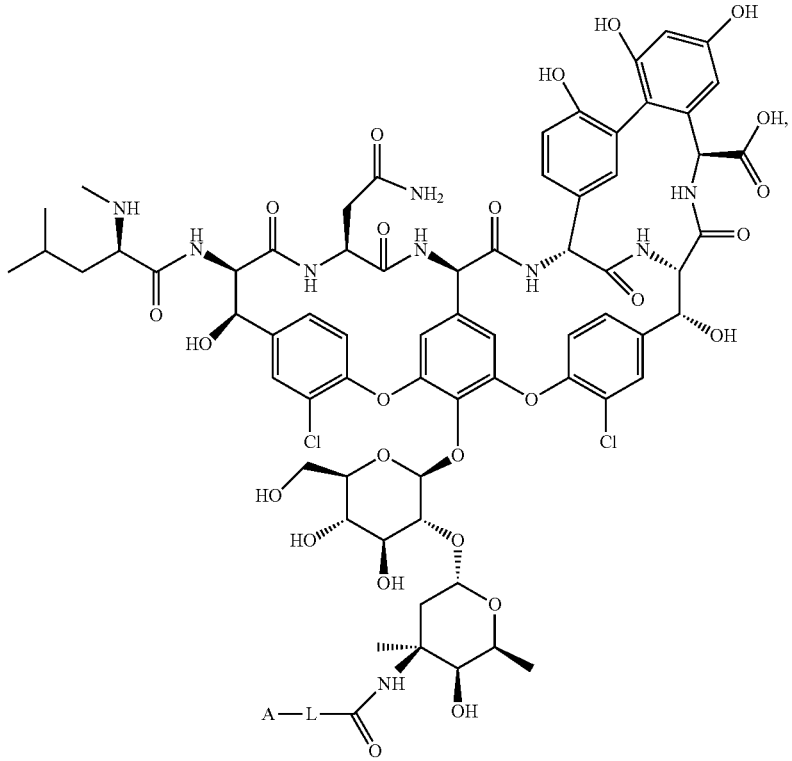

wherein A and L are as described herein for Formula (II).

In some embodiments, the biologically active molecule functionalized with a chemical group reactive in a bioorthogonal chemical reaction is vancomycin-DBCO.

In some embodiments, the biologically active molecule functionalized with a chemical group reactive in a bioorthogonal chemical reaction is vancomycin-alkyne of the following formula:

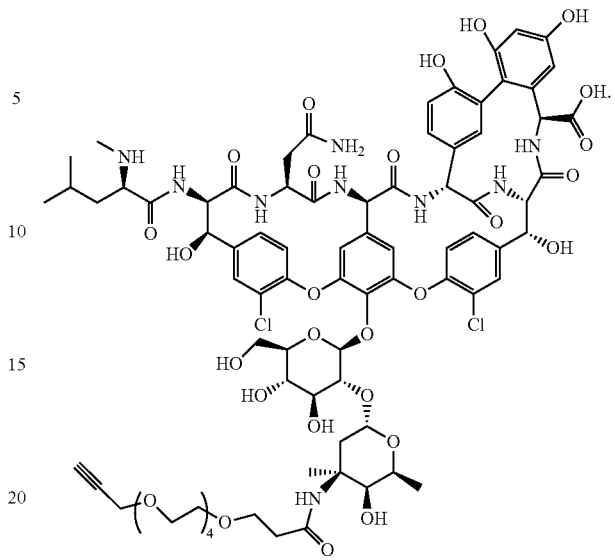

In some embodiments, vancomycin-DBCO has the following formula:

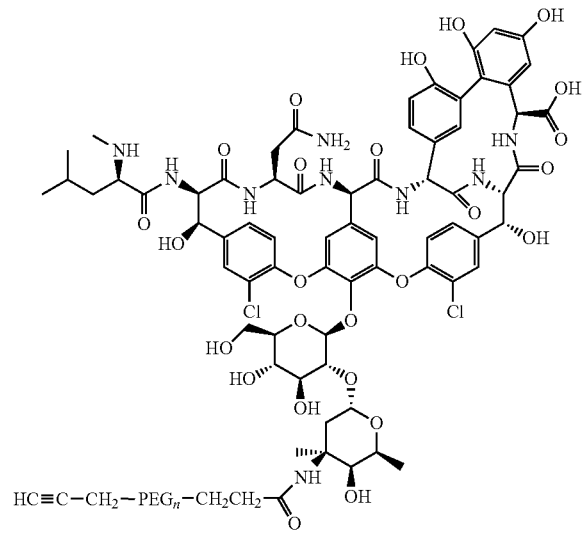

In some embodiments, vancomycin-alkyne or vancomycin-cyclooctyne (e.g., vancomycin-DBCO) may be prepared by reacting a compound of Formula (Ia) or a compound of Formula II with the vancomycin. The reacting may be carried out according to any synthetic method known in the art. For example, vancomycin at a concentration of about 1 mM in a buffer such as Dulbecco's phosphate-buffered saline (DPBS) may be reacted with a reagent of any one of the Formulae as described herein (e.g., alkyne-PEG$_5$-N-hydroxysuccinimidyl ester) for about 24 hours at about room temperature. One of ordinary skill in the art will readily select and implement appropriate synthetic methods.

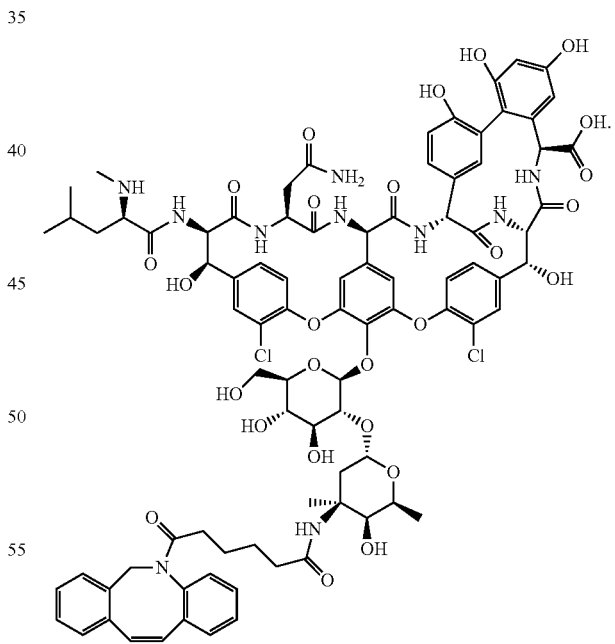

In some embodiments, the vancomycin-alkyne has the following formula:

In some embodiments, vancomycin-DBCO has the following formula:

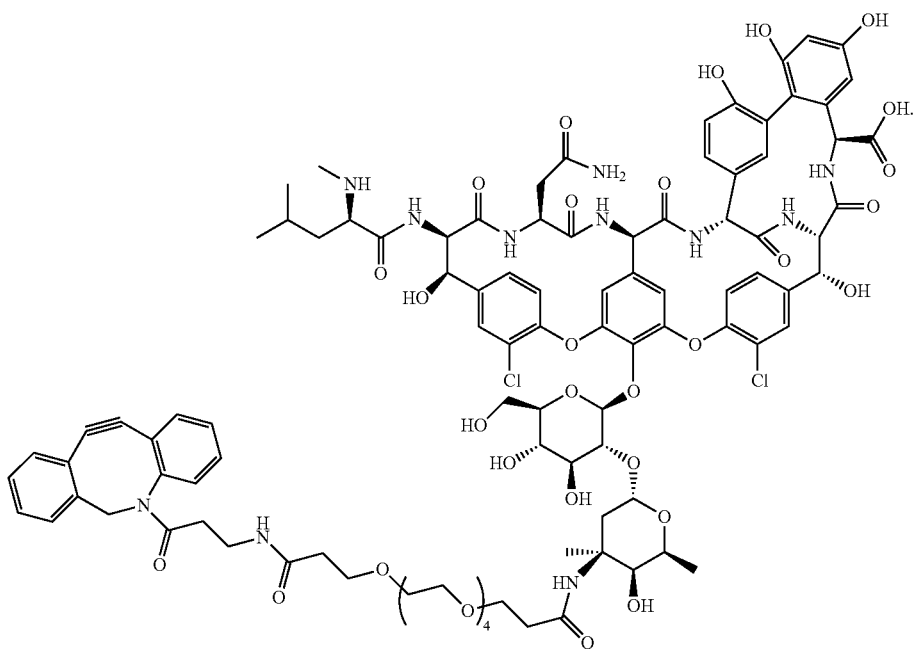

In some embodiments, anticoagulants, such as heparin, may be conjugated with alkyne or cycloalkyne (e.g., DBCO) by partial activation of free carboxyl groups in heparin using 1-ethyl-3-(3-dimethylaminopropyl)carbodiimide (EDC) and N-hydroxysuccinimide (NHS), followed by reaction with alkyne or cycloalkyne-containing reagent comprising an amino functional groups. A PEG linker of various lengths or an alkylene linker, or both, may be introduced between alkyne or cycloalkyne functionality of the reagent and the NHS ester (e.g., as described for compounds of Formula (I), (Ia) and Formula (II)). In other embodiments, the free aldehyde group in deaminated heparin (e.g., heparin deaminated under nitrous acid treatment conditions) can be conjugated with aminooxy alkyne with, e.g., aniline as the catalyst.

In some embodiments, the biologically active molecule functionalized with a chemical group reactive in a bioorthogonal chemical reaction is heparin-azide.

In some embodiments, the biologically active molecule functionalized with a chemical group reactive in a bioorthogonal chemical reaction is heparin-alkyne of any of the following formulae:

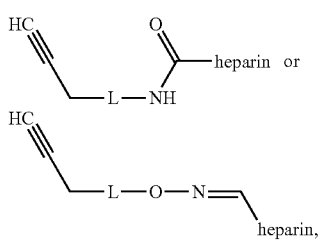

wherein L is as described herein for Formula (Ia).

In some embodiments, the biologically active molecule functionalized with a chemical group reactive in a bioorthogonal chemical reaction is heparin-alkyne-biotin (HeparinAB) of any of the following formulae:

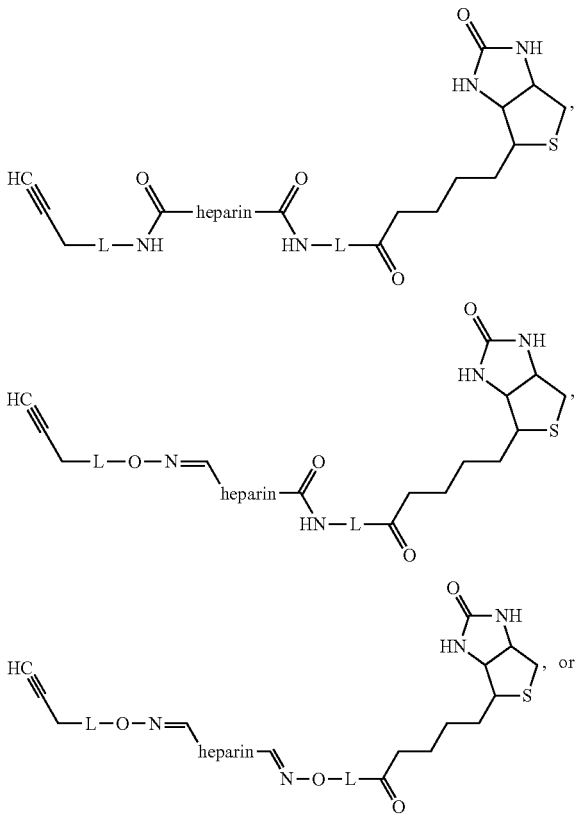

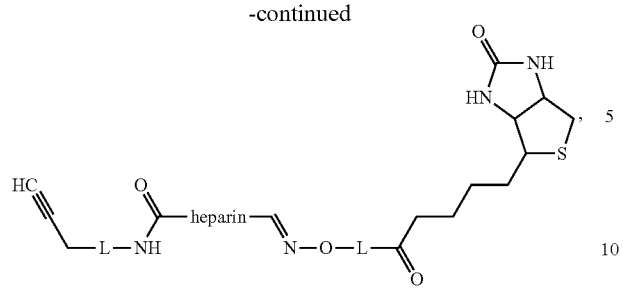

wherein each L is as described herein for Formula (Ia).

In some embodiments, the biologically active molecule functionalized with a chemical group reactive in a bioorthogonal chemical reaction is heparin-alkyne of any one the following formulae:

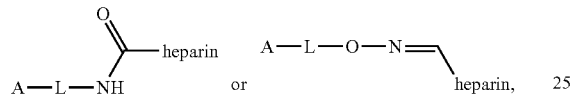

wherein A and L are as described herein for Formula (II).

In some embodiments, the biologically active molecule functionalized with a chemical group reactive in a bioorthogonal chemical reaction is heparin-alkyne-biotin (HeparinAB) of any of the following formulae:

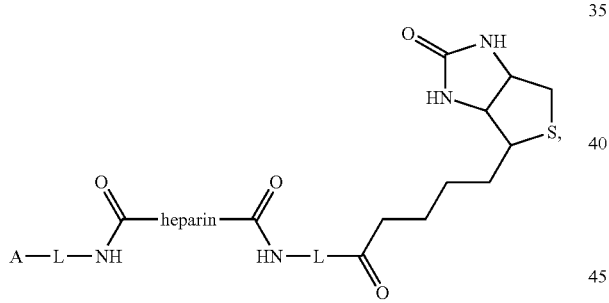

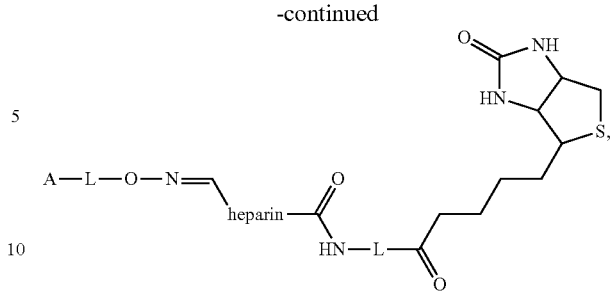

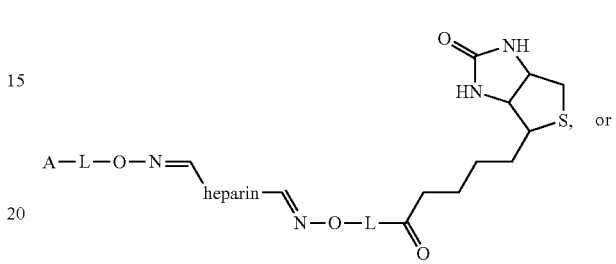

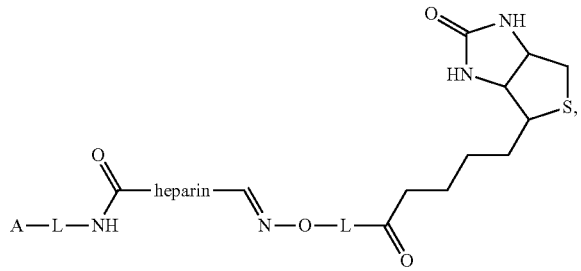

wherein each A and each L are as described herein for Formula (II).

In some embodiments, the biologically active molecule functionalized with a chemical group reactive in a bioorthogonal chemical reaction is heparin-alkyne-biotin (HeparinAB) of the following formula:

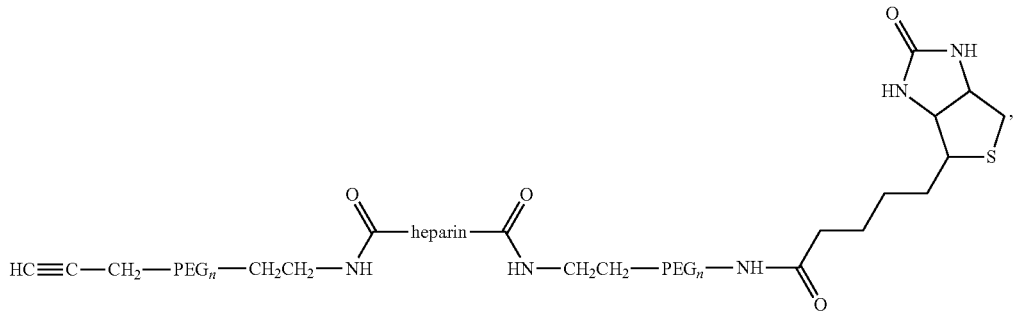

wherein each n is independently an integer form 1 to 20.
In some embodiments, each n is 3.

In some embodiments, the biologically active molecule functionalized with a chemical group reactive in a bioorthogonal chemical reaction is heparin-alkyne-biotin (HeparinAB) of the following formula:

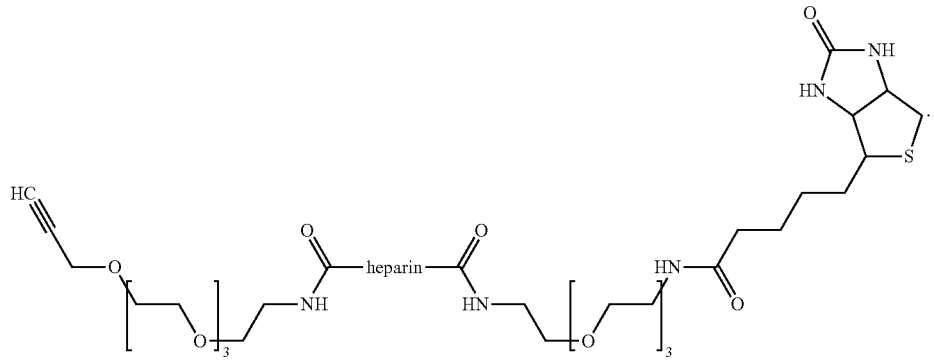

In some embodiments, the biologically active molecule functionalized with a chemical group reactive in a bioorthogonal chemical reaction is heparin-DBCO.

In some embodiments, the biologically active molecule functionalized with a chemical group reactive in a bioorthogonal chemical reaction is heparin-alkyne of any one the following formulae:

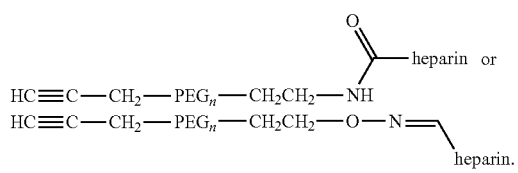

In some embodiments, the heparin-alkyne has the following formula:

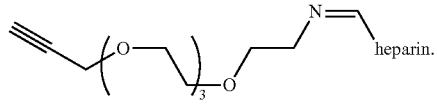

In some embodiments, the heparin-alkyne has the following formula:

In some embodiments, the heparin-DBCO has the following formula:

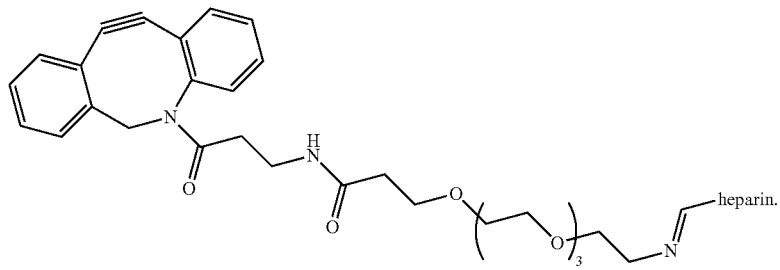

In some embodiments, heparin-alkyne or heparin-cyclooctyne (e.g., heparin-DBCO) may be prepared by reacting a compound of Formula (Ia) or a compound of Formula II with the heparin. The reacting may be carried out according to any synthetic method known in the art. For example, deaminated heparin at a concentration of about 10 mM may be reacted with a reagent of any one of the Formulae as described herein (e.g., o-(prop-2-ynyl)-hydroxylamine hydrochloride at a concentration of about 100 mM) for about 20 hours in a about 0.1M sodium citrate solution at about room temperature in the presence of a catalyst such as p-phenylenediamine. One of ordinary skill in the art will readily select and implement appropriate synthetic methods.

In some embodiments, the biologically active molecule functionalized with a chemical group reactive in a bioorthogonal chemical reaction is an antibody specific against tumor necrosis factor-alpha (TNF-α) (e.g., adalimumab). In some embodiments, the anti-TNF-α antibody is functionalized with an aliphatic alkyne. In some embodiments, the anti-TNF-α antibody is functionalized with a cyclooctyne). In some embodiments, the biologically active molecule functionalized with a chemical group reactive in a bioorthogonal chemical reaction is anti-TNF-α-alkyne. In some embodiments, the biologically active molecule functionalized with a chemical group reactive in a bioorthogonal chemical reaction is anti-TNF-α-DBCO. In some embodiments, the anti-TNF-α antibody is functionalized with an azide.

Other biomolecules, such as immunosuppressants, inhibitors or activators of cell surface receptors, may also be conjugated with alkyne or cycloalkyne in a similar manner to functionalize decellularized native biomaterials In some embodiments, any one of the nutrients described herein may be functionalized with a chemical group that is reactive in a bioorthogonal chemical reaction using a reagent comprising a chemical group that is reactive in a bioorthogonal chemical reaction as described herein (any one of the reagents of Formula I, Ia, Ib, and Formula II).

Functionalization of Organ Scaffolds Using Chemoselective Ligation

In some embodiments, the present disclosure provides a decellularized scaffold of a mammalian organ or tissue comprising an extracellular matrix, wherein the extracellular matrix of the decellularized scaffold is chemoselectively functionalized with a biologically active molecule.

In some embodiments, the present disclosure provides a method of preparing a decellularized scaffold of a mammalian organ or tissue comprising an extracellular matrix bioorthogonally functionalized with a biologically active molecule, the method comprising reacting the decellularized scaffold of a mammalian organ or tissue comprising an extracellular matrix functionalized with a chemical group that is reactive in a biorthogonal chemical reaction with a biologically active molecule functionalized with a reactive chemical group complimentary to the reactive chemical group of the functionalized extracellular matrix.

In some embodiments, the reactive chemical group that is reactive in a biorthogonal chemical reaction is an azide; the biologically active molecule is vancomycin or heparin; and the reactive chemical group complimentary to the reactive chemical group of the functionalized extracellular matrix is an alkyne.

In some embodiments, the reactive chemical group that is reactive in a biorthogonal chemical reaction is an alkyne; the biologically active molecule is vancomycin or heparin; and the reactive chemical group complimentary to the reactive chemical group of the functionalized extracellular matrix is an azide.

In some embodiments, the decellularized scaffold of a mammalian organ or tissue comprises an extracellular matrix functionalized with an azide. In some embodiments, the decellularized scaffold of a mammalian organ or tissue comprises an extracellular matrix functionalized with an alkyne.

In some embodiments, the biologically active molecule is functionalized with an alkyne. In some embodiments, the biologically active molecule is functionalized with an aliphatic alkyne. In some embodiments, the biologically active molecule is functionalized with a cyclooctyne. In some embodiments, the biologically active molecule is functionalized with an azide. In some embodiments, the biologically active molecule is vancomycin-azide. In some embodiments, the biologically active molecule is vancomycin-alkyne. In some embodiments, the biologically active molecule is heparin-azide. In some embodiments, the biologically active molecule is heparin-alkyne.

In some embodiments, the decellularized scaffold of a mammalian organ or tissue comprises an extracellular matrix functionalized with an azide; and the biologically active molecule is functionalized with an alkyne (e.g., aliphatic alkyne or cyclooctyne). In some embodiments, the decellularized scaffold of a mammalian organ or tissue comprises an extracellular matrix functionalized with an alkyne; and the biologically active molecule is functionalized with an azide. In some embodiments, the decellularized scaffold of a mammalian organ or tissue comprises an extracellular matrix functionalized with an azide; and the biologically active molecule is vancomycin-alkyne. In some embodiments, the decellularized scaffold of a mammalian organ or tissue comprises an extracellular matrix functionalized with an alkyne; and the biologically active molecule is vancomycin-azide.

In some embodiments, the decellularized scaffold of a mammalian organ or tissue comprises an extracellular matrix functionalized with an azide; and the biologically active molecule is heparin-alkyne. In some embodiments, the decellularized scaffold of a mammalian organ or tissue comprises an extracellular matrix functionalized with an alkyne; and the biologically active molecule is heparin-azide.

In some embodiments, the reacting is carried out in a solvent (e.g., DMF, acetonitrile, DMSO). In some embodiments, the reacting is carried out in water. In some embodiments, the reacting is carried out in an alcohol, such as ethanol, methanol, or t-butanol. In some embodiments, the reacting is carried out in t-butanol/water. In some embodiments, the reacting is carried out in tetrahydrofuran (THF). In some embodiments, the reacting is carried out in the absence of a solvent (e.g., as described in Applied Catalysis A: General, 453, 26, 2013, 151-158). In some embodiments, the reacting is carried out under any of the conditions described in "Copper-Catalyzed Azide-Alkyne Click Chemistry for Bioconjugation", Curr Protoc Chem Biol. 2011; 3(4): 153-162, the disclosure of which is incorporated herein by reference in its entirety. In some embodiments, the reacting is carried out in air-free conditions. In some embodiments, the reacting is carried out in the atmosphere of air.

In some embodiments, the reacting is carried out in a bioreactor (e.g., any one of the bioreactors described herein) by perfusing the decellularized scaffold of a mammalian organ or tissue comprising an extracellular matrix functionalized with a chemical group that is reactive in a biorthogonal chemical reaction with the buffer or media (e.g., any buffer or media described herein) comprising biologically active molecule functionalized with a reactive chemical group complimentary to the reactive chemical group of the functionalized extracellular matrix. In some aspects of these embodiments, the rate of perfusion is from about 0.1 mL/min to about 20 mL/min, from about 0.2 mL/min to about 15 mL/min, from about 0.3 mL/min to about 10 mL/min, or from about 0.5 mL/min to about 5 mL/min. In other aspects of these embodiments, the rate of perfusion is about 0.1 ml/min, about 0.2 ml/min, about 0.3 ml/min, about 0.4 ml/min, about 0.5 ml/min, about 1 ml/min, about 2 ml/min, about 5 ml/min, or about 10 ml/min.

In some embodiments, the reaction is carried out in a bioreactor by infusing the decellularized scaffold of a mammalian organ or tissue comprising an extracellular matrix functionalized with a chemical group that is reactive in a biorthogonal chemical reaction with the buffer or media (e.g., any buffer or media described herein) comprising biologically active molecule functionalized with a reactive chemical group complimentary to the reactive chemical group of the functionalized extracellular matrix. In some embodiments, the concentration of the functionalized biologically active molecule in the infusion media is from about 1 μM to about 10 M, from about 5 μM to about 5 M, from about 10 μM to about 1 M, from about 10 μM to about 100 mM, from about 20 μM to about 50 mM, from about 50 μM to about 20 mM, or from about 100 μM to about 10 mM. In some embodiments, the infusion is carried out at about room temperature. In some embodiments, the reacting comprises incubating the scaffold post-infusion for a time period form about 10 min to about 24 hours, form about 30 min to about 6 hours, form about 45 min to about 3 hours, or from about 1 hour to about 2 hours.

In some embodiments, the reacting is carried out using Click-iT® Cell Reaction Kit from ThermoFisher (catalog No. C10269).

In some embodiments, when the reactive chemical group is an aliphatic alkyne, the reacting is carried out in the presence of a copper catalyst. In some embodiments, when the reactive chemical group is an aliphatic alkyne, the reacting is carried out in the absence of a copper catalyst. In some embodiments, the copper catalyst is selected from metallic copper, copper (I) compound and copper (II) compound used with a reducing agent. In some embodiments, the copper catalyst is selected from $CuSO_4$, CuAAC, $Cu(MeCN)_4PF_6$, CuBr, and CuI. In some embodiments, the copper catalyst is used with a stabilizing ligand (e.g., TBTA, THPTA). In some embodiments, the reacting is carried out in the presence of sodium ascorbate. In some embodiments, the amount of the copper catalyst is from about 0.1 mol. % to about 5 mol %, from about 0.2 mol. % to about 4 mol %, from about 0.3 mol. % to about 3 mol %, from about 0.5 mol. % to about 2 mol %, or from about 0.7 mol. % to about 1.5 mol %. In some embodiments, the amount of the copper catalyst is about 0.1 mol. %, about 0.2 mol. %, about 0.3 mol. %, about 0.4 mol. %, about 0.5 mol. %, about 0.6 mol. %, about 0.7 mol. %, about 0.8 mol. %, about 0.9 mol. %, about 1.0 mol. %, about 1.1 mol. %, about 1.2 mol. %, about 1.3 mol. %, about 1.5 mol. %, or about 2.0 mol. %.

In some embodiments, when the reactive chemical group is a cyclooctyne, the reacting is carried out in the absence of a copper catalyst. In some embodiments, when the reactive chemical group is a cyclooctyne, the reacting is carried out in the presence of a copper catalyst (e.g., $CuSO_4$, CuAAC, $Cu(MeCN)_4PF_6$, CuBr, and CuI as described herein).

In some embodiments, the reacting is carried out at a temperature from about 0° C. to about 50° C., from about 0° C. to about 40° C., from about 0° C. to about 30° C., from about 0° C. to about 25° C., from about 0° C. to about 20° C., from about 0° C. to about 15° C., from about 0° C. to about 10° C., or from about 0° C. to about 5° C. In some embodiments, the reacting is carried out at about 0° C., about 5° C., about 10° C., about 15° C., about 20° C., about 25° C., or at ambient temperature. In some embodiments, the reacting is carried out at a temperature at about 0° C. In some embodiments, the reacting is carried out at ambient temperature.

In some embodiments, the concentration of the functionalized biologically active molecule is from about 1 μM to about 1000 μM, from about 2 μM to about 900 μM, from about 3 μM to about 800 μM, from about 4 μM to about 700 μM, from about 5 μM to about 600 μM, from about 6 μM to about 500 μM, from about 7 μM to about 400 μM, from about 8 μM to about 300 μM, from about 9 μM to about 200 μM, from about 10 μM to about 100 μM, from about 20 μM to about 90 μM, from about 25 μM to about 80 μM, from about 30 μM to about 70 μM, or from about 40 μM to about 60 μM. In some embodiments, the concentration of the functionalized biologically active molecule is about 10 μM, about 15 μM, about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM or about 100 μM. In some embodiments, the concentration of the functionalized biologically active molecule is from about 1 mM to about 1000 mM, from about 2 mM to about 900 mM, from about 3 mM to about 800 mM, from about 4 mM to about 700 mM, from about 5 mM to about 600 mM, from about 6 mM to about 500 mM, from about 7 mM to about 400 mM, from about 8 mM to about 300 mM, from about 9 mM to about 200 mM, from about 10 mM to about 100 mM, from about 20 mM to about 90 mM, from about 25 mM to about 80 mM, from about 30 mM to about 70 mM, or from about 40 mM to about 60 mM. In some embodiments, the concentration of the functionalized biologically active molecule is about 1 mM, about 2 mM, about 3 mM, about 5 mM, about 7.5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, v, about 80 mM, about 85 mM, about 90 mM or about 100 mM.

In some embodiments, the reacting is carried out for a time period from about 5 min to about 24 hours, from about 15 min to about 18 hours, from about 30 min to about 12 hours, from about 45 min to about 6 hours, or from about 1 hour to about 2 hours. In some embodiments, the reacting is carried out at about 15 min, about 30 min, about 45 min, about 1 hour, about 1.5 hours, about 2 hours, about 2.5 hours, about 3 hours, about 4 hours, about 5 hours, or about 6 hours.

Cell Seeding/Recellularized Organs and Tissues for Transplantation

In some embodiments, the present disclosure provides a method of preparing a mammalian organ or tissue for transplantation comprising seeding the decellularized scaffold of a mammalian organ or tissue comprising extracellular matrix bioorthogonally functionalized with a biologically active molecule as described herein with recipient-derived cells to obtain the organ or tissue for transplantation.

In some embodiments, the recipient-derived cells are differentiated or regenerative cells. Any appropriate regenerative cell type, such as naïve or undifferentiated cell types, can be used to seed the organ or tissue scaffold as described herein. The cells may be seeded at a variety of stages including, but not limited to, stem cell stage (e.g., after induction), progenitor cell stage, hemangioblast stage, or differentiated stage (e.g., CD 31+, vWF+). As used herein, regenerative cells can include, without limitation, progenitor cells, precursor cells, and "adult"-derived stem cells including umbilical cord cells (e.g., human umbilical vein endothelial cells) and fetal stem cells. Regenerative cells also can include differentiated or committed cell types. Stem cells appropriate for the methods and materials provided herein can include human induced pluripotent stem cells (iPSC) (e.g., undifferentiated, differentiated endoderm, anteriolized endoderm, TTF-1 positive lung progenitors), human mesenchymal stem cells, human umbilical vein endothelial cells, multipotent adult progenitor cells (MAPC), iPS derived mesenchymal cells, or embryonic stem cells. In some cases, regenerative cells derived from other tissues also can be used. For example, regenerative cells derived from skin, bone, muscle, bone marrow, synovium, or adipose tissue can be used to develop stem cell-seeded tissue matrices.

In some embodiments, an organ or tissue scaffold provided herein can be alternatively or further seeded with differentiated cell types such as (preferably human) epithelial cells and endothelial cells. For example, a lung matrix can be seeded with endothelial cells via the vasculature (e.g. through the arterial line or the venous line), and, when the organ or tissue is a lung, seeded with epithelial cells via the airway (e.g., through the tracheal line). The organ or tissue scaffold can also be seeded with one or more cell types (e.g., one or more of types of epithelial and mesenchymal cells, adult peripheral blood derived epithelial cells, cord blood-derived epithelial cells, iPS derived epithelial cells, progenitor stage cells (e.g., smooth muscle), adult lung derived cell mixture (e.g., rat human), commercially available small airway epithelial cells or alveolar epithelial cells, Embryonic Stem (ES) cell-derived epithelial cells, and/or human umbilical vein endothelial cells (HUVEC).

Any type of appropriate commercially available media and/or media kits may be used for the seeding and culture of cells. For example, SAGM media may be used for small airway cells (e.g., SAGM BulletKit by Lonza) and EGM-2 kits may be used for endothelial cells (e.g., EGM-2 BulletKit by Lonza). Media customized to the seeded endothelial cell type may be used (e.g., by increasing or decreasing growth factors such as VEGF) as described in, for example, Brudno Y et al. Enhancing microvascular formation and vessel maturation through temporal control over multiple pro-angiogenic and pro-maturation factors. *Biomaterials* 34 (2013) 9201-9209. In the case of endothelial cells, a sequence of different media compositions may be used to induce different phases of seeding, expansion, engraftment, and maturation of cells. For example, in a first phase, a cell seeded constructs may be perfused with an 'angiogenic media' for 2-30 days to increase endothelial cell expansion, migration, and metabolism. This media is characterized by high concentration of cytokines, e.g., VEGF at 5-100 ng/ml and bFGF at 5-100 ng/ml, and the presence of phorbol myristate acetate (PMA), e.g., 5-100 ng/ml PMA, which activates the angiogenic pathway through activation of protein kinase C, and Ang-1, which stimulates endothelial cell sprouting. In a second phase, a cell seeded construct can then be perfused with 'tightening media' that supports endothelial maturation and the formation of tight junctions. Tightening media has lower levels of cytokines, with the same basic composition as the angiogenic media but with decreased levels of VEGF, bFGF and PMA (0.1-5 ng/ml VEGF, FGF, and PMA). Hydrocortisone, which promotes tight junction formation and has been shown to reduce pulmonary edema, can be further added to the tightening media to promote vascular maturation. Further promaturation factors such as PDGF and Ang-2 may be added to the tightening media to enhance vessel formation. Concentrations of these factors may be titrated to support different vessel sizes. Media changes can be performed gradually to avoid detrimental effects of sudden cytokine changes. Similar to endothelial cell supporting media, sequential media changes can be used to guide epithelial cell fate. Initial media may contain, for example, Activin A at 10-200 ng/ml and Pi3K inhibitors such as ZSTK 474 at 0.01-1 uM to induce definite endoderm, subsequently TGF-beta inhibitors such as A-8301 at 01-10 uM and BMP4 antagonists such as DMH-1 at 0.05-1 uM to induce anteriorized endoderm, and finally BMP4 at 1-100 ug/ml, FGF2 at 10-500 ng/ml, GSK-3beta inhibitor such as CHIR 99021 at 10-500 nM, a PI3K inhibitor such as PIK-75 at 1-100 nM and methotrexate at 1-100 nM to induce the generation of lung progenitor cells.

Any appropriate method for isolating and collecting cells for seeding can be used. For example, induced pluripotent stem cells generally can be obtained from somatic cells "reprogrammed" to a pluripotent state by the ectopic expression of transcription factors such as Oct4, Sox2, Klf4, c-MYC, Nanog, and Lin28. See Takahashi et al., *Cell* 131:861-72 (2007); Park et al., *Nature* 451:141-146 (2008); Yu et al., *Science* 318:1917-20 (2007); Zhu et al., *Cell Stem Cell.* 7:651-5 2010; and Li et al., *Cell Res.* 21:196-204 (2011); Malik and Rao, Methods Mol Biol. 2013; 997:23-33; Okano et al., Circ Res. 2013 Feb. 1; 112(3):523-33; Lin and Ying, Methods Mol Biol. 2013; 936:295-312. Peripheral blood-derived mononuclear cells can be isolated from patient blood samples and used to generate induced pluripotent stem cells. In other examples, induced pluripotent stem cells can be obtained by reprogramming with constructs optimized for high co-expression of Oct4, Sox2, Klf4, c-MYC in conjunction with small molecule such as transforming growth factor β (SB431542), MEK/ERK (PD0325901) and Rho-kinase signaling (Thiazovivin). See GroB et al., *Curr Mol Med.* 13:765-76 (2013) and Hou et al., *Science* 341:651:654 (2013). Methods for generating endothelial cells from stem cells are reviewed in Reed et al., *Br J Clin Pharmacol.* 2013 April; 75(4):897-906. Cord blood stem cells can be isolated from fresh or frozen umbilical cord blood. Mesenchymal stem cells can be isolated from, for example, raw unpurified bone marrow or ficoll-purified bone marrow. Epithelial and endothelial cells can be isolated and collected from living or cadaveric donors, e.g., from the subject who will be receiving the organ or tissue as described herein, according to methods known in the art. For example, dermal epithelial cells can be obtained from a skin tissue sample (e.g., a punch biopsy), and endothelial cells can be obtained from a vascular tissue sample. In some embodiments, proteolytic enzymes are perfused into the tissue sample through a catheter placed in the vasculature. Portions of the enzymatically treated tissue can be subjected to further enzymatic and mechanical disruption. The mixture of cells obtained in this manner can be separated to purify epithelial and endothelial cells. In some cases, flow cytometry-based methods (e.g., fluorescence-activated cell sorting) can be used to sort cells based on the presence or absence of specific cell surface markers. For example, organ or tissue cells (epithelial, mesenchymal, and endothelial) can be obtained from organ or tissue biopsies, which, when the organ is lung, can be obtained via transbronchial and endobronchial biopsies, or via surgical biopsies of an organ or tissue. In cases where non-autologous cells are used, the selection of immune type-matched cells should be considered, so that the organ or tissue will not be rejected when implanted into a subject.

Isolated cells can be rinsed in a buffered solution (e.g., phosphate buffered saline at pH 7.4) and resuspended in a cell culture medium. Standard cell culture methods can be used to culture and expand the population of cells. Once obtained, the cells can be used to seed the organ or tissue scaffold, e.g., introduced into the matrix via the arterial or venous lines (endothelial cells) or through the airway (tracheal) line (epithelial cells). For example, a tissue matrix can be seeded with at least one cell type in vitro at any appropriate cell density. For example, cell densities for seeding a matrix can be at least $1\times10^3$ cells/gram matrix. Cell densities can range between about $1\times10^5$ to about $1\times10^{10}$ cells/gram matrix (e.g., at least 100,000, 1,000,000, 10,000,000, 100,000,000, 1,000,000,000, or 10,000,000,000 cells/gram matrix) can be used.

In some embodiments, a decellularized or artificial lung tissue matrix, as provided herein, can be seeded with the cell types and cell densities described above by perfusion seeding. For example, a flow perfusion system can be used to seed the decellularized lung tissue matrix via the vascular system preserved in the tissue matrix (e.g., through the arterial line). In some cases, automated flow perfusion systems can be used under the appropriate conditions. Such perfusion seeding methods can improve seeding efficiencies and provide more uniform distribution of cells throughout the composition. Quantitative biochemical and image analysis techniques can be used to assess the distribution of seeded cells following either static or perfusion seeding methods. In some embodiments, the cell seeding may be carried out according to the methods and procedure described, for example, in U.S. Pat. Nos. 6,479,064, 8,470,520, US 2012/0064537, and US 2013/0156744, the disclosures of the foregoing are incorporated herein by reference in their entirety.

In some embodiments, an organ or tissue scaffold can be impregnated with one or more growth factors to stimulate differentiation of the seeded regenerative cells. For example, an organ or tissue scaffold can be impregnated with growth factors appropriate for the methods and materials provided herein, for example, vascular endothelial growth factor (VEGF), TGF-β growth factors, bone morphogenetic proteins (e.g., BMP-1, BMP-4), platelet-derived growth factor (PDGF), fibroblast growth factor (FGF), e.g., FGF-10, insulin-like growth factor (IGF), epidermal growth factor (EGF), or growth differentiation factor-5 (GDF-5). See, e.g., Desai and Cardoso, Respire. Res. 3:2 (2002). These growth factors can be encapsulated to control temporal release. Different parts of the scaffold can be enhanced with different growth factors to add spatial control of growth factor stimulation.

Seeded tissue matrices can be incubated for a period of time (e.g., from several hours to about 14 days or more) post-seeding to improve engraftment and penetration of the cells in the tissue matrix. The seeded organ or tissue scaffold can be maintained under conditions in which at least some of the regenerative cells can multiply and/or differentiate within and on the acellular tissue matrix. Such conditions can include, without limitation, the appropriate temperature (35-38° C.) and/or pressure (e.g., atmospheric), electrical and/or mechanical activity (e.g., ventilation via positive or negative pressure with positive end expiratory pressure from 1-20 cmH$_2$O, mean airway pressure from 5-50 cmH$_2$O, and peak inspiratory pressure from 5-65 cmH$_2$O), the appropriate amounts of fluid, e.g., O$_2$ (1%-100% FiO$_2$) and/or CO$_2$ (0%-10% FiCO$_2$), an appropriate amount of humidity (10%-100%), and sterile or near-sterile conditions. Such conditions can also include wet ventilation, wet to dry ventilation and dry ventilation. In some cases, nutritional supplements (e.g., nutrients and/or a carbon source such as glucose), exogenous hormones, or growth factors can be added to the seeded tissue matrix. Histology and cell staining can be performed to assay for seeded cell propagation. Any appropriate method can be performed to assay for seeded cell differentiation.

Thus, the methods described herein can be used to generate a transplantable organ or tissue, e.g., for transplanting into a human recipient subject. In some embodiments, the transplantable organ or tissue retains a sufficiently intact vasculature that can be connected to the patient's vascular system.

Prosthetic Mesh

In some embodiments, the present disclosure provides a method of preparing a biological prosthetic mesh comprising reacting the decellularized scaffold of a mammalian organ or tissue comprising an extracellular matrix functionalized with a chemical group that is reactive in a biorthogonal chemical reaction with a biologically active molecule functionalized with a reactive chemical group complimentary to the reactive chemical group of the functionalized extracellular matrix. In some aspects of these embodiments, the reacting is carried out using any of the methods and procedures described herein. In some aspects of these embodiments, the organ or tissue is any one of the organs or tissues described herein. In other aspects of these embodiments, the organ or tissue is a skin flap.

In some embodiments, the present disclosure provides a biological prosthetic mesh comprising decellularized scaffold of a mammalian organ or tissue comprising an extracellular matrix functionalized with a biologically active molecule. In some aspects of these embodiments, the biologically active molecule is vancomycin or heparin. In some aspects of these embodiments, the organ or tissue is any one of the organs or tissues described herein. In other aspects of these embodiments, the organ or tissue is a skin flap.

In some embodiments, the biologic prosthetic mesh further comprises a material selected from Polypropylene (PP), polytetrafluorethylene (PTFE, ePTFE), dacron, orlon, polyethylene, mylar and marlex. In some embodiments, the biological prosthetic mesh further comprises a biodegradable polymer. In some embodiments, the biological prosthetic mesh further comprises poly(lactide-co-glycolide) (PLGA). In some embodiments, the poly(lactide-co-glycolide) (PLGA) comprises a range of ratios of lactic acid to glycolic acid monomers, for example, from about 1:9 to about 9:1, from about 1:4 to about 4:1, from about 3:7 to about 7:3, or from about 3:2 to about 2:3. In some embodiments, the biological prosthetic mesh comprises an aliphatic polyester polymer. In some embodiments, the aliphatic polyester polymer is selected from the group consisting of polycaprolactone (PCL), polybutylene succinate (PBS), and a polyhydroxylalkanoate (PHA), such as polyhydroxybutyrate. In some embodiments, aliphatic polyester polymer is selected from polylactic acid (PLA) and polyglycolic acid (PGA). In some embodiments, the mesh comprises titanium/propylene composite material. In some embodiments, the mesh is a composite mesh. In some embodiments, the biological prosthetic mesh is a multilayer composite. In some embodiments, the mesh is absorbable. In some embodiments, the mesh is permanent. In some embodiments, the mesh comprises barrier coatings. In some embodiments, the mesh comprises glycerol and propylene glycol (e.g., a film comprising these materials).

In some embodiments, the mesh is monofilament. In some embodiments, the mesh is dualfilament. In other embodiments, the mesh is multifilament. In some embodiments, the mesh is lightweight. On other embodiments, the mesh is heavyweight. In some embodiments, the weight of the mesh is from about 1 g/cm$^2$ to about 500 g/cm$^2$, from about 10 g/cm$^2$ to about 400 g/cm$^2$, from about 20 g/cm$^2$ to about 300 g/cm$^2$, from about 30 g/cm$^2$ to about 200 g/cm$^2$, from about 40 g/cm$^2$ to about 150 g/cm$^2$, or from about 50 g/cm$^2$ to about 150 g/cm$^2$. In some embodiments, the weight of the mesh is about 1 g/cm$^2$, about 10 g/cm$^2$, about 20 g/cm$^2$, about 30 g/cm$^2$, about 40 g/cm$^2$, about 50 g/cm$^2$, about 60 g/cm², about 70 g/cm², about 80 g/cm², about 90 g/cm², about 100 g/cm², about 150 g/cm², or about 200 g/cm².

In some embodiments, the pore size of the biological prosthetic mesh which allows infiltration by macrophages, fibroblasts, blood vessels and collagen. In some embodiments, the pore size of the biological prosthetic mesh is from about 1 µm to about 1000 µm, from about 2 µm to about 950 µm, from about 3 µm to about 900 µm, from about 4 µm to about 850 µm, from about 5 µm to about 800 µm, from about 6 µm to about 750 µm, from about 7 µm to about 700 µm, from about 8 µm to about 650 µm, from about 9 µm to about 600 µm, from about 10 µm to about 550 µm, from about 20 µm to about 500 µm, from about 30 µm to about 450 µm, from about 40 µm to about 400 µm, from about 50 µm to about 350 µm, from about 60 µm to about 300 µm, from about 70 µm to about 250 µm, from about 80 µm to about 200 µm, or from about 100 µm to about 200 µm. In some embodiments, the pore size of the biological prosthetic mesh is about 1 µm, about 5 µm, about 7 µm, about 10 µm, about 20 µm, about 30 µm, about 40 µm, about 50 µm, about 75 µm, about 100 µm, about 200 µm, about 300 µm, about 400 µm, about 500 µm, about 600 µm, about 750 µm, or about 1000 µm.

In some embodiments, the elasticity of the mesh at about 32 N/cm is from about 10% to about 80%, from about 20% to about 70%, or from about 30% to about 60%. In some embodiments, the elasticity of the mesh at about 32 N/cm is about 10%, about 20%, about 30%, about 38%, about 40%, about 50%, about 60%, about 70%, or about 80%. In some embodiments, the elasticity of the mesh at about 16 N/cm is from about 1% to about 60%, from about 2% to about 50%, from about 3% to about 40%, from about 4% to about 30%, from about 4% to about 20%, from about 4% to about 15%, or from about 20% to about 40%. In some embodiments, the elasticity of the mesh at about 16 N/cm is about 4%, about 5%, about 6%, about 7%, about 8%, about 9%, about 10%, about 20%, about 30%, or about 40%.

In some embodiments, the tensile strength of the prosthetic mesh is from about 10 N/cm to about 1000 N/cm, from about 20 N/cm to about 900 N/cm, from about 30 N/cm to about 800 N/cm, from about 40 N/cm to about 700 N/cm, from about 50 N/cm to about 600 N/cm, from about 60 N/cm to about 500 N/cm, from about 70 N/cm to about 400 N/cm, from about 80 N/cm to about 300 N/cm, or from about 75 N/cm to about 150 N/cm. In some embodiments, the tensile strength of the prosthetic mesh is about 10 N/cm, about 20 N/cm, about 30 N/cm, about 40 N/cm, about 50 N/cm, about 60 N/cm, about 70 N/cm, about 80 N/cm, about 90 N/cm, about 100 N/cm, about 150 N/cm, about 200 N/cm, about 300 N/cm or about 500 N/cm.

In some embodiments, the biological prosthetic mesh may be prepared using the decellularized scaffold of a mammalian organ or tissue comprising an extracellular matrix functionalized with a biologically active molecule as described herein. In some embodiments, the biological prosthetic mesh may be prepared by any one of methods described, from example, in US 2002/0042658, US 2009/0192528, US 2010/0272782, US 2010/0318108, US 2015/0297798, US 2016/0015503, WO 2013/093921, and WO 2016/061450, the disclosures of which are incorporated herein by reference in their entirety.

The biological prosthetic mesh as described herein advantageously treats most challenging complex hernias involving an open abdomen, contamination, and/or gross infection, conditions that make the use of previously known prosthetic meshes inappropriate. The biological prosthetic mesh as described herein advantageously provide extracellular components necessary for complete healing, allow for the reconstruction of new and healthy tissue, and restore mechanical and functional integrity to the abdominal wall.

Molecular Enhancement of Organ or Tissue Transplant

In some embodiments, the present disclosure provides an organ or tissue for transplantation, wherein the organ or tissue is functionalized with a biologically active molecule (e.g., any one of the biologically active molecules described herein). In some aspects of these embodiments, the biologically active molecule is vancomycin. In other aspects of these embodiments, the biologically active molecule is an antibody specific against tumor necrosis factor-alpha (TNF-α) (e.g., adalimumab).

In some embodiments, the present disclosure provides a method of preparing an organ or tissue for transplantation, the method comprising (i) administering to a donor subject a nutrient functionalized with a chemical group that is reactive in a biorthogonal chemical reaction (e.g., using any of the methods described herein) to obtain an organ or tissue functionalized with a chemical group that is reactive in a biorthogonal chemical reaction; (ii) surgically removing the organ or tissue from the donor subject as described herein; and (iii) treating the isolated organ or tissue with a preservation solution comprising biologically active molecule functionalized with a reactive chemical group complimentary to the reactive chemical group of the functionalized nutrient as described herein to obtain an organ or tissue functionalized with the biologically active molecule. In some embodiments, the method further comprises washing the organ or tissue functionalized with the biologically active molecule with a preservation solution to obtain the organ or tissue prepared for transplantation.

In some embodiments, the reactive chemical group with which the nutrient is functionalized is an azide or an alkyne (e.g., aliphatic alkyne or a cyclooctyne). In some embodiments, the nutrient functionalized with a chemical group that is reactive in a biorthogonal chemical reaction is any one of the nutrients described herein. In some aspects of these embodiments, the nutrient is selected from alkynyl fucose, alkynyl ManNAc, alkyne-labeled galactosamine, an alkyne-labeled glucosamine, an alkyne-labeled mannosamine, alkyne-labeled galactosamine, an alkyne-labeled glucosamine, an alkyne-labeled mannosamine, azide-labeled galactosamine (e.g., Ac4GalNAz), an azide-labeled glucosamine (e.g., Ac4GlcNAz), an azide-labeled mannosamine (e.g., Ac4ManNAz). In some aspects of these embodiments, the nutrient is selected from Ac4GlcNAz, Ac4ManNAz and Ac4GalNAz. In some aspects of these embodiments, the nutrient is Ac4GalNAz.

In some embodiments, the reactive chemical group complimentary to the reactive chemical group of the functionalized nutrient is azide. In some embodiments, the reactive chemical group complimentary to the reactive chemical group of the functionalized nutrient is an aliphatic alkyne. In some embodiments, the reactive chemical group complimentary to the reactive chemical group of the functionalized nutrient is a cyclooctyne. In some embodiments, the cyclooctyne is DBCO. In some embodiments, the DBCO-functionalized biologically active molecule is vancomycin. In some embodiments, the azide-functionalized biologically active molecule is vancomycin. In some embodiments, the alkyne-functionalized biologically active molecule is vancomycin. In some embodiments, the DBCO-functionalized biologically active molecule is heparin. In some embodiments, the azide-functionalized biologically active molecule is heparin. In some embodiments, the alkyne-functionalized biologically active molecule is heparin. In some embodiments, the DBCO-functionalized biologically active molecule is anti-TNF-alpha antibody. In some embodiments, the azide-functionalized biologically active molecule is anti-TNF-alpha antibody. In some embodiments, the alkyne-functionalized biologically active molecule is anti-TNF-alpha antibody. In some embodiments, the recipient subject is not susceptible to a condition selected from ischemia, reperfusion injury and bacterial infection after transplantation of the organ or tissue functionalized with the biological active molecule as described herein.

In some embodiments, the treating is carried out at a temperature from about 0° C. to about 40° C., from about 0° C. to about 37° C., from about 25° C. to about 37° C., from about 0° C. to about 25° C., from about 0° C. to about 20° C., from about 0° C. to about 15° C., from about 0° C. to about 10° C., or from about 0° C. to about 5° C. In some embodiments, the treating is carried out at about 0° C., about 5° C., about 10° C., about 15° C., about 20° C., about 25° C., about 30° C., about 37° C., about 40° C. or ambient temperature. In some embodiments, the treating is carried out at about 0° C. In some embodiments, the treating is carried out at about 25° C. In some embodiments, the treating is carried out at about 37° C.

In some embodiments, the treating is carried out for a time period from about 5 min to about 24 hours, from about 15 min to about 18 hours, from about 30 min to about 12 hours, from about 45 min to about 6 hours, or from about 1 hour to about 2 hours. In some embodiments, the treating is carried out at about 15 min, about 30 min, about 45 min, about 1 hour, about 1.5 hours, about 2 hours, about 2.5 hours, about 3 hours, about 4 hours, about 5 hours, about 6 hours, about 12 hours, about 18 hours, or about 24 hours.

In some embodiments, the treating is carried out in the absence of any catalysts. In some embodiments, the treating is carried out in the absence of copper catalyst. In some embodiments, the treating is carried out in the presence of copper (I) catalyst. In some embodiments, the copper (I) catalyst is selected from $CuSO_4$, CuAAC, $Cu(MeCN)_4PF_6$, CuBr, and CuI. In some aspects of these embodiments, the copper catalyst is used with a stabilizing ligand (e.g., TBTA, THPTA). In some aspects of these embodiments, the treating is carried out in the presence of sodium ascorbate. In some aspects of these embodiments, the amount of the copper catalyst is from about 0.1 mol. % to about 5 mol %, from about 0.2 mol. % to about 4 mol %, from about 0.3 mol. % to about 3 mol %, from about 0.5 mol. % to about 2 mol %, or from about 0.7 mol. % to about 1.5 mol %. In other aspects of these embodiments, the amount of the copper catalyst is about 0.1 mol. %, about 0.2 mol. %, about 0.3 mol. %, about 0.4 mol. %, about 0.5 mol. %, about 0.6 mol. %, about 0.7 mol. %, about 0.8 mol. %, about 0.9 mol. %, about 1.0 mol. %, about 1.1 mol. %, about 1.2 mol. %, about 1.3 mol. %, about 1.5 mol. %, or about 2.0 mol. %.

In some embodiments, the preservation solution is any one of the Perfadex® or CoStorSol® preservation solutions. In some embodiments, the preservation solution is an aqueous solution (injection grade water). In some embodiments, the preservation solution is any one of the preservation solutions known in the art. In some embodiments, the preservation solution comprises an ingredient selected from lactobionic acid, potassium phosphate monobasic, magnesium sulfate heptahydrate, raffinose pentahydrate, adenosine, allopurinol, glutathione, potassium hydroxide, sodium hydroxide and hydrochloric acid.

In some examples, the preservation solution may include low-potassium extracellular-type solutions such as Perfadex® or a composition as shown in Table 1. Amino acids, antibiotics, or agents (e.g., those shown in Table 2 or any one of amino acids, antibiotics, and agents described herein) may also be added to the preservation solution.

TABLE 1

Preservation solution composition

Krebs-Henseleit Buffer (118 mM NaCl, 4.7 mM KCl, 1.2 mM KH2PO4, 1.2 mM MgSO4, 4.2 mM NaHCO3)
0.2%-5% D-Glucose
1-15% human Albumin (optional)
1-20% Hetastarch (optional)
1-10% Dextan 40
Varying concentrations of Glutamine, Antibiotics, and amino acids

TABLE 2

Preservation solution composition

ROS scavenger (Glutathione/N-acetylcysteine)
$2^{nd}$ messenger (dibutryl cAMP (cAMP analogue))
Glucose metabolism (Insulin)
Membrane stabilizer (Hydrocortisone)
Growth factors (VEGF, FGF)
Oxygen carrier (red blood cells, perfluorocarbon, hemoglobin binding oxygen carrier)

In some embodiments, the concentration of the biologically active molecule functionalized with a reactive chemical group complimentary to the reactive chemical group of the functionalized nutrient as described herein in the preservation solution is from about 0.01 µM to about 1000 mM, is from about 0.01 µM to about 100 mM, from about 0.01 µM to about 10 mM, from about 0.01 µM to about 1 mM, from about 0.01 µM to about 500 µM, from about 0.01 µM to about 250 µM, from about 0.01 µM to about 100 µM, from about 0.01 µM to about 50 µM, from about 0.01 µM to about 25 µM, from about 0.01 µM to about 10 µM, from about 0.01 µM to about 1 µM, from about 0.01 µM to about 0.5 µM, from about 0.05 µM to about 10 µM, from about 0.1 µM to about 10 µM, from about 1 µM to about 10 µM, from about 0.05 µM to about 1 mM, from about 0.1 µM to about 1 mM, from about 0.5 µM to about 1 mM, from about 1 µM to about 1 mM, from about 10 µM to about 1 mM, from about 100 µM to about 1 mM, from about 1 mM to about 1000 mM, from about 2 mM to about 900 mM, from about 3 mM to about 800 mM, from about 4 mM to about 700 mM, from about 5 mM to about 600 mM, from about 6 mM to about 500 mM, from about 7 mM to about 400 mM, from about 8 mM to about 300 mM, from about 9 mM to about 200 mM, from about 10 mM to about 100 mM, from about 20 mM to about 90 mM, from about 25 mM to about 80 mM, from about 30 mM to about 70 mM, or from about 40 mM to about 60 mM. In some embodiments, the concentration of the biologically active molecule functionalized with a reactive chemical group complimentary to the reactive chemical group of the functionalized nutrient as described herein in the preservation solution is about 0.01 µM, about 0.05 µM, about 0.1 µM, about 0.5 µM, about 1 µM, about 2 µM, about 5 µM, about 10 µM, about 25 µM, about 50 µM, about 100 µM, about 250 µM, about 500 µM, about 1 mM, about 2 mM, about 3 mM, about 5 mM, about 7.5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, v, about 80 mM, about 85 mM, about 90 mM or about 100 mM. In some embodiments, the concentration of the biologically active molecule functionalized with a reactive chemical group complimentary to the reactive chemical group of the functionalized nutrient as described herein in the preservation solution is from about 1 µM to about 1000 µM, from about 2 µM to about 900 µM, from about 3 µM to about 800 µM, from about 4 µM to about 700 µM, from about 5 µM to about 600 µM, from about 6 µM to about 500 µM, from about 7 µM to about 400 µM, from about 8 µM to about 300 µM, from about 9 µM to about 200 µM, from about 10 µM to about 100 µM, from about 20 µM to about 90 µM, from about 25 µM to about 80 µM, from about 30 µM to about 70 µM, or from about 40 µM to about 60 µM. In some embodiments, the concentration of the biologically active molecule functionalized with a reactive chemical group complimentary to the reactive chemical group of the functionalized nutrient as described herein in the preservation solution is about 10 µM, about 15 µM, about 20 µM, about 25 µM, about 30 µM, about 35 µM, about 40 µM, about 45 µM, about 50 µM, about 55 µM, about 60 µM, about 65 µM, about 70 µM, about 75 µM, about 80 µM, about 85 µM, about 90 µM or about 100 µM.

REFERENCES

1. Chiu, L. L. Y., and Radisic, M. (2010). Scaffolds with covalently immobilized VEGF and Angiopoietin-1 for vascularization of engineered tissues. Biomaterials 31, 226-241.
2. Shen, Y. H., Shoichet, M. S., and Radisic, M. (2008). Vascular endothelial growth factor immobilized in collagen scaffold promotes penetration and proliferation of endothelial cells. Acta Biomaterialia 4, 477-489.
3. Wissink, M. J. B., Beernink, R., Pieper, J. S., Poot, A. A., Engbers, G. H. M., Beugeling, T., van Aken, W. G., and Feij en, J. (2001). Immobilization of heparin to EDC/NHS-crosslinked collagen. Characterization and in vitro evaluation. Biomaterials 22, 151-163.
4. Darehzereshki, A. et al. Biologic versus nonbiologic mesh in ventral hernia repair: a systematic review and meta-analysis. World J. Surg. 38, 40-50 (2014).
5. Bellows, C. F., Wheatley, B. M., Moroz, K., Rosales, S. C. & Morici, L. a. The effect of bacterial infection on the biomechanical properties of biological mesh in a rat model. PLoS One 6, (2011).
6. Collage, R. D. & Rosengart, M. R. Abdominal wall infections with in situ mesh. Surg. Infect. (Larchmt). 11, 311-8 (2010).
7. Ott, H. C. et al. Perfusion-decellularized matrix: using nature's platform to engineer a bioartificial heart. Nat. Med. 14, 213-221 (2008).
8. Halaweish, I. et al. Novel in vitro model for assessing susceptibility of synthetic hernia repair meshes to *Staphylococcus aureus* infection using green fluorescent protein-labeled bacteria and modern imaging techniques. Surg. Infect. (Larchmt). 11, 449-454 (2010).
9. Chiu, L. L. Y. & Radisic, M. Scaffolds with covalently immobilized VEGF and Angiopoietin-1 for vascularization of engineered tissues. *Biomaterials* 31, 226-241 (2010).
10. Yang, C.-H. Evaluation of the release rate of bioactive recombinant human epidermal growth factor from cross-linking collagen sponges. *Journal of Materials Science: Materials in Medicine* 19, 1433-1440 (2008).
11. Grover, C. N. et al. Crosslinking and composition influence the surface properties, mechanical stiffness and cell reactivity of collagen-based films. *Acta Biomaterialia* 8, 3080-3090 (2012).
12. Pieper, J. S., Oosterhof, A., Dijkstra, P. J., Veerkamp, J. H. & van Kuppevelt, T. H. Preparation and characterization of porous crosslinked collagenous matrices containing bioavailable chondroitin sulphate. *Biomaterials* 20, 847-858 (1999).
13. Olde Damink, L. H. H. et al. Cross-linking of dermal sheep collagen using a water-soluble carbodiimide. *Biomaterials* 17, 765-773 (1996).
14. Grover, C. N., Farndale, R. W., Best, S. M. & Cameron, R. E. The interplay between physical and chemical properties of protein films affects their bioactivity. *Journal of Biomedical Materials Research* Part A 100A, 2401-2411 (2012).
15. Davidenko, N. et al. Control of crosslinking for tailoring collagen-based scaffolds stability and mechanics. *Acta Biomaterialia* 25, 131-142 (2015).
16. Chang, P. V. et al. Metabolic Labeling of Sialic Acids in Living Animals with Alkynyl Sugars. *Angewandte Chemie International Edition* 48, 4030-4033 (2009).
17. Hang, H. C., Yu, C., Kato, D. L. & Bertozzi, C. R. A metabolic labeling approach toward proteomic analysis of mucin-type O-linked glycosylation. *Proceedings of the National Academy of Sciences* 100, 14846-14851 (2003).
18. Chang, P. V. et al. Copper-free click chemistry in living animals. *Proceedings of the National Academy of Sciences* 107, 1821-1826 (2010).
19. Salic, A. & Mitchison, T. J. A chemical method for fast and sensitive detection of DNA synthesis in vivo. *Proceedings of the National Academy of Sciences* 105, 2415-2420 (2008).
20. Jao, C. Y., Roth, M., Welti, R. & Salic, A. Metabolic labeling and direct imaging of choline phospholipids in vivo. *Proceedings of the National Academy of Sciences* 106, 15332-15337 (2009).
21. Hinz, F. I., Dieterich, D. C., Tirrell, D. A. & Schuman, E. M. Noncanonical Amino Acid Labeling in Vivo to Visualize and Affinity Purify Newly Synthesized Proteins in Larval Zebrafish. *ACS Chemical Neuroscience* 3, 40-49 (2012).
22. Jao, C. Y. & Salic, A. Exploring RNA transcription and turnover in vivo by using click chemistry. *Proceedings of the National Academy of Sciences* 105, 15779-15784 (2008).
23. Liu, J., Xu, Y., Stoleru, D. & Salic, A. Imaging protein synthesis in cells and tissues with an alkyne analog of puromycin. *Proceedings of the National Academy of Sciences* 109, 413-418 (2012).
24. Ullrich, M. et al. Bio-orthogonal labeling as a tool to visualize and identify newly synthesized proteins in *Caenorhabditis elegans*. Nat. Protocols 9, 2237-2255 (2014).
25. Schiapparelli, L. M. et al. Direct Detection of Biotinylated Proteins by Mass Spectrometry. *Journal of Proteome Research* 13, 3966-3978 (2014).
26. Ott, H. C. et al. Regeneration and orthotopic transplantation of a bioartificial lung. Nat Med 16, 927-933 (2010).
27. Petersen, T. H. et al. Tissue-Engineered Lungs for in Vivo Implantation. *Science* 329, 538-541 (2010).
28. Wilson, G. J., Courtman, D. W., Klement, P., Lee, J. M. & Yeger, H. Acellular Matrix: A Biomaterials Approach for Coronary Artery Bypass and Heart Valve Replacement. Ann Thorac Surg. 60, S353-358 (1995).
29. Badylak, S. F., Taylor, D. & Uygun, K. Whole-Organ Tissue Engineering: Decellularization and Recellularization of Three-Dimensional Matrix Scaffolds. *Annu Rev Biomed Eng.* 13, 27-53, doi:10.1146/annurev-bioeng-071910-124743 (2011).

30. Crapo, P. M., Gilbert, T. W. & Badylak, S. F. An overview of tissue and whole organ decellularization processes. *Biomaterials* 32, 3233-3243 (2011).
31. Hong, V., Presolski, S. I., Ma, C. & Finn, M. G. Analysis and Optimization of Copper-Catalyzed Azide-Alkyne Cycloaddition for Bioconjugation. *Angewandte Chemie (International ed. in English)* 48, 9879-9883 (2009).
32. Presolski, S. I., Hong, V. P. & Finn, M. G. Copper-Catalyzed Azide-Alkyne Click Chemistry for Bioconjugation. *Current Protocols in Chemical Biology* (2011).
33. Dube, D. H., Prescher, J. A., Quang, C. N. & Bertozzi, C. R. Probing mucin-type O-linked glycosylation in living animals. *Proceedings of the National Academy of Sciences of the United States of America* 103, 4819-4824 (2006).
34. Laughlin, S. T. & Bertozzi, C. R. In Vivo Imaging of *Caenorhabditis elegans* Glycans. *ACS Chemical Biology* 4, 1068-1072 (2009).

The invention will be further described in the following examples, which do not limit the scope of the invention described in the claims.

EXAMPLES

Materials and General Methods

In Vivo Metabolic Engineering and Organ/Tissue Decellularization

All animal experiments were approved by the Massachusetts General Hospital Institutional Animal Care and Use Committee and performed in compliance with the Animal Welfare Act. Male Sprague-Dawley rats (100-125 g, Charles River Laboratories) was administered with metabolic labeling reagents (Ac4GalNAz, Ac4GlcNAz or Ac4ManNAz) (30 mg/day, Click Chemistry Tools) via intraperitoneal injection daily for three days. One day after the last administration of the metabolic labeling reagents, organs were harvested from the animals and perfusion decellularized using the following conditions: 0.1% SDS through the pulmonary artery (PA) for the lung; 1% SDS retrograde coronary perfusion through the ascending aorta for the heart; 1% SDS through the renal artery for the kidney; and 1% SDS through the inferior vena cava (with superior vena cava ligated) for the liver. Full-thickness skin grafts were harvested from the abdomen of the animal and decellularized by immersion with agitation in 1% SDS. Decellularized organ and tissue scaffolds were washed sequentially with distilled water, 1% Triton X and PBS.

Ex Vivo Metabolic Engineering and Decellularization of Rat and Porcine Lungs

For ex vivo metabolic engineering of the rat lung, the lung was freshly harvested from a male Sprague-Dawley rat (100-125 g). The isolated rat lung was cultured in 100 ml of DMEM/F12 medium containing 10% fetal bovine serum (DMEM/F12-FBS), with the supplementation of Ac4GalNAz (50 µM) or DMSO (0.1%), for 24 hours in a bioreactor under constant rate perfusion (5 ml/min) through the PA, followed by perfusion decellularization as described above.

For ex vivo metabolic engineering of the porcine lung, the left lung was freshly isolated from a male Yorkshire swine (18-20 kg, Tufts University). The isolated porcine left lung was cultured DMEM/F12-FBS medium, with the supplementation of Ac4GalNAz (50 µM) or DMSO (0.1%), for 24 hours in a bioreactor under constant rate perfusion (300 ml/min) through the left main PA. 3 L of medium was initially used and was refreshed once with another 2 L of medium after the initial 16 hours of culture. A parallel oxygenation loop was used during the culture at a flow rate of 150 ml/min. Following culture, the porcine left lung was decellularized by sequential single-pass perfusion through the left main PA with 0.5% SDS, distilled water, 1% Triton X and PBS, adapted from a previously described method (Zhou, H. et al. Bioengineering Human Lung Grafts on Porcine Matrix. *Annals of Surgery* Publish Ahead of Print (2017)).

Collagen-Azide Well Assay

Wells in a 96-well plate were coated with 200 µg/mL of collagen I (Corning), incubated overnight with 5 mM Azido-PEG4-NHS Ester (Az-HNS, in 10% DMSO) or 10% DMSO (control) in DPBS (pH 8.0), and washed extensively with DPBS (pH 7.0). The Collagen wells with and without Az-NETS conjugation were clicked with 20 µM Heparin-AB for 1 hour at room temperature using the Click-iT Cell Reaction Buffer Kit (Life Technology) containing 1 mM copper (II) sulfate. The wells were sequentially washed with TBS (with 20 mM EDTA, pH 7.4) and PBS (pH 7.4), blocked with 1% BSA in 50 mM Tris-HCl (pH 8.4), and incubated with Antithrombin III (ATIII, 25 µg/ml, Sigma-Aldrich) in 1% BSA in Tris-HCl (pH 8.4) for 1 hour at 37° C. Following washing with Ultrapure Distilled Water (Life Technology), each well was incubated at 37° C. with 30 µl of 2.4 nkat/ml Factor Xa (FXa) in Tris-HCl (pH 8.4) for 5, 15 or 30 minutes. At each time point, the remaining FXa activity in each well was quantified using the S-2222 chromogenic substrate (Chromogenix) according to manufacturer's instruction. The chromogenic reaction was terminated with the addition of 20% acetic acid and the absorbance was read at 405 nm using NanoDrop (Thermo Fisher). For imaging in the wells, Heparin-Biotin (Heparin-B) was stained with Alexa Fluor 594-conjugated Streptavidin (Life Technologies, S-32356, 1:500), ATIII was sequentially stained with Goat-anti-ATIII (Santa Cruz Biotechnology, sc-32453, 1:100) and Alexa Fluor 594-conjugated Donkey-anti-Goat antibodies (Life Technologies, A-11058, 1:500), and Collagen I was sequentially stained with Rabbit-anti-Collagen I (Abcam, ab34710, 1:200) and Alexa Fluor 488-conjugated Donkey-anti-Rabbit antibodies (Life Technologies, A-21206, 1:500). Fluorescence intensity of the wells after staining was quantified using SpectraMax Microplate Reader (Molecular Devices) at 584 nm (ex)/612 nm (em) for Heparin-B and ATIII, and at 485 nm (ex)/538 nm (em) for Collagen I. Fluorescence image scanning of stained wells was performed using a Nikon Eclipse TE200 microscope and NIS-Elements imaging software (Nikon).

Biotin and Heparin-AB Infusion Click Reaction in Acellular Lung

The acellular rat lung with or without ex vivo Ac4GalNAz metabolic engineering was infused with 10 ml of Biotin-Alkyne click reaction mix (containing 10 µM Biotin-Alkyne and Click-iT Cell Reaction Buffer Kit), or with Heparin-AB click reaction mix (containing 20 µM Heparin-AB and Click-iT Cell Reaction Buffer Kit). The trachea was ligated before infusion of the click reaction mix. Following 1-hour incubation at room temperature post-infusion, the trachea ligation was removed, and the acellular lung was washed sequentially with 500 ml of TBS (with 20 mM EDTA, pH 7.4) and 1 L of PBS via single-pass perfusion through the PA.

ATM Immobilization and FXa Inhibition Assay in Heparin-AB-Functionalized Acellular Lungs.

Following Heparin-AB infusion click reaction in the acellular lung with or without ex vivo Ac4GalNAz metabolic engineering, the right cranial and middle lobes were harvested for histological analysis of Heparin-B immobilization. The remaining lung was blocked with 1% BSA in 50 mM Tris-HCl (pH 8.4), and perfused at 3 ml/min with 3 ml of ATIII (25 µg/ml) in 1% BSA in Tris-HCl (pH 8.4) for 1 hour at 37° C. Following ATIII perfusion, the lung was washed three times by perfusion at 3 ml/min with 50 ml Ultrapure Distilled Water for 10 minutes at 37° C. The right caudal and accessary lobes were then harvested for Western blot analysis of ATIII immobilization. The remaining left lung was perfused at 3 ml/min with 3 ml of 2.4 nkat/ml FXa in Tris-HCl (pH 8.4) for 5, 15, 30 and 60 minutes at 37° C. to allow FXa inactivation. At each time point, 50 µl of FXa perfusate was removed from the lung perfusion and the remaining FXa activity in the perfusate was quantified using the S-2222 chromogenic substrate as described above.

Click Reaction on Histological Sections and Histology

All samples were fixed with 4% paraformaldehyde (Boston BioProducts), paraffin-embedded, and sectioned at 5-µm thickness. Following deparaffinization, rehydration and antigen retrieval using Antigen Unmasking Solution (Vector Laboratories), the sections were processed for either on-section click reaction or regular histological staining. For on-section click reaction, sections of acellular organ scaffolds derived from in vivo or ex vivo metabolic engineering were incubated with Biotin-Alkyne click reaction mix, with and without copper (II) sulfate, for 1 hour at room temperature, followed by extensive washing with PBS. For regular histological staining of biotin and Laminin, the sections were incubated with Rabbit-anti-Laminin antibody (Abcam, ab11575, 1:200) overnight at 4° C., followed by staining with Alexa Fluor 488-conjugated Donkey-anti-Rabbit antibody (A-21206, 1:500) and Alexa Fluor 647-conjugated Streptavidin (Life Technologies, S-32357, 1:500). Images were acquired using a Nikon Eclipse TE200 microscope and NIS-Elements imaging software. The fluorescence intensity of Azide-Biotin-Streptavidin and Laminin staining was quantified using ImageJ (NIH).

Click Reaction and Western Blot

To conjugate Biotin-Alkyne onto the azide-labeled acellular lung ECM for Western blot analysis, a small piece of lung tissue was homogenized with gentleMACS Dissociator (Miltenyi Biotec) in PBS, and incubated with 1 ml Biotin-Alkyne click reaction mix for 1 hour at room temperature, followed by extensive washing in PBS. The ECM proteins from the clicked lung tissue was extracted using urea buffer as described below. For direct extraction of lung ECM and ECM-associated proteins, the acellular lung tissue was homogenized with gentleMACS Dissociator in urea buffer (5 M urea, 2 M thiourea, 50 mM DTT, 0.1% SDS and 1% protease inhibitor in PBS, pH 7.4) (see, e.g., Ngoka, L. Sample prep for proteomics of breast cancer: proteomics and gene ontology reveal dramatic differences in protein solubilization preferences of radioimmunoprecipitation assay and urea lysis buffers. *Proteome Science* 6, 30 (2008)), incubated with agitation for 2 hours at room temperature, and dialyzed against PBS using an Amicon Ultracentrifuge filter with 10 kDa molecular weight cut-off (Sigma-Aldrich). Following BCA quantification, the protein samples were analyzed using SDS-PAGE under reducing condition, transferred to nitrocellulose blotting membranes, and incubated with primary antibodies overnight at 4° C., followed by incubation with HRP-conjugated secondary antibodies for 1 hour at room temperature before autoradiography. Primary antibodies used include ATIII (Santa Cruz Biotechnology, sc-32453, 1:400) and Laminin (Abcam, ab11575, 1:1000), and secondary antibodies used include HRP-conjugated Donkey-anti-Rabbit antibody (Abcam, ab98440, 1:10,000) and HRP-conjugated Donkey-anti-Goat antibody (Abcam, ab98519, 1:10,000). For biotin analysis, the blot was incubated with HRP-conjugated Streptavidin (Life Technologies, 434323, 1:10,000).

Statistical Analysis

Statistical analysis was performed by one-way ONOVA with Tukey's multiple comparisons test or Student's t-tests. Statistical significance was defined as * $P<0.05$ and ** $P<0.01$. Values in graphs were presented as means with s.d. Microsoft Excel (Microsoft) and Prism 7 (GraphPad Software) were used for data management, statistical analysis and graph preparation.

Example 1—Comparison of Metabolic Labeling Efficiency of Three Azide-Labeled Sugars (Ac4GalNAz, Ac4GlcNAz and Ac4ManNAz)

The first step in the presently described methods and procedures is to generate ligands (azide tags) on decellularized organ/tissue scaffolds for chemoselective ligation (the click reaction) by metabolic labeling using azide-labeled sugars. In the described method, azide-labeled galactosamine (Ac4GalNAz) was used to metabolically label decellularized native organ/tissue scaffolds. Taking decellularized lung scaffolds as a model, it was demonstrated that Ac4GalNAz displayed superior labeling efficiency comparing to other commercially available azide-labeled sugars, such as Ac4GlcNAz and Ac4ManNAz.

Figure 1A:
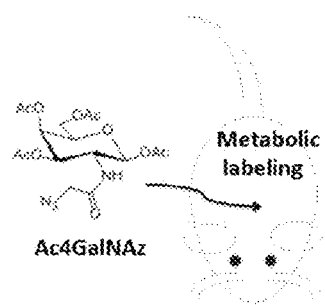
FIG. 1A shows administering azide-labeled sugars to the donor animals.
Figure 1B:
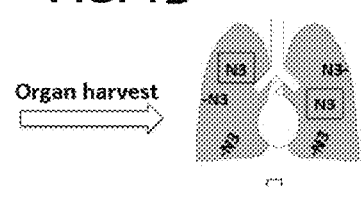
FIG. 1B shows both non-extracellular matrix (ECM) associated glycoproteins and ECM-associated glycoaminoglycans or glycoproteins labeled with azide tags. Diagram shows the lung as an example.
Figure 1D:
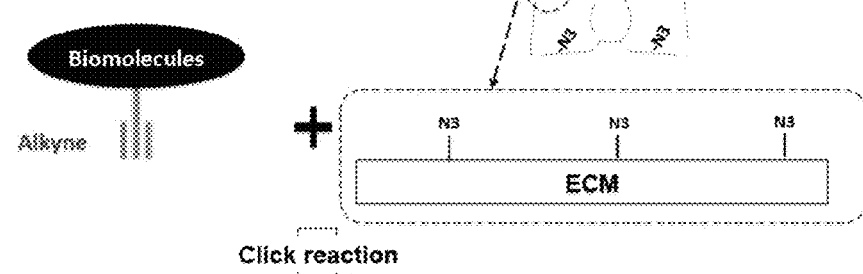
FIG. 1D shows biomolecules with diverse functions conjugated with alkyne functional group.
Figure 1E:
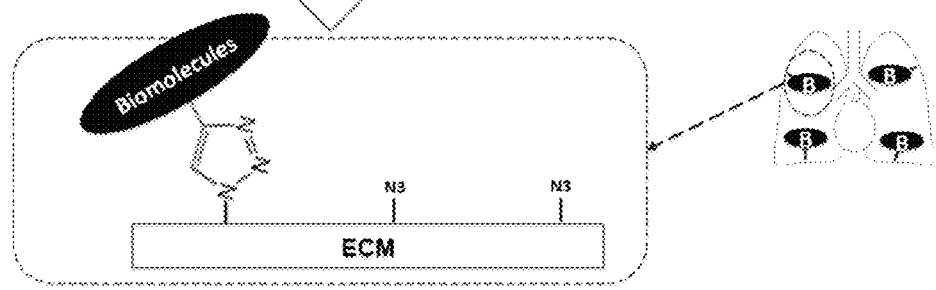
FIG. 1E shows alkyne-conjugated biomolecules immobilized onto decellularized organ scaffolds through the highly selective copper-catalyzed click reaction. Diagram shows the lung as an example.
Figure 2A:
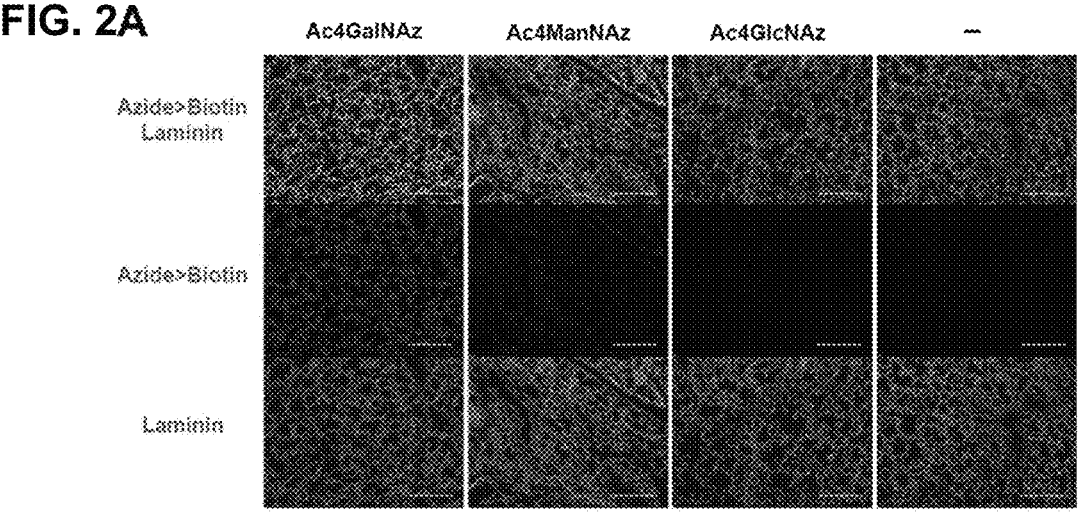
FIG. 2A shows detection of azide labeling in decellularized rat lung scaffolds after in vivo metabolic engineering using Ac4GalNAz, Ac4ManNAz and Ac4GlcNAz.

In FIG. 2A, images showed staining of azide tags (purple) and ECM component Laminin (green) on decellularized rat lungs after 3 days of metabolic labeling in donor rats. Azide tag staining was performed using biotin-alkyne (via click reaction)

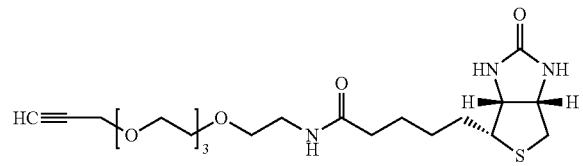

Figure 2B:
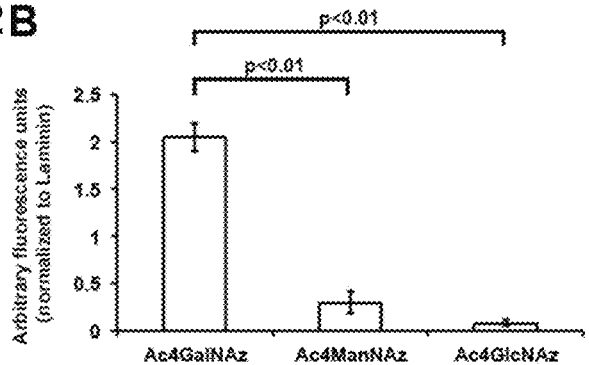
FIG. 2B shows quantification of biotin labeling by measuring the fluorescence intensity of biotin staining (normalized to the fluorescence intensity of ECM laminin staining).
Figure 2C:
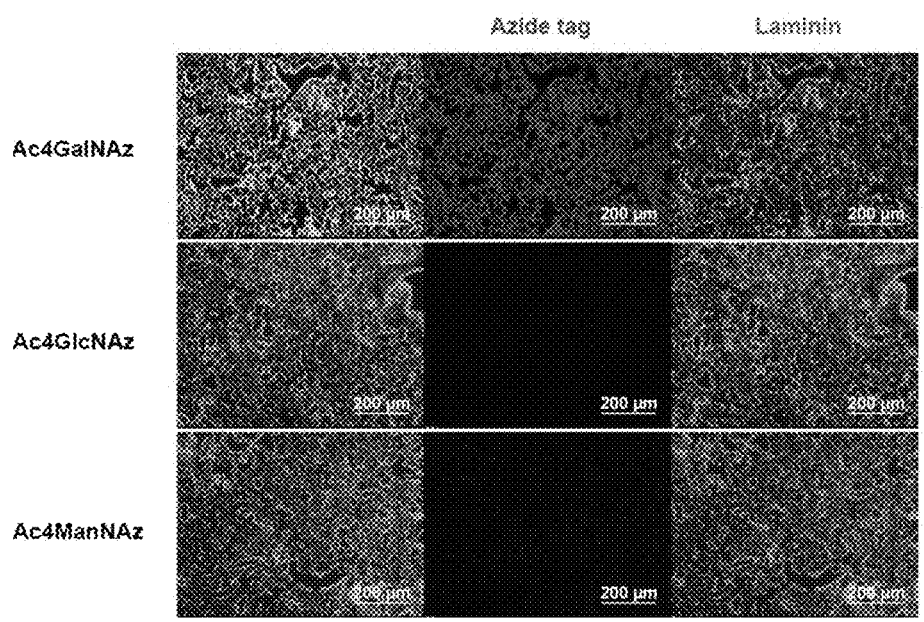
FIG. 2C shows comparison of metabolic labeling efficiency of three azide-labeled sugars (Ac4GlcNAz, Ac4GalNAz and Ac4ManNAz).
Figure 25A:
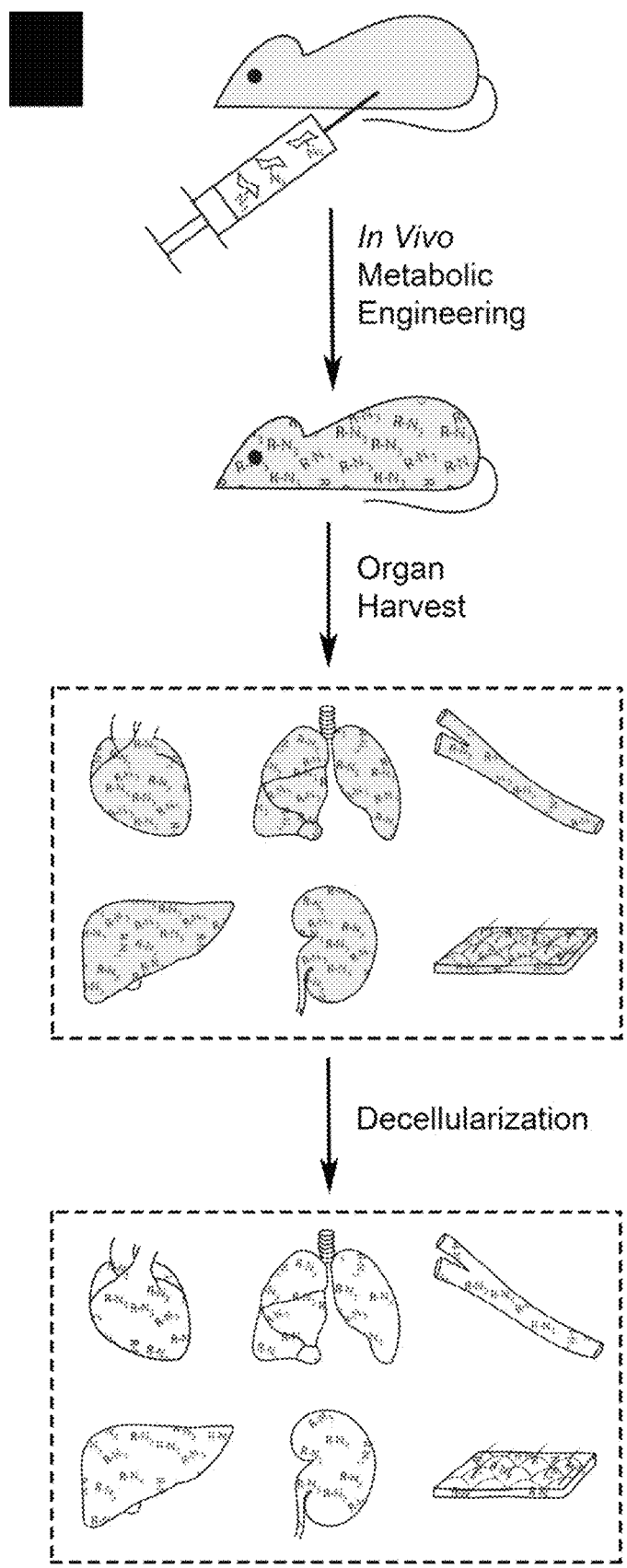
FIG. 25A is a diagram of in vivo metabolic engineering of organ ECM in the rat. Briefly, in vivo metabolic engineering is done by administration of metabolic labeling reagents via intraperitoneal injection daily for three days. The organs were then harvested and decellularized.

(SigmaAldrich, catalog No. 764213) and Alexa Fluor 647-conjugated streptavidin. (ThermoFisher, Catalog number: S21374). Ac4GalNAz displayed superior efficiency in labeling decellularized rat lung scaffolds, comparing to Ac4GlcNAz and Ac4ManNAz (See FIGS. 2A and 2B). Ac4GalNAz produced the strongest metabolic azide labeling intensity in acellular lungs (FIGS. 25C-25D).

Figure 25B:
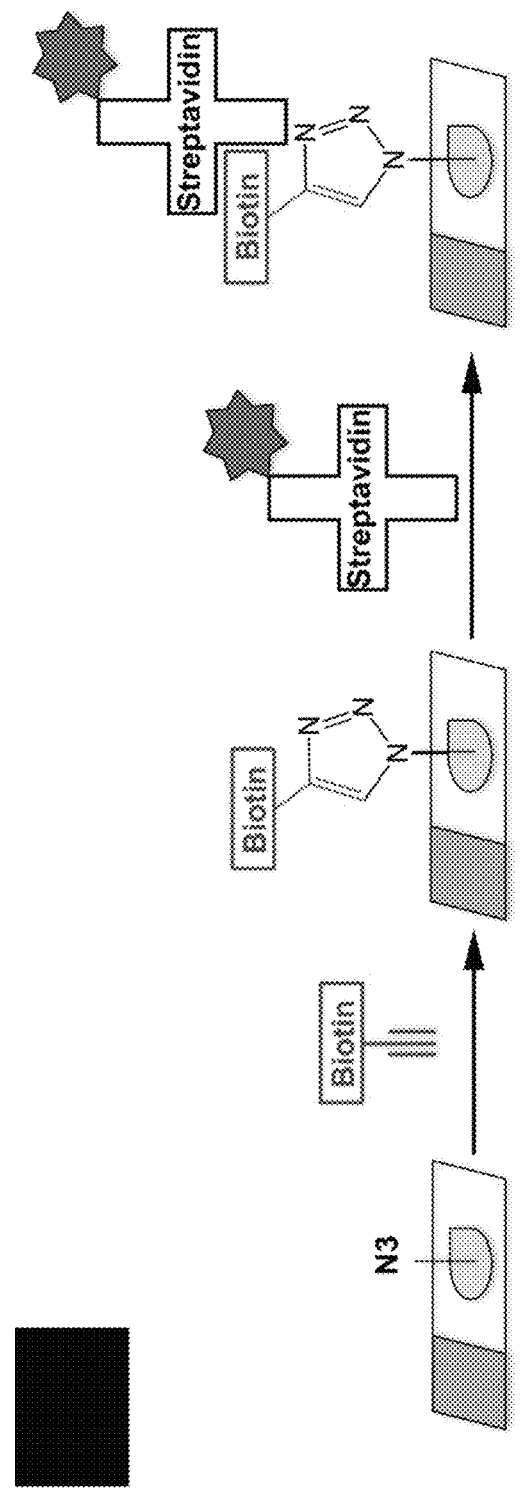
FIG. 25B is a diagram of detecting azide ligands in the ECM on a histological section by conjugating biotin-alkyne onto azide ligands via the click reaction, followed by biotin detection using fluorophore-conjugated streptavidin.
Figure 25C:
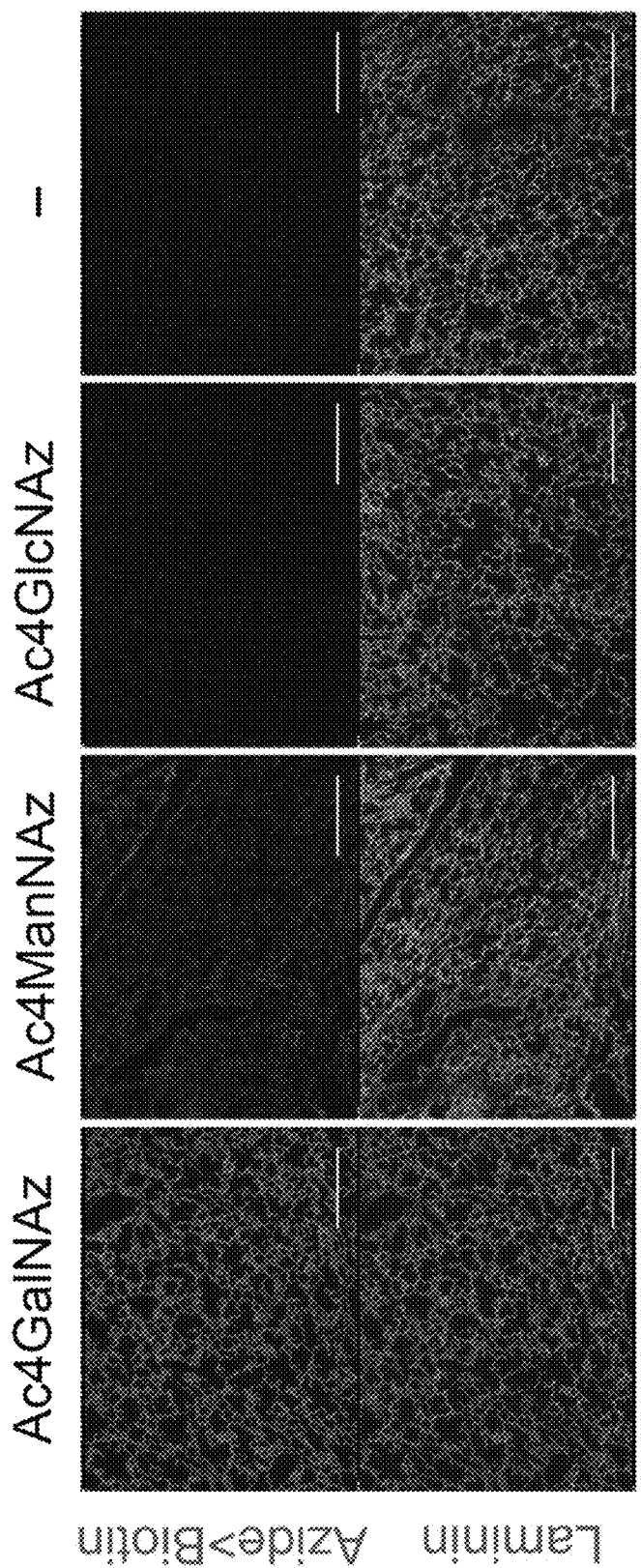
FIG. 25C contains images showing comparison of the in vivo metabolic labeling efficiency of acellular lung ECM by Ac4GalNAz, Ac4ManNAz and Ac4GlcNAz. Imaging detection of azide ligands in acellular lung ECM using biotin-alkyne click reaction and streptavidin staining (as shown in FIG. 25B), acellular lung ECM was co-stained with Laminin (scale bar: 200 μm).
Figure 25D:
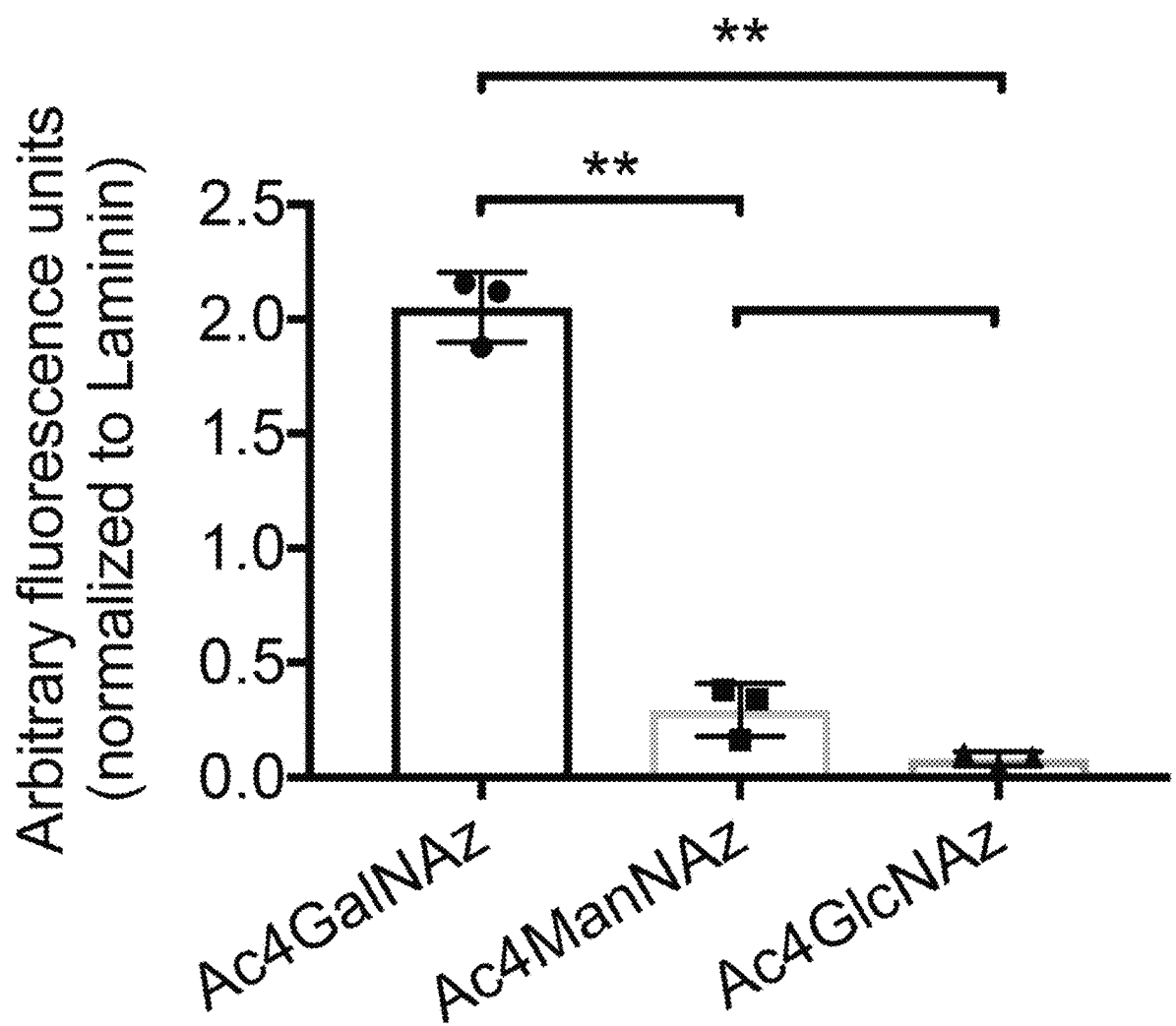
FIG. 25D is a bar graph showing comparison of the in vivo metabolic labeling efficiency of acellular lung ECM by Ac4GalNAz, Ac4ManNAz and Ac4GlcNAz. Quantification of azide-biotin-streptavidin labeling intensity, normalized to the fluorescence intensity of Laminin (n=3 for each metabolic labeling reagent). ** $P<0.01$.
Figure 25E:
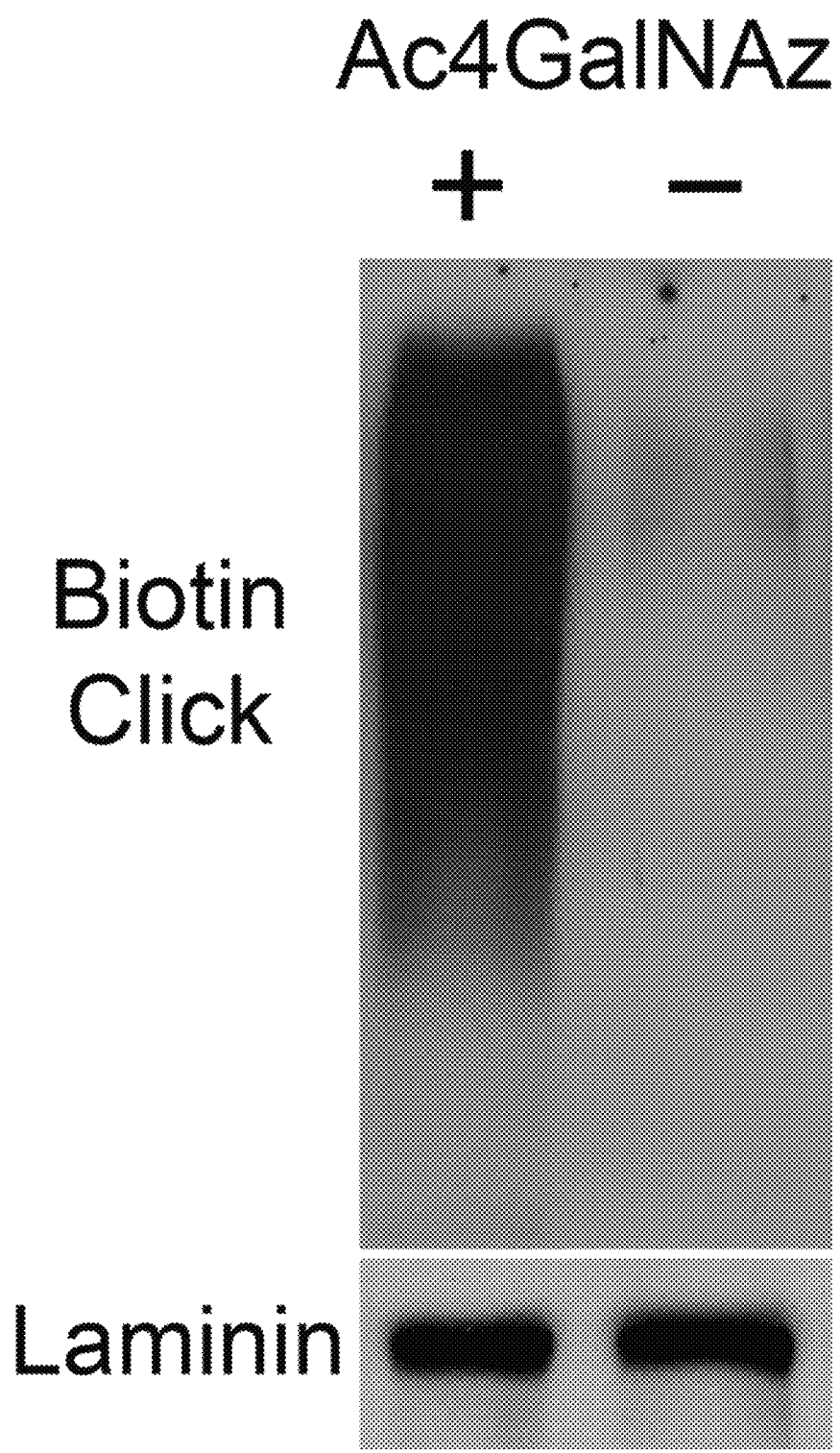
FIG. 25E is a Western blot showing detection of azide-biotin-streptavidin labeling in the ECM proteins extracted from acellular lung ECM after in vivo metabolic engineering using Ac4GalNAz or DMSO (control) (n=3 for each group). Laminin Western blot served as loading control.

Isolated ECM proteins from decellularized lungs labeled with Ac4GalNAz after click conjugation with biotin-alkyne were analyzed, showing the abundance of biotin labeling by western blot, which demonstrated that the azide labeling of the lung ECM is covalent in nature (see FIG. 25E).

Ac4GalNAz was further demonstrated efficient in vivo metabolic azide labeling of decellularized scaffolds of the rat carotid artery, heart, liver, kidney and skin through three-day intraperitoneal administration of Ac4GalNAz (See Example 5).

Figure 3:
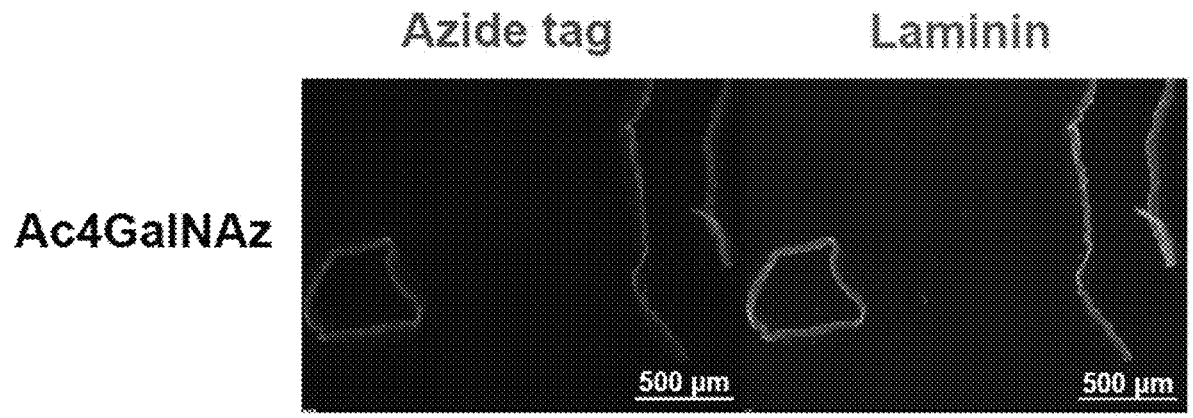
FIG. 3 shows in vivo metabolic labeling of rat carotid arteries using Ac4GalNAz.

It was also demonstrated that the metabolic labeling using Ac4GalNAz can be performed in both growing and aged animals, it can also be performed in isolated organs during ex vivo culture (see Example 4). Besides the lung, efficient metabolic labeling using Ac4GalNAz was also achieved in the decellularized scaffolds of blood vessels (See FIG. 3) and skin flaps. The same labeling technique can be applied to many other organs/tissues, and decellularized products from larger animals, such as porcine scaffolds. In FIG. 3, images showed staining of azide tags (purple) and ECM component Laminin (green) on decellularized rat carotid arteries after 3 days of metabolic labeling in donor rats. Azide tag staining was performed using biotin alkyne (via click reaction) and Alexa Fluor 647-conjugated streptavidin.

Example 2a—Generation of Clickable Heparin (Heparin-Alkyne)

Methods were developed to generate alkyne-conjugated biomolecules of interest, so that these alkyne-biomolecules can be selectively immobilized onto azide-modified decellularized organ scaffolds. For example, clickable heparin was generated by conjugating an alkyne group to the aldehyde termini of deaminated heparin. Briefly, approximately 10 mM of deaminated heparin (Carbomer) was reacted at room temperature for 20 h with 100 mM of o-(prop-2-ynyl)-hydroxylamine hydrochloride (Santa Cruz) in 0.1 M sodium citrate solution (pH 4.5) in the presence of 90 mM of p-phenylenediamine (Sigma) catalyst. The product was dialyzed against water using an Amicon Ultracentrifuge filter with a 3 kDa molecular weight cut off. Successful conjugation of deaminated heparin to o-(prop-2-ynyl)-hydroxylamine hydrochloride was examined by reacting 450 uM of the dialyzed product to 550 uM 30 kDa PEG-azide molecule for 1 hour in two click conditions (with or without copper catalyst), and electrophoresis using 1% (w/v) barium acetate 0.5% agarose gel in 0.05M diaminopropane buffer (pH 9.0). The gel was fixed by immersing it in 0.1% (w/v) N-cetyl-N,N,N-trimethylammonium bromide in water for 15 min, stained with a fresh solution of 0.1% (w/v) toluidine blue in acetic acid:ethanol:water (0.1:5:5 ratio) for 3 hours, and destained in 10% (v/v) ethanol.

Figure 4:
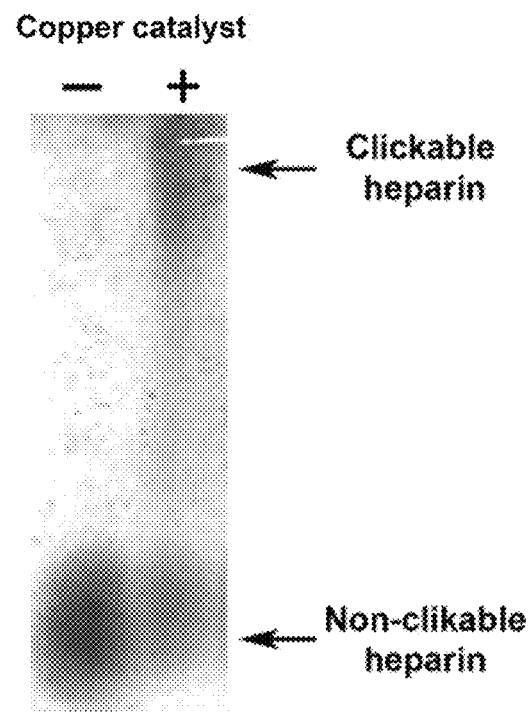
FIG. 4 shows generation of clickable heparin (heparin-alkyne).

In FIG. 4, alkyne-conjugated heparin (heparin-alkyne) was reacted with PEG(30K)-Azide using click reaction with and without copper catalyst. Only in the presence of copper catalyst, heparin-alkyne displayed a molecular shift due to the conjugation between heparin and PEG(30K)-azide via the click reaction between the alkyne on heparin and the azide on PEG(30K).

Example 2b—Synthesis and Properties of Heparin-Alkyne-Biotin (Heparin-AB)

240 mg heparin (Sigma-Aldrich) was mixed with 12 mM EDC (Sigma-Aldrich) and 12 mM Sulfo-NHS (Life Technologies) in MES buffer (pH 4.7, Sigma-Aldrich) for 30 min at room temperature. Subsequently, 20 mM EZ-Link Amine-PEG3-Biotin (Life Technologies) and 20 mM Amine-PEG4-Alkyne (Click Chemistry Tools) were added to the reaction, and the pH was increased to 8.0. After 2-hour incubation with agitation at room temperature, the product was extensively dialyzed against PBS using Amicon Ultracentrifuge filters with 3-kDa molecular weight cut-off (Sigma-Aldrich).

The synthesis of Heparin-Alkyne-Biotin (Heparin-AB) is shown in FIG. 27A.

The biotin modification of heparin allows easy visualization of immobilized heparin. A Collagen-Azide well assay was further developed, where azide was conjugated onto collagen-coated wells, as a simple model of azide-labeled ECM. This allowed click immobilization of Heparin-AB onto azide-labeled ECM for visualization and bioactivity assessment (see diagram in FIG. 27B). Click immobilization of Heparin-AB onto the collagen wells was performed with and without azide labeling, and observed specific immobilization of Heparin-Biotin (Heparin-B) (see FIGS. 27C and 27D), which further immobilized Antithrombin III (ATIII) (see FIG. 27E) and allowed expedited inhibition of Factor Xa (FXa) (see FIG. 27F).

Example 3—Generation of Clickable Vancomycin (Vancomycin-Alkyne)

Methods:

Vancomycin was purchased from Cayman Chemical (catalog No. 15327, CAS No. 1404-93-9). Alkyne-PEG$_5$-N-hydroxysuccinimidyl ester was purchased from Sigma Aldrich (Catalog No. 764191). Alkyne-PEG$_5$-N-hydroxysuccinimidyl ester was prepared as a stock solution of 30 mM in DMSO.

Figure 22:
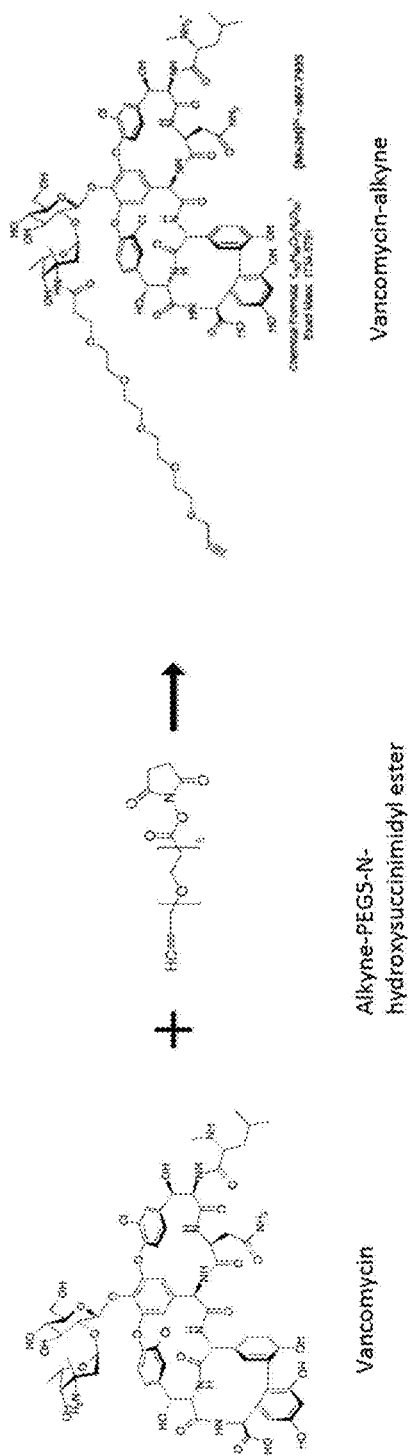
FIG. 22 is a diagram showing the conjugation reaction of vancomycin to alkyne-$PEG_5$-N-hydroxysuccinimidyl ester.
Figure 23:
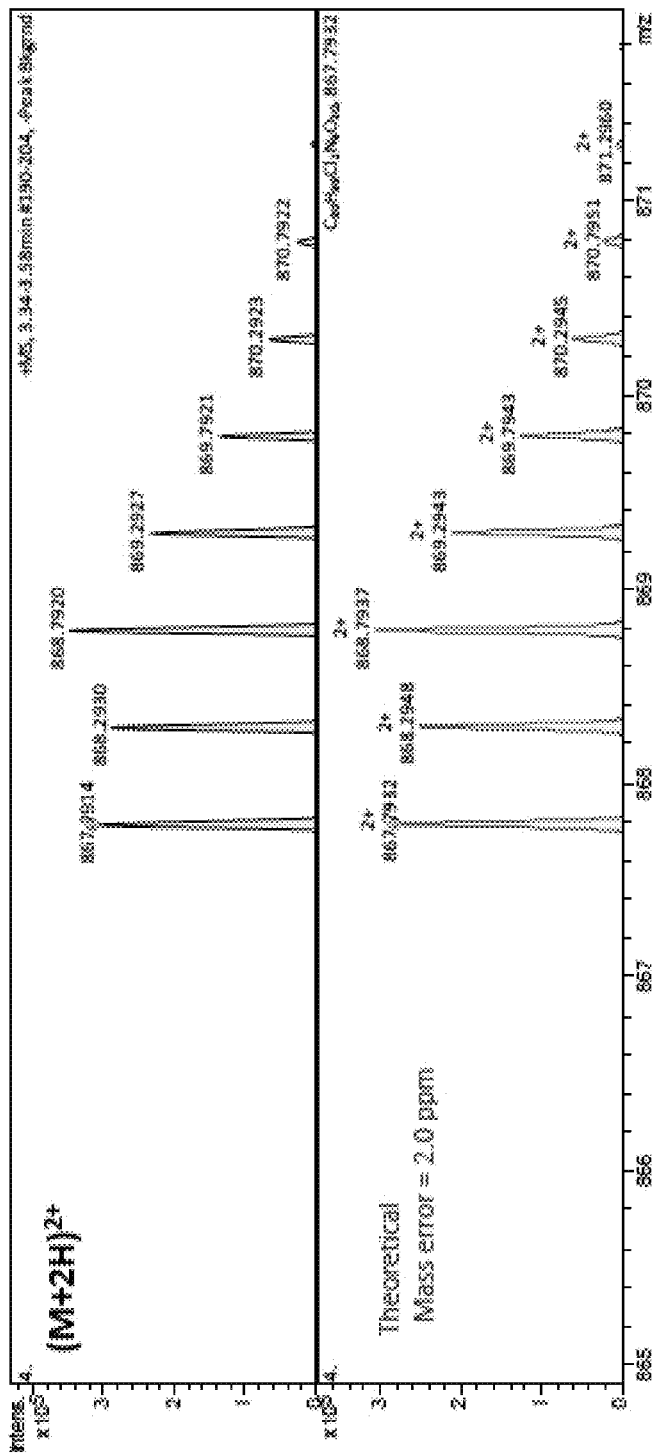
FIG. 23 is LC-MS/MS chromatogram conforming the structure of vancomycin-alkyne.

Preparation of Vancomycin-Alkyne:

Vancomycin (1 mM) was reacted with 3 mM Alkyne-PEG5-N-hydroxysuccinimidyl ester in DPBS (pH 8.3) for 24 hours at room temperature. The resulting vancomycin-alkyne was purified by HPLC. FIG. 22 shows synthetic scheme for the preparation of vancomycin-alkyne from vancomycin and alkyne-PEG$_5$-N-hydroxysuccinimidyl ester. FIG. 23 shows full scan mass spec of the vancomycin-alkyne product.

Example 4. In Vivo Metabolic Labeling of Extracellular Matrix of Organs/Tissues

Methods

Figure 13:
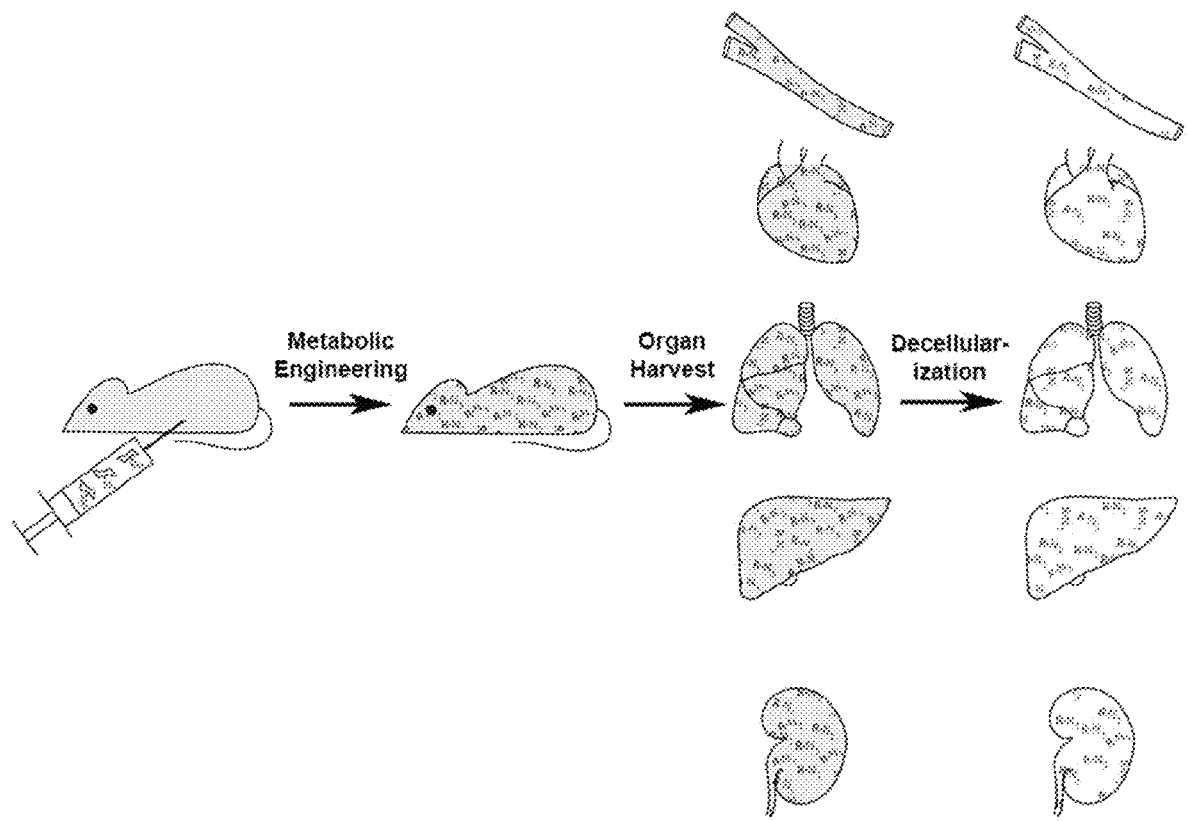
FIG. 13 shows diagram of in vivo metabolic engineering of decellularized scaffolds of rat organs/tissues.

For metabolic engineering of organs/tissues in vivo in the rat model, azide-labeled sugars (300 mg/kg body weight in 70% DMSO) were administered through intraperitoneal injection daily. One day after the last azide-labeled sugar administration, organs/tissues were harvested and perfusion decellularized (See FIGS. 1 and 13). The presence of azide labeling in the decellularized scaffolds were evaluated by performing copper-catalyzed click reaction.

Figure 5:
FIG. 5 shows decellularized rat epigastric dermal matrix flap with deep inferior epigastric artery and vein cannulated.

Animal Feeding, Organ Isolation and Decellularization:

100 gram Sprague Dawley Rats were injected intraperitoneally (300 mg/kg body weight in 70% DMSO) with azide-labeled galactosamine (Ac4GalNAz) for 3 days or 7 days prior to end-point tissue harvest, and perfusion decellularization of whole organs. See diagram in FIG. 25A. After the in vivo incorporation phase was completed, the animals were anesthetized, shaved, and prepared for surgery. Laparotomy was performed and the animals were systematically heparinized and sacrificed by exsanguination. Full thickness skin flaps in the distribution of the deep inferior epigastric artery were harvested with the vascular pedicle intact. The artery was cannulated and all branches were ligated. The flaps were then sterilely moved into a perfusion decellularization biochamber and decellularized according to previously described protocols (e.g., a protocol described in Ott, H. C. et al. Nat. Med., 2008, 14, 213-221) (See FIG. 5). After decellularization, samples were excised and fixed for histologic analysis (See FIGS. 6A-D).

Confirmation of Azide Incorporation:

Decellularized scaffolds after metabolic engineering and decellularization were fixed in 4% paraformaldehyde overnight at 4° C. The scaffolds were then embedded in paraffin and sectioned at 5-μm thickness. The paraffin-embedded sections were deparaffinized and rehydrated according to standard histological staining procedures. Copper-catalyzed click reaction was performed on these sections using alkyne-conjugated biotin (10 μM) and Click-iT® Cell Reaction Buffer Kit (ThermoFisher, Catalog number: C10269) for one hour at room temperature, followed by detection of biotin by fluorophore-conjugated streptavidin.

Figure 7:
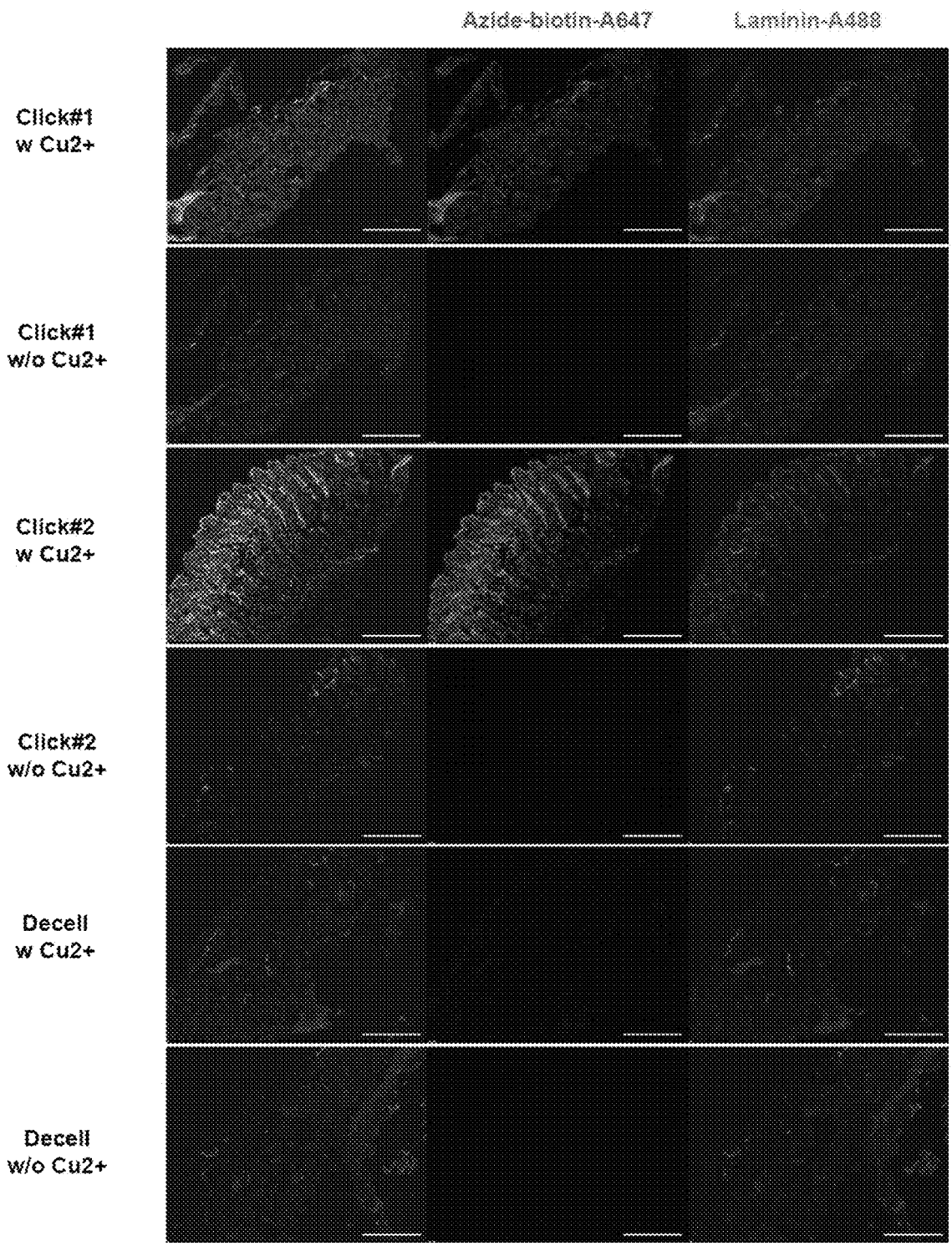
FIG. 7 shows in vivo metabolic labeling of rat epigastric flaps using Ac4GalNAz.

Azide incorporation within the decellularized ECM on histological sections was assessed by conjugating biotin-alkyne onto the azide ligands using the click reaction, followed by biotin detection using fluorophore-conjugated streptavidin, see FIG. 25B. Confirmation of azide incorporation onto the decellularized ECM was confirmed using histologic analysis with immunofluorescence:

In FIG. 7, images demonstrate staining of azide tags (purple) and ECM component Laminin (green) on decellularized rat epigastric flaps after 3 days of metabolic labeling in donor rats (Click #1 and Click #2). Azide tag staining was performed using biotin-alkyne (via click reaction) and Alexa Fluor 647-conjugated streptavidin. Images demonstrate lack of azide tags, with or without Cu on decellularized rat epigastric flaps after 3 days of DMSO injections for negative control (Decell).

Figure 14:
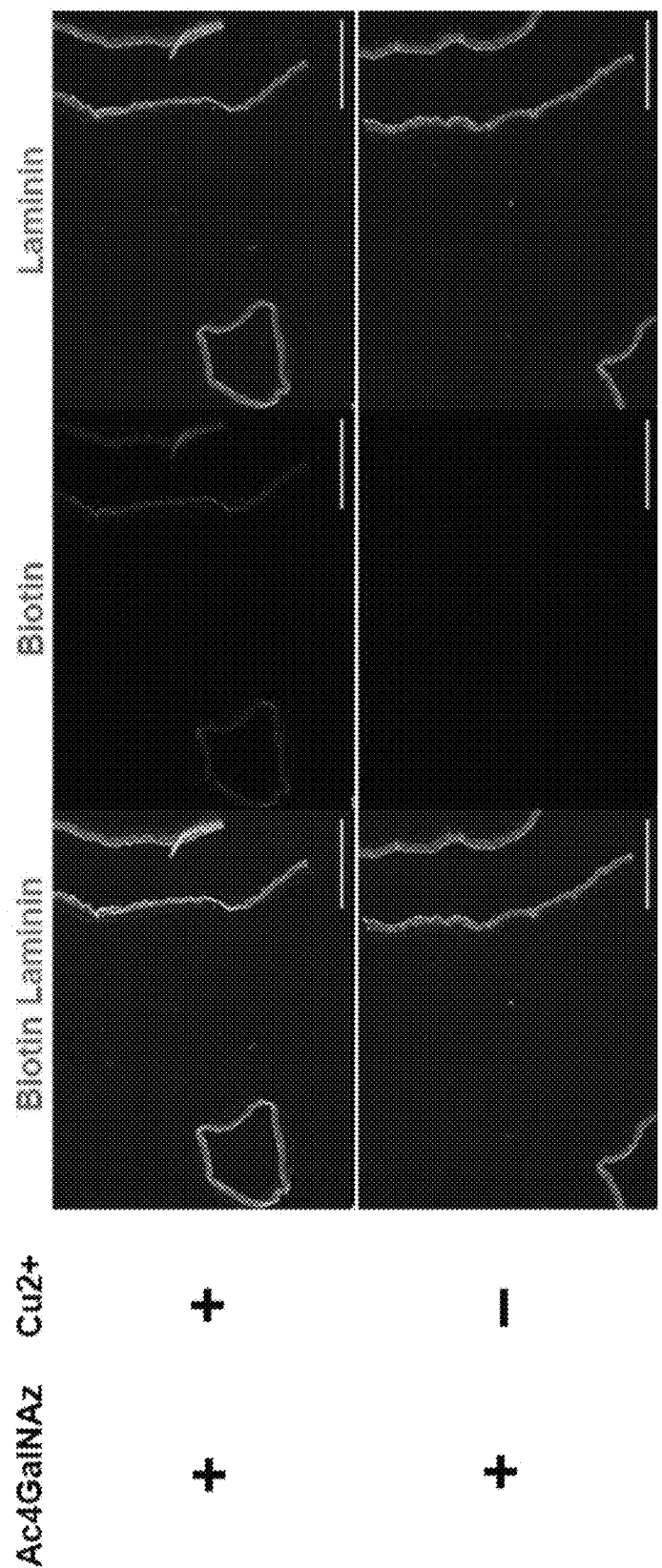
FIG. 14 shows detection of azide labeling in decellularized rat carotid artery scaffolds after in vivo metabolic engineering using Ac4GalNAz.

FIG. 14 shows detection of azide labeling in decellularized rat carotid artery scaffolds after in vivo metabolic engineering using Ac4GalNAz. The samples were co-stained with laminin, which is an abundant ECM protein, to facilitate visualization of the decellularized ECM (Scale: 500 µm).

Figure 15:
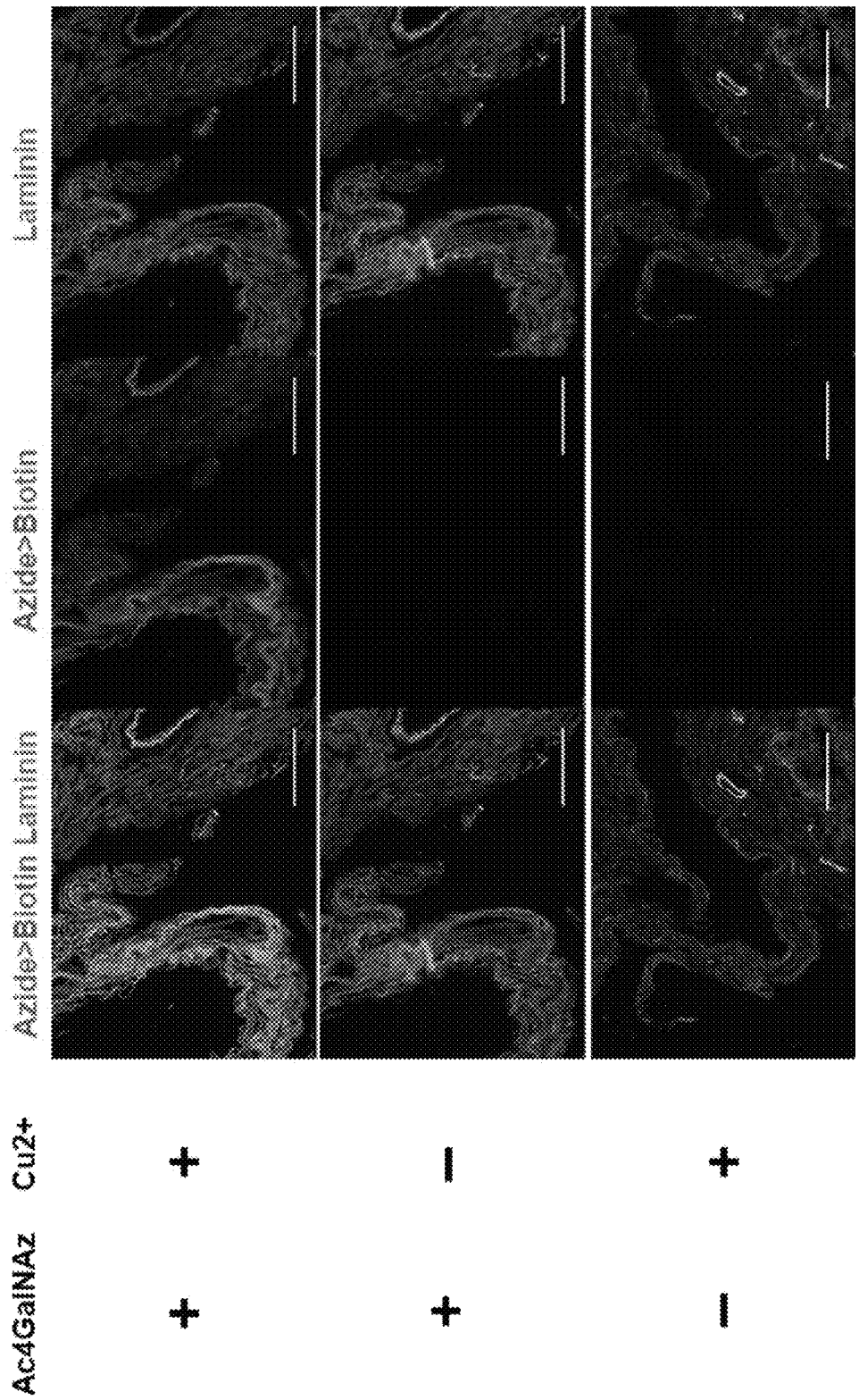
FIG. 15 shows detection of azide labeling in decellularized rat heart scaffolds after in vivo metabolic engineering using Ac4GalNAz.

FIG. 15 shows detection of azide labeling in decellularized rat heart scaffolds after in vivo metabolic engineering using Ac4GalNAz. The samples were co-stained with laminin, which is an abundant ECM protein, to facilitate visualization of the decellularized ECM (Scale: 200 µm).

Figure 16:
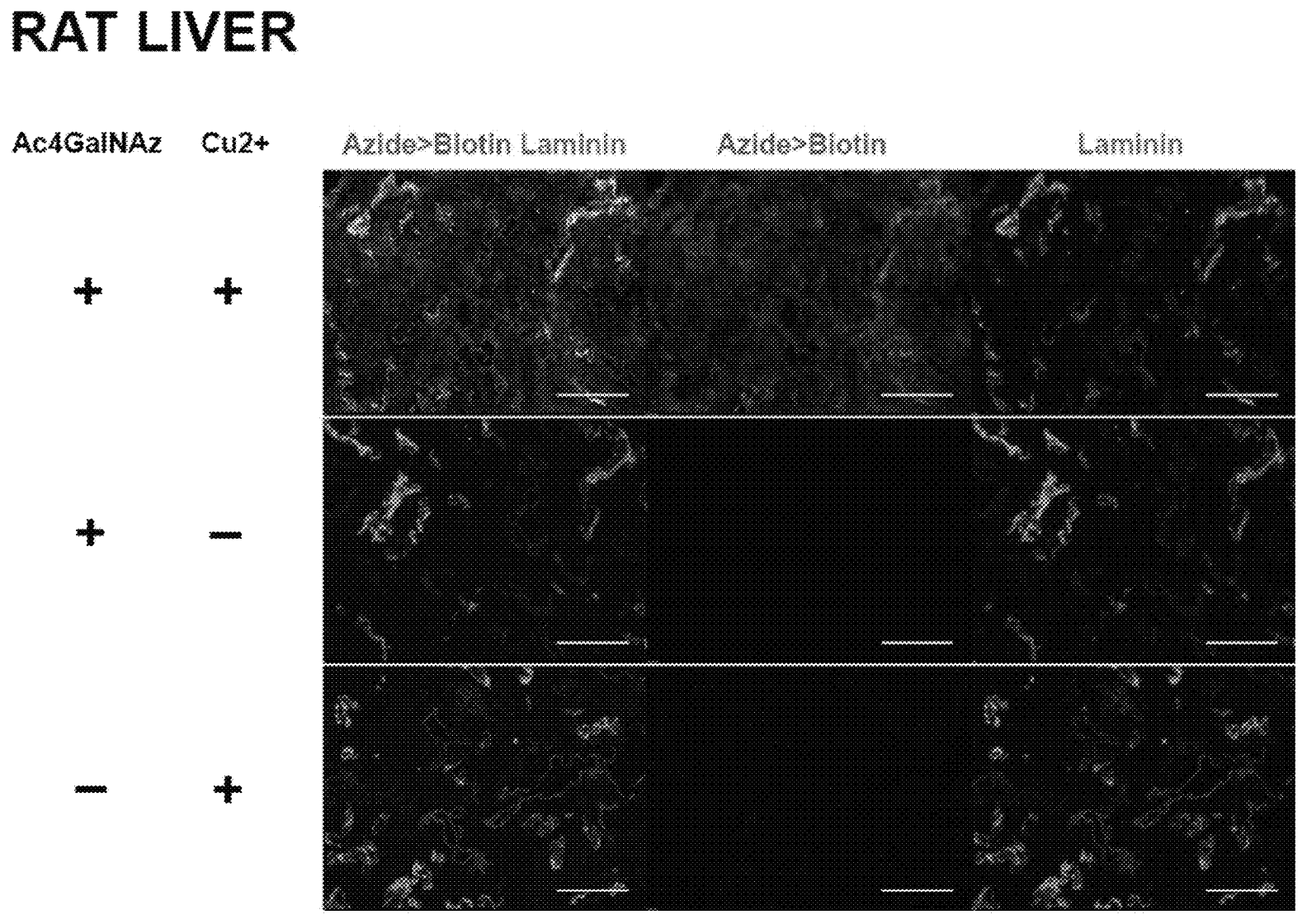

FIG. 16 shows detection of azide labeling in decellularized rat liver scaffolds after in vivo metabolic engineering using Ac4GalNAz. The samples were co-stained with laminin, which is an abundant ECM protein, to facilitate visualization of the decellularized ECM (Scale: 200 µm).

Figure 17:
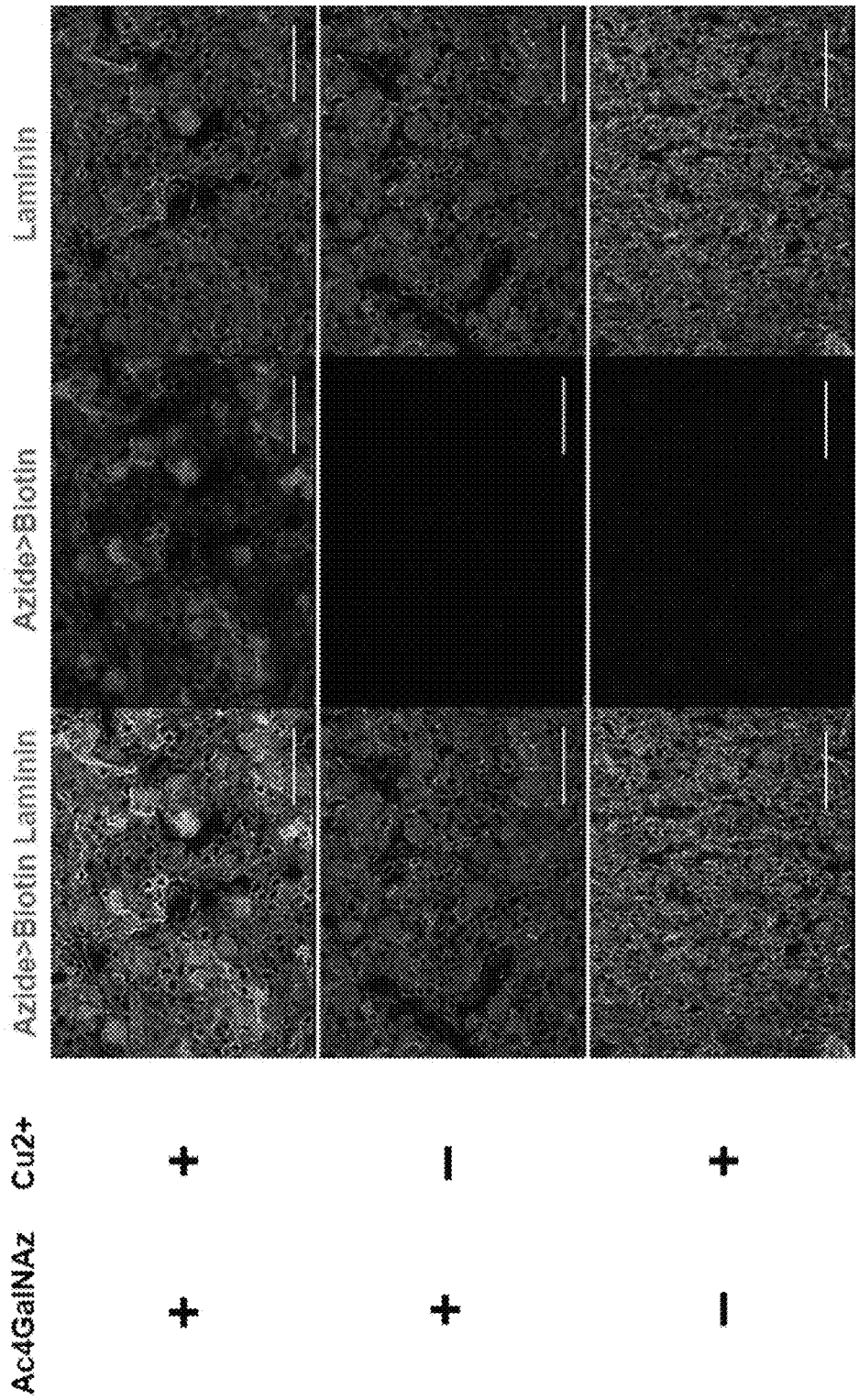
FIG. 17 shows detection of azide labeling in decellularized rat kidney scaffolds after in vivo metabolic engineering using Ac4GalNAz.

FIG. 17 shows detection of azide labeling in decellularized rat kidney scaffolds after in vivo metabolic engineering using Ac4GalNAz. The samples were co-stained with laminin, which is an abundant ECM protein, to facilitate visualization of the decellularized ECM (Scale: 200 µm).

Figure 18:
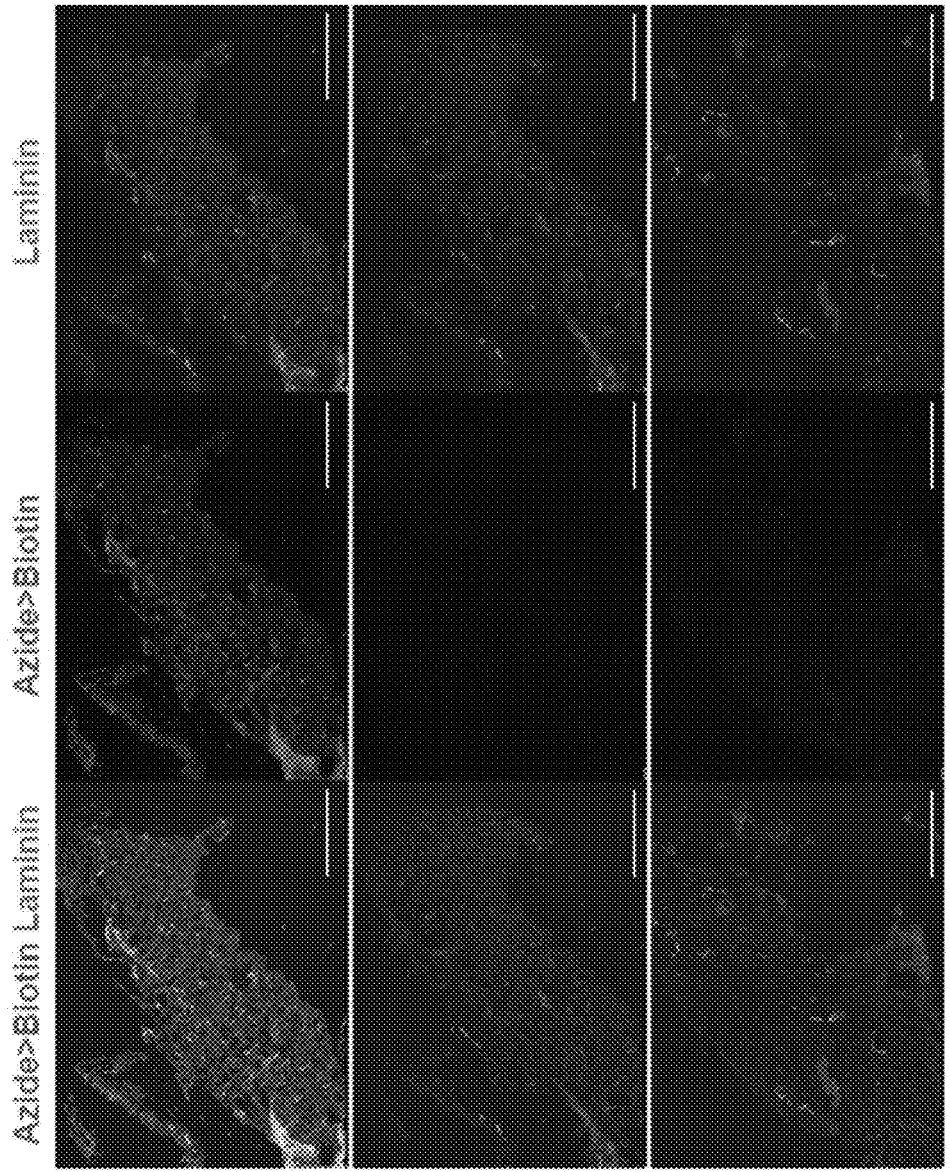
FIG. 18 shows detection of azide labeling in decellularized rat skin scaffolds after in vivo metabolic engineering using Ac4GalNAz.

FIG. 18 shows detection of azide labeling in decellularized rat skin scaffolds after in vivo metabolic engineering using Ac4GalNAz. The samples were co-stained with laminin, which is an abundant ECM protein, to facilitate visualization of the decellularized ECM (Scale: 500 µm).

Experiments shown in FIGS. 28-32 demonstrated strong and specific ECM labeling of the heart, liver, kidney, skin and carotid artery derived from animals administered with Ac4GalNAz. This highlights the broad applicability of the metabolic engineering strategy described herein.

Example 5—Click Reaction of Azide-Labeled Decellularized Scaffolds with Vancomycin-Alkyne Vancomycin is made clickable by conjugating an alkyne group to the only primary amine present as described above (see, e.g., FIG. 22, Example 3). The structure of the resulting clickable vancomycin-alkyne was confirmed by LC-MS/MS analysis (FIG. 23). Using the previously described click reaction, Vancomycin was immobilized onto the ECM. Copper-catalyzed click reaction was performed on decellularized rat epigastric flaps by perfusion (0.5 ml/min) using Vancomycin-alkyne (100 µM) and Click-iT® Cell Reaction Buffer Kit (ThermoFisher, Catalog number: C10269) for one hour at room temperature, followed by intensive washing and detection of immobilized vancomycin using a vancomycin-specific antibody.

Figure 24:
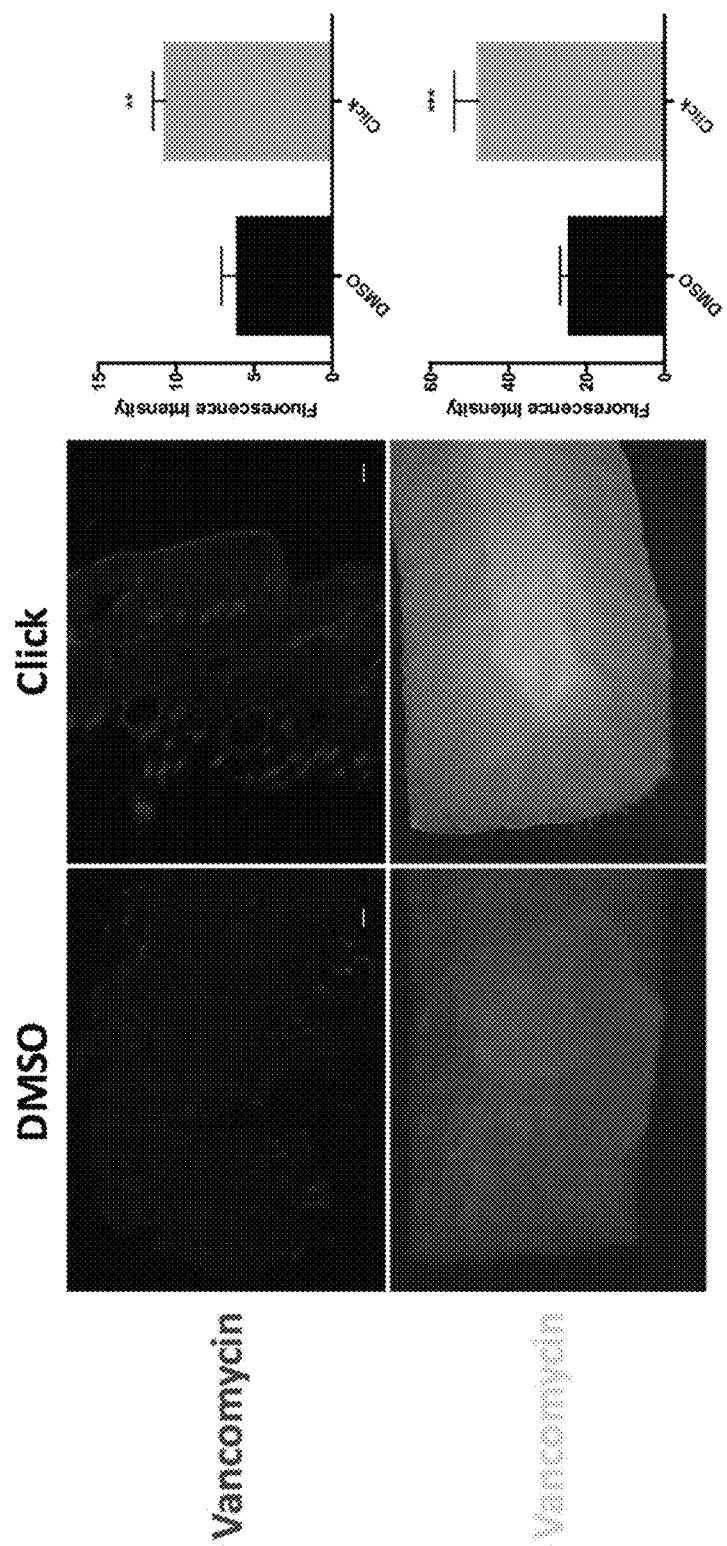
FIG. 24 is an image showing immunofluorescent staining for vancomycin on decellularized rat epigastric flaps (REFs) after click reaction.

In FIG. 24, images show immunofluorescent staining for vancomycin immobilized on decellularized ECM of the rat epigastric flap (REF) after click reaction, DMSO control (A, upper left image) versus Ac4GalNAz-labeled REF (B, upper right image) after staining for vancomycin (red) (scale bar=100 µM). Referring to FIG. 24, fluorescence intensity quantification of staining from AB shows an increase in vancomycin on the Ac4GalNAz-labeled REF (p<0.05). FIG. 24 shows epifluorescent staining for vancomycin (green) on whole mount REF, DMSO control (D, lower left image) versus Ac4GalNAz-labeled REF (E, lower right image). Fluorescence intensity quantification of staining from D/E shows an increase in vancomycin on the Ac4GalNAz-labeled REF (p<0.001). Both on cross-sections and whole-mount staining the level of vancomycin is higher on the ECM with metabolically labeled azide tag, comparing to the ECM without azide labeling (DMSO control). The resulting mesh, is then stored in 20% sucrose at −20° C. for further testing and/or use as described herein.

Conclusions:

There are numerous potential benefits of a dermal matrix mesh with immobilized Vancomycin. The mesh should be much more resistant to Vancomycin-sensitive bacterial infiltration and subsequent biofilm formation. Vancomycin effectively kills the most common bacteria cultured from infected mesh. By eliminating these bacteria the mesh better maintains essential biomechanical properties and is more durable, long-term solution for patients with complex abdominal wall pathology. Moreover, by using this mesh, superficial site infections after abdominal wall reconstruction with mesh would be markedly reduced. Treating patients with Vancomycin is challenging and burdensome to the health care system. It requires patients to have intravenous access and typically demands at least twice daily dosing, in addition to therapeutic drug level monitoring for efficacy and safety. Renal toxicity from vancomycin is a significant health problem. In the system as described herein, the vancomycin-functionalized mesh is immobilized onto the ECM resulting in virtually no Vancomycin in systemic circulation thereby greatly reducing the potential for toxicity. In addition to abdominal wall reconstruction, biologic mesh is widely used in reconstructive surgery to support prosthetic implants. Infection is a rare but devastating complication for these procedures and an infection-resistant mesh provides benefit for use in these procedures.

Advantages

Figure 8:
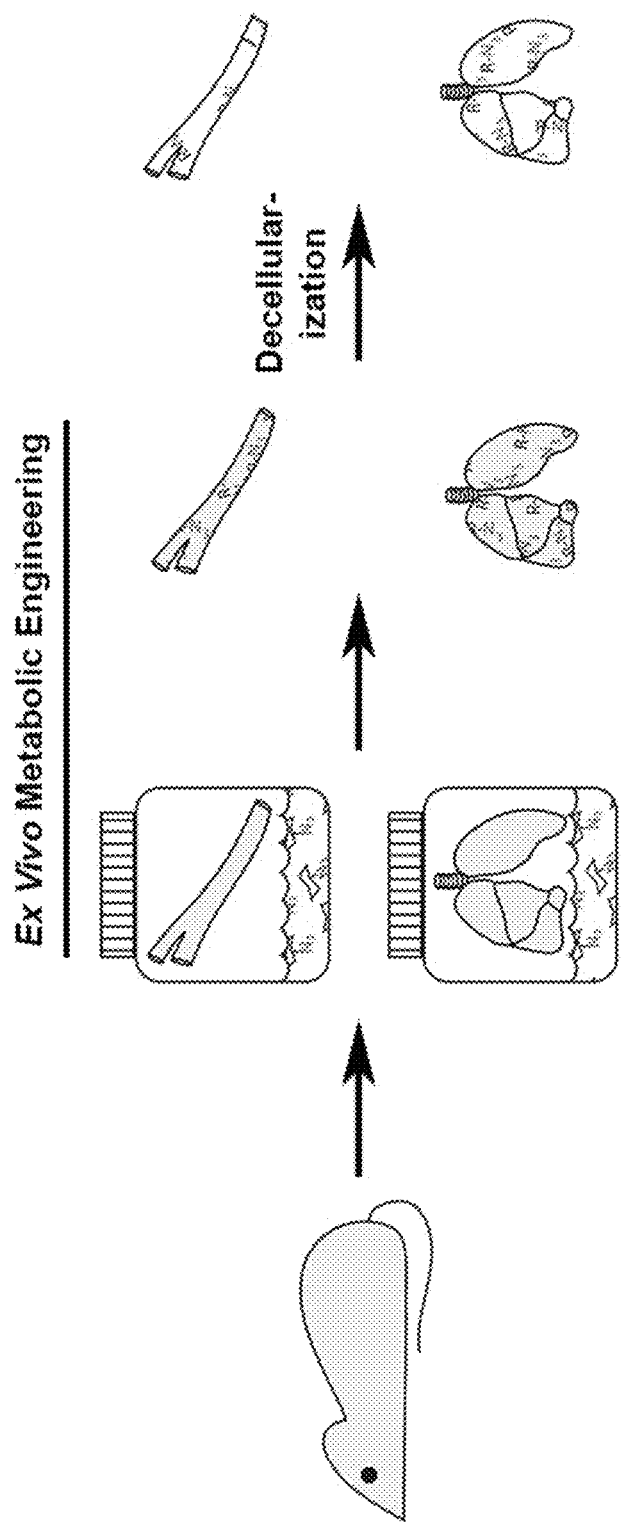
FIG. 8 shows diagram of ex vivo metabolic engineering of decellularized scaffolds of rat organs/tissues.
Figure 9:
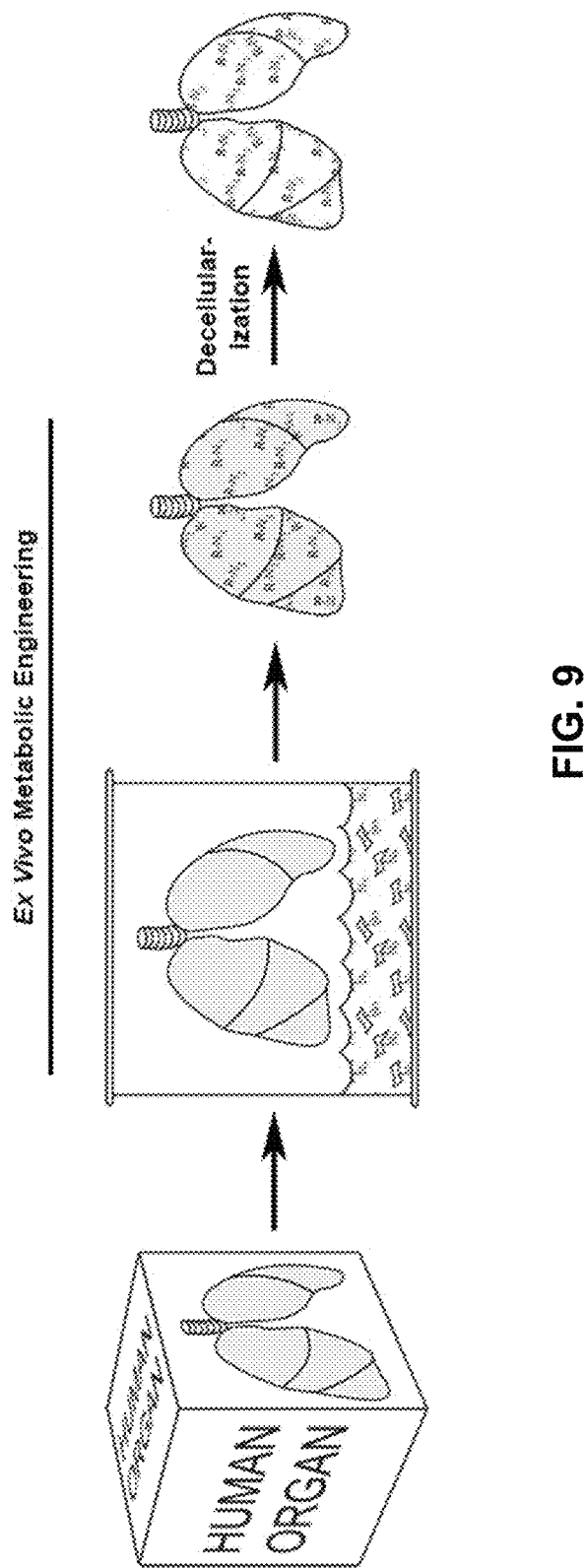
FIG. 9 shows diagram of ex vivo metabolic engineering of decellularized scaffolds of human lungs.

Vancomycin-coated mesh provides significant resistance against bacterial infections resulting in a more durable and functional reconstructive material Example 6a—Ex Vivo Metabolic Labeling of Extracellular Matrix of Organs/Tissues Methods of Incorporation of Biorthogonal Reactive Ligands in ECM For metabolic engineering of isolated organs/tissues during ex vivo culture, DMEM/F12 medium supplemented with 10% fetal bovine serum and 1% Penicillin-Streptomycin (1:100 dilution of a stock of 10,000 units/mL of penicillin and 10,000 µg/mL of streptomycin) was used. Azide-labeled sugar (Ac4GalNAz) was added to the culture medium at 50 µM. The organs/tissues were cultured using constant rate perfusion for one day in a bioreactor (FIG. 21). For rat lung, the perfusion rate was 5 ml/min. For a lobe of human lung, the perfusion rate was 10 ml/min. For rat epigastric flaps, the perfusion rate was 0.2 ml/min. After culture, the organ/tissues were perfusion decellularized (See FIG. 8 and FIG. 9).

See diagram shown in FIG. 26A showing metabolic azide labeling of the ECM during the ex vivo culture of freshly isolated organs. Freshly isolated rat lungs cultured in DMEM/F12 medium containing 10% fetal bovine serum (DMEM/F12-FBS) with and without the supplementation of Ac4GalNAz (50 µM) for one day in a bioreactor under constant rate perfusion (5 ml/min), followed by perfusion decellularization (FIG. 26A) showed robust covalent azide labeling of the lung ECM only in the presence of Ac4GalNAz during the ex vivo culture and Cu(I) catalyst during the click conjugation with biotin-alkyne (see FIGS. 26B and 26C and experiments described herein).

The freshly isolated porcine left lung was cultured in the same DMEM/F12-FBS medium, with and without supplementation of 50 µM Ac4GalNAz, for one day under constant rate perfusion (300 ml/min), followed by perfusion decellularization (FIGS. 26A, 26D and 26E). Consistent with what was observed in the acellular rat lung ECM engineering, specific and covalent azide incorporation into the metabolically engineered acellular porcine lung ECM can be detected using click conjugation with biotin-alkyne (see FIGS. 26F and 26G).

Confirmation of Azide Incorporation:

The presence of azide labeling in the decellularized scaffolds were evaluated by performing copper-catalyzed click reaction. Decellularized scaffolds after metabolic engineering and decellularization were fixed in 4% paraformaldehyde overnight at 4° C. The scaffolds were then embedded in paraffin and sectioned at 5-µm thickness. The paraffin-embedded sections were deparaffinized and rehydrated according to standard histological staining procedures. Copper-catalyzed click reaction was performed on these sections using alkyne-conjugated biotin (10 µM) and Click-iT® Cell Reaction Buffer Kit (ThermoFisher, Catalog number: C10269) for one hour at room temperature, followed by detection of biotin by fluorophore-conjugated streptavidin.

Figure 10:
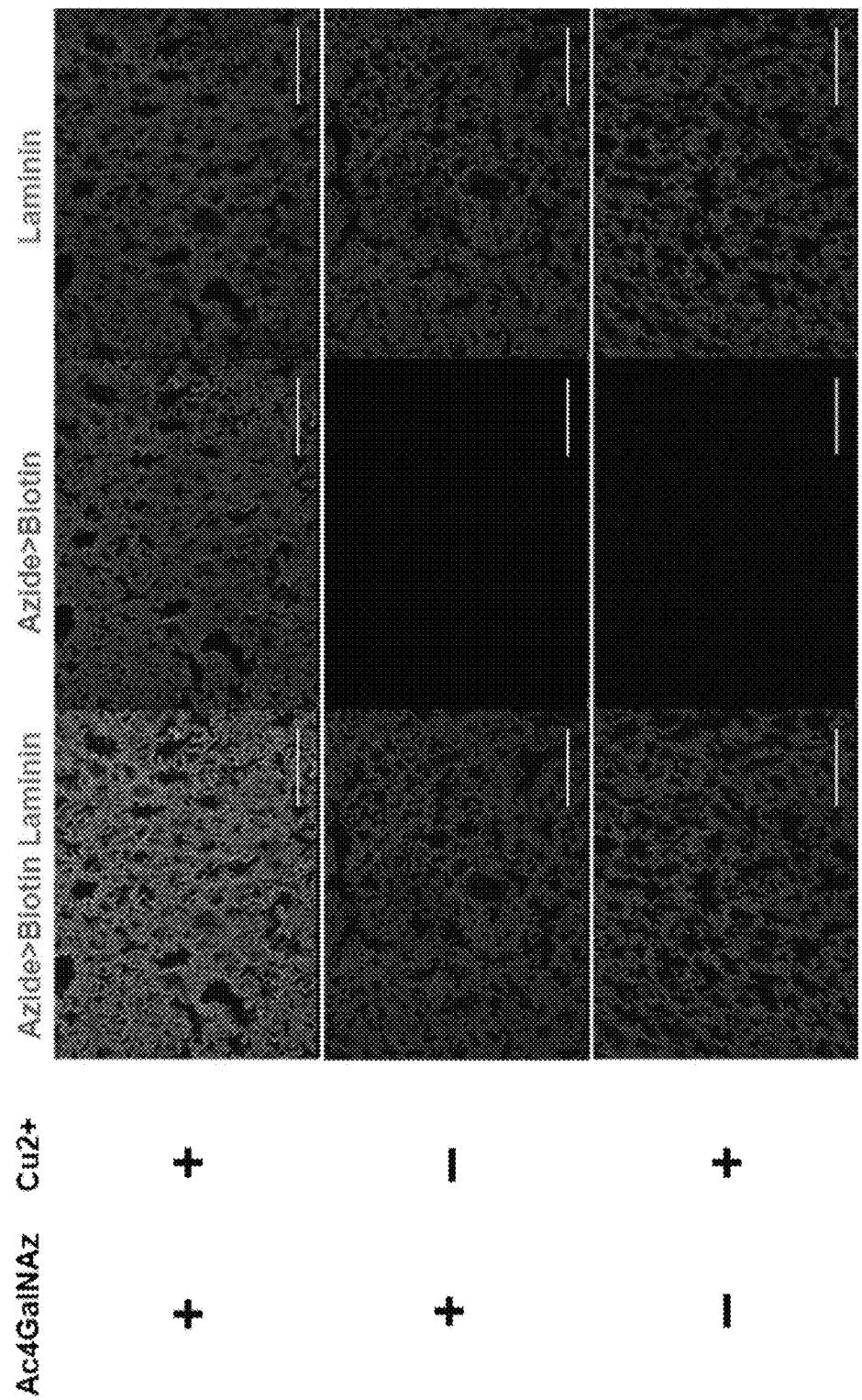
FIG. 10 shows detection of azide labeling in decellularized rat lung scaffolds after ex vivo metabolic engineering.

FIG. 10 shows detection of azide labeling in decellularized rat lung scaffolds after ex vivo metabolic engineering. The samples were co-stained with laminin, which is an abundant extracellular matrix (ECM) protein, to facilitate visualization of the decellularized ECM (Scale: 200 µm).

Figure 11:
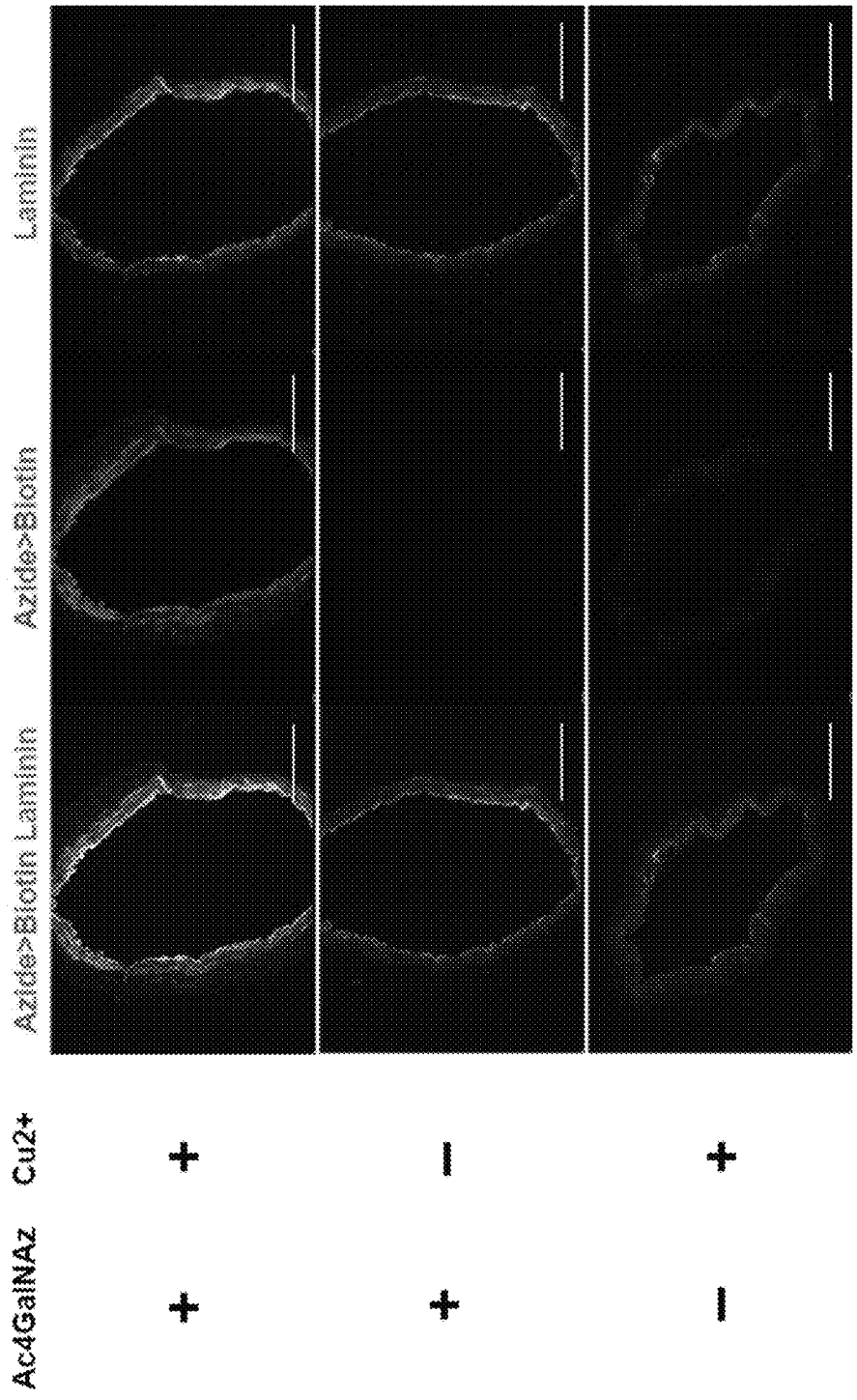
FIG. 11 shows detection of azide labeling in decellularized rat carotid artery scaffolds after ex vivo metabolic engineering.
Figure 12:
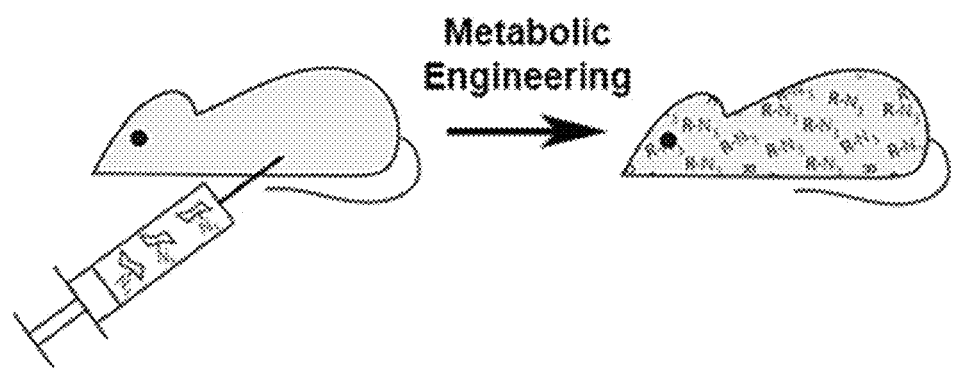
FIG. 12 shows diagram of in vivo metabolic engineering of decellularized scaffolds of rat organs/tissues.

FIG. 11 shows successful labeling of decellularized scaffolds of carotid arteries. The samples were co-stained with laminin, which is an abundant ECM protein, to facilitate visualization of the decellularized ECM (Scale: 200 µm).

Ex vivo metabolic engineering approach can be applied to other organs/tissues of rat, human and other models, such as the porcine model.

Example 6b—Reaction of Metabolically Labeled Extracellular Matrix of Organs/Tissues with Modified Biomolecules Click Reaction During Organ Infusion To enable subsequent biomedical application of functionalized ECM, such as whole-organ engineering, the feasibility of conjugating alkyne-modified biomolecules of interest onto azide-labeled acellular organ scaffolds in whole-mount by infusion click reaction was shown (see FIG. 26H). Using the ex vivo-engineered azide-labeled acellular rat lung and biotin-alkyne as a model, efficient and homogeneous click immobilization of biotin throughout the entire acellular lung after infusing the lung with click reaction mix and incubating for one hour at room temperature was demonstrated (see FIG. 26I).

Biomolecule Immobilization onto Synthetic ECM Surface

Following confirmation of preserved bioactivity of Heparin-AB after its click immobilization onto synthetic ECM surface (See Example 2b), the immobilization of Heparin-AB on azide-labeled acellular lungs was demonstrated (see diagram in FIG. 27G). Infusion click reaction of Heparin-AB in acellular rat lungs with and without ex vivo Ac4GalNAz metabolic engineering was performed, and observed specific and homogeneous immobilization of Heparin-B throughout the entire azide-labeled acellular lungs (see FIG. 27H). Similar to what is observed on the Collagen-Azide wells (See Example 2b), Heparin-B immobilized on azide-labeled acellular lungs led to enhancement of ATIII immobilization (see FIG. 27I) and FXa inhibition (see FIG. 27J). Altogether, these results demonstrated that the azide-labeled, click-reactive acellular lung ECM, derived from Ac4GalNAz metabolic engineering, can be effectively used to immobilize an alkyne-modified biomolecules of interest via the click conjugation while maintaining their bioactivity after immobilization.

Figure 19:
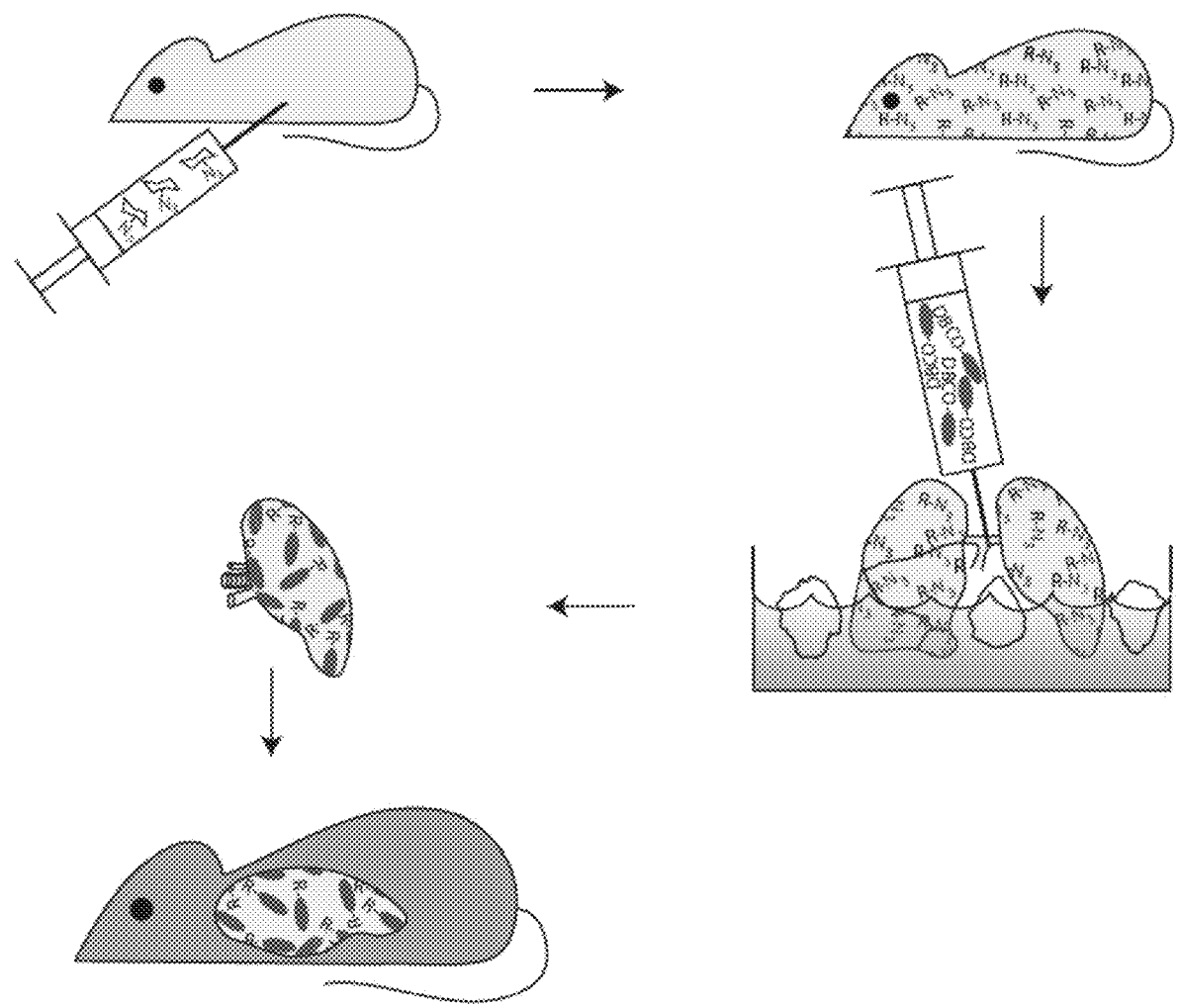
FIG. 19 is a diagram showing the procedure for molecular refinement of donor lung tissue during its cold preservation for transplantation.

Example 7—Bioorthogonal Modification of Donor Organ Grafts to Improve Organ Preservation and Transplantation Procedure The procedure involves two steps. In the first step, the donor rat was injected with Ac4GalNAz for three days (as described in Example 4). This allowed for metabolic labeling of the donor lung with azido tags. In the second step, the donor lung with azido labeling was preserved in preservation solution (Perfadex) containing DBCO-activated biotin at 100 µM concentration on ice for 1 hour. The lung was then intensively washed with preservation solution (Perfadex) and prepared for transplantation. The lung is fixed for histological staining of the immobilized biologically active molecule (as exemplified by biotin). The diagram of the procedure for molecular refinement of donor lung tissue during its cold preservation for transplantation is shown in FIG. 19.

Results

To prove the concept of functionalizing transplantable live lung tissue using copper-free click chemistry in a clinically relevant setting, the click reaction was performed during the phase of cold lung preservation in the clinical preservation solution Perfadex on ice. DBCO-activated biotin was used a proof-of-principle.

Figure 20:
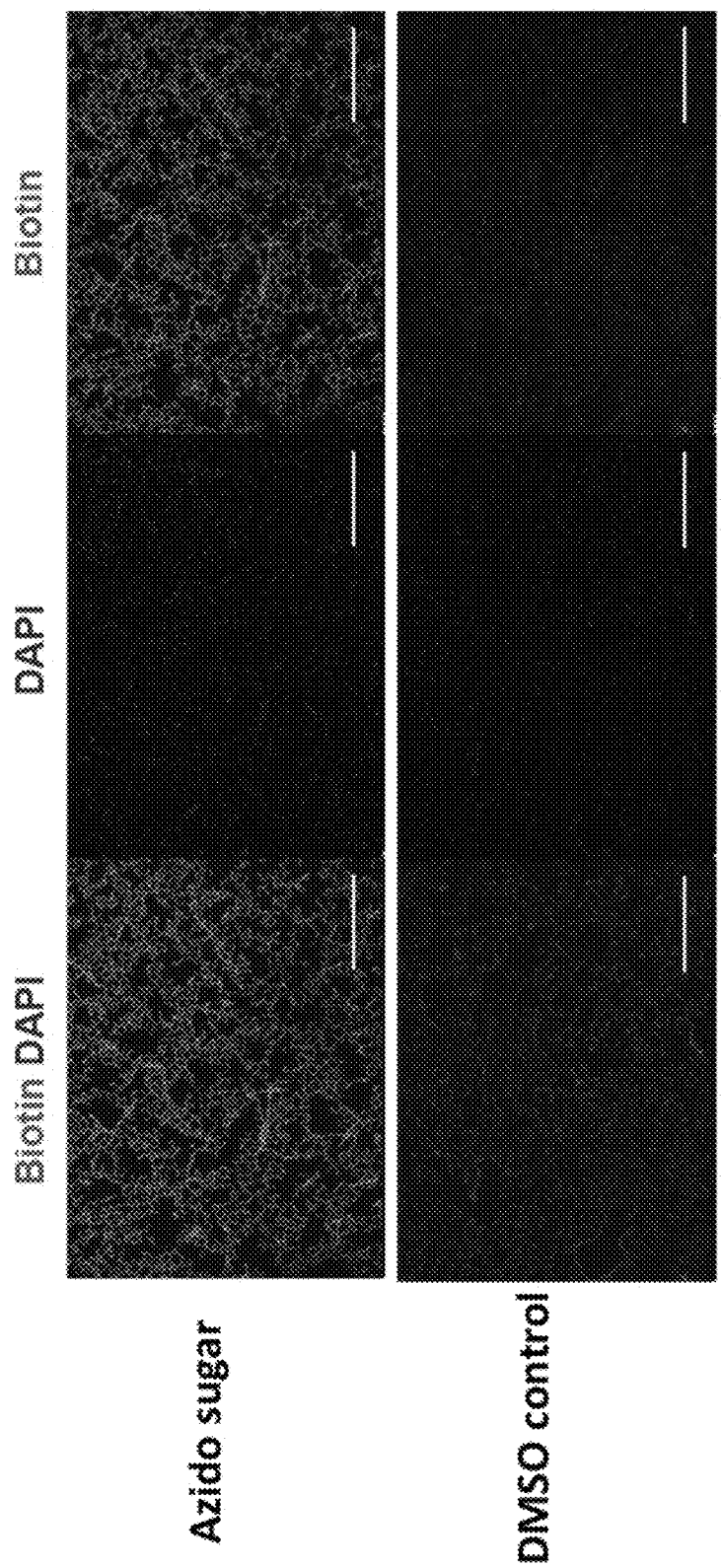
FIG. 20 is a photograph showing copper-free click reaction of DBCO-biotin and azido sugar labelled lung grafts and control lung grafts that were preserved in clinical Perfadex solution on ice.

As shown in FIG. 20, immobilization of biotin onto donor lung tissue using the bioorthogonal and chemoselective reaction occurred with high efficiency within one hour in cold clinical preservation solution.

Described herein is a strategy to metabolically engineer native ECM biomaterials by covalent incorporation of azide ligands in vivo and ex vivo. This enables chemoselective functionalization of these biomaterials with desired features endowed by covalent immobilization of, e.g., alkyne-modified bioactive molecules through the click chemistry. It was shown that click-reactive azide ligands can be efficiently incorporated into the organs' ECM through intraperitoneal administration of Ac4GalNAz. Effective azide incorporation is observed in the ECM of all the tissues and organs that were examined (see Examples), including the lung, heart, kidney, liver, skin and blood vessel. This indicates that the strategy described herein is applicable to a wide range of native ECM biomaterials.

Using the lung as a model, it was shown that efficient Ac4GalNAz metabolic ECM engineering can also be achieved during the ex vivo culture of freshly isolated organs in both the rodent and porcine models. This further broadens the applicability of the described method to circumstances when the administration of Ac4GalNAz to donor animals is not feasible. This also opens up the possibility of applying the metabolic ECM engineering directly to donor human organs. Using Heparin-AB as a model, it was demonstrated that the "clickable" acellular lungs derived from metabolic engineering can be effectively used for immobilization of bioactive molecules, which remained biologically active after their click immobilization onto whole-organ ECM.

Importantly, the approach described herein for native biomaterial functionalization has confirmed biocompatibility. It was shown that azide ligands can be incorporated into the ECM of live and functioning organs in vivo, indicating that the azide incorporation sites can be regarded as "safe sites" that do not cause obvious interference with the organs' regular functions. Following decellularization, alkyne-modified biomolecules of interest can be further conjugated onto these "safe sites" using the click chemistry. Altogether, by combining a biologically selective azide incorporation into the ECM and a subsequent chemoselective click ligation with desired alkyne-modified biomolecules, the methods described herein provide an innovative solution to enable functionalization of native ECM biomaterials with high specificity and biocompatibility.

Moreover, in conventional biomaterial functionalization using crosslinking chemistry, immobilization reactions usually need to be individually developed for each biomolecule of interest due to their distinct chemical properties. Using crosslinking chemistry for biomaterial functionalization, it is also challenging to combine multiple functional biomolecules together in one reaction due to the potential cross reactivity between the biomolecules upon chemical activation and the difference in their reactivity with the biomaterial. In contrast, when using the azide-labeled "clickable" ECM biomaterials, the click chemistry-based conjugation reaction can be applied to most alkyne-modified biomolecules with minimal modifications. It is also possible to combine different alkyne-modified biomolecules together in a single conjugation reaction, given the chemical inertness of these alkyne-modified biomolecules to each other. The development of composite biomaterials carrying multiple desired features is thus possible.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of preparing a decellularized scaffold of an organ or tissue of a mammal comprising an extracellular matrix functionalized with a chemical group that is reactive in a biorthogonal chemical reaction, the method comprising:
   (i) selecting the mammal for functionalizing the extracellular matrix of the organ or tissue of the mammal with the chemical group that is reactive in the biorthogonal chemical reaction; and
   (ii) administering a nutrient functionalized with the chemical group that is reactive in the biorthogonal chemical reaction to the mammal in an amount from about 10 mg/kg to about 10 g/kg that is sufficient to functionalize the extracellular matrix of the organ or tissue of the mammal with the chemical group that is reactive in the biorthogonal chemical reaction;
   (iii) surgically removing from the mammal the organ or tissue comprising the extracellular matrix functionalized with a chemical group that is reactive in a biorthogonal chemical reaction; and
   (iv) decellularizing the organ or tissue to obtain the decellularized scaffold comprising the extracellular matrix functionalized with a chemical group that is reactive in a biorthogonal chemical reaction.

2. The method of claim 1, wherein the organ or tissue is bovine, porcine, murine or human organ or tissue.

3. The method of claim 1, wherein the organ or tissue is selected from the group consisting of carotid artery, lung, heart, liver, kidney and skin.

4. The method of claim 1, wherein the chemical group that is reactive in the biorthogonal chemical reaction is selected from the group consisting of an azide ($N_3$), an alkyne, a nitrone, an isocyanide, a cyclopropene and a tetrazine.

5. The method of claim 1, wherein the chemical group that is reactive in the biorthogonal chemical reaction is selected from an azide (—$N_3$) and an alkyne.

6. The method of claim 1, wherein the chemical group that is reactive in the biorthogonal chemical reaction is an azide (—$N_3$).

7. The method of claim 1, wherein the nutrient is selected from the group consisting of saccharide, amino acid, fatty acid, and triglyceride.

8. The method of claim 1, wherein the nutrient is a monosaccharide.

9. The method of claim 1, wherein the nutrient functionalized with the chemical group that is reactive in a biorthogonal chemical reaction is selected from the group consisting of azide-labeled galactosamine, azide-labeled glucosamine and azide-labeled mannosamine.

10. The method of claim 1, wherein the nutrient functionalized with the chemical group that is reactive in a biorthogonal chemical reaction is selected from tetraacylated N-azidoacetylgalactosamine ($Ac_4$GalNAz), tetraacylated N-azidoacetylmannosamine ($Ac_4$ManNAz), and tetraacylated N-azidoacetylglucosamine ($Ac_4$GlcNAz).

11. The method of claim 1, wherein the nutrient functionalized with the chemical group that is reactive in a biorthogonal chemical reaction is tetraacylated N-azidoacetylgalactosamine ($Ac_4$GalNAz).

12. The method of claim 1, wherein the nutrient is administered by intraperitoneal injection, subcutaneous injection or by the intratracheal route.

13. The method of claim 1, wherein the nutrient is administered by intraperitoneal injection.

* * * * *